US009990625B2

(12) United States Patent
Pitroda et al.

(10) Patent No.: US 9,990,625 B2
(45) Date of Patent: *Jun. 5, 2018

(54) ESTABLISHING TRUST FOR CONDUCTING DIRECT SECURE ELECTRONIC TRANSACTIONS BETWEEN A USER AND SERVICE PROVIDERS

(71) Applicant: MasterCard Mobile Transactions Solutions, Inc., Purchase, NY (US)

(72) Inventors: Satyan G. Pitroda, Oak Brook, IL (US); Mehul Desai, Oak Brook, IL (US)

(73) Assignee: MASTERCARD MOBILE TRANSACTIONS SOLUTIONS, INC., Purchase, NY (US)

( * ) Notice: Subject to any disclaimer, the term of this patent is extended or adjusted under 35 U.S.C. 154(b) by 298 days.

This patent is subject to a terminal disclaimer.

(21) Appl. No.: 14/983,877

(22) Filed: Dec. 30, 2015

(65) Prior Publication Data

US 2016/0117668 A1 Apr. 28, 2016

Related U.S. Application Data

(63) Continuation of application No. 13/168,764, filed on Jun. 24, 2011, now Pat. No. 9,330,388, which is a
(Continued)

(51) Int. Cl.
*G06Q 20/32* (2012.01)
*G06Q 20/02* (2012.01)
(Continued)

(52) U.S. Cl.
CPC ....... *G06Q 20/3227* (2013.01); *G06F 19/322* (2013.01); *G06F 21/606* (2013.01);
(Continued)

(58) Field of Classification Search
CPC .................................................. G06Q 20/3227
See application file for complete search history.

(56) References Cited

U.S. PATENT DOCUMENTS 3,999,050 A 12/1976 Pitroda
4,227,253 A 10/1980 Ehrsam et al.
(Continued)

FOREIGN PATENT DOCUMENTS

EP 1006469 A1 6/2000
WO 8304327 A1 12/1983
(Continued)

OTHER PUBLICATIONS 13165007.9, "European Application Serial No. 13165007.9, Extended European Search Report dated Jul. 30, 2014", C-Sam, Inc., 7 Pages.
(Continued)

*Primary Examiner* — Jacob C Coppola
(74) *Attorney, Agent, or Firm* — GTC Law Group PC & Affiliates

(57) ABSTRACT

Ensuring security of electronic transactions between a user and a service provider involves establishing electronic trust among a user, device, transaction service provider, and service providers through OTAC processing, key generation and exchange, and verification.

7 Claims, 80 Drawing Sheets

Related U.S. Application Data continuation of application No. 11/539,024, filed on Oct. 5, 2006.

(60) Provisional application No. 60/724,066, filed on Oct. 6, 2005.

(51) Int. Cl.

| | |
|---|---|
| *G06Q 20/04* | (2012.01) |
| *G06Q 20/10* | (2012.01) |
| *G06Q 20/12* | (2012.01) |
| *G06Q 20/36* | (2012.01) |
| *G06Q 20/38* | (2012.01) |
| *G06Q 20/40* | (2012.01) |
| *G06Q 20/42* | (2012.01) |
| *G06Q 30/06* | (2012.01) |
| *G06Q 20/14* | (2012.01) |
| *G06F 21/60* | (2013.01) |
| *H04L 29/06* | (2006.01) |
| *G06F 19/00* | (2018.01) |

(52) U.S. Cl.
CPC ........... *G06Q 20/02* (2013.01); *G06Q 20/045* (2013.01); *G06Q 20/0453* (2013.01); *G06Q 20/10* (2013.01); *G06Q 20/12* (2013.01); *G06Q 20/145* (2013.01); *G06Q 20/32* (2013.01); *G06Q 20/322* (2013.01); *G06Q 20/325* (2013.01); *G06Q 20/327* (2013.01); *G06Q 20/3223* (2013.01); *G06Q 20/3226* (2013.01); *G06Q 20/367* (2013.01); *G06Q 20/3674* (2013.01); *G06Q 20/382* (2013.01); *G06Q 20/385* (2013.01); *G06Q 20/3821* (2013.01); *G06Q 20/3829* (2013.01); *G06Q 20/38215* (2013.01); *G06Q 20/40* (2013.01); *G06Q 20/401* (2013.01); *G06Q 20/4014* (2013.01); *G06Q 20/42* (2013.01); *G06Q 30/06* (2013.01); *H04L 63/0838* (2013.01); *G06Q 2220/00* (2013.01); *H04L 63/0428* (2013.01); *H04L 63/06* (2013.01); *H04L 63/08* (2013.01)

(56) References Cited

U.S. PATENT DOCUMENTS

| | | |
|---|---|---|
| 4,238,854 A | 12/1980 | Ehrsam et al. |
| 4,302,810 A | 11/1981 | Bouricius et al. |
| 4,992,940 A | 2/1991 | Dworkin et al. |
| 5,175,416 A | 12/1992 | Mansvelt et al. |
| 5,239,462 A | 8/1993 | Jones et al. |
| 5,241,594 A | 8/1993 | Kung |
| 5,276,311 A | 1/1994 | Hennige |
| 5,283,731 A | 2/1994 | Lalonde et al. |
| 5,461,217 A | 10/1995 | Claus |
| 5,578,808 A | 11/1996 | Taylor |
| 5,590,038 A | 12/1996 | Pitroda |
| 5,592,375 A | 1/1997 | Borgman et al. |
| 5,600,708 A | 2/1997 | Meche et al. |
| 5,664,115 A | 9/1997 | Fraser et al. |
| 5,671,279 A | 9/1997 | Elgamal |
| 5,671,280 A | 9/1997 | Rosen |
| 5,699,527 A | 12/1997 | Davidson et al. |
| 5,732,400 A | 3/1998 | Mandler et al. |
| 5,761,306 A | 6/1998 | Lewis |
| 5,765,144 A | 6/1998 | Larche et al. |
| 5,794,207 A | 8/1998 | Walker et al. |
| 5,797,133 A | 8/1998 | Jones et al. |
| 5,815,657 A | 9/1998 | Williams et al. |
| 5,826,245 A | 10/1998 | Sandberg-Diment |
| 5,855,008 A | 12/1998 | Goldhaber et al. |
| 5,859,419 A | 1/1999 | Wynn |
| 5,864,667 A | 1/1999 | Barkan |
| 5,870,721 A | 2/1999 | Norris |
| 5,878,403 A | 3/1999 | Defrancesco et al. |
| H001794 H | 4/1999 | Claus |
| 5,895,903 A | 4/1999 | Abe et al. |
| 5,903,881 A | 5/1999 | Schrader et al. |
| 5,910,987 A | 6/1999 | Ginter et al. |
| 5,930,776 A | 7/1999 | Wade et al. |
| 5,932,859 A | 8/1999 | Ijichi et al. |
| 5,940,807 A | 8/1999 | Purcell et al. |
| 5,940,811 A | 8/1999 | Norris et al. |
| 5,940,812 A | 8/1999 | Tengel et al. |
| 5,943,423 A | 8/1999 | Muftic |
| 5,945,652 A | 8/1999 | Ohki et al. |
| 5,952,641 A | 9/1999 | Korshun et al. |
| 5,955,961 A | 9/1999 | Wallerstein |
| 5,974,396 A | 10/1999 | Anderson et al. |
| 5,979,797 A | 11/1999 | Castellano |
| 5,987,611 A | 11/1999 | Freund |
| 5,995,947 A | 11/1999 | Payankannur Suresh et al. |
| 6,000,607 A | 12/1999 | Ohki et al. |
| 6,014,645 A | 1/2000 | Cunningham et al. |
| 6,016,476 A | 1/2000 | Maes et al. |
| 6,026,430 A | 2/2000 | Butman et al. |
| 6,061,692 A | 5/2000 | Thomas et al. |
| 6,067,528 A | 5/2000 | Breed et al. |
| 6,078,888 A | 6/2000 | Johnson, Jr. |
| 6,085,976 A | 7/2000 | Sehr |
| 6,128,602 A | 10/2000 | Northington et al. |
| 6,141,653 A | 10/2000 | Foucher et al. |
| 6,142,368 A | 11/2000 | Mullins et al. |
| 6,142,369 A | 11/2000 | Jonstromer |
| 6,145,739 A | 11/2000 | Bertina et al. |
| 6,149,055 A | 11/2000 | Gatto |
| 6,167,396 A | 12/2000 | Lokken |
| 6,185,599 B1 | 2/2001 | Salimando et al. |
| 6,208,979 B1 | 3/2001 | Sinclair et al. |
| 6,233,341 B1 | 5/2001 | Riggins |
| 6,243,443 B1 | 6/2001 | Low et al. |
| 6,250,557 B1 | 6/2001 | Forslund et al. |
| 6,264,108 B1 | 7/2001 | Baentsch |
| 6,308,887 B1 | 10/2001 | Korman et al. |
| 6,327,578 B1 | 12/2001 | Linehan |
| 6,339,638 B1 | 1/2002 | Ohki et al. |
| 6,370,514 B1 | 4/2002 | Messner et al. |
| 6,385,594 B1 | 5/2002 | Stiegler et al. |
| 6,393,411 B1 | 5/2002 | Bishop et al. |
| 6,418,326 B1 | 7/2002 | Heinonen et al. |
| 6,431,439 B1 | 8/2002 | Suer et al. |
| 6,442,532 B1 | 8/2002 | Kawan |
| 6,505,164 B1 | 1/2003 | Brunsting et al. |
| 6,505,176 B2 | 1/2003 | Freiman et al. |
| 6,505,773 B1 | 1/2003 | Palmer et al. |
| 6,510,236 B1 | 1/2003 | Crane et al. |
| 6,513,117 B2 | 1/2003 | Tarpenning et al. |
| 6,523,027 B1 | 2/2003 | Underwood et al. |
| 6,577,861 B2 | 6/2003 | Ogasawara |
| 6,581,068 B1 | 6/2003 | Bensoussan et al. |
| 6,611,869 B1 | 8/2003 | Eschelbeck et al. |
| 6,622,015 B1 | 9/2003 | Himmel et al. |
| 6,675,153 B1 | 1/2004 | Cook et al. |
| 6,705,520 B1 | 3/2004 | Pitroda et al. |
| 6,732,919 B2 | 5/2004 | Macklin et al. |
| 6,738,749 B1 | 5/2004 | Chasko |
| 6,745,326 B1 | 6/2004 | Wary |
| 6,760,752 B1 | 7/2004 | Liu et al. |
| 6,761,319 B2 | 7/2004 | Peachman |
| 6,769,607 B1 | 8/2004 | Pitroda et al. |
| 6,789,193 B1 | 9/2004 | Heiden |
| 6,862,607 B1 | 3/2005 | Vermeulen |
| 6,871,276 B1 | 3/2005 | Simon et al. |
| 6,880,761 B1 | 4/2005 | Ritter et al. |
| 6,885,877 B1 | 4/2005 | Ozaki et al. |
| 6,925,439 B1 | 8/2005 | Pitroda |
| 6,941,342 B1 | 9/2005 | Nelson et al. |
| 6,948,063 B1 | 9/2005 | Ganesan et al. |
| 6,999,943 B1 | 2/2006 | Johnson et al. |
| 7,010,582 B1 | 3/2006 | Cheng et al. |
| 7,039,802 B1 | 5/2006 | Eskicioglu et al. |
| 7,103,575 B1 | 9/2006 | Linehan |

(56) References Cited

U.S. PATENT DOCUMENTS

| | | |
|---|---|---|
| 7,120,609 B1 | 10/2006 | Kerkdijk et al. |
| 7,124,092 B2 | 10/2006 | O'Toole, Jr. et al. |
| 7,158,948 B1 | 1/2007 | Rodriguez et al. |
| 7,167,711 B1 | 1/2007 | Dennis |
| 7,177,836 B1 | 2/2007 | German et al. |
| 7,200,578 B2 | 4/2007 | Paltenghe et al. |
| 7,216,091 B1 | 5/2007 | Blandina et al. |
| 7,225,147 B1 | 5/2007 | Kley |
| 7,240,028 B1 | 7/2007 | Rugge |
| 7,249,092 B2 | 7/2007 | Dunn et al. |
| 7,257,636 B2 | 8/2007 | Lee et al. |
| 7,263,515 B1 | 8/2007 | Tenorio et al. |
| 7,287,271 B1 | 10/2007 | Riggins |
| 7,330,826 B1 | 2/2008 | Porat et al. |
| 7,343,351 B1 | 3/2008 | Bishop et al. |
| 7,366,682 B1 | 4/2008 | Katiyar et al. |
| 7,366,990 B2 | 4/2008 | Pitroda |
| 7,373,515 B2 | 5/2008 | Owen et al. |
| 7,379,913 B2 | 5/2008 | Steele et al. |
| 7,484,246 B2 | 1/2009 | Matsuyama et al. |
| 7,516,103 B1 | 4/2009 | Peitrucha, Jr. et al. |
| 7,590,570 B2 | 9/2009 | Harrison et al. |
| 7,630,986 B1 | 12/2009 | Kannan et al. |
| 7,646,874 B2 | 1/2010 | Iwamoto et al. |
| 7,664,672 B1 | 2/2010 | Walker et al. |
| 7,734,661 B2 | 6/2010 | Jordan et al. |
| 7,822,635 B1 | 10/2010 | Brown et al. |
| 7,822,688 B2 | 10/2010 | Labrou et al. |
| 7,827,057 B1 | 11/2010 | Walker et al. |
| 7,844,500 B2 | 11/2010 | Ran |
| 7,925,878 B2 | 4/2011 | Merrien et al. |
| 7,970,690 B2 | 6/2011 | Diana et al. |
| 8,055,548 B2 | 11/2011 | Staib et al. |
| 8,291,085 B2 | 10/2012 | Shiigi et al. |
| 8,781,923 B2 | 7/2014 | Pitroda et al. |
| 9,070,127 B2 | 6/2015 | Pitroda et al. |
| 9,177,315 B2 | 11/2015 | Pitroda et al. |
| 9,208,490 B2 | 12/2015 | Pitroda et al. |
| 9,317,849 B2 | 4/2016 | Pitroda et al. |
| 9,330,388 B2 | 5/2016 | Pitroda et al. |
| 9,330,389 B2 | 5/2016 | Pitroda et al. |
| 9,330,390 B2 | 5/2016 | Pitroda et al. |
| 9,400,980 B2 | 7/2016 | Satyan et al. |
| 9,471,914 B2 | 10/2016 | Pitroda et al. |
| 9,697,512 B2 | 7/2017 | Pitroda et al. |
| 9,811,820 B2 | 11/2017 | Pitroda |
| 2001/0007983 A1 | 7/2001 | Lee |
| 2001/0011250 A1 | 8/2001 | Paltenghe et al. |
| 2001/0014868 A1 | 8/2001 | Herz et al. |
| 2001/0029496 A1 | 10/2001 | Otto et al. |
| 2001/0032878 A1 | 10/2001 | Tsiounis et al. |
| 2001/0034604 A1 | 10/2001 | Yagasaki et al. |
| 2001/0034720 A1 | 10/2001 | Armes |
| 2001/0034725 A1 | 10/2001 | Park et al. |
| 2001/0037294 A1 | 11/2001 | Freishtat et al. |
| 2001/0037451 A1 | 11/2001 | Bhagavatula et al. |
| 2001/0044762 A1 | 11/2001 | Nault |
| 2001/0045451 A1 | 11/2001 | Tan et al. |
| 2001/0051917 A1 | 12/2001 | Bissonette et al. |
| 2001/0051923 A1 | 12/2001 | Kosuda |
| 2002/0004783 A1 | 1/2002 | Paltenghe et al. |
| 2002/0023010 A1 | 2/2002 | Rittmaster et al. |
| 2002/0026410 A1 | 2/2002 | Woloshin et al. |
| 2002/0026419 A1 | 2/2002 | Maritzen et al. |
| 2002/0026582 A1 | 2/2002 | Futamura |
| 2002/0029207 A1 | 3/2002 | Bakalash et al. |
| 2002/0032633 A1 | 3/2002 | Okumura et al. |
| 2002/0046162 A1 | 4/2002 | Sakashita et al. |
| 2002/0049622 A1 | 4/2002 | Lettich et al. |
| 2002/0052825 A1 | 5/2002 | Bensemana |
| 2002/0053035 A1* | 5/2002 | Schutzer ............... G06F 21/32 726/5 |
| 2002/0062249 A1 | 5/2002 | Iannacci |
| 2002/0062280 A1 | 5/2002 | Zachariassen et al. |
| 2002/0065774 A1 | 5/2002 | Young et al. |
| 2002/0072986 A1 | 6/2002 | Aram |
| 2002/0077964 A1 | 6/2002 | Brody et al. |
| 2002/0080974 A1 | 6/2002 | Grawrock |
| 2002/0087388 A1 | 7/2002 | Keil et al. |
| 2002/0091646 A1 | 7/2002 | Lake et al. |
| 2002/0095331 A1 | 7/2002 | Osman et al. |
| 2002/0107730 A1 | 8/2002 | Bernstein |
| 2002/0108041 A1 | 8/2002 | Watanabe et al. |
| 2002/0111907 A1 | 8/2002 | Ling |
| 2002/0138455 A1 | 9/2002 | Abdel-Moneim et al. |
| 2002/0147047 A1 | 10/2002 | Letovsky et al. |
| 2002/0147920 A1 | 10/2002 | Mauro |
| 2002/0152179 A1 | 10/2002 | Racov et al. |
| 2002/0169626 A1 | 11/2002 | Walker et al. |
| 2002/0169737 A1 | 11/2002 | Armstrong et al. |
| 2002/0177433 A1 | 11/2002 | Bravo et al. |
| 2003/0023880 A1 | 1/2003 | Edwards et al. |
| 2003/0028451 A1 | 2/2003 | Ananian |
| 2003/0028470 A1 | 2/2003 | Dutta |
| 2003/0038707 A1 | 2/2003 | Geller |
| 2003/0052865 A1 | 3/2003 | Miller et al. |
| 2003/0055652 A1 | 3/2003 | Nichols et al. |
| 2003/0055785 A1 | 3/2003 | Lahiri et al. |
| 2003/0060286 A1 | 3/2003 | Walker et al. |
| 2003/0074253 A1 | 4/2003 | Scheuring et al. |
| 2003/0078788 A1 | 4/2003 | Sussman et al. |
| 2003/0084172 A1 | 5/2003 | Dejong et al. |
| 2003/0084302 A1 | 5/2003 | De Jong et al. |
| 2003/0093414 A1 | 5/2003 | Litzow et al. |
| 2003/0105722 A1 | 6/2003 | Welt |
| 2003/0110133 A1 | 6/2003 | Maritzen et al. |
| 2003/0115126 A1 | 6/2003 | Pitroda |
| 2003/0126075 A1 | 7/2003 | Mascavage, III et al. |
| 2003/0149876 A1 | 8/2003 | McGough |
| 2003/0154135 A1 | 8/2003 | Covington et al. |
| 2003/0159040 A1 | 8/2003 | Hashimoto et al. |
| 2003/0162565 A1 | 8/2003 | Al-Khaja et al. |
| 2003/0163700 A1 | 8/2003 | Paatero |
| 2003/0163701 A1 | 8/2003 | Ochi et al. |
| 2003/0163739 A1 | 8/2003 | Armington et al. |
| 2003/0167226 A1 | 9/2003 | Britton et al. |
| 2003/0172039 A1 | 9/2003 | Guy et al. |
| 2003/0172272 A1 | 9/2003 | Ehlers et al. |
| 2003/0187795 A1 | 10/2003 | Lee et al. |
| 2003/0197058 A1 | 10/2003 | Benkert et al. |
| 2003/0204725 A1 | 10/2003 | Itoi et al. |
| 2003/0212632 A1 | 11/2003 | Keogh et al. |
| 2003/0220884 A1 | 11/2003 | Choi et al. |
| 2003/0229548 A1 | 12/2003 | Kakuta |
| 2004/0002878 A1 | 1/2004 | Hinton |
| 2004/0025053 A1 | 2/2004 | Hayward et al. |
| 2004/0029569 A1 | 2/2004 | Khan et al. |
| 2004/0030887 A1 | 2/2004 | Harrisville-Wolff et al. |
| 2004/0039651 A1 | 2/2004 | Grunzig et al. |
| 2004/0044627 A1 | 3/2004 | Russell et al. |
| 2004/0059672 A1 | 3/2004 | Baig et al. |
| 2004/0062399 A1 | 4/2004 | Takase |
| 2004/0083184 A1 | 4/2004 | Tsuei et al. |
| 2004/0098349 A1 | 5/2004 | Tolson et al. |
| 2004/0117460 A1 | 6/2004 | Walsh et al. |
| 2004/0143552 A1 | 7/2004 | Weichert et al. |
| 2004/0176134 A1 | 9/2004 | Goldthwaite et al. |
| 2004/0177248 A1 | 9/2004 | Yoshida |
| 2004/0181665 A1 | 9/2004 | Houser |
| 2004/0187018 A1 | 9/2004 | Owen et al. |
| 2004/0210597 A1 | 10/2004 | Wanish |
| 2004/0254881 A1 | 12/2004 | Kumar et al. |
| 2004/0268127 A1 | 12/2004 | Sahota |
| 2005/0021488 A1 | 1/2005 | Agrawal et al. |
| 2005/0021975 A1 | 1/2005 | Liu |
| 2005/0044410 A1 | 2/2005 | Yan et al. |
| 2005/0055275 A1 | 3/2005 | Newman et al. |
| 2005/0055316 A1 | 3/2005 | Williams et al. |
| 2005/0060248 A1 | 3/2005 | O'Neal |
| 2005/0071349 A1 | 3/2005 | Jordan et al. |
| 2005/0081044 A1 | 4/2005 | Giles et al. |
| 2005/0108157 A1 | 5/2005 | Bushman et al. |
| 2005/0171898 A1 | 8/2005 | Bishop et al. |
| 2005/0177518 A1 | 8/2005 | Brown et al. |

(56) References Cited

U.S. PATENT DOCUMENTS

| | | |
|---|---|---|
| 2005/0228874 A1 | 10/2005 | Edgett et al. |
| 2005/0250473 A1 | 11/2005 | Brown et al. |
| 2005/0261959 A1 | 11/2005 | Moyer |
| 2005/0273406 A1 | 12/2005 | Lebda et al. |
| 2005/0273431 A1 | 12/2005 | Abel et al. |
| 2006/0004656 A1 | 1/2006 | Lee |
| 2006/0015358 A1 | 1/2006 | Chua |
| 2006/0041761 A1 | 2/2006 | Neumann et al. |
| 2006/0059344 A1 | 3/2006 | Mononen |
| 2006/0069585 A1 | 3/2006 | Springfield et al. |
| 2006/0069916 A1 | 3/2006 | Jenisch et al. |
| 2006/0074779 A1 | 4/2006 | Washizuka et al. |
| 2006/0080545 A1 | 4/2006 | Bagley |
| 2006/0094403 A1 | 5/2006 | Norefors et al. |
| 2006/0106700 A1 | 5/2006 | Boren et al. |
| 2006/0129454 A1 | 6/2006 | Moon et al. |
| 2006/0136739 A1 | 6/2006 | Brock et al. |
| 2006/0167823 A1 | 7/2006 | York et al. |
| 2006/0174105 A1 | 8/2006 | Park |
| 2006/0179304 A1 | 8/2006 | Han |
| 2006/0235761 A1 | 10/2006 | Johnson |
| 2006/0235796 A1 | 10/2006 | Johnson et al. |
| 2006/0262929 A1 | 11/2006 | Vatanen et al. |
| 2006/0269061 A1 | 11/2006 | Balasubramanian et al. |
| 2006/0271457 A1 | 11/2006 | Romain et al. |
| 2006/0276171 A1 | 12/2006 | Pousti et al. |
| 2007/0016941 A1 | 1/2007 | Gonzalez et al. |
| 2007/0033642 A1 | 2/2007 | Ganesan et al. |
| 2007/0038680 A1 | 2/2007 | Casey et al. |
| 2007/0079333 A1 | 4/2007 | Murakami et al. |
| 2007/0083441 A1 | 4/2007 | Harper |
| 2007/0125838 A1 | 6/2007 | Law et al. |
| 2007/0130463 A1 | 6/2007 | Law et al. |
| 2007/0136800 A1 | 6/2007 | Chan et al. |
| 2007/0198432 A1 | 8/2007 | Pitroda et al. |
| 2007/0214037 A1 | 9/2007 | Shubert et al. |
| 2007/0239476 A1 | 10/2007 | Rohan et al. |
| 2007/0248091 A1 | 10/2007 | Khalid et al. |
| 2008/0015942 A1 | 1/2008 | Harper et al. |
| 2008/0033869 A1 | 2/2008 | Steele et al. |
| 2008/0059297 A1 | 3/2008 | Vallier et al. |
| 2008/0137861 A1 | 6/2008 | Lindmo et al. |
| 2008/0177826 A1 | 7/2008 | Pitroda |
| 2008/0313079 A1 | 12/2008 | Van Bosch et al. |
| 2009/0254971 A1 | 10/2009 | Herz et al. |
| 2009/0271317 A1 | 10/2009 | Walker et al. |
| 2010/0095120 A1 | 4/2010 | Thom et al. |
| 2011/0182268 A1 | 7/2011 | Akhtar et al. |
| 2011/0251870 A1 | 10/2011 | Tavares et al. |
| 2011/0321127 A1 | 12/2011 | Pitroda et al. |
| 2012/0005077 A1 | 1/2012 | Pitroda et al. |
| 2012/0005078 A1 | 1/2012 | Pitroda et al. |
| 2012/0005079 A1 | 1/2012 | Pitroda et al. |
| 2012/0005080 A1 | 1/2012 | Pitroda et al. |
| 2012/0005081 A1 | 1/2012 | Pitroda et al. |
| 2012/0005082 A1 | 1/2012 | Pitroda et al. |
| 2012/0005083 A1 | 1/2012 | Pitroda et al. |
| 2012/0005084 A1 | 1/2012 | Pitroda et al. |
| 2012/0005085 A1 | 1/2012 | Pitroda et al. |
| 2012/0005086 A1 | 1/2012 | Pitroda et al. |
| 2012/0005087 A1 | 1/2012 | Pitroda et al. |
| 2012/0005088 A1 | 1/2012 | Pitroda et al. |
| 2012/0005089 A1 | 1/2012 | Pitroda et al. |
| 2012/0005090 A1 | 1/2012 | Pitroda et al. |
| 2012/0005091 A1 | 1/2012 | Pitroda et al. |
| 2012/0005092 A1 | 1/2012 | Pitroda et al. |
| 2012/0005725 A1 | 1/2012 | Pitroda et al. |
| 2012/0005726 A1 | 1/2012 | Pitroda et al. |
| 2012/0011058 A1 | 1/2012 | Pitroda et al. |
| 2012/0101831 A1 | 4/2012 | Pitroda et al. |
| 2012/0101832 A1 | 4/2012 | Pitroda et al. |
| 2012/0101833 A1 | 4/2012 | Pitroda et al. |
| 2012/0101834 A1 | 4/2012 | Pitroda et al. |
| 2012/0101835 A1 | 4/2012 | Pitroda et al. |
| 2012/0101836 A1 | 4/2012 | Pitroda et al. |
| 2012/0109667 A1 | 5/2012 | Pitroda et al. |
| 2012/0109668 A1 | 5/2012 | Pitroda et al. |
| 2012/0109669 A1 | 5/2012 | Pitroda et al. |
| 2012/0109670 A1 | 5/2012 | Pitroda et al. |
| 2012/0109671 A1 | 5/2012 | Pitroda et al. |
| 2012/0109672 A1 | 5/2012 | Pitroda et al. |
| 2012/0109673 A1 | 5/2012 | Pitroda et al. |
| 2012/0109674 A1 | 5/2012 | Pitroda et al. |
| 2012/0116790 A1 | 5/2012 | Pitroda et al. |
| 2012/0116959 A1 | 5/2012 | Pitroda et al. |
| 2013/0226721 A1 | 8/2013 | Chmara et al. |
| 2014/0052623 A1 | 2/2014 | Pitroda et al. |
| 2014/0052640 A1 | 2/2014 | Pitroda et al. |
| 2014/0067690 A1 | 3/2014 | Pitroda et al. |
| 2014/0067691 A1 | 3/2014 | Pitroda et al. |
| 2016/0110717 A1 | 4/2016 | Pitroda et al. |
| 2016/0117669 A1 | 4/2016 | Pitroda et al. |
| 2016/0117674 A1 | 4/2016 | Pitroda et al. |
| 2016/0119332 A1 | 4/2016 | Pitroda et al. |
| 2016/0217258 A1 | 7/2016 | Pitroda et al. |

FOREIGN PATENT DOCUMENTS

| | | |
|---|---|---|
| WO | 9535546 A1 | 12/1995 |
| WO | 9922326 A1 | 5/1999 |
| WO | 9934314 A1 | 7/1999 |
| WO | 2000045243 A1 | 8/2000 |
| WO | 0118629 A2 | 3/2001 |
| WO | 0137199 A1 | 5/2001 |
| WO | 0137200 A1 | 5/2001 |
| WO | 2001052212 A1 | 7/2001 |
| WO | 2001067333 A1 | 9/2001 |
| WO | 0193172 A1 | 12/2001 |
| WO | 02057899 A1 | 7/2002 |
| WO | 03012717 A1 | 2/2003 |
| WO | 03092348 A2 | 11/2003 |
| WO | 2006075917 A2 | 7/2006 |
| WO | 2007044500 A2 | 4/2007 |

OTHER PUBLICATIONS

Derfler, Frank J. et al., "How Networks Work", Bestseller Edition, Ziff-Davis Press, Emeryville, CA, 1996, 69 pages.

EP06836203.7, "European Application Serial No. EP06836203.7, Supplementary European Search Report dated Aug. 31, 2010", 5 pages.

EP13165006.1, "European Application Serial No. 13165006.1, Extended European Search Report dated Jul. 24, 2014", C-Sam, Inc., 9 Pages.

Gralla, Preston, "How the Internet Works", Millennium Edition, Que Corporation, Indianapolis, IN, 1999, 35 pages.

Hwang, Jin-Bum et al., "Two Layered PKI Model for Device Authentication in Multi-Domain Home Networks", 2006 IEEE Tenth International Symposium, IEEE, Jun. 28, 2006, 6 Pages.

Muller, Nathan J., "Desktop Encyclopedia of the Internet", Artech House Inc., Norwood, MA, 1999, 51 pages.

PCT/US2006/039091, "International Application Serial No. PCT/US2006/039091, International Preliminary Report on Patentability issued on Mar. 17, 2009", 4 pages.

PCT/US2006/039091, "International Application Serial No. PCT/US2006/039091, International Search Report and Written Opinion dated Jun. 26, 2008", 4 pages.

Shimaoka, M. et al., "Memorandum for multi-domain Public Key Infrastructure (PKI) Interoperability", SECOM; N Hastings, NIST, Network Working Group Request for Comments: Draft <draft-shimaoka-multidomain-pki-05.txt>, Jul. 2005, 32 Pages.

White, Ron, "How Computers Work", Millennium Edition, Que Corporation, Indianapolis, IN, 1999, 83 pages.

White, Ron, "How Software Works", Ziff-Davis Press, 1993, 194 pages.

Microsoft, "Computer Dictionary", Fifth Edition, 648 pages.

* cited by examiner

ESTABLISHING TRUST FOR CONDUCTING DIRECT SECURE ELECTRONIC TRANSACTIONS BETWEEN A USER AND SERVICE PROVIDERS

CROSS-REFERENCE TO RELATED APPLICATIONS

This application is a continuation of U.S. patent application Ser. No. 13/168,764, filed Jun. 24, 2011, that is a continuation of U.S. patent application Ser. No. 11/539,024, filed Oct. 5, 2006, now abandoned, and each of which is incorporated herein by reference in its entirety. U.S. patent application Ser. No. 11/539,024 also claims the benefit of U.S. Provisional Patent Application No. 60/724,066, filed Oct. 6, 2005, naming Satyan Pitroda and Mehul Desai as inventors.

Certain systems and methods are described in PCT Pub. No. PCT WO 95/35546 to Satyan Pitroda and entitled "Universal Electronic Transaction Card and system and Methods of Conducting Electronic Transactions," (referred to herein as "Pitroda") the entire teachings of which are hereby incorporated by reference.

This application is related to the following U.S. patents, each of which is incorporated herein by reference in its entirety: U.S. Pat. No. 8,527,380, filed Oct. 31, 2002, entitled "System and methods for servicing electronic transactions"; U.S. Pat. No. 7,366,990 filed Jan. 19, 2001, entitled "Method and system for managing user activities and information using a customized computer interface"; U.S. Pat. No. 5,952,641, filed Nov. 21, 1996, entitled "Security device for controlling the access to a personal computer or to a computer terminal"; U.S. Pat. No. 6,925,439, filed Mar. 10, 1999, entitled "Device, system and methods of conducting paperless transactions"; U.S. Pat. No. 6,769,607, filed Jun. 6, 2000, entitled "Point of sale and display adapter for electronic transaction device"; U.S. Pat. No. 6,705,520, filed Nov. 15, 1999, entitled "Point of sale adapter for electronic transaction device"; U.S. Pat. No. 5,590,038, filed Jun. 20, 1994, entitled "Universal electronic transaction card including receipt storage and system and methods of conducting electronic transactions"; U.S. Pat. No. 3,999,050, filed Oct. 10, 1975, entitled "Electronic diary"; and U.S. Pat. No. 5,884,271, filed Sep. 6, 1996, entitled "Device, system and methods of conducting paperless transactions device".

This application is also related to the following published PCT applications, each of which is incorporated herein by reference in its entirety: PCT Pub. No. WO 02/057899, filed Jan. 17, 2002, entitled "Method and system for managing user activities and information using a customized computer interface"; PTC Pub. No. WO 03/012717, filed Jul. 30, 2001, entitled "System for distribution and use of virtual stored value cards"; PCT Pub. No. WO 01/93172, filed Jun. 1, 2001, entitled "Doctor service provider"; PCT Pub. No. WO 01/37200, filed Sep. 21, 2000, entitled "Point of sale and display adapter for electronic transaction device"; PCT Pub. No. WO 01/37199, filed Sep. 8, 2000, entitled "Point of sale adapter for electronic transaction device"; PCT Pub. No. WO 01/18629, filed Aug. 10, 2000, entitled "System and method for servicing electronic transactions"; PCT Pub. No. WO 01/18629, filed Aug. 10, 2000, entitled "System and method for servicing electronic transactions"; PCT WO 99/34314, filed Dec. 30, 1998, entitled "Universal electronic communications card"; PCT WO 95/35546, filed Jun. 7, 1995, entitled "Universal electronic transaction card and system and methods of conducting electronic transactions"; and PCT WO 83/04327, filed May 21, 1982, entitled "System with remote computer data entry device, associated apparatus and method of using same".

All patents, patent applications and other documents referenced herein are hereby incorporated by reference.

BACKGROUND

Field

This application relates to methods and systems of electronic transactions and particularly relates to mobile secure electronic transactions.

Description of the Related Art

Mobile devices with increasing capabilities enable users to communicate with each other and to perform other computing functions. However, while the widespread use of these devices can enable business transactions, it also increases the difficulty of supporting those transactions in a secure way. A need exists for improved methods and systems for enabling a wide variety of electronic transactions.

SUMMARY

Provided herein are methods and systems for supporting secure electronic transactions, including those that support security at the domain, user and device level.

Methods and systems disclosed herein include methods and systems for receiving a request from a first facility at a second facility; and transmitting an acknowledgement to the request from the second facility to the first facility. In some embodiments the first facility is capable of being initialized, and in some embodiments the initialization of the first facility comprises entering one or more of a code, personal identifier, password, personal identification number, signature, or similar identifier. In some embodiments the first facility is a universal electronic transaction facility. In some embodiments the second facility is a service facility. In some embodiments the service facility is a transaction service facility. Some embodiments include a method for providing the first facility with a financial transaction service. In some instances the request from the first facility is a transaction request. The methods and systems may also include the first step of establishing communications between the universal electronic transaction facility and the transaction service facility. In some embodiments the service facility is a wallet service facility. A wallet service center may include a service facility that provides various services related to the features and functions of an electronic transaction facility, including services that can be accessed by user devices, merchant devices, and devices of various service providers. A wallet service center may include one or more servers, one or more databases, and one or more other computing facilities. In embodiments, a wallet service center may include one or more security facilities, which may be multidimensional security facilities. In some instances, such security facilities may operate in accordance with a variety of distinct security protocols, such as security protocols that are native to one or more user devices, one or more network or transport domains or facilities, one or more merchant systems, or one or more service provider systems. Other features of a wallet service center may be understood by reference to the embodiments described herein and in the documents incorporated by reference herein.

Methods and systems disclosed herein include methods and systems for transmitting a request from a second facility to a first facility and receiving an acknowledgement of the request at the second facility. In some embodiments the first facility is capable of being initialized, and in some embodiments the initialization of the first facility comprises entering one or more of a code, personal identifier, password, personal identification number, signature, or similar identifier. In some embodiments the first facility is a transaction facility. In some embodiments the second facility is a service facility. In some embodiments the service facility is a transaction service facility. In some embodiments the method is a method for providing the first facility with a financial transaction service. In some embodiments the request from the second facility is a transaction request. In some embodiments the transaction facility is a universal electronic transaction facility.

Methods and systems disclosed herein include methods and systems for transmitting an alert associated with a pending transaction to a first facility from a second facility; and receiving, at the second facility, a response to the alert. In some instances, the response is a request for direct settlement of the transaction at the second facility; receiving from a third facility a message comprising information pertaining to the transaction; transmitting, from the second facility to the first facility, a request for a code; receiving, at the second facility, the code from the first facility; determining the validity of the code; settling the transaction; and transmitting, from the second facility and to both the first facility and the third facility, an acknowledgement of the transaction being settled. In some embodiments the first facility is a transaction facility. In some embodiments the second facility is a service facility. In some embodiments the service facility is a transaction service facility. In some embodiments the transaction facility is a universal electronic transaction facility. In some embodiments the third facility is a merchant facility. In some embodiments the message received from the third facility further comprises an identifier that is unique to the third facility. In some embodiments the method is a method for providing the first facility with the capability of transacting with the third facility. In some embodiments the method is a method for providing the third facility with the capability of first sending a bill to the first facility and then receiving payment of the bill from the first facility. In some embodiments the service facility is a wallet service center. In some embodiments the alert of a transaction is a bill. In some embodiments the code is a personal identifier.

Methods and systems disclosed herein include methods and systems for conducting a transaction, including receiving from a first facility a reference to a second facility; sending a request to the first facility; receiving from the first facility a response; determining the validity of the response; settling a transaction between the first facility and the second facility; and sending a confirmation of the transaction to both the first facility and the second facility. In some embodiments the first facility is capable of being initialized, and in some embodiments the initialization of the first facility comprises entering one or more of a code, personal identifier, password, personal identification number, signature, or similar identifier. In some embodiments the first facility is a source facility. In some embodiments the source facility is a transaction facility. In some embodiments the transaction facility is a universal electronic transaction facility. In some embodiments the second facility is a recipient facility. In some embodiments the recipient facility is a transaction facility. In some embodiments the transaction facility is a universal electronic transaction facility. In some embodiments the method is a method for enabling a person-to-person asset transfer from the first facility to the second facility. In some embodiments the reference to the second facility is an identifier. In some embodiments the identifier is a unique identifier.

Methods and systems disclosed herein include methods and systems for transferring money from one financial account to another, including receiving from a first facility a request for a funds transfer, the request comprising a reference to a source account, a reference to a destination account, and a transfer amount in response to the request for a funds transfer; requesting a code from the first facility; receiving the code from the first facility; and sending a confirmation of a funds transfer to the first facility. In some embodiments the first facility is capable of being initialized, and in some embodiments the initialization of the first facility comprises entering one or more of a code, personal identifier, password, personal identification number, signature, or similar identifier. In some embodiments the reference to the source account is an identifier. In some embodiments the identifier is a unique identifier. In some embodiments the reference to the destination account is an identifier. In some embodiments this destination identifier is a unique identifier. In some embodiments the first facility is a transaction facility. In some embodiments the transaction facility is a universal electronic transaction facility.

Methods and systems disclosed herein include methods and systems for receiving from a first facility a request to transfer funds to a second facility, the request comprising a reference to the first facility, a reference to the second facility, and a transfer amount; in response to the request for a funds transfer, requesting a code from the first facility; receiving the code from the first facility; receiving from the second facility a request for a funds transfer from the first facility to the second facility; in response to the request from the second facility, transmitting a request to the second facility requesting the unique identifier of the second facility and a code receiving from the second facility the unique identifier of the second facility and the code; and transmitting to the second facility an approval to release funds to the second facility. In some embodiments the first facility is capable of being initialized, and in some embodiments the initialization of the first facility comprises entering one or more of a code, personal identifier, password, personal identification number, signature, or similar identifier. In some embodiments the first facility is a sender facility. In some embodiments the sender facility is a merchant. In some embodiments the second facility is a destination facility. In some embodiments the destination facility is a merchant. In some embodiments the reference to the first facility is an identifier. In some embodiments the identifier is a unique identifier. In some embodiments the reference to the second facility is an identifier. In some embodiments the identifier is a unique identifier.

Methods and systems disclosed herein include methods and systems for conducting a transaction. In some embodiments the method is a method for a wire transfer. In some embodiments the method is a method for a money order. In some embodiments the first facility is a transaction facility. In some embodiments the first facility is a universal electronic transaction facility. In some embodiments the second facility is a transaction facility. In some embodiments the second facility is a universal electronic transaction facility.

Methods and systems disclosed herein include methods and systems for conducting a transaction, including receiving a transaction request from a second facility. In some embodiments the transaction request is associated with a first facility and a third facility; in response to receiving the transaction request, sending a request for a code to the first facility; receiving the code from the first facility; verifying the validity of the code sending the transaction request to the third facility; receiving from the third facility a confirmation of the transaction; and sending a transaction authorization to the second facility. In some embodiments the first facility is capable of being initialized, and in some embodiments the initialization of the first facility comprises entering a code, personal identifier, password, personal identification number, signature, or similar identifier. In some embodiments the transaction is a purchase. In some embodiments the transaction is an activation of a prepaid shopping card. In some embodiments the transaction is a recharge of a prepaid shopping card. In some embodiments the transaction is a top-up (that is, increasing the amount of prepaid minutes) of a prepaid cell phone. In some embodiments the second facility is a merchant facility. In some embodiments the first facility is a customer facility. In some embodiments the third facility is a supplier facility. In some embodiments the first facility is a transaction facility. In some embodiments the transaction facility is a universal electronic transaction facility.

Methods and systems disclosed herein include methods and systems for providing an incentive to a consumer, including transmitting an electronic coupon to a first facility. In some embodiments the first facility is capable of being initialized, and in some embodiments the initialization of the first facility comprises entering one or more of a code, personal identifier, password, personal identification number, signature, or similar identifier. In some embodiments the first facility is a consumer facility. In some embodiments the consumer facility is a transaction facility. In some embodiments the consumer facility is a universal electronic transaction facility.

Methods and systems disclosed herein include methods and systems for transmitting an electronic coupon to a first facility; receiving a unique identifier of the first facility from a second facility; receiving data associated with the coupon from the merchant facility; sending a request for a code to the first facility; receiving the code from the first facility; verifying the validity of the code; and sending an electronic coupon redemption approval to the second facility. In some embodiments the first facility is capable of being initialized, and in some embodiments the initialization of the first facility comprises entering a code, personal identifier, password, personal identification number, signature, or similar identifier. In some embodiments the first facility is a consumer facility. In some embodiments the consumer facility is a transaction facility. In some embodiments the transaction facility is a universal electronic transaction facility. In some embodiments the second facility is a merchant facility.

In various embodiments, a merchant facility can include or be hosted by any device with a processor, such as a point of sale terminal, cash register, personal computer, laptop computer, cellular phone, PDA, processor-equipped retail display, kiosk, ATM, processor-equipped shelving, sign, billboard, barcode scanner, RFID device, scanner, machine vision system, camera, card reader, magnetic stripe reader or other device.

Methods and systems disclosed herein include methods and systems for conducting a transaction, including establishing a session with a first facility; requesting an inventory status report from a second facility; transmitting the inventory status report to the first facility; receiving a purchase request from the first facility; executing the purchase request with the second facility; and issuing a receipt to the first facility. In some embodiments the first facility is capable of being initialized, and in some embodiments the initialization of the first facility comprises entering one or more of a code, personal identifier, password, personal identification number, signature, or similar identifier. In some embodiments the first facility is a consumer facility. In some embodiments the consumer facility is a transaction facility. In some embodiments the transaction facility is a universal electronic transaction facility. In some embodiments the second facility is a supplier facility. In some embodiments the supplier facility is a ticket retail facility. In some embodiments the supplier facility is a ticket issuing facility. The methods and systems may also include issuing a ticket to the first facility. In some embodiments the purchase request is a ticket order. In some embodiments the inventory status report is a ticket availability report. In some embodiments the session is a secure session.

Methods and systems disclosed herein include methods and systems for withdrawing money from an account, including receiving a request for a withdrawal from an account associated with first facility; sending a request for a code to the first facility; receiving the code from the first facility; transmitting to a second facility an approval to accept funds from the first facility; and sending a confirmation of the withdrawal to the first facility. In some embodiments the first facility is capable of being initialized, and in some embodiments the initialization of the first facility comprises entering one or more of a code, personal identifier, password, personal identification number, signature, or similar identifier. In some embodiments the first facility is a consumer facility. In some embodiments the consumer facility is a transaction facility. In some embodiments the transaction facility is a universal electronic transaction facility. In some embodiments the second facility is a merchant facility. In some embodiments the merchant facility is a bank.

Methods and systems disclosed herein include methods and systems for depositing money into an account, including receiving a request from a second facility to deposit funds into an account associated with a first facility. In some embodiments the request comprises a unique identifier of the first facility, an identifier of the account associated with the first facility, and an amount to be deposited. The methods and systems may include sending a request for a code to the second facility; receiving the code from the second facility; transmitting to the second facility a confirmation of the deposit into the account associated with the first facility; and sending a confirmation of the deposit to the first facility. In some embodiments the first facility is capable of being initialized, and in some embodiments the initialization of the first facility comprises entering one or more of a code, personal identifier, password, personal identification number, signature, or similar identifier. In some embodiments the first facility is a consumer facility. In some embodiments the consumer facility is a transaction facility. In some embodiments the transaction facility is a universal electronic transaction facility. In some embodiments the second facility is a merchant facility.

Universal electronic transaction facilities as described herein may have any and all features and attributes in various embodiments disclosed herein. In some embodiments the universal electronic transaction facility provides a user with "electronic wallet" capabilities. Like a person's leather, physical wallet, an electronic wallet contains one or more identification cards, credit cards, or the like. The electronic wallet is an electronic collection of one or more of these types of physical materials that can be reviewed, viewed and used electronically to achieve similar results to the physical analogs. In this manner, in some embodiments the electronic wallet contains a credit card. In some embodiments the electronic wallet contains a medical card. In some embodiments the electronic wallet contains a membership card. In some embodiments the electronic wallet contains a promotional card. In some embodiments the electronic wallet contains a coupon. In some embodiments the electronic wallet is paperless. In some embodiments the electronic wallet provides a data security feature. In some embodiments the universal electronic transaction facility contains a component that enables a service. In some embodiments enabling a service comprises an interaction with a service facility. In some embodiments the service facility authenticates a participant in a transaction. In some embodiments the service facility is the final authority as to the settlement of a transaction. In some embodiments the service facility comprises a main service facility. In some embodiments the interaction with a service facility comprises utilizing a communication facility to transmit data to a main service facility. In some embodiments utilizing the communication facility comprises utilizing a network communication facility. In some embodiments the service comprises a transactional method. In some embodiments the transactional method comprises a financial transactional method. In some embodiments the service comprises a transaction. In some embodiments the transaction comprises a financial transaction. In some embodiments the service is supplied by a service partner. In some embodiments the service is delivered through a Web services oriented architecture. In some embodiments the service comprises a premium service associated with a financial charge. In some embodiments the service comprises a free service. In some embodiments the service is bill payment. In some embodiments the bill payment comprises bill receipt. In some embodiments the bill payment comprises bill payment. In some embodiments the bill payment comprises bill receipt and bill payment. In some embodiments the service is personal data management. In some embodiments the service is security. In some embodiments the security is associated with a function of the universal electronic transaction facility. In some embodiments the security comprises a privacy feature associated with the universal electronic transaction facility. In some embodiments the security comprises theft determent. In some embodiments the security comprises transaction integrity. In some embodiments the security comprises data integrity. In some embodiments the security comprises identity authentication. In some embodiments the security comprises non-repudiation. In some embodiments the security comprises revocation. In some embodiments the security comprises renewability. In some embodiments the security is associated with the universal electronic transaction facility. In some embodiments the service is promotion. In some embodiments the promotion is associated with a loyalty card. In some embodiments the promotion is associated with a coupon. In some embodiments the promotion comprises an incentive program. In some embodiments the promotion is associated with the universal electronic transaction facility. In some embodiments the promotion is directly distributed. In some embodiments the directly distributed promotion is distributed by a vendor. In some embodiments the promotion is distributed by a merchant. In some embodiments the merchant comprises a retailer. In some embodiments the service is banking. In some embodiments the banking comprises an account transfer. In some embodiments the banking comprises access to an ATM facility. In some embodiments the banking comprises a microcredit transaction. In some embodiments the banking comprises a microcredit settlement. In some embodiments the banking comprises a function provided to the user of the universal electronic transaction facility. In some embodiments the service comprises applying for a new account. In some embodiments applying for a new account comprises provided needed information to a service facility. In some embodiments the service facility comprises a bank. In some embodiments the service facility comprises a credit card company. In some embodiments the service is renewing an existing account. In some embodiments the service is issuing a credit card. In some embodiments the service is management of a sub-account. In some embodiments the service is removing an account. In some embodiments the service is canceling an account. In some embodiments the service is shopping. In some embodiments shopping comprises the providing personal information. In some embodiments the personal information assists in browsing merchandise. In some embodiments the personal information assists in product selection. In some embodiments shopping is associated with a shopping action. In some embodiments the shopping action comprises checking for a bargain. In some embodiments the shopping action comprises checking for a discount. In some embodiments the shopping action comprises checking for a related product. In some embodiments the shopping action comprises receiving promotional information. In some embodiments the shopping action associated with browsing merchandise. In some embodiments the service comprises a purchasing agent. In some embodiments the service comprises a government service. In some embodiments the government service is associated with a passport. In some embodiments the government service is associated with a visa. In some embodiments the government service is associated with a social security number. In some embodiments the government service is associated with a motor vehicle. In some embodiments the government service is associated with voting. In some embodiments the service is customer profiling. In some embodiments customer profiling benefits a user of the universal electronic transaction facility. In some embodiments customer profiling benefits a vendor. In some embodiments customer profiling comprises profiling a group of users. In some embodiments the service is inter-vendor cooperation. In some embodiments the service is inter-vendor collaboration. In some embodiments the service comprises a financial service. In some embodiments the financial service is associated with a person-to-person money transfer. In some embodiments the financial service is associated with a money order. In some embodiments the financial service is associated with a wire transfer. In some embodiments the service comprises a prepaid service. In some embodiments the prepaid service comprises a prepaid calling card. In some embodiments the prepaid service comprises a prepaid cell phone. In some embodiments the prepaid service comprises a debit card. In some embodiments the service is ticketing. In some embodiments ticketing is associated with an airline. In some embodiments ticketing is associated with a play. In some embodiments ticketing is associated with a sporting event. In some embodiments ticketing is associated with an auction. In some embodiments ticketing is associated with a charitable function. In some embodiments ticketing is associated with an educational function. In some embodiments ticketing is associated with a ceremony. In some embodiments ticketing is associated with a speech. In some embodiments ticketing is associated with an entertainment event. In some embodiments ticketing is associated with a hospitality facility. In some embodiments a hospitality facility comprises a hotel. In some embodiments ticketing is associated with paperless tickets. In some embodiments paperless tickets are issued directly to the universal electronic transaction facility. In some embodiments the service comprises a manned ATM. In some embodiments the service comprises a proximity transaction. In some embodiments the service is associated with the universal electronic transaction facility. In some embodiments the service comprises allowing an authorized user of the universal electronic transaction facility to conduct a transaction with a merchant. In some embodiments the service comprises allowing an authorized user of the universal electronic transaction facility to conduct a transaction with a peer. In some embodiments the service comprises allowing an authorized user of the universal electronic transaction facility to conduct a transaction with a supplier. In some embodiments the service comprises allowing an authorized user of the universal electronic transaction facility to conduct a transaction with a transaction participant. In some embodiments the service comprises a Web server. In some embodiments the service comprises a transaction service. In some embodiments the service comprises a user interface User interfaces as disclosed herein may include a wide variety of features and attributes. In some embodiments the user interface comprises a display. In some embodiments the display comprises an LCD. In some embodiments the display comprises a touch screen. In some embodiments the display comprises an organic light emitting diode. In some embodiments the display comprises a flexible organic light emitting diode. In some embodiments the display comprises a projection display. In some embodiments the display renders an identifier. In some embodiments the identifier comprises a signature. In some embodiments the identifier comprises a bar code. In some embodiments the identifier provides information to an operator of a support computer. In some embodiments the display renders a signature. In some embodiments the display provides visual feedback to a user of the universal electronic transaction facility. In some embodiments the display provides information to a user of the universal electronic transaction facility. In some embodiments the display comprises a full size display. In some embodiments the full size display is the size of a tablet PC. In some embodiments the full size display is the size of a desktop PC. In some embodiments the full size display comprises a remote display. In some embodiments the remote display is associated with a remote computer. In some embodiments the display comprises a small size display. In some embodiments the small size display is the size of that of a PDA. In some embodiments the small size display is the size of that of a cell phone. In some embodiments the small size display is the size of that of a camera. In some embodiments the small size display is the size of that of a digital watch display. In some embodiments the display is small enough to be portable. In some embodiments the display is large enough to display user-readable messages. In some embodiments the display is large enough to display touch controls. In some embodiments the display is small enough to be portable, large enough to display user-readable messages, and large enough to display touch controls. In some embodiments the display is embodied in a remote device. In some embodiments the remote device comprises a Web browser. In some embodiments the component comprises a control facility. In some embodiments the control facility controls functions of the universal electronic transaction facility. In some embodiments the control facility comprises a processor. In some embodiments the control facility comprises a microprocessor. In some embodiments the control facility comprises a computer. In some embodiments the control facility comprises a display controller. In some embodiments the control facility comprises a memory component. In some embodiments the memory component stores a value associated with a transactional method associated with the functionality of the universal electronic transaction facility. In some embodiments the value comprises a unique identifier. In some embodiments the unique identifier is used to discriminate one universal electronic transaction facility from another. In some embodiments the value comprises access control information. In some embodiments the access control information is used to prevent unauthorized use of the universal electronic transaction facility. In some embodiments the access control information comprises an encoded signature. In some embodiments the access control information comprises a personal identification number. In some embodiments the access control information comprises a biometric measure, such as a fingerprint or iris scan. These and other biometric measures may also be encoded to further enhance security.

In some embodiments the value comprises personal information identifying an owner of the universal electronic transaction facility. This personal information may comprise an individual's name, a business's name, a home address, a home telephone number, a home fax number, a home e-mail address, an office address, an office phone number, an office fax number, an office e-mail address, a URL, a URI, height, weight, birth date, a social security number, blood type, and/or marital status. In some embodiments the value comprises financial account information, such as a credit card number, a date of issue, a date of expiration, a credit limit, a savings account number, a checking account number, an investment account number, a username associated with a financial account. In some embodiments the value comprises medical and health information associated with an owner of the universal electronic transaction facility. this may comprises an indication of an allergy, a medical history, a medical condition, a health insurance number associated with a health insurance plan, a physician name, a hospital name, a pharmacy name. In some embodiments the value comprises a stored cash value. In some embodiments the value comprises branding information. In some embodiments the branding information comprises a logo. In some embodiments the branding information comprises an image of a credit card.

In some embodiments the memory component comprises RAM. In some embodiments the memory component comprises ROM. In some embodiments the memory component comprises non-volatile RAM. In some embodiments the memory component comprises a data storage facility. In some embodiments the data storage facility comprises a file. In some embodiments the data storage facility comprises an object-oriented database. In some embodiments the data storage facility comprises a relational database. In some embodiments the data storage facility comprises an object. In some embodiments the data storage facility comprises a facility for storing data. In some embodiments the data storage facility comprises a facility for storing an application. In some embodiments the data storage facility comprises a facility for storing a program. In some embodiments the data storage facility comprises a facility for storing an item associated with the electronic facility. In some embodiments the memory component is sufficient to store all data associated with the participation of the universal electronic transaction facility in the execution of a transactional method. In some embodiments the memory component comprises a leak-resistant cryptography facility. In some embodiments the leak-resistant cryptography facility is a smart card. In some embodiments the memory component comprises a magnetic facility. In some embodiments the memory component comprises an optical facility. In some embodiments the memory component comprises an electronic facility. In some embodiments the memory component stores content. In some embodiments the content is uploaded in whole to a support computer. In some embodiments the content is stored in a multidimensional database. In some embodiments the content is associated with a transactional method. In some embodiments the memory component is operatively coupled to a software conduit. In some embodiments the software conduit uploads the content in part to a support computer. In some embodiments the software conduit uploads the content in part to a local computer. In some embodiments the software conduit uploads the content in part to a main service facility. In some embodiments the software conduit uploads the content in whole to a main service facility. In some embodiments the software conduit uploads the content in whole to a local computer. In some embodiments the software conduit uploads the content in whole to a main service facility. In some embodiments the content is uploaded to a backup facility. In some embodiments the backup facility is a main service facility. In some embodiments the content is a type of data that is the same as a type of data stored by a main service facility. In some embodiments the control facility comprises input/output port management. In some embodiments the control facility comprises a light emitting diode. In some embodiments the light emitting diode indicates on/off status. In some embodiments the on/off status is determined by a switch. In some embodiments the control facility comprises a beeper. In some embodiments the control facility comprises a speaker. In some embodiments the control facility comprises a contact facility. In some embodiments the contact facility connects to an external facility. In some embodiments the contact facility is associated with charging a battery. In some embodiments the battery is integral to the universal electronic transaction facility. In some embodiments the contact facility provides power to the universal electronic transaction facility. In some embodiments the contact facility provides data communications capability to the universal electronic transaction facility. In some embodiments the contact facility comprises a power pin. In some embodiments the contact facility comprises a magnetic stripe. In some embodiments the contact facility comprises a contact smart card facility. In some embodiments the contact facility comprises a power facility. In some embodiments the contact facility comprises a data facility. In some embodiments the control facility comprises a battery. In some embodiments the control facility comprises a contactless facility. In some embodiments the control facility comprises a communication facility. In some embodiments the communication facility comprises a contact facility. In some embodiments the communication facility comprises a contactless facility. In some embodiments the contactless facility comprises interacting with an external facility. In some embodiments the contactless facility comprises an infrared facility. In some embodiments the infrared facility comprises an IrDA facility. In some embodiments the contactless facility comprises an RF facility. In some embodiments the RF facility is an RFID facility. In some embodiments the contactless facility comprises a contactless smartcard facility. In some embodiments the communication facility comprises a direct communication facility. In some embodiments the communication facility comprises a local communication facility. In some embodiments the communication facility comprises a network communication facility. In some embodiments the network communication facility comprises a connection to a PSTN. In some embodiments the connection to the PSTN comprises a modem. In some embodiments the network communication facility comprises a connection to a data network. In some embodiments the connection to a data network may comprise an Ethernet card, an 802.11 wireless card, a Bluetooth facility, a cellular network (utilizing protocols such as CDPD, GPRS, GSM, CSD, HSCSD, and SMS). In some embodiments the network communication facility comprises a connection to a special interface. In some embodiments the special interface is a data communications interface that is operatively coupled to a main service facility. In some embodiments the network communication facility comprises a secure data connection (such as a VPN, an IPSec connection, or an SSH connection). In some embodiments the communication facility comprises a physical component. In some embodiments the physical component is a category 5e cable or other network component. In some embodiments the communication facility comprises an application-oriented component. In some embodiments the application-oriented component is a Web server. In some embodiments the application-oriented component is a Web browser. In some embodiments the application-oriented component is associated with the universal electronic transaction facility.

In some embodiments the communication facility comprises a facility providing a direct connection to a main service facility through an external facility. In some embodiments the facility providing a direct connection to a main service facility through an external facility is an application implementing the Telnet protocol, the FTP protocol, or the SSH protocol. In some embodiments the facility providing a direct connection to a main service facility through an external facility comprises an application providing a connection-based tunnel through the external facility to the main service facility. In some embodiments the facility providing a direct connection to a main service facility through an external facility comprises an application providing a session-based tunnel through the external facility to the main service facility. In some embodiments the communication facility comprises an application-oriented communication facility. In some embodiments the application-oriented communication facility comprises a facility for connecting to a service provider's Web server. In some embodiments the service provider is a retailer. In some embodiments connecting to a service provider comprises utilizing HTTP or HTTPS. In some embodiments the communication is associated with the embodiment of the universal electronic transaction facility. In some embodiments the control facility comprises a power facility (e.g. a battery, a DC power supply, a solar cell, a fuel cell, a recharger, an inductive charger and/or a cigarette-lighter adapter). In some embodiments the power facility comprises a practicable source of power. In some embodiments the power facility comprises a wireless interaction with an external facility. In some embodiments the interaction with the external facility comprises electromagnetic induction.

In some embodiments the universal electronic transaction facility is embodied in a form. In some embodiments the form is 3.5 inches by 2.5 inches. In some embodiments the form is the size of a credit card. In some embodiments the form is the size of a stack of credit cards. In some embodiments the form comprises a mobile device. In some embodiments the mobile device comprises a PDA. In some embodiments the mobile device comprises a smart card. In some embodiments the mobile device comprises a cell phone. In some embodiments the mobile device comprises a wearable computer. In some embodiments the mobile device comprises a watch. In some embodiments the mobile device comprises a Blackberry. In some embodiments the mobile device comprises a Sidekick. In some embodiments the mobile device comprises a ring. In some embodiments the mobile device comprises a bracelet. In some embodiments the mobile device comprises a pendant. In some embodiments the mobile device comprises a shoe. In some embodiments the mobile device comprises an eyeglasses rim. In some embodiments the mobile device comprises a barrette. In some embodiments the mobile device comprises a personal item that a user wears. In some embodiments the form comprises a cash register. In some embodiments the form comprises a point of sale system. In some embodiments the form comprises a personal computer. In some embodiments the form comprises a portable digital music player. In some embodiments the form comprises a digital camera. In some embodiments the form comprises a set-top box. In some embodiments the form comprises a digital video recorder. In some embodiments the form comprises a satellite receiver. In some embodiments the form comprises an automobile. In some embodiments the form comprises a utility meter. In some embodiments the utility meter comprises an electric meter. In some embodiments the utility meter comprises a gas meter. In some embodiments the form is associated with a sale of a thing. In some embodiments the form is associated with a transfer of funds.

In some embodiments the component comprises an interface to an automobile. In some embodiments the component comprises a GPS receiver. In some embodiments the component comprises a facility enabling a mobile, location-sensitive transaction. In some embodiments the component comprises a user interface. In some embodiments the component comprises a brightness adjustment facility. In some embodiments the component comprises an enclosure. In some embodiments the enclosure moderates an environmental lighting condition. In some embodiments the environment lighting condition would otherwise hinder the usability of the universal electronic transaction facility. In some embodiments the component comprises a visible light sensor capable of sensing an environment lighting condition. In some embodiments a display is integral to the universal electronic transaction facility and operatively coupled to the visible light sensor. In some embodiments the brightness of the display is adjusted based upon the luminosity of the environmental lighting condition, wherein the adjustment of the brightness of the display enhances the readability of the display by a user of the universal electronic transaction facility.

In some embodiments the component comprises software to support methods associated with transactions. In some embodiments the software comprises an operating system. This software may include a memory display manager, a database display manager, an analysis algorithm, an analysis procedure, an interface controller, a day planner, an I/O driver, a display driver, a scheduler, a command manager, a clock, a calendar, a universal electronic transaction facility initialization program, an authorization program, a security manager, and a signature manager. In some embodiments the software comprises an operational application that emulates a physical card. In some embodiments the physical card is a credit card. In some embodiments the operational application operates on an input value. In some embodiments the input value is a gratuity. In some embodiments the input value is a cash back quantity. In some embodiments the input value is a monetary quantity associated with a transaction. In some embodiments the physical card is a bank card. In some embodiments an operational application operates on an input value. In some embodiments the input value is a gratuity. In some embodiments the input value is a cash back quantity. In some embodiments the input value is a monetary quantity associated with a transaction.

In some embodiments the physical card is a medical card. In some embodiments the operational application is associated with information associated with the medical aspect of a person. In some embodiments the person is associated with the universal electronic transaction facility. In some embodiments the information associated with the medical aspect of the person is a medical history. In some embodiments the information associated with the medical aspect of the person is insurance information. In some embodiments the information associated with the medical aspect of the person is photo identification. In some embodiments the physical card is a driver's license. In some embodiments the physical card is a phone card. In some embodiments the physical card is an airline travel card. In some embodiments the operational application interfaces with an airline reservation facility. In some embodiments the operational application interfaces with a facility associated with airline travel. In some embodiments the physical card is a car rental card. In some embodiments the physical card is a universal integrated card. In some embodiments the universal integrated card comprises: the integration of a plurality of operational applications; an identity of a user associated with the universal electronic transaction facility; and an account associated with both the identity of the user and a transaction. In some embodiments the transaction is associated with at least one of the plurality of operational applications. In some embodiments the component comprises a smartcard facility. In some embodiments the component comprises a microphone with speech recognition. In some embodiments the component comprises a Bluetooth facility. In some embodiments the component comprises a virtual private network. In some embodiments the component comprises a holographic memory facility. In some embodiments the component comprises a removable RAM facility. In some embodiments the component comprises a removable ROM facility. In some embodiments the component comprises a registration facility capable of registering with a central security facility. In some embodiments the component comprises an activation facility capable of interacting with the service facility. In some embodiments the universal electronic transaction facility may be a Linux, Macintosh or a Windows computer. In some embodiments the universal electronic transaction facility supports an additional features associated with one of a transactional method and a general activity. In some embodiments said additional feature comprises the entry of a code. In some embodiments the code is an alphanumeric code. In some embodiments the code is a personal identifier. In some embodiments the code is a password. In some embodiments the code is a personal identification number. In some embodiments the code is a signature. In some embodiments said additional feature comprises the display of a universal electronic transaction facility option. In some embodiments the option is an account summary. In some embodiments said additional feature comprises the display of a status associated with a transaction. In some embodiments said status is indicative of a completed transaction. In some embodiments said additional feature comprises the display of a numeric keypad. In some embodiments said numeric keypad responsive to a user's touch input. In some embodiments said additional feature comprises a notepad. In some embodiments said additional feature comprises a to-do list. In some embodiments said additional feature comprises a contact. In some embodiments said additional feature comprises an email program. In some embodiments said additional feature comprises a task. In some embodiments said additional feature comprises a message. In some embodiments said additional feature comprises an instant message. In some embodiments said additional feature comprises an alarm. In some embodiments said additional feature comprises a reminder. In some embodiments said additional feature is associated with a general computing capability. In some embodiments said additional feature is associated with a transactional method. In some embodiments said additional feature is associated with a general user activity.

In some embodiments the universal electronic transaction facility interacts with a main service facility. In some embodiments the main service facility is an HTTP server. In some embodiments the main service facility is a personal computer. In some embodiments the main service facility is a workstation. In some embodiments the main service facility is a laptop computer. In some embodiments the main service facility provides functions as a service in a service oriented architecture. In some embodiments the service is listed in a registry of such services. In some embodiments the registry is accessed by a client of the main service facility. In some embodiments the client is a universal electronic transaction facility. In some embodiments the main service facility is a distributed computer. In some embodiments the main service facility is a cluster computer. In some embodiments the main service facility is a network of workstations. In some embodiments the main service facility is a server. In some embodiments the main service facility is a supercomputer. In some embodiments the main service facility is a mainframe computer. In some embodiments the main service facility is a server farm. In some embodiments the main service facility is a set of servers deployed at different geographic locations. In some embodiments the interaction occurs via an external connector. In some embodiments the external connector is employed in association with the universal electronic transaction facility and the main service facility during the execution of a transactional method. In some embodiments the external connector comprises a telecommunications facility. In some embodiments the external connector comprises an Internet facility. In some embodiments the external connector comprises an information processing facility. In some embodiments the external connector comprises a user input key. In some embodiments the external connector comprises a liquid crystal display. In some embodiments the external connector comprises a personal computer interface facility. In some embodiments the external connector enables a transactional method between the universal electronic transaction facility and the main service facility. In some embodiments the external connector comprises an RF facility. In some embodiments the external connector comprises an IR facility. In some embodiments the external connector facilitates communication between the universal electronic transaction facility and the main service facility. In some embodiments the external connector is associated with a merchant. In some embodiments the external connector is associated with a transaction participant.

In some embodiments the universal electronic transaction facility requires the completion of an initialization procedure prior to use. In some embodiments the initialization procedure associates a user with the universal electronic transaction facility. In some embodiments one step in the initialization process requires a user to enter a signature. In some embodiments the signature becomes a permanent record. In some embodiments the signature is used for verification. In some embodiments the signature is used for identification. In some embodiments the signature is used for security purposes. In some embodiments the signature is stored in nonvolatile RAM. In some embodiments the signature is automatically displayed on a display associated with the universal electronic transaction facility during the exercise of a transactional method. In some embodiments the universal electronic transaction facility is ready for normal use only after the user has entered the signature. In some embodiments one step in the initialization process requires a user to select a code. In some embodiments the code is up to 10 digits. In some embodiments the code is a personal identification number. In some embodiments later recalling and providing the code is a prerequisite to accessing information stored in the universal electronic transaction facility. In some embodiments the user's later failing to recall and provide the code results in the partial disablement of the universal electronic transaction facility. In some embodiments the user's later failing to recall and provide the code results in the total disablement of the universal electronic transaction facility. In some embodiments the universal electronic transaction facility is ready for normal use only after the user has selected a code.

In some embodiments the universal electronic transaction facility displays a command box on a display integral to the universal electronic transaction facility. In some embodiments the command box appears at the top of the display. In some embodiments the command box is associated with a command. In some embodiments the command is "type". In some embodiments the command is "print". In some embodiments the command is "erase". In some embodiments the command is "security". In some embodiments the command is "shift". In some embodiments the command is supported by the universal electronic transaction facility. In some embodiments the remaining part of the display is available for the display of information associated with a transactional method. In some embodiments the universal electronic transaction facility comprises a specific area that is assigned for an original signature. In some embodiments the original signature is entered by a user into the universal electronic transaction facility during an initialization procedure. In some embodiments the signature is permanently stored in the universal electronic transaction facility. In some embodiments the signature is used for identification purposes. In some embodiments the specific area is subsequently utilized by a user to write a signature. In some embodiments the user writes the signature during the exercise of a transactional method.

In some embodiments the universal electronic transaction facility provides for the digitization of a physical (or biometric) trait associated with a user, such as captured in a photograph, a fingerprint, a voice print, and/or an iris scan. In some embodiments the physical trait is likely to be unique to the user and not associated with another user. In some embodiments the digitization of the physical trait provides for identification of the user. In some embodiments the digitization of the physical trait provides for authorization of the user. In some embodiments the universal electronic transaction facility displays a simulation of a physical card. In some embodiments the simulation is a simulacrum. In some embodiments the physical card is a credit card. In some embodiments a signature collected during an initialization procedure associated with the universal electronic transaction facility is displayed during an exercise of a transactional method. In some embodiments the signature is inspected by a merchant. In some embodiments the signature is inspected by a participant in the transactional method. In some embodiments the simulacrum comprises basic card information. In some embodiments the basic card information may comprise a name, a card number, a date of issue, and/or an expiration date. In some embodiments the basic card information is stored within the universal electronic transaction facility. In some embodiments the basic card information is presented in the form of a bar code. In some embodiments the bar code is read by a bar code reader.

Embodiments of a user interface may include many features and attributes. A user interface may include a touch screen. In some embodiments the user interface comprises a touch memory button. In some embodiments the user interface comprises a touch memory reader. In some embodiments the user interface comprises a mouse. In some embodiments the user interface comprises a trackball. In some embodiments the trackball is integral to the universal electronic transaction facility. In some embodiments the user interface comprises a microphone. In some embodiments the microphone enabled speech recognition. In some embodiments the user interface comprises an RFID scanner. In some embodiments the user interface comprises a Bluetooth interface to an external user interface. In some embodiments the user interface comprises a network interface. In some embodiments the user interface comprises a remote Web browser operatively coupled to the universal electronic transaction facility via a network. In some embodiments the user interface comprises a keyboard. In some embodiments the user interface comprises a click wheel. In some embodiments the user interface comprises a track wheel. In some embodiments the user interface comprises a pointer. In some embodiments the user interface comprises a slider. In some embodiments the user interface comprises a button. In some embodiments the user interface comprises a voice-activated interface. In some embodiments the user interface comprises a stylus. In some embodiments the user interface comprises a smart pen. In some embodiments the user interface comprises a remote control. In some embodiments the user interface comprises a network interface. In some embodiments the user interface comprises a software interface. In some embodiments the user interface comprises a Web page. In some embodiments the user interface comprises a browser. In some embodiments the user interface comprises a camera. In some embodiments the camera is a video camera. In some embodiments the camera is a Web camera.

A UET or universal electronic transaction facility may be capable of performing many functions and may have many attributes. In some embodiments the universal electronic transaction facility is capable of storing a user's signature as an essential part of an initialization process of the universal electronic transaction facility. In some embodiments the universal electronic transaction facility is capable of storing a security code as a part of an initialization process of the universal electronic transaction facility. In some embodiments the universal electronic transaction facility is capable of being initialized, and in some embodiments the initialization of the universal electronic transaction facility comprises entering a code, personal identifier, password, personal identification number, signature, or similar identifier. In some embodiments the initialization of the universal electronic transaction facility further comprises creating a client profile. In some embodiments the initialization of the universal electronic transaction facility further comprises selecting a transaction service provider. In some embodiments the initialization of the universal electronic transaction facility further comprises registering with a central security agency.

Methods and systems disclosed herein include methods and systems for making a payment, including issuing a representation of a check to an electronic transaction facility; storing the representation in memory associated with the electronic transaction facility; and causing the representation to be transmitted in connection with a transaction. The methods and systems may also include the step of assessing information that is associated with the representation and processing at least some of the information through a financial institution. In some embodiments the financial institution is an ACH processing facility. The methods and systems may also include the step of transmitting at least one of a cancelled check and a transaction receipt back to the electronic transaction facility in response to a competed transaction. In some embodiments the electronic transaction facility comprises at least one of a cell phone, PDA, combination PDA cell phone, satellite phone, mobile phone, mobile communication facility, laptop computer, handheld computer, desktop computer, and a computer.

Methods and systems disclosed herein include methods and systems for making a payment, including issuing a representation of a money order to an electronic transaction facility; storing the representation in memory associated with the electronic transaction facility; and causing the representation to be transmitted in connection with a transaction. The methods and systems may also include the step of transmitting a transaction receipt back to the electronic transaction facility in response to a competed transaction. The methods and systems may also include the step of storing the transaction receipt in the memory.

Methods and systems disclosed herein include methods and systems for transacting, including issuing personal health care information to a universal electronic transaction facility in a form that represents an actual record. In some embodiments the personal health care information is a patient's electronic medical record. In some embodiments the electronic medical record is stored on a user device. In some embodiments the electronic medical record includes information relating to at least one of a patient's address, phone number, email address, emergency contact information, primary care physician, age, height, weight, blood type, medical conditions (e.g., disease, blood pressure, cholesterol levels), currently prescribed medications, allergies, previous surgeries, previous health care providers, current health insurance provider and policy number. In some embodiments a user initiates a transaction relating to the personal health care information with a health care provider. In some embodiments a user transmits his electronic medical record to the electronic network of a health care provider. In some embodiments a user transmits his electronic medical record to the electronic network of a health insurer. In some embodiments a health care provider transmits new information to the user's electronic medical record. In some embodiments the personal health care information relates to health insurance carrier information. In some embodiments the health insurance carrier information includes information relating to at least one of a health maintenance organization, preferred provider organization, policy number, primary care physician automated referral authorization and service approval. In some embodiments the personal health care information relates to a prescription. In some embodiments the prescription includes at least one of a link with pharmacy; doctor; link with a patient, link with hospital, link with a doctor's office, pay for prescription on phone itself and just pick up at the pharmacist, link to health insurance, and a link to a reimbursor. In some embodiments the record comprises an electronic medical record. In some embodiments the medical record includes information related to at least one of a complete medical record containing treatment history, current medications, physicians, disease, and morbidities. In some embodiments the record comprises an informed consent. In some embodiments the informed consent includes information related to at least one of treatment, health care proxy, and participation in clinical trials. In some embodiments the record comprises organ donor information. In some embodiments the organ donor information relates to at least one of what is to be donated, an appropriate signed consent, and witness form. In some embodiments the record comprises medical emergency contact information. In some embodiments the medical emergency contact information includes at least one of an address, phone, location of medical records, allergies to medications, list of current medications person is taking, blood type, disease, and morbidities present in person.

Methods and systems disclosed herein include methods and systems for transacting, including issuing a secure voting ballot to a universal electronic transaction facility. In some embodiments the ballot comprises a representation of an actual ballot. The methods and systems may also include the step of using the universal transaction facility to make a vote. The methods and systems may also include the step of issuing a receipt in response to the vote. In some embodiments a user uses the universal electronic transaction facility to make a voting transaction in connection with a vote. In some embodiments the vote is for a public election. In some embodiments the vote is for public elected officials. In some embodiments the elected officials comprise local, municipal, county, state, and federal government. In some embodiments the vote is for referendum items. In some embodiments the vote is for a corporate election. In some embodiments voting comprises directors, shareholders, proxies, and tender offers. In some embodiments the vote is for a product. In some embodiments a user votes as part of a survey. In some embodiments a corporation conducts a product survey. In some embodiments a product survey is conducted while at home. In some embodiments the product survey is conducted while in a store. In some embodiments the product survey is conducted while viewing an advertisement. In some embodiments the vote is for entertainment. In some embodiments the entertainment vote is part of a show. In some embodiments the vote is by the attending audience. In some embodiments the vote is by television viewers. In some embodiments a vote is for a favorite show. In some embodiments the show is on television. In some embodiments the show is in the movies. In some embodiments a vote is for an alternate ending to a show. In some embodiments the vote is for a bill or legislation. In some embodiments the vote is by elected officials. In some embodiments the elected officials vote in a senate. In some embodiments the elected officials vote in a house of representatives. In some embodiments there is an acknowledgement to the vote. In some embodiments the user client facility receives a receipt. In some embodiments the receipt is a facsimile of the ballot. In some embodiments the ballot is marked to indicate a recorded vote. In some embodiments the vote is recorded late. In some embodiments the vote receipt to the user indicates the vote was received late. In some embodiments the user is informed when the next election is. In some embodiments the users identification is marked as voted. In some embodiments the user is not able to vote in the same election more than once. In some embodiments at least one ballot is stored on the client facility. In some embodiments a ballot comprises local, municipal, county, state, federal, corporate, entertainment, product, or bill elections. In some embodiments the user selects a ballot to vote. In some embodiments a voter is reminded to vote. The methods and systems may also include a user being issued an actual ballot facsimile. In some embodiments the organization taking the vote sends the ballot facsimile. In some embodiments the user request a ballot facsimile from a vote organization. The methods and systems may also include the user client facility stores at least one ballot facsimile. In some embodiments the ballot has attributes. In some embodiments the attributes comprise name, address, personal identification, vote date, vote start time, vote end time, or other attribute for voting. The methods and systems may also include the user transacts a vote. In some embodiments the user selects a ballot. In some embodiments the user marks a ballot with the users vote. The methods and systems may also include the polling location issues a receipt of voting. In some embodiments the receipt is a facsimile of the ballot marked with a voting acknowledgement. In some embodiments the receipt is a facsimile of an acknowledgement of voting. The methods and systems may also include the user archiving the receipt of the voting. In some embodiments the archive is by user-defined category. In some embodiments at least one receipt is archived. The methods and systems may also include secure transaction capability, using a client facility and supported by a secure distributed web-based platform. In some embodiments secure transaction through any client facility. The methods and systems may also include the ability to issue, securely and electronically, entire token. In some embodiments the token has all necessary images, branding, and/or data for conducting transactions. In some embodiments the token is transmitted directly to a user. In some embodiments transmitted through a wired and/or wireless medium. In some embodiments transmitted to a personal client facility including PCs, mobile phones, etc., and/or a public device for temporary personal use. The methods and systems may also include the ability to reproduce, securely and electronically, multiple existing card, account, and vendor information. In some embodiments the reproduction contains branding and images, with necessary data for conducting transactions. In some embodiments reproduction is on client facility. The methods and systems may also include the ability to conduct secure transactions, such as using Infrared, RF, and Bar-Codes, or using various forms of over-the-air transactions. The methods and systems may also include the ability to issue to client facility securely and electronically, a receipt or acknowledgement related to transactions conducted. In some embodiments transactions may be performed locally. In some embodiments transactions are performed using over-the-air transactions. The methods and systems may also include the ability to securely and electronically interact with multiple domains, through any wired and/or wireless medium. In some embodiments transactions are used to procure personalized tokens. In some embodiments a UET is used to initiate and complete transactions. In some embodiments to a user receives receipt or acknowledgement of transaction.

The methods and systems may also include the ability to secure all proximity and over-the-air transactions, including issuance of tokens and receipts, using three-dimensional authentication. In some embodiments the three dimensional verifying is the identification of the user, device and domain for every transaction. In some embodiments this includes using cryptography tools. In some embodiments a user may customize the public/private key infrastructure on a per user, per device and per domain basis. The methods and systems may also include the ability to securely encrypt tokens and receipts, where tokens and receipts are issued. In some embodiments when tokens and receipts are stored on the client facility.

The methods and systems may also include the ability to configure the user-interface and personalized/non-personalized applications on the client facility, optionally based on the user's preferences and in some embodiments through the support of an Expert system. In some embodiments an expert system operates over a period of time based on the user's behavior, usage patterns, transaction history and qualified external inputs.

Methods and systems disclosed herein include methods and systems for enabling a security transaction, including issuing personal information to a universal electronic transaction facility, wherein the personal information is adapted to be used in connection with a transaction; wherein the transaction may involve the communication of a facsimile of an actual object. In some embodiments the personal information includes information about the user. In some embodiments the personal information is at least one of a phone number, address, email address, social security number, drivers license, credit card accounts, debit card accounts, business card information, address book, and email address book. In some embodiments the personal information is communicated through a security facility. In some embodiments the personal information is encrypted. In some embodiments the personal information is stored encrypted. In some embodiments the personal information is transmitted encrypted. In some embodiments the personal information includes information about user acquaintances. In some embodiments the personal information is at least one of a phone number, address, email address, and business card information. In some embodiments the acquaintance's personal information is communicated with security methods. In some embodiments the personal information is encrypted. In some embodiments the personal information is stored in an encrypted form. In some embodiments the personal information is transmitted in an encrypted form. In some embodiments the personal information manager tracks user activity. In some embodiments the personal information manager tracks monetary transactions. In some embodiments the personal information manager tracks acquaintance communications. In some embodiments the personal information manager recognizes groups of acquaintances as being associated. In some embodiments the personal information manager provides additional contacts. In some embodiments the additional contacts are determined by the user contact of an acquaintance group. In some embodiments the contacts are by email. In some embodiments the contacts are by phone. In some embodiments the personal information manager interacts with a user's location. In some embodiments the user's location is determined by GPS. In some embodiments the user's location is by cell tower triangulation. In some embodiments the personal information manager determines a user's proximity to acquaintances. In some embodiments the proximity is determined at least in part by comparing the user's location to people in close proximity that match the information in the user's address book. In some embodiments the object comprises at least one of a driver license, social security card, credit card, debit card, personal ID, and other personal document. The methods and systems may also include the step of storing one or more replicas of personal information in memory associated with the universal electronic transaction facility. In some embodiments the replicas include associated attributes. In some embodiments an attribute comprises at least one of a name, address, valid dates, height, weight, and ID number. The methods and systems may also include the transmission of personal information at a point of a transaction. In some embodiments the point of transaction is remote from recipient. In some embodiments the point of transaction is local to the recipient. The methods and systems may also include the user receiving a reply from a transaction. In some embodiments the reply comprises an email, a message, a business card, an address card, or a phone number. The methods and systems may also include the step of the user archiving the replica of a reply. In some embodiments the reply is by type of document. In some embodiments a type of document comprises at least one of an email, a message, an address, a phone number, and a business card. In some embodiments the archive is initiated by an acquaintance. The methods and systems may also include providing a secure transaction capability, wherein the secure transaction capability includes using a client facility supported by a secure distributed web-based platform. The methods and systems may also include the step of the ability to issue, securely and electronically, an entire token. In some embodiments the token includes images, branding, and/or data for conducting transactions. In some embodiments the token is transmitted directly to a user. In some embodiments the transmission includes transmission through a wired and/or wireless medium. In some embodiments the token is transmitted to a personal client facility including at least one of a PC, mobile phone, and a public device for temporary personal use. The methods and systems may also include the step of providing the ability to reproduce, securely and electronically, multiple existing card, account, and vendor information. In some embodiments the reproduction contains branding and images. In some embodiments the step of reproduction is accomplished on client facility. The methods and systems may also include the step of providing the ability to conduct secure transactions. In some embodiments the secure transactions include the use of at least one of Infrared, RF, and Bar-Codes. In some embodiments the secure transactions include the use of at least one of using wireless transactions. The methods and systems may also include the step of providing the ability to issue a receipt or acknowledgement related to transactions conducted to a client facility securely.

Methods and systems disclosed herein include methods and systems for enabling a security transaction, including issuing a secure loyalty card to a universal electronic transaction facility. In some embodiments the loyalty card relates to at least one of an airline frequent flyer miles, rail frequent miles, hotel frequent stay rewards, store rewards, store coupons, service business promotions, and store promotions. In some embodiments the loyalty card is adapted to be redeemed at a merchant. In some embodiments loyalty card is adapted to be redeemed for money. In some embodiments loyalty card is adapted to be redeemed for products. In some embodiments loyalty card is adapted to be redeemed for services. In some embodiments a user initiates a loyalty information transaction through the universal electronic transaction facility. In some embodiments the transaction is targeted to a merchant. In some embodiments transaction is targeted to a common set of merchants. In some embodiments transaction is targeted to all available merchants. In some embodiments a merchant initiates a loyalty information transaction through the universal electronic transaction facility. In some embodiments the merchant transmits loyalty information to a predetermined list of users. In some embodiments a merchant transmits loyalty information to a common set of users. In some embodiments a merchant transmits loyalty information to all associated users. The methods and systems may also include the step of storing a loyalty card replica with associated attributes. The methods and systems may also include the step of transmitting a redemption communication from the universal electronic transaction facility. In some embodiments the redemption takes place remotely. In some embodiments the redemption takes place at the business location. In some embodiments the redemption takes place in real time. The methods and systems may also include the step of providing a transaction receipt by a merchant of the transaction. In some embodiments the receipt takes place remotely. In some embodiments the receipt takes place at the business location. In some embodiments the receipt is in real time. The methods and systems may also include the step of storing the receipt in memory associated with the universal electronic transaction facility. In some embodiments more than one receipt is stored. The methods and systems may also include providing secure transaction capability, using a client facility supported by a secure distributed web-based platform. In some embodiments secure transaction through any client facility. The methods and systems may also include the step of issuing an entire token, securely and electronically. In some embodiments the token has all necessary images, branding, and/or data for conducting transactions. In some embodiments the token is transmitted directly to a user. In some embodiments transmitted through a wired and/or wireless medium. In some embodiments transmitted to a personal client facility including PCs, mobile phones, etc., and/or a public device for temporary personal use. The methods and systems may also include the step of providing a reproduction facility adapted to reproduce, securely and electronically, multiple existing card, account, and vendor information. In some embodiments the reproduction contains branding and images, with necessary data for conducting transactions. In some embodiments reproduction is on client facility. The methods and systems may also include the step of enabling the universal electronic transaction facility with the ability to conduct secure transactions, such as through Infrared, RF, and Bar-Codes or various forms of wireless transactions. The methods and systems may also include the step of providing a receipt. The methods and systems may also include the step of adapting the transaction facility to securely and electronically interact with multiple domains, through any wired and/or wireless medium. In some embodiments methods and systems are used to procure personalized tokens. In some embodiments methods and systems are used to initiate and complete transactions. In some embodiments methods and systems are used to receive receipt or acknowledgement of transaction. The methods and systems may also include the step of adapting the transaction facility to secure all proximity and wireless transactions, including issuance of tokens and receipts, using three-dimensional authentication. In some embodiments the three dimensional verifying is the identification of the user, device and domain for every transaction. In some embodiments using cryptography tools. In some embodiments methods and systems are used to customize the public/private key infrastructure on a per user, per device and per domain basis. The methods and systems may also include the step of adapting the transaction facility with the ability to securely encrypt tokens and receipts. In some embodiments when tokens and receipts are issued. In some embodiments tokens and receipts are stored on the client facility. The methods and systems may also include the step of adapting the transaction facility ability to configure the user-interface and personalized/non-personalized applications on the client facility. In some embodiments a device is configured based on the user's preferences. In some embodiments a device is configured through the support of an expert system (e.g. over a period of time a device is automatically configured based on the user's behavior, usage patterns, transaction history and qualified external inputs). The methods and systems may also include the adapting the transaction facility with the ability to provision multiple tokens, multiple services and multiple personalized/non-personalized applications, with a high level of throughput, efficiency, and fault tolerance. In some embodiments based on the User's preferences and through the support of an expert system. In some embodiments based on the user's behavior, usage patterns, transaction history and qualified external inputs.

Methods and systems disclosed herein include methods and systems for enabling a transaction, including issuing an infotainment file to a universal electronic transaction facility and making a transaction associated with the infotainment. In some embodiments infotainment is from a group comprising movies, movie clips, radio programming, electronic books, video, games, video games, music, and music clips. In some embodiments the infotainment is played on the user client facility. In some embodiments the infotainment has a license. The methods and systems may also include the storage of infotainment replicas. In some embodiments at least one version of infotainment replica is stored. In some embodiments at least one type of infotainment replica is stored. The methods and systems may also include the transmission of a purchase request is made. In some embodiments the purchase is made remotely. In some embodiments the purchase is made at a sales location. In some embodiments funds are transferred from the user during a purchase request. In some embodiments the fund transaction is in real time. The methods and systems may also include the transmission of a receipt from a merchant. In some embodiments the receipt is transmitted remotely. In some embodiments the receipt is transmitted at the sales location. In some embodiments the receipt is transmitted in real time. The methods and systems may also include the archive of the receipt replica by the user. In some embodiments the user client may store at least one replica. In some embodiments the user client may store replicas for at least one merchant. The methods and systems may also include providing secure transaction capability, using a client facility and supported by a secure distributed web-based platform. In some embodiments secure transaction through any client facility. The methods and systems may also include adapting the transaction facility with the ability to issue, securely and electronically, an entire token. In some embodiments the token has all necessary images, branding, and/or data for conducting transactions. In some embodiments the token is transmitted directly to a user. In some embodiments the token is transmitted through a wired and/or wireless medium. In some embodiments the token is transmitted to a personal client facility including PCs, mobile phones, etc., and/or a public device for temporary personal use.

The methods and systems may also include adapting the transaction facility with the ability to reproduce, securely and electronically, multiple existing card, account, and vendor information. In some embodiments the reproduction contains branding and images, with necessary data for conducting transactions. In some embodiments reproduction is on a client facility. The methods and systems may also include adapting the transaction facility with the ability to conduct secure transactions, such as using Infrared, RF, and bar codes, using over-the-air transactions or the like. The methods and systems may also include adapting the transaction facility with the ability to issue to client facility securely and electronically, a receipt or acknowledgement related to transactions conducted. In some embodiments a receipt or acknowledgement is issued at a location of the user, such as a merchant location, optionally using over-the-air transactions. The methods and systems may also include adapting the transaction facility with the ability to securely and electronically interact with multiple domains, through any wired and/or wireless medium, such as to procure personalized tokens, to initiate and complete transactions or to receive receipt or acknowledgement of transaction. The methods and systems may also include adapting the transaction facility with the ability to secure all proximity and over-the-air transactions, including issuance of tokens and receipts, using three-dimensional authentication. In some embodiments the three-dimensional verifying is the identification of the user, device and domain for every transaction, optionally using known cryptography tools, such as DES encryption, PGP encryption, public key-private key techniques, or other cryptography tools. In some embodiments a host may customize the public/private key infrastructure on a per user, per device and per domain basis. The methods and systems may also include adapting the transaction facility with the ability to securely encrypt tokens and receipts when tokens and receipts are issued. In some embodiments when tokens and receipts are stored on the client facility. The methods and systems may also include adapting the transaction facility with the ability to configure the user-interface and personalized/non-personalized applications on the client facility, such as based on preferences, such as through an expert system. Personalization or configuration may take place over a period of time based on the user's behavior, usage patterns, transaction history and qualified external inputs. The methods and systems may also include adapting the transaction facility with the ability to provision multiple tokens, multiple services and multiple personalized/non-personalized applications, with a high level of throughput, efficiency, and fault tolerance, optionally based on the User's preferences and through the support of an expert system. In some embodiments based on the user's behavior, usage patterns, transaction history and qualified external inputs. These and other systems, methods, objects, features, and advantages of the present invention will be apparent to those skilled in the art from the following detailed description of the preferred embodiment and the drawings. All documents mentioned herein are hereby incorporated in their entirety by reference.

Provided herein may be methods and systems for providing universal electronic transactions. In an aspect of the invention, a method may involve providing a universal electronic transaction facility. In variations of this method, the universal electronic transaction facility may be capable of providing a separate security protocol based on at least a domain, a device and a user of the universal electronic transaction facility. In variations of this method, the method may further comprise providing a secure, distributed web-based platform that is associated with the universal electronic transaction facility. In versions of this variation, the method may further comprise providing a secure transaction capability to a user via the universal electronic transaction facility and in association with the web-based platform.

In variations of this method, the method may further comprise providing a secure transaction capability to a user via the universal electronic transaction facility. In versions of this variation, the transaction capability is associated with a payment application. In versions of this variation, the transaction capability is associated with a non-payment application. In versions of this variation, the secure transaction capability may comprise an ability to issue an acknowledgement of a transaction to the universal electronic transaction facility. The acknowledgement may be a receipt.

In variations of this method, the universal electronic transaction facility may be a client device. In variations of this method, the universal electronic transaction facility may operate in accordance with a wallet metaphor. In variations of this method, the universal electronic transaction facility may not operate in accordance with a wallet metaphor.

In variations of this method, the universal electronic transaction facility may be a personal device. In variations of this method, the universal electronic transaction facility may be a public device. In variations of this method, the universal electronic transaction facility may be capable of interacting with multiple domains.

In variations of this method, the method may further comprise transmitting data to the universal transaction facility. In versions of this variation, the data may be at least one of an acknowledgement, a receipt, a token. In versions of this variation, the universal electronic transaction facility is capable of encrypting the data at the universal electronic transaction facility. The universal electronic transaction facility may further be capable of storing the encrypted data at the universal electronic transaction facility. The data may be one or more instances of one or more of the following things: a bill, an acknowledgement, a receipt, a statement, a loyalty statement, a coupon, a promotion, a transaction summary, a violation record, a ticket, a driver's license, a check book, a check, a token.

In an aspect of the invention, a system may comprise a universal electronic transaction facility. In variations of this system, the universal electronic transaction facility may include a generator of a separate security protocol based on at least a domain, a device and a user of the universal electronic transaction facility. In variations of this system, the system may further comprise a secure, distributed web-based platform that is associated with the universal electronic transaction facility. In versions of this variation, the system may further comprise a secure transaction capability associated with the universal electronic transaction facility and the web-based platform In variations of this system, the system may further comprise a secure transaction capability in association with the universal electronic transaction facility. In versions of this variation, the transaction capability is associated with a payment application. In versions of this variation, the transaction capability is associated with a non-payment application. In versions of this variation, the secure transaction capability may comprise a transaction acknowledgement facility in communication with the universal electronic transaction facility. The acknowledgement facility may include a receipt.

In variations of this system, the universal electronic transaction facility may be a client device. In variations of this system, the universal electronic transaction facility may be operable in accordance with a wallet metaphor. In variations of this method, the universal electronic transaction facility may not be operable in accordance with a wallet metaphor.

In variations of this system, the universal electronic transaction facility may be a personal device. In variations of this system, the universal electronic transaction facility may be a public device. In variations of this system, the universal electronic transaction facility includes interaction capability for multiple domains.

In variations of this system, the system may further comprise a data transmission facility in communication with the universal transaction facility. In versions of this variation, the data transmission facility includes at least one of an acknowledgement, a receipt, a token. In versions of this variation, the universal electronic transaction facility includes a data encryption facility. The universal electronic transaction facility may further include an encrypted data storage facility. The data storage facility may include data storage capacity for at least one of a bill, an acknowledgement, a receipt, a statement, a loyalty statement, a coupon, a promotion, a transaction summary, a violation record, a ticket, a driver's license, a check book, a check, a token.

In an aspect of the invention, methods and systems may include providing an operative coupling between a universal electronic transaction facility and an external system. In a variation of this method, the universal electronic transaction facility may be capable of providing a separate security protocol based on at least a domain, a device and a user of the universal electronic transaction facility. In a variation of this method, the external system is a transactional system. In versions of this variation, the transactional system is a point-of-sale system.

In variations of this method, the operative coupling is secure. In variations of this method, the operative coupling is wireless. In variations of this method, the operative coupling is wired.

In an aspect of the invention, a system may include a universal electronic transaction facility and an external system operatively coupled thereto. In an embodiment of the system, the universal electronic transaction facility may include a separate security protocol facility based on at least a domain, a device and a user of the universal electronic transaction facility. In an embodiment of the system, the external system is a transactional system. In versions of this embodiment, the transactional system is a point-of-sale system.

In embodiments of the system, operatively coupled is securely coupled. In embodiments of the system, operatively coupled is wirelessly coupled. In embodiments of the system, operatively coupled is wired.

In another aspect of the invention, a method may comprise receiving data from a universal electronic transaction facility and conducting an action in response to the data received from a universal electronic transaction facility. In a variation of this method, the universal electronic transaction facility may be capable of providing a separate security protocol based on at least a domain, a device and a user of the universal electronic transaction facility.

In a variation of this method, the method further comprises issuing a token to a user of a universal electronic transaction facility prior to receiving the data, wherein the data is associated with the token. In versions of this variation, the action may be a transaction that is based on verification of the token. The transaction may be conducted in a real world. The real world may contain a device-to-device communication. The real world may contain a bar code and bar code reader. The transaction conducted in a real world may be a proximity transaction. The transaction may be conducted in a virtual world. The transaction conducted in a virtual world may be an over-the-air transaction. The transaction may be associated with a biometric parameter. The transaction may not be associated with a biometric parameter. In versions of this variation, issuing the token may be done securely and electronically. In versions of this variation, the token may be personalized to the user. In versions of this variation, the token may not be personalized to the user. In versions of this variation, the token may encompass necessary data for conducting the action. In versions of this variation, the token may encode at least one of an image or branding. In versions of this variation, issuing the token may be done over a wired medium. In versions of this variation, issuing the token may be done over a wireless medium. In versions of this variation, the token may be associated with at least one of a credit card, a bank account, a frequent flyer card, a stored value card, a loyalty card, an insurance card, a driver's license, a bill, or a coupon.

In a variation of this method, the method may further comprise issuing a plurality of tokens to a user of a universal electronic transaction facility prior to receiving the data, wherein the data is associated with the token. In a variation of this method, the method may further comprise securing the action using three-dimensional authentication. In versions of this variation, three-dimensional authentication may involve verifying the identity of a user, the universal electronic transaction facility, and a domain.

In another aspect of the invention, a system may comprise a universal electronic transaction facility and a data receiver in communication with the universal electronic transaction facility, wherein the data receiver is responsive to data received from the universal electronic transaction facility. In a variation of this method, the universal electronic transaction facility may include a separate security protocol facility based on at least a domain, a device and a user of the universal electronic transaction facility. In a variation of this method, the method may further comprise a data token associated with the universal electronic transaction facility. Versions of this variation may further comprise a token verification transaction. The token verification transaction may be a real world transaction. The real world transaction may include device-to-device communication. The real world transaction may include a bar code reader and a bar code. The real world transaction may be a proximity transaction. The token verification transaction may be a virtual world transaction. The virtual world transaction may be an over-the-air transaction. The token verification transaction may be associated with a biometric parameter. The token verification transaction may not be associated with a biometric parameter. The token verification transaction may further be associated with three-dimensional authentication security. Three-dimensional authentication may include a user identity verification facility, a universal electronic transaction verification facility, and a domain verification facility. In versions of this variation, the data token may be secure and electronic. The version may further comprise a plurality of user data tokens associated with the universal electronic transaction, wherein data is associated with each user data token. In versions of this variation, the data token may be personalized to a user. In versions of this variation, the data token may not be personalized to a user. In versions of this variation, the data token may include necessary data for an action. In versions of this variation, the data token may include encoding for at least one of an image or branding. In versions of this variation, the association of the data token may be over a wired medium. In versions of this variation, the association of the data token may be over a wireless medium. In versions of this variation, the association of the data token may be with at least one of a credit card, a bank account, a frequent flyer card, a stored value card, a loyalty card, an insurance card, a driver's license, a bill, or a coupon.

In another aspect of the invention, a method of providing a service may include communicating with a universal electronic transaction facility and communicating with a service provider. In a variation of this method, the communication may be associated with the provision of a service that is provided by the service provider. In versions of this variation, the service is provided to the user via the universal electronic transaction facility. In versions of this variation, the service may be one of the following services: bill payment, person-to-person transaction, money order/transfer, prepaid airtime top-up, ticketing, marketing, electronic checking, licensing, health service, travel service, infotainment service, personal information management service, training, a lottery, voting.

In a variation of this method, the universal electronic transaction facility may be capable of providing a separate security protocol based on at least a domain, a device and a user of the universal electronic transaction facility. In a variation of this method, the communication may be secure. In versions of this variation, the secure communication is provided according to three-dimensional authentication.

In a variation of this method, the communication may be associated with the provision of a plurality of services that are provided by at least one of the service provider and a second service provider. In a variation of this method, the communication may be associated with a plurality of applications. In versions of this variation, at least one of the applications may be personalized. In versions of this variation, at least one of the applications may be non-personalized.

In a variation of this method, the communication may be in accordance with a user preference. In a variation of this method, the communication may be in accordance with data that is provided by an expert system.

In another aspect of the invention, a system may comprise a universal electronic transaction facility and a service provider in communication therewith. In a variation of the system, the service provider may include a service facility responsive to said communication. In a version of this variation, the service facility may include one of the following services: bill payment, person-to-person transaction, money order/transfer, prepaid airtime top-up, ticketing, marketing, electronic checking, licensing, health service, travel service, infotainment service, personal information management service, training, a lottery, voting. In a variation of the system, the universal electronic transaction facility may include a separate security protocol capacity based on at least a domain, a device and a user of the universal electronic transaction facility. In versions of this variation, the service provider may be in communication with a user via the universal electronic transaction facility.

In a variation of the system, the communication is secure. In versions of this variation, the secure communication is three-dimensional authentication. In a variation of the system, the system may further comprise a second service provider and a plurality of services associated with the at least one of the service provider and a second service provider. In a variation of the system, the system may further comprise a plurality of applications associated with the service provider. In versions of this variation, at least one of the applications may be personalized. In versions of this variation, at least one of the applications may be non-personalized.

In a variation of the system, the communication may be in accordance with a user preference. In a variation of the system, the communication may be in accordance with data that are provided by an expert system.

In an aspect of the invention, a method may include providing a multidimensional database in association with a universal electronic transaction facility. In a variation of this method, the universal electronic transaction facility may be capable of providing a separate security protocol based on at least a domain, a device and a user of the universal electronic transaction facility.

In another aspect of the invention, a system may include a multidimensional database and a universal electronic transaction facility in association therewith. In an embodiment of this system, the universal electronic transaction facility may include a separate security protocol based on at least a domain, a device and a user of the universal electronic transaction facility.

In an aspect of the invention, a method may include providing a personalized token in association with a universal electronic transaction facility. In a variation of this method, the universal electronic transaction facility may be capable of providing a separate security protocol based on at least a domain, a device and a user of the universal electronic transaction facility. In a variation of this method, the personalized token may be an official electronic identifier of the user. In versions of this variation, the personalized token may be associated with at least one of the following things: a driver's license, a passport. In versions of this variation, the personalized token may be at least one of the following kinds of token: a secure and electronic token, a branded token. In a variation of this method, the personalized token may be provided at a point of transaction. In a variation of this method, the personalized token may be provided in real time.

In an aspect of the invention, a system may include a universal electronic transaction facility and a personalized token in association therewith. In a variation of this system, the universal electronic transaction facility may include a separate security protocol based on at least a domain, a device and a user of the universal electronic transaction facility. In a variation of this system, the personalized token may be an official electronic identifier of a user. In versions of this variation, the personalized token may be associated with at least one of the following: a driver's license, a passport. In versions of this variation, the personalized token may be at least one of the following: a secure and electronic token, a branded token.

In a variation of this system, the personalized token may be a point of transaction token. In a variation of this system, the personalized token may be a real time token.

In another aspect of the invention, a method may include providing a merchant-oriented user interface in association with a universal electronic transaction facility, wherein the user interface allows the merchant to issue a token to a user of the universal electronic transaction facility. In a variation of this method, the universal electronic transaction facility may be capable of providing a separate security protocol based on at least a domain, a device and a user of the universal electronic transaction facility. In a variation of this method, the token is a branded token. In a version of this variation, the branded token may be secure and electronic. In a version of this variation, the branded token may be associated with at least one of the following things: a driver's license, a passport, a statement, a coupon, a promotion, a ticket, a ticket associated with a violation, a check book, a check, a secure and electronic token, a branded token, a credit card, a bank account, a frequent flyer card, a stored value card, a loyalty card, an insurance card, a bill, a bill, a merchant-issued credit card, a merchant-issued loyalty card, prepaid airtime, a money order, a money transfer, an account In another aspect of the invention, a system may comprise a universal electronic transaction facility and a merchant-oriented user interface in association therewith, wherein the merchant-oriented user interface includes a user token issuing facility in communication with the universal electronic transaction facility. In a variation of this system, the universal electronic transaction facility may include a separate security protocol based on at least a domain, a device and a user of the universal electronic transaction facility. In a variation of this system, the user token issuing facility may include a branded token issuing facility. In a version of this variation, the branded token issuing facility may be secure and electronic. In a version of this variation, the branded token issuing facility may be associated with at least one of the following: a driver's license, a passport, a statement, a coupon, a promotion, a ticket, a ticket associated with a violation, a check book, a check, a secure and electronic token, a branded token, a credit card, a bank account, a frequent flyer card, a stored value card, a loyalty card, an insurance card, a bill, a bill, a merchant-issued credit card, a merchant-issued loyalty card, prepaid airtime, a money order, a money transfer, an account.

In an aspect of the invention, a method may include providing a user interface for initializing a universal electronic transaction facility. In a variation of this method, the universal electronic transaction facility may be capable of providing a separate security protocol based on at least a domain, a device and a user of the universal electronic transaction facility. In a variation of this method, the user interface may allow a user to manage at least one parameter of the universal electronic transaction facility. In versions of this variation, the at least one parameter may be associated with at least one of the following things: a domain, a device, a user identifier, a password, a security protocol. In a variation of this method, the user may be an administrator.

In an aspect of the invention, a system may include a user interface, wherein the user interface includes an initializing facility for a universal electronic transaction facility. In a variation of this system, the system may further comprise a separate security protocol based on at least a domain, a device and a universal electronic transaction facility user. In a variation of this system, the user interface may include a management facility in association with at least one universal electronic transaction facility parameter. In versions of this variation, the at least one universal electronic transaction facility parameter may be associated with at least one of the following: a domain, a device, a user identifier, a password, a security protocol. In a variation of the system, the user interface may be an administrator interface.

In an aspect of the invention, a method may include providing a mobile wallet in association with a universal electronic transaction facility. In a variation of this method, the universal electronic transaction facility may be capable of providing a separate security protocol based on at least a domain, a device and a user of the universal electronic transaction facility. In a variation of this method, the mobile wallet may include an electronic representation of an item that is associated with a user. In a version of this variation, the item may be at least one of the following things: a driver's license, a passport, a statement, a coupon, a promotion, a ticket, a ticket associated with a violation, a check book, a check, a secure and electronic token, a branded token, a credit card, a back card, a bank account, a frequent flyer card, a stored value card, a loyalty card, an insurance card, a bill, a bill, a merchant-issued credit card, a merchant-issued loyalty card, prepaid airtime, a money order, a money transfer, an account. In a version of this variation, the item may be an official identity document of the user.

In an aspect of the invention, a system may include a universal electronic transaction facility and a mobile wallet in association therewith. In a variation of this system, the system may further comprise a separate security protocol based on at least a domain, a device and a user of the universal electronic transaction facility, wherein the separate security protocol is associated with the universal electronic transaction facility. In a variation of this system, the mobile wallet may include an electronic representation of a user item. In versions of this variation, the user item may be at least one of the following: a driver's license, a passport, a statement, a coupon, a promotion, a ticket, a ticket associated with a violation, a check book, a check, a secure and electronic token, a branded token, a credit card, a back card, a bank account, a frequent flyer card, a stored value card, a loyalty card, an insurance card, a bill, a bill, a merchant-issued credit card, a merchant-issued loyalty card, prepaid airtime, a money order, a money transfer, an account. In versions of this variation, the user item may be an official identity document of a user.

In an aspect of the invention, a method may include providing a universal electronic transaction facility that is adapted to support a transaction within a non-standard transaction domain. In a variation of this method, the universal electronic transaction facility may be capable of providing a separate security protocol based on at least a domain, a device and a user of the universal electronic transaction facility. In a variation of this method, the non-standard transaction domain may be the Web and the universal electronic transaction facility supports transactions using a secure, Web-based, personalized portal. In a variation of this method, the non-standard transaction domain may be associated with gaming and the universal electronic transaction facility supports transactions using a secure gaming portal. In a variation of this method, the non-standard transaction domain may be associated with a merchant and the universal electronic transaction facility supports transactions using a secure merchant portal. In a variation of this method, the non-standard transaction domain may be associated with a government and the universal electronic transaction facility supports transactions using a secure governmental portal. In a variation of this method, the non-standard transaction domain may be associated with an enterprise and the universal electronic transaction facility supports transactions using a secure enterprise portal. In a variation of this method, the non-standard transaction domain may be associated with health/fitness and the universal electronic transaction facility supports transactions using a secure health/fitness portal. In a variation of this method, the non-standard transaction domain may be associated with a religion and the universal electronic transaction facility supports transactions using a secure religious portal. In a variation of this method, the non-standard transaction domain may be associated with a sport and the universal electronic transaction facility supports transactions using a secure sports portal. In a variation of this method, the non-standard transaction domain may be associated with insurance and the universal electronic transaction facility supports transactions using a secure insurance portal. In a variation of this method, the non-standard transaction domain may be associated with a university and the universal electronic transaction facility supports transactions using a secure university portal. In a variation of this method, the non-standard transaction domain may be associated with a party and the universal electronic transaction facility supports transactions using a secure party portal. In versions of this variation, the party may be a political party.

In a variation of this method, the non-standard transaction domain may be associated with a pharma-exchange and the universal electronic transaction facility supports transactions using a secure pharma-exchange portal. In a variation of this method, the non-standard transaction domain may be associated with a commodity exchange and the universal electronic transaction facility supports transactions using a secure commodity exchange portal. In a variation of this method, the non-standard transaction domain may be associated with an airline and the universal electronic transaction facility supports transactions using a secure airline portal. In a variation of this method, the non-standard transaction domain may be associated with transportation and the universal electronic transaction facility supports transactions using a secure transportation portal.

In an aspect of the invention, a system may include a universal electronic transaction facility adapted to support a transaction within a non-standard transaction domain. In a variation of this system, the system may further comprise a separate security protocol based on at least a domain, a device and a universal electronic transaction facility user, wherein the separate security protocol is associated with the universal electronic transaction facility. In a variation of this system, the non-standard transaction domain may be the Web and the universal electronic transaction facility may include a secure, Web-based, personalized portal. In a variation of this system, the non-standard transaction domain may be associated with gaming and the universal electronic transaction facility may include a secure gaming portal. In a variation of this system, the non-standard transaction domain may be associated with a merchant and the universal electronic transaction facility may include a secure merchant portal. In a variation of this system, the non-standard transaction domain may be associated with a government and the universal electronic transaction facility may include a secure governmental portal. In a variation of this system, the non-standard transaction domain may be associated with an enterprise and the universal electronic transaction facility may include a secure enterprise portal. In a variation of this system, the non-standard transaction domain may be associated with health/fitness and the universal electronic transaction facility may include a secure health/fitness portal. In a variation of this system, the non-standard transaction domain may be associated with a religion and the universal electronic transaction facility may include a secure religious portal. In a variation of this system, the non-standard transaction domain may be associated with a sport and the universal electronic transaction may include a secure sports portal. In a variation of this system, the non-standard transaction domain may be associated with insurance and the universal electronic transaction facility system may include a secure insurance portal. In a variation of this system, the non-standard transaction domain may be associated with a university and the universal electronic transaction facility may include a secure university portal. In a variation of this system, the non-standard transaction domain may be associated with a party and the universal electronic transaction facility may include a secure party portal. In versions of this variation, the party may be a political party. In a variation of this system, the non-standard transaction domain may be associated with a pharma-exchange and the universal electronic transaction facility may include a secure pharma-exchange portal. In a variation of this system, the non-standard transaction domain may be associated with a commodity exchange and the universal electronic transaction facility may include a secure commodity exchange portal. In a variation of this system, the non-standard transaction domain may be associated with an airline and the universal electronic transaction facility may include a secure airline portal. In a variation of this system, the non-standard transaction domain may be associated with transportation and the universal electronic transaction facility may include a secure transportation portal.

In another aspect of the invention, a method may comprise providing a financial service in association with a universal electronic transaction facility. In a variation of this method, the universal electronic transaction facility may be capable of providing a separate security protocol based on at least a domain, a device and a user of the universal electronic transaction facility. In a variation of this method, the financial service may be selected from the group consisting of bill payment, person-to-person payment, money order payment, funds transfer, a top-up transaction, a ticketing transaction, issuance of a coupon, and resolution of a check.

In a variation of this method, the financial service may include securely issuing, to the universal electronic transaction facility, at least one electronic replica of at least one of the following items: a bill from a bill issuer, a payment token, money order, money transfer token, a prepaid airtime token, a ticket, a ticket associated with a violation, a loyalty card, an account, a coupon, a promotion, a check book, a check, a license, a driver's license.

In a version of this variation, the financial service may further include communicating at least one of branding, an image, information required to complete a transaction. The transaction may involve procuring a service from a merchant. The transaction may be a procurement of a service from a ticket issuer.

In a version of this variation, the financial service may further include alerting a user based on at least one attribute of the at least one item. The attribute may be associated with at least one of a date of expiry, a change of address, a number of a check, a number of checks remaining, a number of days before a coupon can be redeemed, a redemption date, a date of travel, a due date, a time, a time of issuance, a financial balance.

In a version of this variation, the financial service may further include enabling a user to securely pay the bill using universal electronic transaction facility. Paying the bill may occur in real time. Paying the bill may be associated with an on-line settlement of the bill paying the bill is associated with an off-line settlement of the bill. Paying the bill may be associated with at least one of a preferred mode of payment, a preferred time, a preferred location.

In a version of this variation, the financial service may further comprise securely issuing, to the universal electronic transaction facility, an electronic replica of at least one of the following confirmations: a receipt that is associated with a bill; a transaction summary statement; a marketing vehicle; a ticket associated with a violation; a license. The license may be at least one of a driver's license, a gun license, a liquor license, a fishing license, a hunting license. The marketing vehicle may be at least one of a loyalty card, an account, a coupon, a promotion. The transaction summary statement may be associated with a transaction between a user of the universal transaction facility and another user. The electronic replica may contain a payment stamp. The financial service may further include enabling a user to pay another user. The other user may have a universal electronic transaction facility. Paying another user may occur securely and in real time. Paying another user may be associated with an on-line settlement. Paying another user may be associated with an off-line settlement. The electronic replica may be delivered to a universal electronic transaction facility of a user that receives funds according to the financial service. The electronic replica may contain a summary that is associated with the financial service. The summary may be a frequent flyer summary. The electronic replica may include a cancelled check.

In a version of this variation, the financial service may further include enabling a transfer of units that is securely initiated at the universal electronic transaction facility. The financial service may include debiting units from a first account and crediting at units to a second account, wherein at least one of the debiting or crediting is contingent on validating a user and a request. Enabling the financial service may include issuing a request to a service provider, wherein the request is associated with completing the crediting and debiting under the control of the service provider. Issuing the transfer may be initiated via wireless communications. Issuing the transfer may be initiated via proximity-based communications. The units may be financial units. The units may be airtime units. The financial service may further comprise enabling a use of the funds by the user that receives the funds. The financial service is a ticket issuance service.

In a version of this variation, the financial service may further include enabling a top-up of an account, wherein the top-up is securely initiated at the universal electronic transaction facility.

In a version of this variation, the financial service may further include securely redeeming the electronic replica. A wireless communication may initiate securely redeeming the electronic replica. A proximity-based communication may initiate securely redeeming the electronic replica.

In a version of this variation, the financial service may further include securely receiving the electronic replica.

In a version of this variation, the financial service may be the issuance of a ticket that is associated with a violation, and wherein the electronic replica is of a driver's license.

In a version of this variation, the financial service may further include a unit transfer enabling facility, wherein the unit transfer enabling facility is in secure communication with the universal electronic transaction facility. The financial service may include a unit debiting facility in association with a first account and a unit crediting facility in association with a second account, wherein at least one of the unit debiting facility or unit crediting facility is contingent on a user and request validation. The financial service may further comprise a service provider request issuance facility associated with a service provider crediting and debiting facility. The unit transfer enabling facility may be in communication via wireless communications. The unit transfer enabling facility may be in communication via proximity-based communications. The unit transfer enabling facility may include financial units. The unit transfer enabling facility may include financial units. The unit transfer enabling facility may include airtime units. The financial service may further comprise a user funds enablement and receipt facility.

In a variation of this method, the universal electronic transaction facility may be a client device.

In an aspect of the invention, a system may comprise a universal electronic transaction facility and a financial service in association therewith. In a variation of this system, the universal electronic transaction facility may include a separate security protocol based on at least a domain, a device and a universal electronic transaction facility user. In a variation of this system, the financial service may be selected from the group consisting of bill payment, person-to-person payment, money order payment, funds transfer, a top-up transaction, a ticketing transaction, issuance of a coupon, and resolution of a check.

In a variation of this system, the financial service includes: a secure issuance facility in association with the universal electronic transaction facility and at least one electronic replica of at least one of the following items: a bill from a bill issuer, a payment token, money order, money transfer token, a prepaid airtime token, a ticket, a ticket associated with a violation, a loyalty card, an account, a coupon, a promotion, a check book, a check, a license, a driver's license.

In a version of this variation, the financial service may further include a communication facility comprising at least one of branding, an image, information required to complete a transaction. The transaction may involve merchant service procurement. The transaction may include ticket issuer service procurement.

In a version of this variation, the financial service further includes a user alert based on at least one attribute of the at least one item. The attribute may be associated with at least one of a date of expiry, a change of address, a number of a check, a number of checks remaining, a number of days before a coupon can be redeemed, a redemption date, a date of travel, a due date, a time, a time of issuance, a financial balance.

In a version of this variation, the financial service may further include a secure bill payment facility in association with the universal electronic transaction facility. The secure bill payment facility may be real time based. The secure bill payment facility may be associated with an on-line settlement of the bill. The secure bill payment facility may be associated with an off-line settlement of the bill. The secure bill payment facility may be associated with at least one of a preferred mode of payment, a preferred time, a preferred location. The secure bill payment facility may further include a secure electronic replica redemption facility. The secure electronic replica redemption facility may be proximity-based.

In a version of this variation, the financial service may further comprise a secure electronic replica issuance facility, in communication with the universal electronic transaction facility, wherein the secure electronic replica issuance facility includes an electronic replica of at least one of the following confirmations: a receipt that is associated with a bill; a transaction summary statement; a marketing vehicle; a ticket associated with a violation; a license. The license may be at least one of a driver's license, a gun license, a liquor license, a fishing license, a hunting license. The marketing vehicle may be at least one of a loyalty card, an account, a coupon, a promotion. The transaction summary statement may be associated with a transaction between a user of the universal transaction facility and another user. The electronic replica may contain a payment stamp. The financial service may further include a user-to-user payment enabling facility for a plurality of users. At least one additional user of the plurality of users may have a universal electronic transaction facility. The user-to-user payment enabling facility may be secure and in real time. The user-to-user payment enabling facility may be associated with an on-line settlement. The user-to-user payment enabling facility may be associated with an off-line settlement. The secure electronic replica issuance facility may include an electronic replica delivery facility responsive to: a) the universal electronic transaction facility and b) a user fund receipt facility associated with the financial service. The electronic replica may contain a summary that is associated with the financial service. The summary may be a frequent flyer summary. The electronic replica may include a cancelled check.

In a version of this variation, the financial service may further include secure account top-up enablement, responsive to the universal electronic transaction facility.

In a version of this variation, the financial service may further include secure redemption of the electronic replica.

In a version of this variation, the financial service may further include a secure electronic replica receiving facility.

In a version of this variation, the financial service may include a ticket issuance facility associated with a violation, and wherein the electronic replica is of a driver's license.

In a variation of this system, the universal electronic transaction facility may be a client device.

Informational Systems and Methods for Universal Electronic Transaction Facilities In another aspect of the invention, a method may include providing an informational service in association with a universal electronic transaction facility. In a variation of this method, the universal electronic transaction facility may be capable of providing a separate security protocol based on at least a domain, a device and a user of the universal electronic transaction facility. In a variation of this method, the informational service may be provided upon completion of the separate security protocols. In a variation of this method, the informational service may be provided upon completion of the separate security protocols.

In another aspect of the invention, a system may include a universal electronic transaction facility and an informational service in association therewith. In a variation of this system, the universal electronic transaction facility includes a separate security protocol based on at least a domain, a device and a universal electronic transaction facility user. In a variation of this system, the informational service may be responsive to the separate security protocols. In a variation of this system, the informational service may include a personalization facility responsive to a universal electronic transaction facility user.

In another aspect of the invention, a method may comprise implementing a universal electronic transaction facility on a handheld device of the user. In a variation of this method, the universal electronic transaction facility may be capable of providing a separate security protocol based on at least a domain, a device and a user of the universal electronic transaction facility. In a variation of this method, the handheld device may be a handset.

In another aspect of the invention, a system may include a universal electronic transaction facility and a hand-held device implementation facility in association therewith. In a variation of this system, the universal electronic transaction facility may include a separate security protocol based on at least a domain, a device and a user of the universal electronic transaction facility. In a variation of this system, the handheld device implementation facility may be a handset implementation facility.

In another aspect of the invention, a method may comprise providing a universal electronic transaction facility and displaying a user's financial account information on the universal electronic transaction facility. In a variation of this method, the universal electronic transaction facility may be capable of providing a separate security protocol based on at least a domain, a device and a user of the universal electronic transaction facility.

In a variation of this method, the universal electronic transaction facility may encompass a handheld device of the user. In versions of this variation, the handheld device may be a handset.

In another aspect of the invention, a system may include a universal electronic transaction facility and a user financial account information display facility in association therewith. In a variation of this system, the universal electronic transaction facility may include a separate security protocol based on at least a domain, a device and a user of the universal electronic transaction facility. In a variation of this system, the universal electronic transaction facility may include a user handheld device. In versions of this variation, the user handheld device may be a handset.

In another aspect of the invention, a method may include providing a universal electronic transaction facility and providing a train ticket on the universal electronic transaction facility of a user. In a variation of this method, the universal electronic transaction facility may be capable of providing a separate security protocol based on at least a domain, a device and a user of the universal electronic transaction facility. In a variation of this method, the universal electronic transaction facility may encompass a handheld device of the user. In versions of this variation, the handheld device may be a handset.

In another aspect of the invention, a system may include a universal electronic transaction facility and a user train ticket in association therewith. In a variation of this system, the universal electronic transaction facility may include a separate security protocol based on at least a domain, a device and a universal electronic transaction facility user. In a variation of this system, the universal electronic transaction facility may include a user handheld device. In versions of this variation, the user handheld device may be a handset In another aspect of the invention, a method may include providing a universal electronic transaction facility, and providing a secure transaction facility in association with the universal electronic transaction facility. In a variation of this method, the method may further comprise a client device that interfaces with the secure transaction facility. In a variation of this method, the secure transaction facility may be supported by a secure distributed web-based platform. In a variation of this method, the universal electronic transaction facility may operate in accordance with a wallet metaphor. In a variation of this method, the universal electronic transaction facility may be associated with a payment application. In a variation of this method, the universal electronic transaction facility may be personalized for a user. In versions of this variation, the user may be identified to the system via a RFID.

In another aspect of the invention, a system may include a universal electronic transaction facility, and a secure transaction facility in association with the universal electronic transaction facility. In a variation of this system, the system further comprises a client device that interfaces with the secure transaction facility. In a variation of this system, the secure transaction facility may be supported by a secure distributed web-based platform. In a variation of this system, the universal electronic transaction facility may operate in accordance with a wallet metaphor. In a variation of this system, the universal electronic transaction facility may operate in accordance with a wallet metaphor. In a variation of this system, the universal electronic transaction facility may be personalized for a user. In versions of this variation, the user may be identified to the system via a RFID.

In another aspect of the invention, a method may include providing a universal electronic transaction facility, wherein the user interface allows a user electronically to obtain a token for conducting transactions In a variation of this method, the universal electronic transaction facility may be capable of providing a separate security protocol associated with obtaining the token. In a variation of this method, the token may be a branded token. In versions of this variation, the branded token may be associated with at least one of the following things: a driver's license, a passport, a statement, a coupon, a promotion, a ticket, a ticket associated with a violation, a check book, a check, a secure and electronic token, a branded token, a credit card, a bank account, a frequent flyer card, a stored value card, a loyalty card, an insurance card, a bill, a bill, a merchant-issued credit card, a merchant-issued loyalty card, prepaid airtime, a money order, a money transfer, an account. In a variation of this method, the token may be issued directly to a personal client device of the user. In versions of this variation, the personal client device may be selected from the group consisting of a PC, a mobile phone, and a mobile personal computer. In a variation of this method, the token may be issued directly to a public client device of the user. In a variation of this method, the token may be issued through a wireless medium. In a variation of this method, the token may be issued through a wired medium.

In another aspect of the invention, a system may include a universal electronic transaction facility, wherein the user interface allows a user electronically to obtain a token for conducting transactions. In a variation of this system, the universal electronic transaction facility may be capable of providing a separate security protocol associated with obtaining the token. In a variation of this system, the token may be a branded token. In versions of this variation, the branded token may be associated with at least one of the following things: a driver's license, a passport, a statement, a coupon, a promotion, a ticket, a ticket associated with a violation, a check book, a check, a secure and electronic token, a branded token, a credit card, a bank account, a frequent flyer card, a stored value card, a loyalty card, an insurance card, a bill, a bill, a merchant-issued credit card, a merchant-issued loyalty card, prepaid airtime, a money order, a money transfer, an account. In a variation of this system, the token may be issued directly to a personal client device of the user. In versions of this variation, the personal client device may be selected from the group consisting of a PC, a mobile phone, and a mobile personal computer. In a variation of this system, the token may be issued directly to a public client device of the user. In a variation of this system, the token may be issued through a wireless medium. In a variation of this system, the token may be issued through a wired medium.

In another aspect of the invention, a method may include providing a universal electronic transaction facility, wherein the user interface allows a user securely and electronically to reproduce data for conducting transactions on a client device. In a variation of this method, the data for conducting transactions may comprise at least one data set associated with a first existing account. In versions of this variation, the first existing account may be selected from the group consisting of a credit card account, a debit account, a bank account, a brokerage firm account, and a vendor account. Versions of this variation may further comprise a second data set associated with a second existing account. The second existing account may be selected from the group consisting of a credit card account, a debit account, a bank account, a brokerage firm account, and a vendor account.

In a variation of this method, the user interface may display branding data in association with the data for conducting transactions on the client device. In a variation of this method, the data for conducting transactions may be reproduced on a personal client device of the user. In a variation of this method, the data for conducting transactions may be reproduced on a public client device of the user. In versions of this variation, the public client device may be designated for temporary personal use.

In a variation of this method, the data reproduced on the client device may be directly displayed on the client device. In a variation of this method, the data reproduced on the client device may be indicated by an on-screen icon. In versions of this variation, the on-screen icon may be associated with branding data.

In another aspect of the invention, a system may include a universal electronic transaction facility, wherein the user interface allows a user securely and electronically to reproduce data for conducting transactions on a client device. In a variation of this system, the data for conducting transactions may comprise at least one data set associated with a first existing account. In versions of this variation, the first existing account may be selected from the group consisting of a credit card account, a debit account, a bank account, a brokerage firm account, and a vendor account. Versions of this variation may further comprise a second data set associated with a second existing account. The second existing account may be selected from the group consisting of a credit card account, a debit account, a bank account, a brokerage firm account, and a vendor account.

In a variation of this system, the user interface may display branding data in association with the data for conducting transactions on the client device. In a variation of this system, the data for conducting transactions may be reproduced on a personal client device of the user. In versions of this variation, the personal client device may be selected from the group consisting of a PC, a mobile phone, and a mobile personal computer.

In a variation of this system, the data for conducting transactions may be reproduced on a public client device of the user. In versions of this variation, the public client device may be designated for temporary personal use.

In a variation of this system, the data reproduced on the client device may be directly displayed on the client device. In a variation of this method, the data reproduced on the client device may be indicated by an on-screen icon. In versions of this variation, the on-screen icon may be associated with branding data.

In another aspect of the invention, providing a universal electronic transaction facility and providing a secure transaction facility in association with the universal electronic transaction facility, wherein the secure transaction facility permits a user to conduct a secure transaction.

In a variation of this method, the secure transaction facility may permit the user to conduct the secure transaction using a client device with a real-world security capability selected from the group consisting of infrared, RF, bar code and proximity sensor. In versions of this variation, the real-world security capability may be adapted for a proximity transaction. In versions of this variation, client device may be a personal device. In versions of this variation, the client device may be a public device for temporary personal use.

In a variation of this method, the secure transaction facility may permit the user to conduct the secure transaction using a client device with a virtual-world security capability. In versions of this variation, the virtual-world security capability may be adapted for an over-the-air transaction. In versions of this variation, the client device may be a personal device. In versions of this variation, the client device may be a public device for temporary personal use.

In a variation of this method, the method further comprises providing biometric parameters for access to the secure transaction facility. In a variation of this method, the method further comprises providing a secure, personalized web-based portal that is associated with the universal electronic transaction facility. In versions of this variation, the secure, personalized web-based portal may provide access to an additional transactional service.

In another aspect of the invention, a system may include a universal electronic transaction facility and a secure transaction facility in association with the universal electronic transaction facility, wherein the secure transaction facility permits a user to conduct a secure transaction.

In a variation of this system, the secure transaction facility may permit the user to conduct the secure transaction using a client device with a real-world security capability selected from the group consisting of infrared, RF, bar code and proximity sensor. In versions of this variation, the real-world security capability may be adapted for a proximity transaction. In versions of this variation, client device may be a personal device. In versions of this variation, the client device may be a public device for temporary personal use.

In a variation of this system, the secure transaction facility may permit the user to conduct the secure transaction using a client device with a virtual-world security capability. In versions of this variation, the virtual-world security capability may be adapted for an over-the-air transaction. In versions of this variation, the client device may be a personal device. In versions of this variation, the client device may be a public device for temporary personal use.

In a variation of this system, the method further comprises providing biometric parameters for access to the secure transaction facility. In a variation of this method, the method further comprises providing a secure, personalized web-based portal that is associated with the universal electronic transaction facility. In versions of this variation, the secure, personalized web-based portal may provide access to an additional transactional service.

In another aspect of the invention, a method may include providing a universal electronic transaction facility, wherein the user interface allows a user electronically to obtain a response to an executed transaction. In a variation of this method, the response to the executed transaction comprises a receipt for the executed transaction. In a variation of this method, the response to the executed transaction may comprise an acknowledgement for the executed transaction. In a variation of this method, the response to the executed transaction may comprise a confirmation for the executed transaction. In a variation of this method, the response may be issued directly to a client device of the user. In versions of this variation, the client device may be a personal client device. In versions of this variation, client device is a public device configured for temporary use. In versions of this variation, an electronic replica of the response may be stored on the client device. The electronic replica may be archived in an addressable archive.

In a variation of this method, a secure, personalized web-based portal may be associated with the universal electronic transaction facility to receive the response. In versions of this variation, an electronic replica of the response may be stored in association with the web-based portal. The electronic replica may be archived in an addressable archive.

In another aspect of the invention, a system may include a universal electronic transaction facility, wherein the user interface allows a user electronically to obtain a response to an executed transaction. In a variation of this system, the response to the executed transaction comprises a receipt for the executed transaction. In a variation of this system, the response to the executed transaction may comprise an acknowledgement for the executed transaction. In a variation of this system, the response to the executed transaction may comprise a confirmation for the executed transaction. In a variation of this system, the response may be issued directly to a client device of the user. In versions of this variation, the client device may be a personal client device. In versions of this variation, client device is a public device configured for temporary use. In versions of this variation, an electronic replica of the response may be stored on the client device. The electronic replica may be archived in an addressable archive.

In a variation of this system, a secure, personalized web-based portal may be associated with the universal electronic transaction facility to receive the response. In versions of this variation, an electronic replica of the response may be stored in association with the web-based portal. The electronic replica may be archived in an addressable archive.

In another aspect of the invention, a method may include providing a universal electronic transaction facility, wherein the universal electronic transaction facility is capable of interacting securely with multiple domains. In a variation of this method, the universal electronic transaction facility may interact with multiple domains wirelessly. In a variation of this method, the universal electronic transaction facility may interact with multiple domains via wired connections. In a variation of this method, the universal electronic transaction facility may provide a personalized token to a user via a client device. In versions of this variation, the client device may be a personal client device. In versions of this variation, the client device may be a public device for temporary personal use.

In a variation of this method, the universal electronic transaction facility may initiate a transaction from a client device. In a variation of this method, the universal electronic transaction facility may complete a transaction from the client device.

In a variation of this method, the universal electronic transaction facility may transmit to the client device a response for an executed transaction. In versions of this variation, the response may comprise an acknowledgement of the executed transaction. In versions of this variation, the response may comprise a receipt for an executed transaction.

In another aspect of the invention, a system may include a universal electronic transaction facility, wherein the universal electronic transaction facility is capable of interacting securely with multiple domains. In a variation of this system, the universal electronic transaction facility may interact with multiple domains wirelessly. In a variation of this system, the universal electronic transaction facility may interact with multiple domains via wired connections. In a variation of this system, the universal electronic transaction facility may provide a personalized token to a user via a client device. In versions of this variation, the client device may be a personal client device. In versions of this variation, the client device may be a public device for temporary personal use.

In a variation of this system, the universal electronic transaction facility may initiate a transaction from a client device. In a variation of this method, the universal electronic transaction facility may complete a transaction from the client device.

In a variation of this system, the universal electronic transaction facility may transmit to the client device a response for an executed transaction. In versions of this variation, the response may comprise an acknowledgement of the executed transaction. In versions of this variation, the response may comprise a receipt for an executed transaction.

In another aspect of the invention, a method may include receiving data from a universal electronic transaction facility and carrying out a transaction in response to the data received from a universal electronic transaction facility. In a variation of this method, the method may further comprise providing a separate security protocol based on at least a domain, a device and a user of the universal electronic transaction facility. In a version of this variation, the method may further comprise applying the security protocol to the transaction to secure the transaction. The security protocol may employ three-dimensional authentication to secure the transaction. The three dimensional authentication may involve verifying the identity of the user, the universal transaction facility and the domain. In a version of this variation, the separate security protocol may employ cryptographic tools. In a version of this variation, the separate security protocol may employ strength of encryption. In a version of this variation, the method further comprises customizing the nature of Public/Private Key Infrastructure on a per user, per device and per domain basis.

In a variation of this method, the transaction may be a proximity transaction. In a variation of this method, the transaction may be an over-the-air transaction. In a variation of this method, the transaction may comprise issuance of a token. In a variation of this method, the transaction may comprise issuance of a receipt.

In another aspect of the invention, a method may include providing a universal electronic transaction facility having a user interface, wherein the user interface allows a user to execute a transaction. In a variation of this method, the method further comprises providing a secure transaction capability to a user via the universal electronic transaction facility. In versions of this variation, the secure transaction capability may protect electronic data stored on the universal electronic transaction facility. The electronic data may comprise a token. The electronic data may comprise a receipt. The electronic data may comprise a transaction acknowledgement. In versions of this variation, the secure transaction capability may comprise an encryption protocol. The encryption protocol may encrypt electronic data stored on the universal electronic transaction facility.

In a variation of this method, the universal electronic transaction facility may be a client device. In a variation of this method, the user interface may allow the user to obtain an electronic token for executing the transaction. In a variation of this method, the user interface may allow the user to obtain a response after executing the transaction.

In another aspect of the invention, a method may include providing a universal electronic transaction facility having a user interface, wherein the user interface is configurable by a user.

In a variation of this method, the universal transaction facility may be a client device. In versions of this variation, the client device may be a personal device. In versions of this variation, the client device may be a public device for temporary personal use. In versions of this variation, at least one personalized application may reside on the client device.

In versions of this variation, at least one non-personalized application may reside on the client device.

In a variation of this method, the user may configure the user interface in accordance with a set of user preferences. In a variation of this method, the user may configure the user interface through interaction with an expert system. In versions of this variation, the expert system may be capable of self-modification. The self-modification may comprise a learning behavior. The self-modification may be based on an input selected from the group consisting of user behavior, usage patterns, transaction history and a qualified external input. The self-modification may be based on a plurality of inputs. The self-modification may further comprise suggesting parameters for a subsequent transaction.

In another aspect of the invention, a method may include providing a universal electronic transaction facility having a user interface configurable by a user, wherein the user interface allows the user securely and electronically to reproduce data on a client device. In a variation of this method, the user may configure the user interface in accordance with a set of user preferences. In a variation of this method, the user may configure the user interface through interaction with an expert system. In versions of this variation, the expert system may be capable of self-modification based on an input selected from the group consisting of user behavior, user usage pattern, user transaction history and qualified external inputs.

In a variation of this method, the client device may be a personal device. In a variation of this method, the client device may be a public device for temporary personal use. In a variation of this method, the data may comprise a token for conducting a transaction. In a variation of this method, the data may comprise a service for conducting a transaction. In a variation of this method, the data may comprise an application. In versions of this variation, the application may be personalized. In versions of this variation, the application may be non-personalized.

In a variation of this method, the data may be selected from the group consisting of multiple tokens, multiple services, multiple personalized applications, and multiple non-personalized applications. In versions of this variation, the data may be managed in accordance with user preferences. In versions of this variation, the data may be managed in accordance with an expert system. The expert system may be capable of self-modification based on an input selected from the group consisting of user behavior, user usage pattern, user transaction history and qualified external inputs. In versions of this variation, the data may comprise a plurality of data sets, the data sets being selected from the group consisting of multiple tokens, multiple services, multiple personalized applications, and multiple non-personalized applications.

In another aspect of the invention, methods and systems may include providing a bill payment service in association with a universal electronic transaction facility. The service may include taking a payment out of an offline bank, in time for a bill to be paid on time.

In another aspect of the invention, methods and systems may include providing a person-to-person transaction service in association with a universal electronic transaction facility.

In another aspect of the invention, methods and systems may include providing a money order/transfer service in association with a universal electronic transaction facility. In the methods and systems an electronic token may include an electronic replica of a money order or a transfer. The transaction may be associated with a money order or a transfer. In the methods and systems the service may securely credit a user's account and debit a financial service provider's account. The service provider may be a bank, a credit union, or a financial institution. In the methods and systems, the service may issue a request to a financial service provider to complete a money order/transfer transaction though a settlement/acquisition network. The service may be associated with a transaction history. The value added service may also be associated with the transaction history.

In another aspect of the invention, methods and systems may include a prepaid airtime service in association with a universal electronic transaction facility. In the methods and systems an electronic token may include an electronic replica of a prepaid airtime card. The transaction may be associated with a prepaid airtime card. The service may include securely replenishing a prepaid airtime account. The act of replenishing is accomplished by at least one of the following: selecting pre-configured time/amount packages, specifying a desired amount/time packages, selecting a preferred mode of payment. The service may securely credit a user's account, debits a telecommunication service provider's account, and replenishes the user's airtime account.

In another aspect of the invention, methods and systems may include a ticketing service in association with a universal electronic transaction facility. In the methods and systems an electronic token may include an electronic replica of a ticket. The transaction may be associated with a ticket.

In another aspect of the invention, methods and systems may include a loyalty coupon/promotion service in association with a universal electronic transaction facility. In the methods and systems an electronic token may include an electronic replica of an account, a loyalty statement, or a transaction summary. The transaction may be associated with an account, a loyalty statement, or a transaction summary.

In another aspect of the invention, methods and systems may include an electronic checkbook service in association with a universal electronic transaction facility. In the methods and systems an electronic token may include an electronic replica of a checkbook, a check, a summary statement, an activity statement, a cancelled check. The transaction may be associated with a checkbook, a check, a summary statement, an activity statement, a cancelled check. In the methods and systems, an attribute of the universal electronic transaction facility may include a number of checks remaining, a pre-designated check number, or a balance in the checkbook's ledger.

In another aspect of the invention, methods and systems may include a driver's license service in association with a universal electronic transaction facility. In the methods and systems, the service may be associated with at least one of a device at a point of transaction, and a law enforcement agent's client device.

In another aspect of the invention, methods and systems may include health service in association with a universal electronic transaction facility. In the methods and systems an electronic token may include an electronic replica of a health record, a health insurance card, a prescription, laboratory instructions, a medical referral, approval of medical necessity, an x-ray, a sonogram, a CAT scan, an examination report, a diagnosis, a prognosis, a treatment plan, an MRI result, a laboratory result, a list of over-the-counter items, an approval to return to work, a physical activity permission, or an insurance coverage approval. The transaction may be associated with a health record, a health insurance card, a prescription, laboratory instructions, a medical referral, approval of medical necessity, an x-ray, a sonogram, a CAT scan, an examination report, a diagnosis, a prognosis, a treatment plan, an MRI result, a laboratory result, a list of over-the-counter items, an approval to return to work, a physical activity permission, or an insurance coverage approval. In the methods and systems, an attribute of the universal electronic transaction facility may include availability of a completed prescription for pickup, receipt of a prescription at a pharmacy, shipment of a completed prescription, availability of laboratory results, laboratory results meeting a criteria, a follow-up visit request from a doctor, a time, a date, a time for administration of a prescription, a number of doses of a prescription remaining, a number of refills of a prescription remaining, a number of appointments remaining, or an appointment. The service may be associated with a patient, a doctor, a hospital, a pharmacy, a durable medical goods provider, a physical therapy provider, a laboratory, an insurer, or a researcher.

In another aspect of the invention, methods and systems may include a travel service in association with a universal electronic transaction facility. In the methods and systems an electronic token may include an electronic replica of a ticket, a reservation, a travel voucher, a passport, a travel visa, a travel itinerary, a boarding pass, a map, an immigration document, a menu, a summary statement, a hotel bill, a car rental bill, an air travel bill, a loyalty club accrual, a list of business expenses, or a list of personal expenses. The transaction may be associated with a ticket, a reservation, a travel voucher, a passport, a travel visa, a travel itinerary, a boarding pass, a map, an immigration document, a menu, a summary statement, a hotel bill, a car rental bill, an air travel bill, a loyalty club accrual, a list of business expenses, or a list of personal expenses. In the methods and systems, an attribute of the universal electronic transaction facility may include weather at a travel destination, weather at an airport, traffic conditions, a flight schedule, a flight check in, a seating assignment, a gate assignment, a travel itinerary, a meeting time, a time, a date, a contact local to a travel destination, currency conversion rates, availability of a flight, a time until departure, a train schedule, or a change in flight times.

In another aspect of the invention, methods and systems may include an infotainment service in association with a universal electronic transaction facility. In the methods and systems an electronic token may include an electronic replica of video, images, audio, text, or information required to complete a transaction. The transaction may be associated with video, images, audio, text, or information required to complete a transaction. The electronic replica may be adapted for mobile viewing.

In another aspect of the invention, methods and systems may include a personal information management service in association with a universal electronic transaction facility. In the methods and systems an electronic token may include an electronic replica of a calendar, an appointment, contact information, a mail message, a to-do list, a note, an expense, or information required to complete a transaction. The transaction may be associated with a calendar, an appointment, contact information, a mail message, a to-do list, a note, an expense, or information required to complete a transaction.

In another aspect of the invention, methods and systems may include a training service in association with a universal electronic transaction facility. In the methods and systems an electronic token may include an electronic replica of a video, an image, audio, text, a part number, a part cost, a diagnostic instruction, a repair instruction, an assembly instruction, a disassembly instruction, information required to complete a transaction, a purchase order, or an inventory check. The transaction may be associated with a video, an image, audio, text, a part number, a part cost, a diagnostic instruction, a repair instruction, an assembly instruction, a disassembly instruction, information required to complete a transaction, a purchase order, or an inventory check.

In another aspect of the invention, methods and systems may include a lottery service in association with a universal electronic transaction facility. In the methods and systems an electronic token may include an electronic replica of a lottery ticket. The transaction may be associated with a lottery ticket.

In another aspect of the invention, methods and systems may include a voting service in association with a universal electronic transaction facility. In the methods and systems an electronic token may include an electronic replica of a ballot, an election candidate's information, a ballot number, or a voter identification information. The transaction may be associated with a ballot, an election candidate's information, a ballot number, or a voter identification information. In the methods and systems, an attribute of the universal electronic transaction facility may include a voting date, a voting time, candidate information, voter information, election information, votes cast by phone, votes cast electronically, or votes cast traditionally.

In another aspect of the invention, methods and systems may include a gaming portal in association with a universal electronic transaction facility. In the methods and systems an electronic token may include an electronic replica of a game. The transaction may be associated with a game. In the methods and systems, the gaming portal may be associated with a game that is played, at least in part, on the universal electronic transaction facility. The gaming portal may distribute the game. In the methods and systems, a secure transaction associated with the portal may be associated with betting on the outcome of a game, purchasing a game, purchasing a game from a publisher of the game, purchasing a game from a user of a second universal electronic transaction facility, or selling a game to a user of a second universal electronic transaction facility. In the methods and systems, an original publisher of the game may receive a payment that is associated with the transaction.

In another aspect of the invention, methods and systems may include a merchant portal in association with a universal electronic transaction facility. In the methods and systems an electronic token may include an electronic replica of an invoice, an inventory statement, a financial statement, a request for quote, a bid, a promotion, or a purchase. The transaction may be associated with an invoice, an inventory statement, a financial statement, a request for quote, a bid, a promotion, or a purchase. The merchant portal may distribute a promotion to a consumer using the universal electronic transaction facility. The promotion may be based on past transaction behavior.

In another aspect of the invention, methods and systems may include a government portal in association with a universal electronic transaction facility. In the methods and systems an electronic token may include an electronic replica of a governmental record. The transaction may be associated with a governmental record. The government portal may enable a user to access government services using the universal electronic facility. The government service may be a land record, a sales tax, a procurement contract. In the methods and systems, the universal electronic transaction facility may be used to securely log in to a kiosk to access the government services.

In another aspect of the invention, methods and systems may include an enterprise portal in association with a universal electronic transaction facility. The enterprise portal may enable a user to access enterprise services using the universal electronic transaction facility. The user may securely log time to an enterprise timesheet, or securely track enterprise expenses for reimbursement determination. The timesheet may be used to track at least employee and contractor work times. The enterprise services may be associated with third-party quotes and bids. Securely transmitting the quotes and bids may be associated with the portal. The enterprise portal may enable the secure transmission of disaster management information. The disaster management information may be an available disaster-related service, a required action report, an action prioritization, or an infrastructure requirement.

In another aspect of the invention, methods and systems may include a health/fitness portal in association with a universal electronic transaction facility. In the methods and systems an electronic token may include an electronic replica of health/fitness information, diet information, weight training information, aerobic training information, or personal training information. The transaction may be associated with health/fitness information, diet information, weight training information, aerobic training information, or personal training information. The health and fitness portal may provide access to health and fitness information used with the universal electronic transaction facility.

In another aspect of the invention, methods and systems may include a religious portal in association with a universal electronic transaction facility. In the methods and systems an electronic token may include an electronic replica of religious information, or a charitable collection. The transaction may be associated with religious information, or a charitable collection. The religious information may be passage of the day, access to a religious text, a result of a search of a religious text, or an event calendar.

In another aspect of the invention, methods and systems may include a sports portal in association with a universal electronic transaction facility. In the methods and systems an electronic token may include an electronic replica of a sporting event ticket, a bet, a scorecard, a lineup, a seating chart, a parking pass, a clubhouse pass, a season pass, a standing room only pass, or a line score. The transaction may be associated with a sporting event ticket, a bet, a scorecard, a lineup, a seating chart, a parking pass, a clubhouse pass, a season pass, a standing room only pass, or a line score. In the methods and systems a secure transaction may be associated with sports institution back-end systems, gambling organizations, casinos, financial services providers, payment systems, service providers.

In another aspect of the invention, methods and systems may include an insurance portal in association with a universal electronic transaction facility. In the methods and systems an electronic token may include an electronic replica of an insurance quotation, a claim, a policy, an insurance appraisal, a voucher, a surcharge, a premium, or an application. The transaction may be associated with an insurance quotation, a claim, a policy, an insurance appraisal, a voucher, a surcharge, a premium, or an application. In the methods and systems a secure transaction may be associated with a premium payment, a claim payment, coverage denial, coverage approval, waiver of coverage, patient information, subrogation, a policy change, or an insurance application.

In another aspect of the invention, methods and systems may include a university portal in association with a universal electronic transaction facility. In the methods and systems an electronic token may include an electronic replica of a transcript, an admission application, an acceptance of admission, a rejection of admission, an exam, a course grade, a course schedule, a lab assignment, a lab report, a lab reservation, a book reservation, a library card, a student identification card, a meal card, residence hall key, a room key, a parking pass, a course registration, or a diploma. The transaction may be associated with a transcript, an admission application, an acceptance of admission, a rejection of admission, an exam, a course grade, a course schedule, a lab assignment, a lab report, a lab reservation, a book reservation, a library card, a student identification card, a meal card, residence hall key, a room key, a parking pass, a course registration, or a diploma. In the methods and systems a secure transaction may be associated with matriculation, graduation, a tuition payment, a financial aid application, a financial aid award, a financial aid payment, a course registration, a lab reservation, university store purchase, a student event, a course evaluation, a professor evaluation, an assignment, a test, a housing request, a meal plan selection, a declaration of major.

In another aspect of the invention, methods and systems may include a political party portal in association with a universal electronic transaction facility. In the methods and systems an electronic token may include an electronic replica of a voter registration card, a political party affiliation card. The transaction may be associated with a voter registration card, a political party affiliation card. In the methods and systems a secure transaction may be associated with voting, registering, lobbying, poling, ballot counting, donating, or fundraising.

In another aspect of the invention, methods and systems may include a pharma-exchange portal in association with a universal electronic transaction facility. In the methods and systems an electronic token may include an electronic replica of a prescription, a refill request, or a drug information insert. The transaction may be associated with a prescription, a refill request, or a drug information insert. In the methods and systems a secure transaction may be associated with prescribing, refilling, drug order, generic substitution.

In another aspect of the invention, methods and systems may include a commodity exchange portal in association with a universal electronic transaction facility. In the methods and systems an electronic token may include an electronic replica of a commodity purchase order. The transaction may be associated with a commodity purchase order. In the methods and systems a secure transaction may be associated with placing a bid for a commodity purchase, paying for a commodity purchase, scheduling a shipment of commodities, registering with a commodity bidding system.

In another aspect of the invention, methods and systems may include an airline portal in association with a universal electronic transaction facility. In the methods and systems an electronic token may include an electronic replica of a seat assignment, a seating chart, a manifest, or a class upgrade. The transaction may be associated with a seat assignment, a seating chart, a manifest, or a class upgrade. In the methods and systems a secure transaction may be associated with registering, booking, checking in, or deplaning.

In another aspect of the invention, methods and systems may include a transportation industry portal in association with a universal electronic transaction facility. In the methods and systems an electronic token may include an electronic replica of a registration, a daily schedule, an inspection certificate, or an insurance coverage card. The transaction may be associated with a registration, a daily schedule, an inspection certificate, or an insurance coverage card. In the methods and systems a secure transaction may be associated with registering, paying excise tax, applying for a license, a road test, paying sales tax.

In any and all of the embodiments of services or portals, any and all of the following may be true: The service or portal may be associated with a secure transaction. The service or portal may be associated with a token that may include branding, images, required information for completing a transaction that may be associated with the service or portal. The service or portal may include securely and electronically conducting at least one of communicating the token, communicating the token in real time, reproducing the token, or storing the token. The token may be an electronic replica of at least one of a frequent flyer card, a stored value card, a loyalty card, an insurance card, a driver's license, a bill, a promotion, a coupon, a receipt, an acknowledgement, a paid stamp, or a credit card. The secure transaction may be conducted using at least one of infrared communication, radiofrequency communication, a bar code, an over-the-air communication, or a biometric parameter. The service or portal may be associated with multiple domains. The transaction may be a proximity transaction, an over-the-air transaction or both. The transaction may be secured using a three-dimensional security protocol that may be based upon at least a domain, the universal electronic transaction facility, and a user. The service or portal includes securely and electronically storing at least one of a receipt, and an acknowledgement. The service or portal may be associated with at least one of the following configurable things: a user interface, a personalized application, a non-personalized application, and a web-based personalized portal, each of which may be configured based upon at least one of a user's preference, an expert system, and a usage monitoring facility. The configurable things may provide a profile-driven, value-added service or portal. The service or portal may include provisioning at least one of multiple tokens, multiple service or portals, multiple personalized applications, and multiple non-personalized applications. The service or portal may include securely issuing the token to a user. The universal electronic transaction facility may store the token. The transaction may be associated with at least one of a frequent flyer card, a stored value card, a loyalty card, an insurance card, a driver's license, a bill, a promotion, a coupon, a receipt, an acknowledgement, a paid stamp, and a credit card. The transaction may be at least one of secure, in real time, provided in association with an on-line settlement, provided in association with an off-line settlement, provided using a preferred mode of payment, provided at a preferred time, and provided at a preferred location. The universal electronic transaction facility may be adapted to alert 1a user based upon at least one of an attribute of the token, and a determination by an expert system. The attribute may be at least one of an issuance data, a number of days prior to a date, a date, an amount, and a time. The service or portal may be associated with presenting an electronic replica of the portal or service or portal to a user via the portal or service or portal inbox user interface.

In another aspect of the invention, methods and systems may include providing a financial service in association with a universal electronic transaction facility. The financial service may include securely issuing, to the universal electronic transaction facility, at least one electronic replica of at least one of the following items: a bill from a bill issuer, a loyalty card, an account, a coupon, a promotion, a check book, a check, a license, a driver's license. In the methods and systems, the financial service may include alerting a user based on an attribute of the at least one item. The attribute may be associated with at least one of a date of expiry, a change of address, a number of a check, a number of checks remaining, a number of days before a coupon can be redeemed, a redemption date a due date, a time, a time of issuance, a financial balance. The financial service may further include securely issuing, to the universal electronic transaction facility, an electronic replica of at least one of the following confirmations: a receipt that is associated with a bill; a transaction summary statement; a marketing vehicle; a license; a cancelled check.

In another aspect of the invention, methods and systems may include providing a coupon issuance financial service in association with a universal electronic transaction facility.

In another aspect of the invention, methods and systems may include providing a ticketing financial service in association with a universal electronic transaction facility. The ticketing service may include securely issuing, to the universal electronic transaction facility, at least one electronic replica of at least one of a ticket, and a ticket associated with a violation. The financial service further comprises securely issuing, to the universal electronic transaction facility, an electronic replica of a ticket associated with a violation. The electronic replica may contain a summary that is associated with the ticketing service. The summary may be associated with a frequent flyer summary. The electronic replica may include a cancelled check. The ticket service may be the issuance of a ticket that is associated with a violation, and the electronic replica may be of a driver's license.

In another aspect of the invention, methods and systems may include providing a top-up transaction financial service in association with a universal electronic transaction facility.

In another aspect of the invention, methods and systems may include providing a funds transfer financial service in association with a universal electronic transaction facility.

In another aspect of the invention, methods and systems may include providing a money order payment in association with a universal electronic transaction facility.

In another aspect of the invention, methods and systems may include providing a person-to-person payment financial service in association with a universal electronic transaction facility.

In another aspect of the invention, methods and systems may include providing bill payment financial service in association with a universal electronic transaction facility.

In any and all of the embodiments of financial services, any and all of the following may be true: The universal electronic transaction facility may be capable of providing a separate security protocol based on at least a domain, a device and a user of the universal electronic transaction facility. The financial service may be selected from the group consisting of bill payment, person-to-person payment, money order payment, funds transfer, a top-up transaction, a ticketing transaction, issuance of a coupon, and resolution of a check. The financial service may include securely issuing, to the universal electronic transaction facility, at least one electronic replica of at least one of the following items: a bill from a bill issuer, a payment token, money order, money transfer token, a prepaid airtime token, a ticket, a ticket associated with a violation, a loyalty card, an account, a coupon, a promotion, a check book, a check, a license, a driver's license. The financial service may further include communicating at least one of branding, an image, information required to complete a transaction. The universal electronic transaction facility may be a client device. The financial service may further include alerting a user based on at least one attribute of the at least one item. The attribute may be associated with at least one of a date of expiry, a change of address, a number of a check, a number of checks remaining, a number of days before a coupon can be redeemed, a redemption date, a date of travel, a due date, a time, a time of issuance, a financial balance. The financial service may include enabling a user to securely pay the bill using universal electronic transaction facility. Paying the bill may occur in real time. Paying the bill may be associated with an on-line settlement of the bill, an off-line settlement of the bill, at least one of a preferred mode of payment, a preferred time, and a preferred location. The financial service may further include securely issuing, to the universal electronic transaction facility, an electronic replica of at least one of the following confirmations: a receipt that is associated with a bill; a transaction summary statement; a marketing vehicle; a ticket associated with a violation; a license. The license may include at least one of a driver's license, a gun license, a liquor license, a fishing license, a hunting license. The marketing vehicle may be at least one of a loyalty card, an account, a coupon, a promotion. The transaction summary statement may be associated with a transaction between a user of the universal transaction facility and another user. The electronic replica may include a payment stamp. The financial service may further include enabling a user to pay another user. The another user may have a universal electronic transaction facility. Paying another user may occur securely and in real time. Paying another user may be associated with on-line settlement or off-line settlement. The financial service may further include enabling a transfer of units that is securely initiated at the universal electronic transaction facility. The financial service may include debiting units from a first account and crediting at units to a second account, wherein at least one of the debiting or crediting is contingent on validating a user and a request. The financial service may include issuing a request to a service provider, wherein the request is associated with completing the crediting and debiting under the control of the service provider. Issuing the transfer may be initiated via wireless communications or via proximity-based communications. Transferred units may be financial units or airtime units. The electronic replica may be delivered to a universal electronic transaction facility of a user that receives funds according to the financial service. The financial service may further include enabling a use of the funds by the user that receives the funds. The electronic replica may contain a summary that is associated with the financial service. The financial service maybe a ticket issuance service. The summary may be a frequent flyer summary. The electronic replica may include a cancelled check. The transaction may include procuring a service from a merchant. The financial service may include securely redeeming the electronic replica. Securely redeeming the electronic replica may be initiated by a wireless communication or a proximity based communication. The financial service may include securely receiving the electronic replica. The transaction may be a procurement of a service from a financial service provider.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

The invention and the following detailed description of certain embodiments thereof may be understood by reference to the following figures.

DETAILED DESCRIPTION

Figure 1:
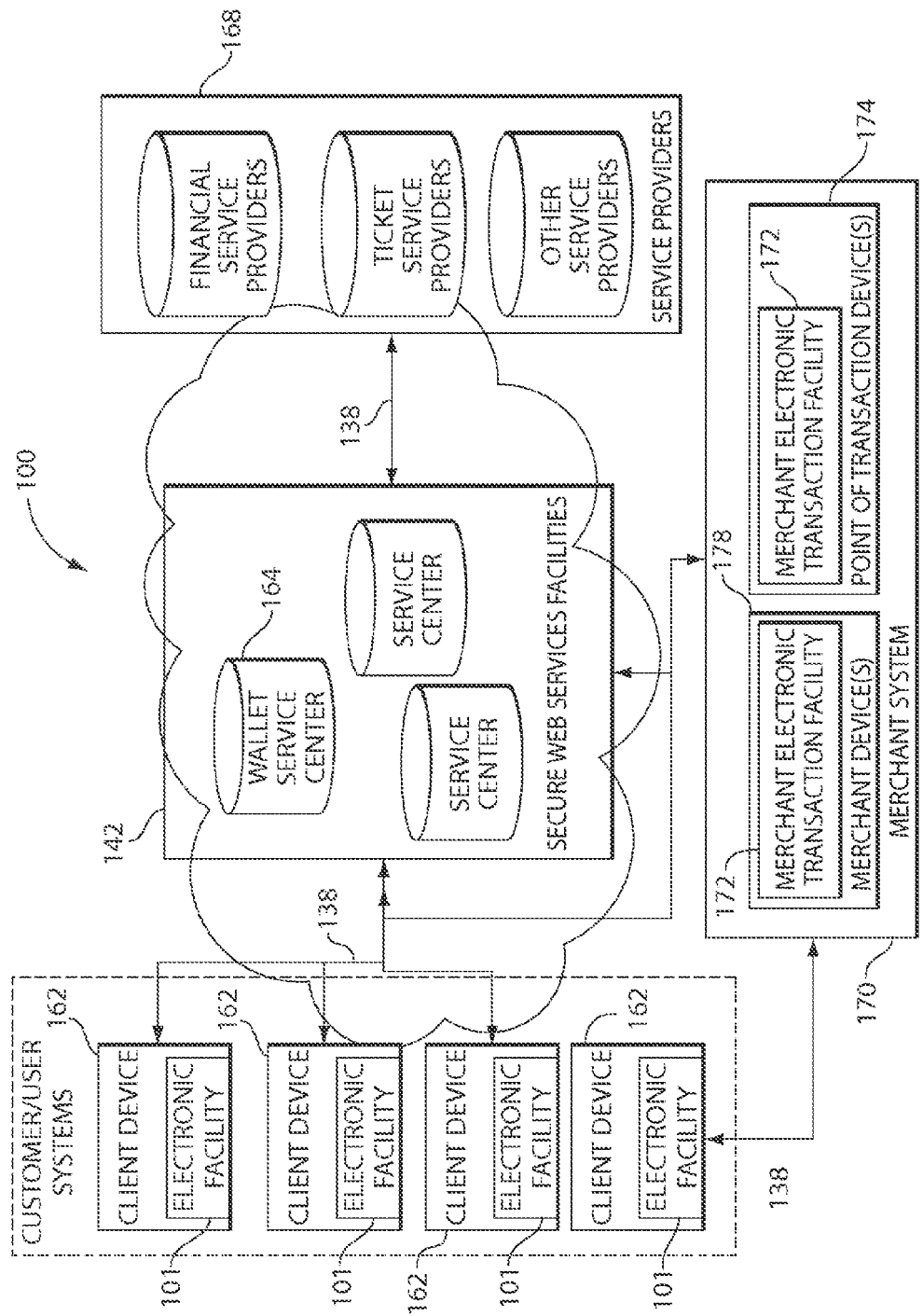
FIG. 1 is a high-level system diagram of the major system components of an electronic transaction platform exemplifying one potential embodiment of the present invention.

FIG. 1 depicts a high-level electronic transaction platform 100, with components for methods and systems for enabling electronic transactions, including transactions that support or include a wide range of specific services, including secure, web-based services. At the center of the platform 100 are one or more main service facilities 142, which are alternatively referred to throughout this disclosure as web services facilities, wallet service centers, wallet service facilities, and the like. The main service facilities 142 include conventional components for enabling web services, such as one or more servers (which may be hardware, software, or a combination of the same, one or more network facilities 138 (which may be local networks, wide area networks, the Internet, wired or wireless networks or any components thereof, as described in more detail below), one or more data storage facilities (as described below), one or more processors, and other components suitable for enabling web services. The methods and systems disclosed herein may also include one or more electronic facilities 101 (as described throughout this disclosure and including universal electronic transaction cards, electronic wallets, and other electronic transaction facilities), which may reside on one or more client devices 162a, 162b, 162c, 162d or merchant devices 178 (such as point of transaction devices 174 or other devices that are part of a merchant's computer system). The electronic facilities 101 may be configured to be compatible with a wide range of client devices 162 and merchant systems 170, and the various functions ascribed to the methods and systems disclosed herein may, in embodiments, alternately reside on client devices 162, on merchant systems 178 and/or on servers or other systems, such as main service facilities 142. Client devices 162 may include (for example, in addition to other examples provided below and in documents referenced herein), cellular phones, PDAs, handheld devices and other mobile computing devices, laptops, desktops and other client computers, servers, appliances and other machines that are equipped with processors (such as kitchen appliances, televisions, set-top boxes and other similar devices), and any other devices capable of running software applications. Client devices 162 may include, for example, public devices that are taken for temporary private use, such as billboards, signs, kiosks, POS terminals, ATMs, processor-equipped shelves, processor-equipped retail displays, processor-equipped transportation systems (such as buses, cars, taxis, boats, airplanes, trains, subways and the like), airport equipment, telephones, equipment for bus or train terminals and platforms, and any other processor-equipped devices found in any public environment). Merchant systems 170 may similarly include a wide range of merchant devices 170, such as point of transaction devices 174, such as cash registers, ATM machines, credit card acceptance facilities, bar code readers, scanners, ticket scanners, laptop and desktop computers, handheld devices, servers, and any other devices that are capable of supporting software applications. In embodiments, the methods and systems disclosed herein are enabled by web service applications, which can be accessed by a range of client devices 162 and merchant systems 170. Methods and systems disclosed herein may also support interactions with service providers 168, such as financial service providers (banks, credit card institutions, and the like), ticket issuers (including ticket merchants, government entities, and others), content providers (such as providing computer games, digital media, music, video and other content) and a wide range of other service providers. In embodiments, the main service facilities 142 are configured to interface with computer systems of such service providers 168, including legacy computing systems. In embodiments, such systems interact with the system as web services in a services oriented architecture.

The platform 100 depicted in FIG. 1 allows a wide range of service-based transactions, as described in more detail below, for a wide range of transactional environments, also described in more detail below.

Figure 2:
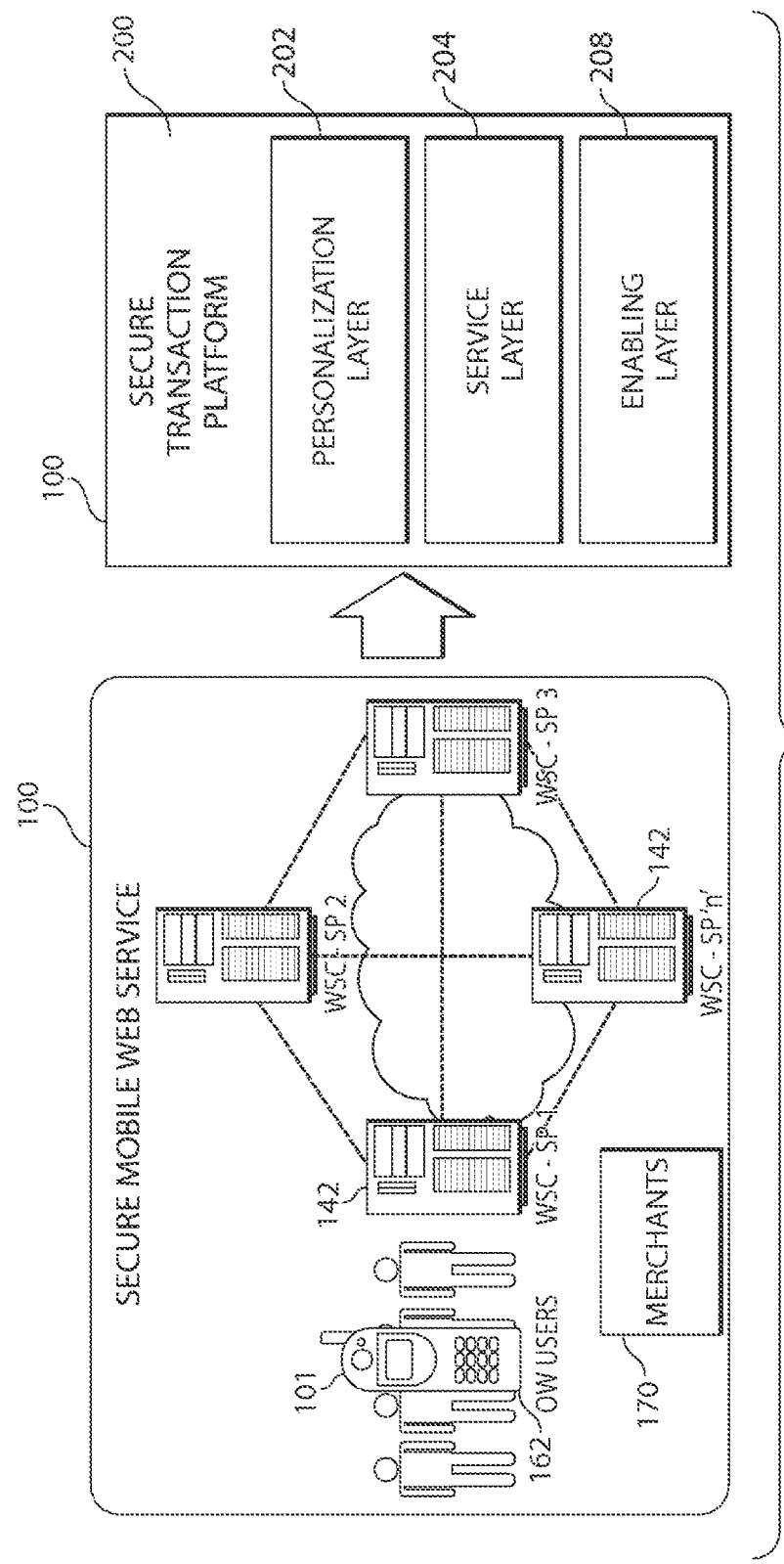
FIG. 2 is a general, logical diagram of the major service components of one potential exemplary embodiment of the electronic transaction platform.

Referring to FIG. 2, the platform 100 can include the main services facilities 142, the merchant systems 170 and the client devices 162, each of which may have components of an electronic transaction facility 101, which may be a software application (or combination of software and hardware), running on any of them. In various embodiments, different components of the platform 100 may be enabled on different devices, using web services or other applications. For example, a billing application may reside on a main service facility 142, on a merchant system 170, or on a client device 162, or it may reside on a service provider system that interacts with the platform 100. The interchangeability of the system components from the hardware standpoint allows deployment of the platform 100 in a wide range of configurations, suitable for particular transactional environments, as described herein. For example, referring to FIG. 2, the platform 100 includes software and signals that can be depicted as a set of layers that make up a secure transaction platform 200, including a personalization layer 202, a service layer 204 and an enabling layer 208. Each of those layers may be embodied on different computer systems, depending on the needs of a particular transaction environment. The presence of these layers thus allows the convenient configuration of the platform 100 to the environment.

Platform 100 may be written to work with the Windows® operating system, Macintosh® operating system, Linux, Windows CE, Unix, or a Java® based operating system, to name a few. Methods or processes in accordance with the various embodiments of the invention may be implemented by computer readable instructions stored in any media that is readable and executable by a processor. A machine-readable medium having stored thereon instructions, which when executed by one or more processors, may cause those processors to perform the methods of the invention. A machine-readable medium may include any mechanism for storing or transmitting information in a form readable by a machine (e.g., a computer). A machine-readable medium may include read only memory (ROM); random access memory (RAM); magnetic disk storage media; optical storage media; flash memory devices; electrical, optical, acoustical or other form of propagated signals (e.g., carrier waves, infrared signals, digital signals, etc.).

Figure 3:
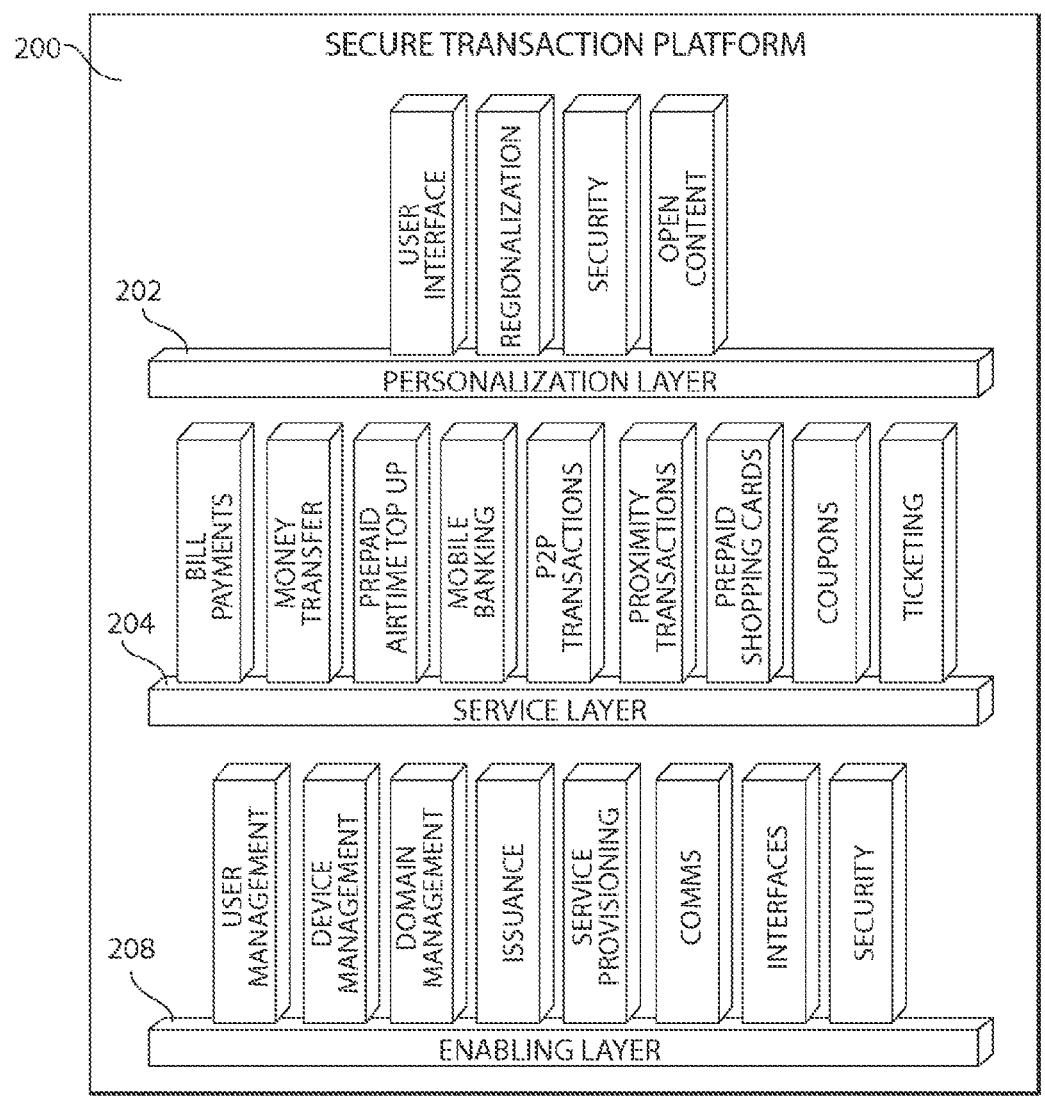
FIG. 3 is a logical diagram of the major components and hierarchy of a secure transaction platform provided by one potential exemplary embodiment of the electronic transaction platform.

FIG. 3 depicts additional detail for an embodiment of a secure electronic transaction platform 200 that corresponds to the platform 100 of FIG. 1, showing additional details of the personalization layer 202, service layer 204 and enabling layer 208, in this case reflecting components that could be enabled by the main service facility 142, electronic facility 101 and merchant systems 170 in various configurations that are suitable for a variety of transactions. For example, the secure electronic transaction platform 200 includes a service layer 204 that includes bill payments services, money transfer services, prepaid airtime top-up services, mobile banking services, peer-to-peer transaction services, proximity transactions services, prepaid shopping card services, coupon services, and ticketing services. The nature of these specific services, which can be enabled by the secure electronic transaction platform 200, are described in more detail below, but respective components of them can reside on the various systems described in connection with FIG. 1. The secure electronic transaction platform 200 also includes an enabling layer, 208 which enables the provision of the various services in the service layer 204. Thus, residing on a main services facility 142 or on a client device 162, merchant system 170 or the system of a service provider 168, the enabling layer 208 enables various components necessary to support services, such as user management, device management, domain management, issuance, service provisioning, communications, interface features and security features. In embodiments, as described more particularly below, the enabling layer has advantageous core features and attributes, such as providing multi-dimensional levels of security, at the user level, device level and domain level. The secure electronic transaction platform 200 may also include a personalization layer 202, which allows the configuration of the secure electronic transaction platform 200 for a particular user, whether it be a customer, a merchant, or a service provider. For example, the personalization layer 202 may include personalization of user interface features (such as allowing a user to depict particular configurations of virtual or physical entities on a client device), personalization based on user histories (such as based on use of the device, absence of use, or the like), regionalization of content, such as to provide a different language, personalized security features, such as password enablement and encryption more generally, and content personalization, such as presenting or delivering content based on a user's expressed preferences or preferences determined by user history, such as past transactions.

Figure 4:
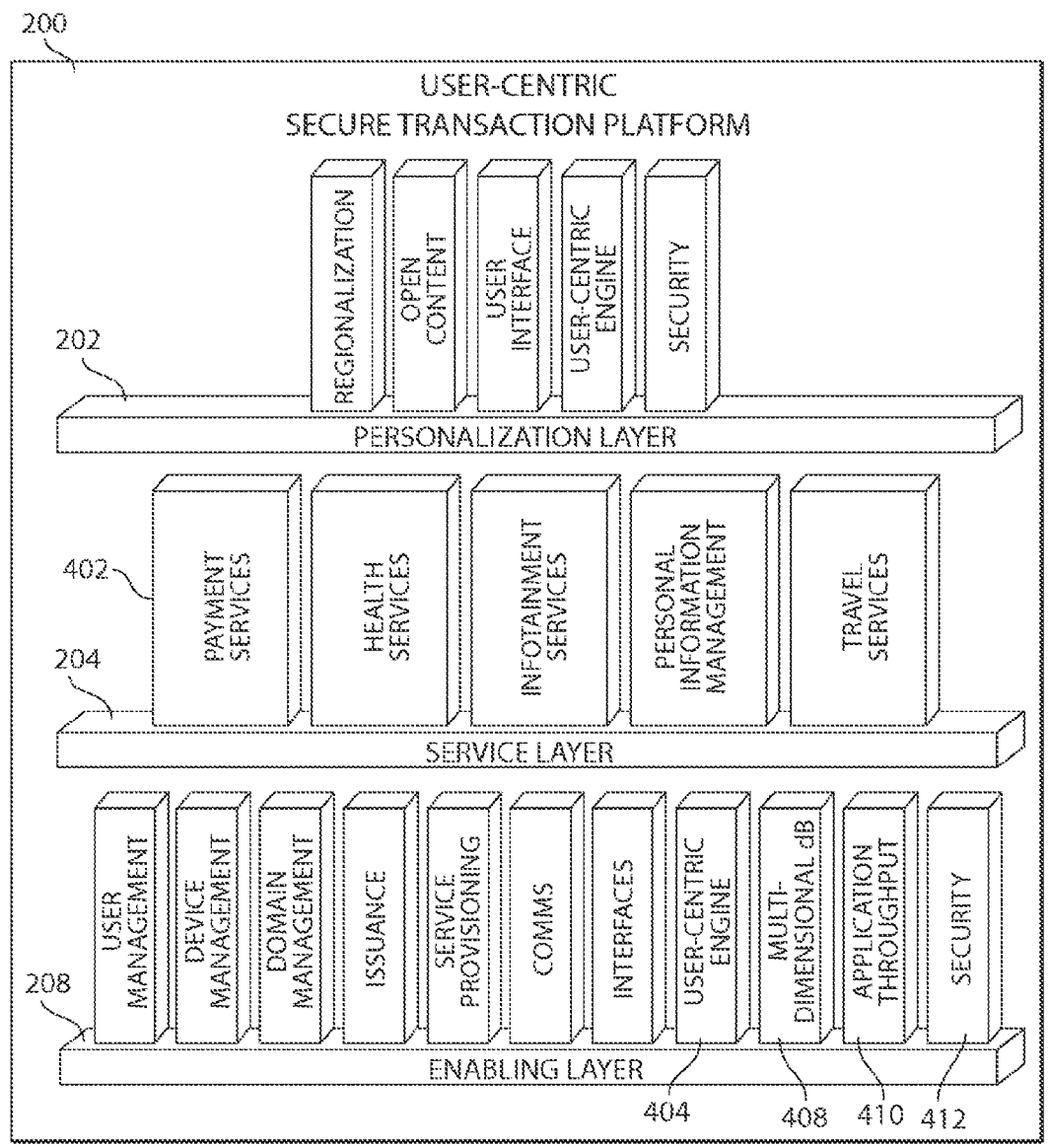
FIG. 4 depicts a user-centric embodiment of one potential exemplary embodiment of the secure transaction platform.

FIG. 4 depicts an embodiment of the platform 100, which is a user-centric secure transaction platform 200, in this case including the personalization layer 202, the service layer 204 and the enabling layer 208. In this case the services illustrated in connection with FIG. 3 are all classified as "payment services" 402, thus here the services layers have been expanded to indicate some of the host of other services domains that can be enabled by the secure transaction platform 200, such as health services, infotainment services, personal information management services and travel services, among many others. Again, these services may be provided with the features and attributes described in more detail elsewhere herein and in the documents incorporated by reference herein. The secure transaction platform 200 also includes the enabling layer 208, which in addition to the capabilities described in connection with FIG. 3 includes other enabling components, including a user-centric engine 404, a multidimensional database 408 (the structure of which is described hereinafter in association with FIG. 62), application throughput facilities 410, and security facilities 412.

The user-centric secure transaction platform may also include additional features at the personalization layer 202, such as capabilities for supporting a personalized user interface, a user-centric engine, and personalized security.

The platform 100 described in connection with FIGS. 1 through 4 enables a number of important features. First, the platform 100 provides secure transaction capability, optionally using a client device 162 and supported by a secure distributed web-based platform, such as main service facility 142. In embodiments, the transaction capability may be provided with a wallet-based metaphor, so that a client device 162, such as a cellular phone, essentially duplicates in software key features of a physical wallet. Key features of a physical wallet may include, but are not limited to including many items in a compact size that allows an end user to carry these items while traveling through daily activities as well as in the home, office or other setting.

In other embodiments, the transaction capability is provided apart from a wallet metaphor; for example, the platform 100 may be provided in connection with client devices 162 of any type or size, as described elsewhere herein. The platform 100 may be used, as described herein, for payment and non-payment applications. In embodiments, the platform 100 also provides the ability to issue, securely and electronically, an entire transaction token (which may be personalized or non-personalized) with all necessary images, branding, and/or data for selecting and conducting transactions, directly with a user, through a wired and/or wireless medium, to a personal client device 162. In embodiments the client device 162 may be a public device that is taken over for temporary personal use, such as a kiosk, public access computer, ATM, billboard, sign, appliance, or other public device equipped with computing capabilities. A transaction token may be any facility for enabling or embodying a transaction, including, but not limited to, credit cards, bank account cards, frequent flyer cards, stored value or other debit cards, loyalty cards, insurance cards, drivers licenses and other licenses, membership cards, professional credentials, bills, invoices and similar instruments, coupons, tickets, and promotional flyers. Platform 100 may also provide the ability to reproduce, securely and electronically, multiple existing card, account, and vendor information, or similar information, with branding and/or images, with necessary data for conducting transactions, on client device of choice (including a personal device or a public device taken for temporary personal use). A platform 100 may also provide the ability to conduct secure transactions in the physical world using proximity communication systems, such as infrared, RF, scanners, bar code readers, ultra-wideband network facilities, Bluetooth facilities, 802.11x facilities, WIFI facilities and the like between any client device 162 and any merchant system 170. In embodiments such transactions may include use of bio-metric parameters.

Platform 100 may further include the ability to securely access personalized web-based user interface facilities for accessing various value added services. A platform 100 may also include the ability for a user-, merchant- or client-centric facility, such as a wallet to "top-up" the amount of another payment token, by transferring funds, on the same client device 162. The funds may be located in the electronic wallet, or may be stored in another facility of the client device 162. The platform 100 may also include the ability to issue to, and reproduce on, a client device 162 (which may be a personal device or public device for temporary personal use), securely and electronically, a receipt or acknowledgement related to transactions conducted in the real world and/or virtual world. Platform 100 may also provide the ability to store and archive electronic replica of receipts on a client device 162 and/or on a personalized web-based portal. In embodiments such receipts may be stored with a merchant acknowledgment of a transaction, such as a "PAID" stamp.

In embodiments platform 100 may enable the ability to securely and electronically interact with multiple domains, through any wired and/or wireless medium, to procure personalized tokens, initiate and complete transactions, receive receipt or acknowledgement of transaction, directly from client device of choice (personal device or public device for temporary personal use).

Platform 100 as described herein also enables the ability to secure proximity and over-the-air transactions, including issuance of tokens and receipts, using multidimensional authentication, verifying the identity of, for example, the user of a client device 162, merchant system 170 or other device, verifying the identity of the device itself, and verifying the identity of the domain for one or more transactions, in each case using appropriate cryptography tools and an appropriate strength of encryption, optionally with the ability to customize the nature of the Public/Private Key Infrastructure on a per user, per device and per domain basis. For example, a user might provide a private key that corresponds to a public key that a merchant obtains from a public key registry in order to send an item, such as a receipt, to the user that is encrypted with the public key. Platform 100 also provides the ability to securely encrypt tokens and receipts, not only when they are issued, but also when they are stored on the client device. Platform 100 as described herein also includes the ability to configure the user-Interface and various personalized and/or non-personalized applications on the client device 162 (which may be a personal device or a public device taken for temporary personal use) based on the user's preferences and/or through the support of an expert system capable of learning over a period of time based on the user's behavior, usage patterns, transaction history and qualified external inputs.

Platform 100 may also enable the ability to provision multiple tokens, multiple services and multiple personalized and/or non-personalized applications, with a high level of throughput, efficiency, and fault tolerance, to the user's client device 162 (which may be a personal device or a public device taken for temporary personal use) based on the user's preferences and/or through the support of an expert system capable of learning over a period of time based on the user's behavior, usage patterns, transaction history and qualified external inputs. In embodiments, the platform 100 has a distributed infrastructure, so that the various attributes described herein can be embodied on a client device 162, merchant system 170, main service facility 142 or other device or system, such as a service provider system.

Figure 5:
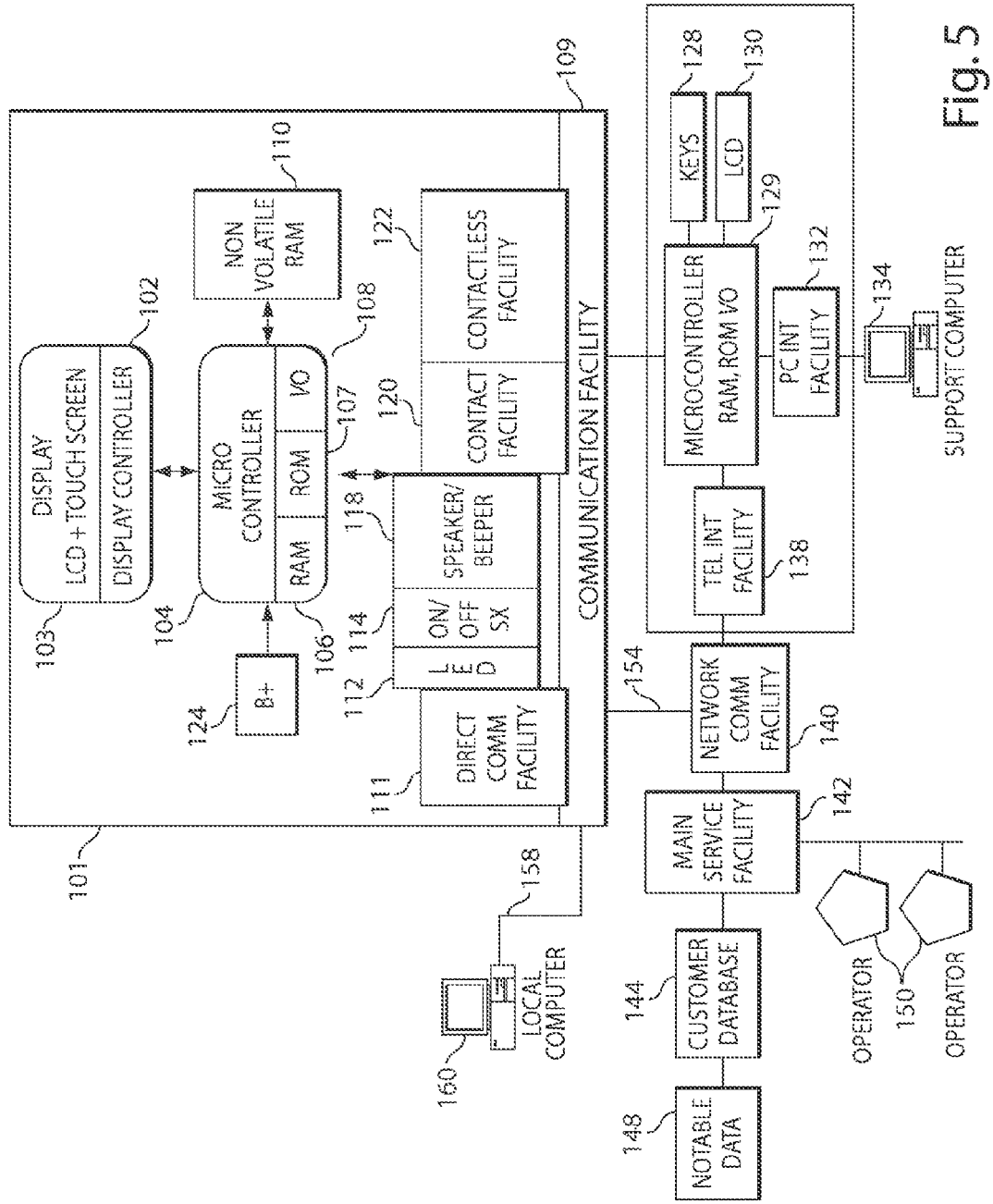
FIG. 5 is a detailed system diagram of one potential exemplary embodiment of an embodiment of the electronic transaction platform.

Referring to FIG. 5, methods and systems are provided herein for enabling a variety of transactions, including transactions that a user engages in through a electronic wallet. In FIG. 5, one embodiment is provided of a computer-based system that may provide a service to a user of an electronic facility 101. As indicated in connection with FIG. 1 above, many different embodiments are possible, depending on the particular services to be provided, or the environment in which a service is to be provided. The electronic facility 101 may be, may comprise, or may be a component of a client facility. This service may be a virtual "electronic wallet." The electronic wallet may replace a traditional wallet and its contents, such as cash, credit cards, medical cards, membership cards, professional credentials, promotional cards and coupons, and so forth. The user of the electronic wallet may experience benefits as compared with using a traditional wallet, such as increased convenience, the elimination of paper transactions, and added security.

Generally, but not always, the service provided by the electronic facility 101 depicted in FIGS. 1 through 5 may relate to a transaction and, in particular, to a financial transaction. This service may be delivered through a variety of software architectures and platforms, as well as a variety of business models. For example, the service may be supplied by a service partner, may be delivered through a Web services oriented architecture, may be a premium service associated with a financial charge to the user, or may be free to the user. The Web services may be delivered via a distributed infrastructure and/or a secure Web services protocol, such as distributed servers that (1) may be utilizing XML digital signatures and/or XML encryption and/or that (2) may be in functional communication via SOAP. The Web services may be associated with a secure application throughput management facility, such as that provided by the AppMetrics® products of Xtremesoft, Inc., Woburn, Mass. The service may relate to a number of different financial and/or information transactions. For example, the service may be a service relating to or including bill payment, personal data management, security, promotion, banking, an application for a new account, a renewal of an existing account, an issuance of a credit card, a management of a sub-account (for example, management of a credit card for a child), an account removal, an account cancellation, shopping, purchasing agent services, a government service, customer profiling, inter-vendor cooperation or collaboration, a financial service, a prepaid service, ticketing, a manned ATM service, a proximity transaction, or any other service that can be usefully associated with the electronic facility 101. The transaction may be a secure transaction, wherein data that may be associated with the transaction may be transmitted and/or stored in a secure fashion such as protected with cryptographic facilities. The secure transaction may be associated with a secure distributed Web-based platform; may or may not be associated with a wallet metaphor; and may have payment or non-payment applications. The secure transaction may be conducted as a proximity transaction in the real world using infrared, RF, bar codes, and so forth. The secure transaction may additionally or alternatively be conducted in the electronic world (e.g. wide area network and perhaps the Internet). The secure transaction may or may not comprise a biometric parameter, the ability to securely access a personalized Web portal for a value-added service, a client-centric wallet to "top-up" the amount of a token perhaps by associating funds, which may be in electronic facility 101 but which may or may not be in the wallet, with the token, wherein the associating the funds with the token may comprise a funds transfer.

In embodiments the transactions may be conducted over-the-air, such as in the proximity transaction. In these embodiments, the transaction may be secured using three-dimensional authentication, which may comprise verifying the identity of the user, the electronic facility 101, and the domain for the transaction. This authentication may comprise the use of a cryptographic facility, such as an implementation of 3DES, AES, and so forth, to secure and protect the transaction from eavesdropping, spoofing, replaying, and so forth. The cryptographic facility may alternately or additionally comprise a public key infrastructure that may be customized on the basis of the user, the electronic facility 101, or the transactional domain basis.

Generally, in the following disclosure, sending, receiving, or transmitting is referred to as being secure when it is protected by well known cryptographic facilities, such as SSL, SSH, DES, AES, XML Encryption, HTTPS, and so forth.

In embodiments, the methods, systems and services supported by the electronic facility 101 may include a wide range of services. For example, and without limitation, the methods and systems may enable a bill payment service, which may include the issuance of a bill and the issuance of a receipt and/or acknowledgement and payment. The payment may be conducted in the real world or the virtual world. The receipt or acknowledgement may be reproduced or stored, securely and electronically, on the electronic facility 101. The receipt or acknowledgement may comprise a "PAID" stamp. The receipt may be procured from one of a plurality of domains, through any wired or wireless medium, and may be used during the initiation or completion of a transaction. Methods and systems may also, or alternatively, enable a security service, which may be associated with any function (including multiple functions) of the electronic facility system and may facilitate a privacy feature or enable electronic facility theft determent. The security service may also provide transaction integrity, data integrity, authentication, non-repudiation, revocation, renewability, and/or any other function associated with security of the electronic facility 101.

A promotion service may be associated with a function of the electronic facility 101 and provide a promotion service associated with a loyalty card, a coupon, a promotion, an incentive program, or any other promotional method. The promotion service may involve direct distribution (from a vendor) or merchant distribution (from a retailer). Methods and systems may also, or instead, support a banking service, which may be associated with an account transfer, access to an ATM facility, a microcredit transaction and/or settlement, or any other method providing banking functionality to the user. Methods and systems described herein may also, or instead, support an application service for enabling an application to qualify for another service or other type of application for a new account service, wherein the application service may comprise providing needed information to a service facility such as a bank or credit card company. Methods and systems may also, or instead, support a shopping service, which may comprise the user providing personal information to assist in browsing merchandise and product selection. An action associated with browsing merchandise may be checking for a bargain, checking for a discount, checking for a related product, receiving promotional information, and any other action providing the user with merchandise browsing capability via the electronic facility 101.

The methods and systems disclosed herein may also, or instead, support a government service, which may be associated with one or more of a passport, a visa, a social security number, a taxpayer identification number, a motor vehicle, and voting. Methods and systems disclosed herein may also, or instead, support a customer profiling service, which may be for the benefit of the user or vendor, and may be associated for example with the profiling of a group of users. Methods and systems disclosed herein may also, or instead, support a financial service, which may be associated with, for example, a person-to-person money transfer, a money order, a purchase, sale, or other transaction of a stock or other equity, a credit or debit card transaction, an account transfer, or a wire transfer. Methods and systems disclosed herein may also, or instead, support a prepaid service associated with, for example, replenishing prepaid airtime or a prepaid shopping card. Method and systems disclosed herein may also, or instead, support a ticketing service, which may be associated with an airline, a movie, a play, a sporting event, an auction, a charitable function, an educational function, a ceremony, a speech, an entertainment event, or a hospitality facility. In the ticketing service, paperless tickets may be issued directly to and securely stored in association with the electronic facility 101.

The electronic facility 101 may include components that collectively support transactional methods, allowing an authorized user of the facility to conduct various transactions with merchants, peers, suppliers, and any other transaction participant. In one embodiment, the electronic facility 101 may include a user interface, which may be any kind of user interface, such as a keyboard, a mouse, a click wheel, a track wheel, a pointer, a slider, a button, a voice activated interface, a stylus, a smart pen, a remote control, a touch screen, a network interface, a software interface, a web page, a browser, or other interface suitable for receiving user input and/or providing information to the user. In one embodiment, the user interface may be an LCD and touch screen display 100. The display provides visual feedback and information to the user. The display 100 may be full size (for example, the size of a tablet or desktop PC) or it may be a smaller size (for example, the size of a PDA, cell phone, camera, or digital watch display). In embodiments the display 100 may be small enough to be portable and/or large enough to display user-readable messages and touch controls.

Referring again to FIG. 5, the electronic facility 101 may also comprise a control facility for controlling the functions of the electronic facility 101, which may be any type of control facility, such as a processor, a microprocessor, a computer, or the like. In embodiments the control facility may comprise an associated display controller 102; a microcontroller 104, which may be a microprocessor, along with RAM 106, ROM 107, and Input/Output port management 108; a non-volatile RAM 110; a light emitting diode 112 to indicate the status of the on/off switch 114, or other status of the electronic facility 101; a speaker/beeper 118, one or more contact facilities 120 to connect to an optional external facility 131 and/or to charge a battery 124; an optional contact-less facility 122 to be used, for example, in wireless communications and/or power applications; and a direct communication facility 111. The electronic facility 101 may be powered by a power facility 124, such as a battery, a power supply, a solar cell, a fuel cell, a recharger, an inductive charger, a cigarette-lighter adapter, or any other source of power.

The electronic facility 101 may be supported by a variety of technology platforms and may take many different forms. For example, the electronic facility 101 may be about 3.5 inches by 2.5 inches, or about the size of a credit card. Alternately, it may integrated into a mobile device, such as a PDA, a smart card, a cell phone, a wearable computer, a watch, a Blackberry®, a Sidekick®, or any other device having a small, portable form. In other embodiments, the technology may be included in a cash register, point of sale system, personal computer, portable digital music player, digital camera, set-top box, digital video recorder, satellite receiver, automobile, utility meter (such as an electric meter or gas meter), or any other device involved in a sale of goods, the transfer of funds, or other transactions described herein. The technology used in the electronic facility 101 may include an interface to an automobile, GPS, cellular phone or any other facility that allows the electronic facility 101 to perform mobile, location-based transactions.

The display 103, as described above, may include an LCD and a touch screen. Alternatively, the display 103 may be a light emitting diode display, an organic light emitting diode array, a flexible organic light emitting diode array, a projection display, or any other display suitable for use with the electronic facility 101. On the display 103 or in the image projected by the display 103 may appear bar codes or signatures. These bar codes and signatures may, for example, provide information to the operator of a support computer 134 who may require a computer-readable or human-readable visual reference to information stored with the electronic facility 101, or information relating to a transaction using the electronic facility 101.

Alternatively, the display 103 portion of the electronic facility 101 may be embodied in a remote device. For example, the electronic facility 101 may further comprise a Web server to which a PC-based Web browser may connect. Displayed on the browser may be the visual interface of the electronic facility 101. Thus in certain embodiments, there is no physical size restriction on the electronic facility 101, as it would only provide the content to be displayed on the display 103, rather than the physical display itself. Here, technology comprising the electronic facility 101 could be embedded in a ring, bracelet, pendant, shoe, eyeglass rim, barrette, or any other personal item that the user may wear.

The electronic facility 101 may comprise a user interface to receive user input. In this respect, the user interface may include an input device such as a touch memory button, a touch memory reader, a mouse, an integrated trackball, a microphone with speech recognition capabilities, an RFID scanner, a Bluetooth® interface to external user input devices, a network interface, a camera, a video or Web camera, or any other user input device, including any of the input facilities described herein. In an alternate embodiment, the user input may be supplied over a network, for example, via a remote Web browser that connects to a Web server, which may be integral to the electronic facility 101.

The electronic facility 101 may communicate with other facilities during a transaction. Integral to the electronic facility 101 may be a communication facility 109, which may comprise a contact facility 120, a contact-less facility 122, a direct communication facility 111, a local communication facility 152, a network communication facility 154, an application-oriented communication facility, or any other communication facility appropriate for use with the electronic facility 101.

Transactions may involve the user engaging the electronic facility 101 in an interaction with the service facility. The service facility may authenticate one or more participants in a transaction and may be a final authority as to the settlement of the transaction. The service facility may include a main service facility 142. The communication facility 109 may facilitate data transmission with the main service facility 142 via the network communication facility 154.

Power or communications to the electronic facility 101 may be provided via direct physical contact with an external object. This is achieved via the contact facility 120, which may comprise a power pin, a magnetic stripe, a contact smart card facility, or any other facility suitable for providing contact-based data communication or power to the electronic facility 101. To the extent that the contact facility 120 may be utilized to provide communications capability to the electronic facility 101, it may be part of the communication facility 109.

The power or communications to the electronic facility 101 may also, or instead, be via a wireless interaction with an external object, such as through the infrared or contact-less facility 122, which may comprise an IrDA facility, a proximity RF facility such as RFID, a contact-less smartcard facility, an electromagnetic induction facility, or any other facility capable of providing contact-less data communication or power to the electronic facility 101. To the extent that the contact-less facility 122 may be utilized to provide communications capability to the electronic facility 101, it may be part of the communication facility 109.

Communications to the electronic facility 101 may also, or instead, be provided via the network communication facility 154, which may include an interface facility to the PSTN (such as a modem), an interface facility to a data network (such as an Ethernet card or 802.11 wireless card or Bluetooth® facility), an interface facility to a cellular network (utilizing protocols such as CDPD, GPRS, GSM, CSD, HSCSD, or SMS), or any other facility providing communications to a special interface 140, which may be a data communications interface to the main service facility 142. To ensure the security of data transmitted, the network communication facility 154 may employ a secure connection (such as a VPN over IPSec or SSH).

In any case, the communications to the electronic facility 101 may enable a secure transaction.

In general, networked computing may include the use of a physical medium, a protocol stack, and one or more applications (such as a Web server and Web browser). The physical medium may include, for example, category 5e cable used for wired Ethernet communications, coaxial cable, fiber optics, or any other physical medium, including, in the case of wireless communications, air or a vacuum, as well as various combinations of these used to complete end-to-end communications between network participants. The protocol stack may include any number of processes used to process communications between network participants, such as, for example, a TCP/IP protocol stack or an OSI protocol stack. The applications may include any programs, program modules, services, or other software executing on a processor or other hardware, including common desktop applications such as work processing software, spreadsheets, presentation software, and web browsers, as well as proprietary software or services that may be transparent to a user. It will be appreciated that in some conceptual descriptions, the roles and structures of these components vary, as for example where the OSI protocol stack includes a physical layer to describe use of a physical medium and an application layer to describe an interface with applications. Similarly, in certain conceptual frameworks, a device operating system may be considered an application or a component of a protocol stack. Thus, still more generally, a networked computing system may include any combination of physical media and processing resources to enable one directional or multi-directional communication between applications, services, or other software components executing on processors or other hardware. All such networked computing systems are intended to fall within the scope of the following description, except where specific programs, protocols, or communication media are specified.

To support the user of an electronic facility 101, an application-oriented communication facility 109 may be associated with the electronic facility 101. This communication facility 109 may comprise a facility allowing direct connection to the main service facility 142 through the external facility 131 (such as Telnet, FTP, SSH), or any other facility providing an application with a connection-based or session-based capability to tunnel data through the external facility 131 to the main service facility 142. In one example, the application-oriented communication facility 109 may include a facility for connecting to a retailer's Web server using Web protocols such as HTTP and HTTPS.

The memory in the electronic facility 101 may comprise RAM 106, ROM 107, and/or nonvolatile RAM 110, or any other kind of data storage facility. The memory may be sufficient to store all data associated with the participation of the electronic facility in the execution of a transactional method herein described. The contents of this memory may be uploaded in whole or in part, optionally via a software conduit, to the support computer 134, the local computer 160, and/or the main service facility 142. To support methods associated with transactions, the memory in electronic facility 101 may contain a multidimensional database, may be implemented utilizing a package and methods that provide leak-resistant cryptography (such as a smart card), and may be embodied in any magnetic, optical, or electronic storage medium. In embodiments the data storage facility may include a file, database (object oriented or relational), object, or other data storage facility for storing data, applications, programs, and other items associated with the electronic facility.

The memory in electronic facility 101 may store a value associated with transactional methods herein described. This value may include: a unique identifier to discriminate one electronic facility 101 from another; access-control information to prevent unauthorized use of electronic facility 101; personal information identifying the owner of the electronic facility 101; financial account information; medical and health information associated with the owner of the electronic facility 101; stored cash value; logos and branding information; or any other value associated with transactional methods.

The access-control information may comprise an encoded signature, a personal identification number, an encoded fingerprint, an encoded iris scan, or any other information (biometric or otherwise) associated with access control, identification, security, or authorization.

The personal information may comprise an individual's name, a business's name, a home address, a home telephone number, a home fax number, a home e-mail address, an office address, an office phone number, an office fax number, an office e-mail address, a uniform resource locator ("URL"), a uniform resource identifier ("URI"), a height, a weight, a birth date, a social security number, a blood type, a marital status, or any other information associated with a person, or used to uniquely identify, contact, or locate a person.

The financial account information may comprise a credit card number, a date of issue, a date of expiration, a credit limit, a savings account number, a checking account number, an investment account number, a username and/or password associated with a financial account, or any other information associated with one or more financial accounts such as brokerage accounts, savings accounts, checking accounts, credit card accounts, and so on.

The medical and health information may comprise an indication of an allergy, a medical history, a medical condition, a health insurance member number associated with a health insurance plan, a physician name, a hospital name, a pharmacy name, current medications or prescriptions, or any other information associated with a medical or health condition.

The logos and branding information may comprise a credit card image or any other image associated with logos and branding that might be used in association with services provided using the electronic facility 101.

To allow the electronic facility 101 to be adaptable to different environmental lighting conditions, the electronic facility 101 may further comprise a display brightness adjustment to control, for example, backlighting or display intensity, and an enclosure. Alternatively, the electronic facility 101 may include a visible light sensor capable of sensing an environmental lighting condition, along with a facility to automatically adjust the display brightness based upon the sensed environmental lighting condition.

The electronic facility 101 may yet further comprise software to support methods associated with transactions. This software may comprise an operating system, a memory display manager, a database display manager, an analysis algorithm, an analysis procedure, an interface controller, a day planner, an I/O driver, a display driver, a scheduler, a command manager, a clock, a calendar, a universal electronic transaction facility initialization program, an authorization program, a security manager, a signature manager, or any other software feature associated with transactions or associated data that is associated with transactions.

By emulating a physical entity (such as a credit card), the electronic facility 101 may provide a user with an alternative to carrying the physical entity. By emulating a plurality of physical entities (such as a credit card, driver's license, event ticket and phone card), the electronic facility 101 may act as an electronic wallet that may relieve its user of the need to carry physical entities, such as cards, in a physical wallet. To support this functionality, the electronic facility 101 may further comprise an application that emulates a physical entity, such as graphically emulating the physical entity, or emulating the entity using audio or video, for example. This application may emulate a credit card, a bank card, a medical card, a driver's license, a phone card, an airline travel card, a car rental card, a universal integrated card, a loyalty program or rewards card, or any other physical entity associated with the user of an electronic facility 101, such as any entity used in the services, applications, environments and transactions described herein. In embodiments, emulating a physical entity includes emulating visual physical characteristics of the entity, such as a brand, logo, trademark, font, format, shape or the like. In other embodiments, emulating a physical entity may include storing digital information associated with the entity, such as identification numbers, pass codes, serial numbers, or the like. In embodiments digital information may be associated with a visual representation of the entity.

Applications described herein, such as those supporting credit card and bank card transactions, for example, may enable numeric entry by the user, such as entry of a personal identification number ("PIN"), a dollar amount, or any other entry that may enable features such as paying a gratuity, requesting a cash back quantity, or specifying any other monetary quantity associated with a transaction.

The medical card application may comprise an associated medical history, insurance information, photo identification, or any other information associated with the medical aspect of a person.

The airline travel card application may comprise an interface with an airline reservation system or an interface with any other system associated with airline travel.

The universal integrated card application may integrate a number of different applications, associated identifications, accounts, or any other items associated with universal integrated card methods.

To support methods associated with the electronic facility 101 or a general activity of the user of the electronic facility 101, the electronic facility 101 may support one or more additional features. An additional feature may include, for example, an entry of a code, which may be an alphanumeric code, a personal identifier, a password, a personal identification number, or a signature. The additional feature may also, or alternatively, include a display of an electronic facility option (such as an account summary), a display of a status associated with a transaction (such as "transaction complete"), a display of a numeric keypad (such as for numeric entry of a gratuity on a restaurant purchase), a notepad, a to-do list, a contact list, an email program, a task manager, a message manager, an instant messaging program, an alarm, a reminder feature, or any other feature that might be usefully included with the electronic facility 101, or methods and services provided thereby.

To enable a transactional method, the electronic facility 101 may need to interact with a main service facility 142. The main service facility 142 may be a server, such as an HTTP server, a personal computer, a workstation, a laptop computer, or any other computer or computing device. In embodiments, the main service facility 142 may provide functions as services in a services-oriented architecture, where the services are listed in a registry of such services that can be accessed by clients of the main service facility 142, such as the electronic facility 101, to use the services. In embodiments the main service facility 142 may comprise a distributed computer, a cluster computer, a network of workstations, a server, a supercomputer, a mainframe computer, a server farm, and/or any combination of these deployed at one or more geographic locations.

The interaction with the main service facility 142 may occur via the external connector 131, which may be employed in association with the electronic facility 101 and the main service facility 142 during the execution of a transactional method herein described. The external connector 131 may comprise a telecommunications/Internet facility 138, an information processing facility 129, user input keys 128, liquid crystal display (LCD) 130, a personal computer (PC) interface facility 132, or any other feature or facility associated with supporting a transactional method between the electronic facility 101 and the main service facility 142. The information processing facility 124 may comprise a microcontroller, RAM, ROM, I/O facility, and any other facility associated with information processing. The external connector 131 may interface with a local communication facility 152 via an RF facility, an IR facility, or any other appropriate facility allowing communication between the electronic facility 101 and the external connector 131. The communication facility 152 may be passive or active, or may include any combination of active and passive components.

A participant may desire a capability associated with the transaction, such as scanning a coupon presented by the user, scanning a ticket held by the user, or the like. To support this capability, the connector 131 may also interface with a support computer 134 via a PC interface facility 132. The external connector 131 may be associated with a merchant or other transaction participant. The communication facility 109 may facilitate data transmission with the external facility 131 via the local communication facility 152. The local communication facility 152 may include a contact facility 120 and/or a contact-less facility 122. The PC interface facility 132 may be passive or active. The PC interface facility 132 may comprise any practicable data transfer facility, including USB, parallel, serial, Ethernet, PSTN, 802.11, WiFi, WiMax, IrDA, or Bluetooth, or any other wired or wireless facility. The PC interface facility 132 may be alterable after the deployment of the external connector 131 to an environment, allowing the interface to be adapted to its environment as the environment may change, for example, due to a modification to the support computer 134. The support computer 134 may provide any facility desired by the user of the support computer 134 that is associated with a transaction involving the user of the electronic facility 101 and the user of the support computer 134.

The external connector 131, independently or in association with the support computer 134, may provide a verification feature when used in association with electronic facility 101. This verification feature may include displaying a photograph; comparing a photograph to a reference photograph; comparing a fingerprint to a reference fingerprint; comparing a voice print to a reference voice print; comparing a signature to a reference signature; displaying a signature; comparing an iris scan to a reference iris scan, or any other feature allowing the comparison of two data sets, one associated with a candidate user and another associated with a known user. The verification feature may also, or instead, employ any combination of PINs, passwords, usernames, and digital keys or certificates to verify identity. Any of the physical entities required for verification may also be stored in or emulated in the electronic transaction facility 101, such as a photograph of the user, fingerprint, voice print, iris scan, or other biometric data, such as a CT scan, MRI result, or the like.

The technology comprising the external connector 131 may be integrated, in whole or in part, into the support computer 134.

The support computer 134, as has been mentioned, may interface with the external connector 131. Through the external connector 131, the support computer 134 may communicate with the electronic facility 101. The support computer 134 may also communicate with the main service facility 142 through the telecommunications/Internet facility 138 of the external connector 131. The communication of the support computer 134 with the electronic facility 101 and the main service facility 142 may support or enable a transactional method with the support computer 134 playing a participant's role in the transaction.

When communicating with the main service facility 142, the support computer 134 may send a code; send a transaction request; send an authorization request; receive an authorization; receive a receipt; receive an acknowledgement; send a coupon; receive approval to redeem a coupon; check for available inventory (for example, the availability of tickets to a theatrical event); request a purchase of available inventory; or request a cell phone top-up. The support computer 134 may also send and receive other communications from the main service facility 142 as specified in the transactional methods herein described. In each case, items that are associated with a transaction may be stored and accessed in a manner that allows access to an emulated format version of their physical format, such as showing a "PAID" stamp on a receipt, showing an official logo on a ticket, or showing an actual physical signature on a signed document. This emulated physical form may be associated with digital data, such as data to ensure uniqueness of a particular representation of an item. Thus, the methods and systems described herein may support storing, manipulating, retrieving, exchanging and otherwise using a close (if not identical) graphical depiction of an actual entity (e.g., an actual driver's license, as opposed to a picture of a driver's license, an actual ticket, as opposed to evidence of having purchased it, or the like), as opposed to mere information about the represented entity.

The support computer 134 may be a point-of-sale (POS) computer. The POS computer may be installed at a store, a fuel pump, a restaurant, a bar, a hotel, a tollbooth, a doctor's office, an airport or other ticketing location, or any other location where a transaction may take place. In embodiments, the POS computer may be equipped with a facility designed to interact with the electronic facility 101. The POS computer may be an automated teller machine (ATM), may be installed in an ATM, or may take any other practicable form. The support computer 134 may be an e-commerce server connected to the Internet. The support computer 134 may be a server connected to the PSTN. In this case, the server may comprise functions that allow for voice interaction with the user, DTMF decoding, SMS reception, SMS transmission, or any other method facilitating data transmission via the PSTN.

The support computer 134 may be capable of conducting proximity transactions in association with the electronic facility 101 and the main service facility 142. The support computer 134 may also be capable of accessing from the main service facility 142 information associated with the transactional methods herein described.

The user of an electronic facility 101 may want to utilize a local computer 160, such as the user's personal computer, to perform an action associated with a transaction, herein described.

To support the utilization of the local computer 160, the communication facility 109 may further comprise a personal connection 158 to the local computer 160. The personal connection 158 may comprise a USB connection, a Firewire connection, an Ethernet connection, an AT keyboard connection, a PS/2 keyboard or mouse connection, a MIDI connection, a game port connection, an IEEE 1284 parallel connection, or any other practicable serial or parallel connection. The personal connection 158 may also, or instead, include a local area networking facility supporting wired or wireless network protocols such as 802.11 and Ethernet. The personal connection 158 may yet further comprise a short range wireless communication facility supporting protocols such as Bluetooth®, IrDA, or any other infrared, radio frequency or other method supporting the wireless transmission of data over a short range.

The local computer 160 may be a personal computer. The personal computer may interface with the electronic facility 101 via a connection such as the above-described physical connection 158. The personal computer may support transactional analysis, which may comprise analysis associated with personal taxation; analysis associated with personal budgeting; analysis associated with compiling a personal financial summary; or any other analysis associated with a transaction. The personal computer may further comprise software to access a remote computer. This remote computer may be associated with a transactional service company and may be the main service facility 142. When accessing a remote computer, the local computer 160 may access or review information associated with a financial account wherein the information is stored in the remove computer. The local computer 160 may also change at the remote computer information associated with a financial account.

In one application of this invention, a health service may be provided in which an electronic facility 101 may be used for inputting, storing, processing, and/or transmitting personal information, including personal medical history (including radiological images memory-availability permitting), account information, and transactional information. At least one central health care information processing facility is provided, which may comprise a main service facility 142, a customer database 155, an operator station 150, a notable data 148, a network communication facility 154, and/or a special interface 140. In Pitroda (included above by reference), the central health care information processing facility is disclosed as a "health care management system" and, within the context of Pitroda's description of the health care management system, the electronic facility 101 is referred to as a "UET card" and a "universal electronic transaction card."

In another application of this invention, an electronic credit transaction service may be provided in which an electronic facility 101 may be used for conducing electronic credit transactions. At least one credit transaction processing facility may be provided, which may comprise a main service facility 142, a customer database 155, an operator station 150, a notable datum or data 148, a network communication facility 154, and/or a special interface 140. In addition, a point of transaction system may be provided, which may comprise an external connector 131. In embodiments, the credit transaction processing facility may be a "service institution system" as described in the documents incorporated herein by reference, and, within the context of a service institution system pertaining to the electronic credit transaction, the electronic facility 101 may be referred to as a "UET card" and a "universal electronic transaction card."

In a general application, some or all the items in FIG. 1 may be combined to provide a transactional service to a user. The transactional service may comprise, without limitation, a payment service, a non-payment service, a health-related service, an infotainment service, a personal information management service, a travel service, a person-to-person service, a money order service, a money transfer service, a prepaid airtime top-up service, a ticketing service, a loyalty service, a coupon service, a promotional service, an electronic checkbook service, a driver's license service, a gaming portal service, a government portal service, an enterprise portal service, a health/fitness portal service, a religious portal service, a sports portal service, an insurance portal service, a university portal service, a user-centric interface facility, a user-centric engine facility, and a security facility. Some of these transactional services are herein described, and the entire teachings of the documents referenced herein are incorporated by reference.

In some applications, the main service facility 142 may comprise a special interface 140 for aggregating telephone lines. In this case, the special interface 140 may provide caller ID functionality for identifying the source of a dial-in; may receive dial-in from a POS computer; may be accessed by a credit card company or other service provider; or may support any method associated with a transaction. Alternatively, in modern applications, the special interface 140 may comprise an Internet connection. In this case, the special interface 140 may receive IP packets from a client computer; provide the IP address of the client computer; may receive incoming data packets from a POS computer; may be accessed by a credit card company or other service provider; or may support any method associated with a transaction. Thus, the main service facility 142 may be coupled to a telecommunications network or the Internet via the special interface 140. More generally, the special interface 140 may provide any needed degree of connectivity between incompatible physical, programming, protocol-based or other interfaces to a main service facility 142

To support the transactional methods herein described; methods associated with a transaction; or any other transactional method, the main service facility 142 may further comprise software ("main service facility software"). The main service facility 142 may still further comprise a customer database 144, such as any relational database or other database, data store, file, mass storage device, or other storage facility, which may be associated with the main service facility software. The main service facility 142 may be capable of storing and processing notable data 148 that is associated with the electronic facility 101. This notable data 218, which may be stored in the database 214, may pertain to transactions, reports, analysis, account authorization, credit card issuance and cancellation, or any other thing associated with the electronic facility 101. The central computer software may also comprise applications and programs for accomplishing a variety of functions and services. In embodiments, services may be deployed in an application-oriented architecture, wherein clients of the services (including the main service facility 142, the support computer 134 and the local computer 160) may access the services to achieve the functions. Services may be listed in a registry of such services, discussed below in detail. In embodiments the services may be deployed with user interfaces that are optimized for use by particular client facilities, such as a particular type of support computer, local computer, or user device. More generally, the software may include any combination of programming languages, environments, and/or other software platforms, modules, or other technologies suitable for providing the functionality described herein, in source code form, executable form, or some intermediate form.

Figure 19:
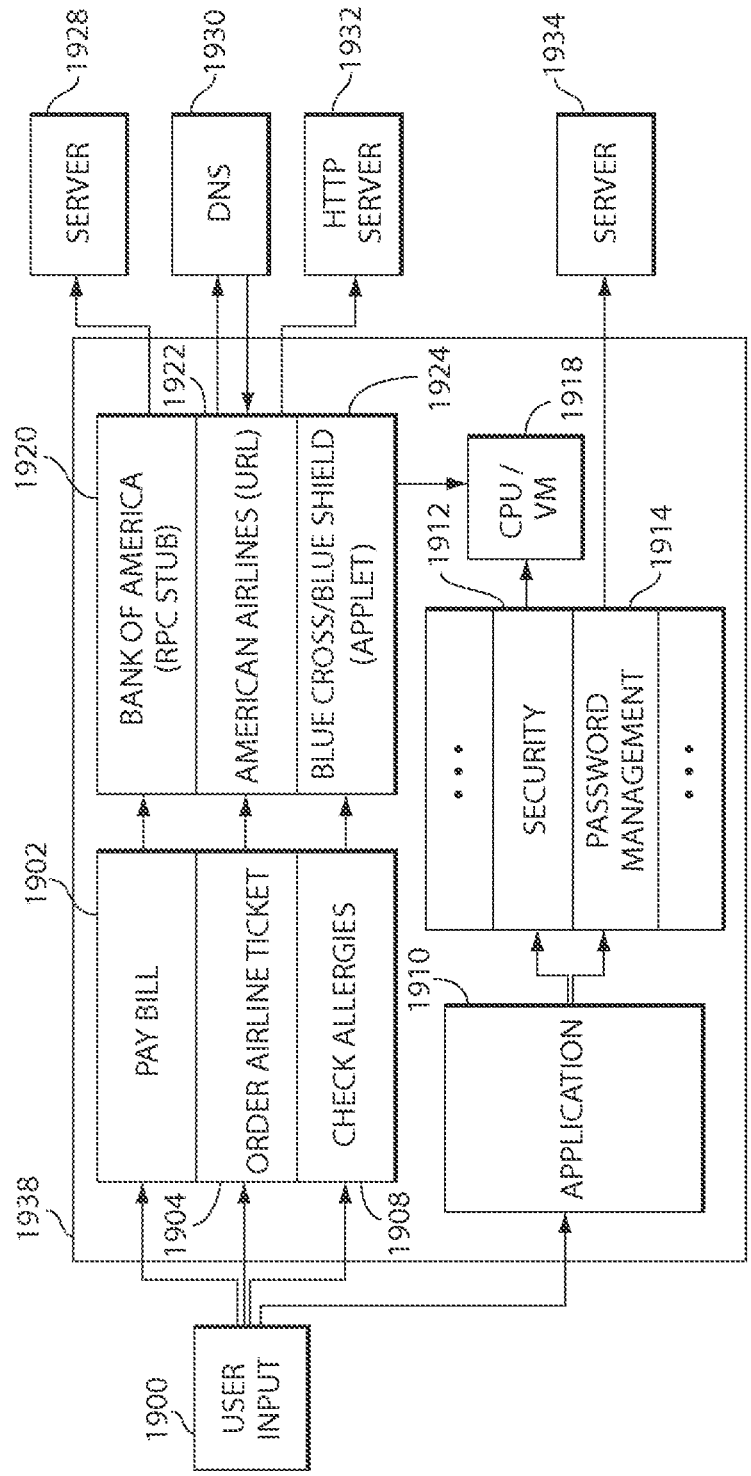
FIG. 19 depicts logical aspects of an embodiment an electronic facility.

Referring now to FIG. 19, an assortment of logical aspects of an embodiment 1938 of an electronic facility 101 is depicted. The embodiment 1938 is capable of receiving a user input 1900 that may be directed to any number of transactional service references or applications 1910. One such user input 1900 is directed to the transactional service reference "Pay Bill" 1902, another is directed to the transactional service reference "Order Airline Ticket" 1904, another is directed to the transactional service reference "Check Allergies" 1908, and another is directed to the application 1910.

As is shown, the transactional service reference "Pay Bill" 1902 refers to an RPC client stub 1920 that is associated, for example, with the company Bank of America. Likewise, the transactional service reference Order Airline Ticket 1904 refers to a URL 1922 associated, for instance, with the company American Airlines and the transactional service reference Check Allergies 1908 is associated with an applet 1924 that is associated, for example, with the health insurance company Blue Cross/Blue Shield.

A number of the objects to which these transactional service references refer are associated with facilities that are external to the embodiment 1938. The Bank of America RPC client stub 1920 is associated with a server 1928 that is associated with the company Bank of America, wherein the server 1928 may be associated with an RPC server stub that is compatible with RPC client stub 1920. The American Airlines URL 1922 is indirectly associated with an HTTP server 1932 that is associated with the company American Airlines.

The indirect association between the American Airlines URL 1922 is due to the need to resolve the URL 1922 to an IP address of the HTTP server 1932. The benefits of this indirection are well known in the art, and include the ability to decouple the name of a Web site from the physical address of the Web site.

The resolution of the URL 1922 is depicted as a first arrow pointing from the URL 1922 to DNS server 1930 representative of a query from the embodiment 1938 to the DNS server 1930; a second arrow pointing from the DNS server 1930 to the URL 1922 representative of a name resolution from the DNS server 1930 to the embodiment 1938; and a third arrow pointing from the URL 1922 to HTTP server 1932 representative of a HTTP request from the embodiment 1938 to the HTTP server 1932.

One of the objects to which a transactional service refers is associated with a facility that is internal to the embodiment 1938: The Blue Cross/Blue Shield applet 1924 is associated with a machine command processing facility 1918. In practice, the machine command processing facility 1918 is likely to be a central processing unit providing either a native machine command processing function or a virtual machine command processing function. The machine command processing facility 1918 may be microcontroller 104.

Within the embodiment 1938, an application 1910 may invoke an additional service reference. Two such references are depicted, additional service reference Security 1912 and additional service reference Password Management 1914. Security 1912 references an applet which may be executed by the machine command processing facility 1918. Password Management 1914 is an RPC client stub associated with a server 1934 that performs as a password management facility.

One distinction between a transactional service reference and an application is that the former is associated with a transactional service and the latter is not. This qualitative distinction illustrates that the systems described herein may perform both transactional and non-transactional functions, some of which are herein described and others of which will be readily apparent to one of ordinary skill in the art. However, as a matter of implementation, there may not be a distinction between the two, as both may be responsive to user input; both may refer to a URL, an RPC stub, an applet, or any other executable or informational object; both may be invoked by the user or automatically by the embodiment 1938; and both may be embodied as an executable, interpreted, or static byte sequence.

In some circumstances, it may be useful for a transactional service reference to indirectly reference a service provider facility. One example of this, disclosed above, is the URL 1922 that may be de-referenced via the DNS server 1930 to an IP address associated with the HTTP server 1932. More generally any system may be used for de-referencing external objects in a digital, networked environment, such as the Digital Object Identifier system, which is a system for identifying content objects in the digital environment developed by the International DOI Foundation. Other name or object resolution systems and methods are also well known in the art and may be utilized in the embodiment 1938 or the electronic facility 101.

Figure 20:
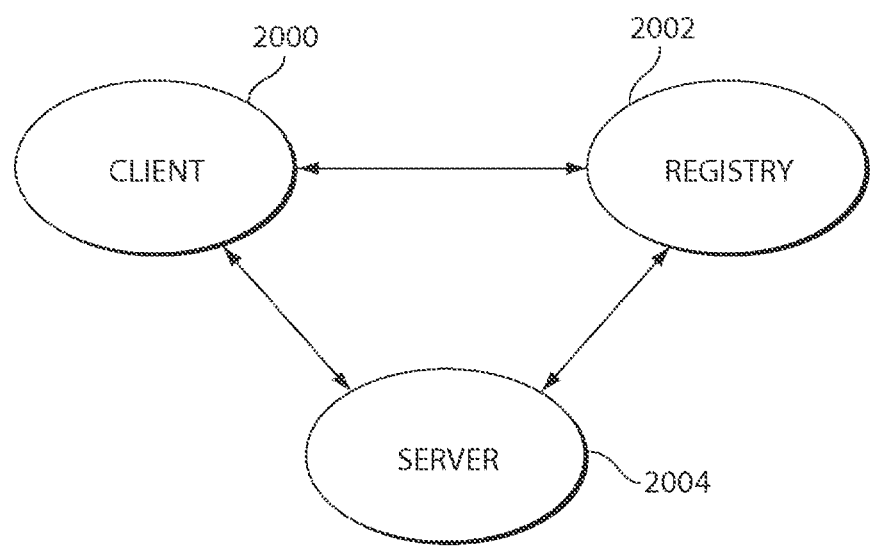
FIG. 20 depicts functional associations between aspects of the electronic transaction platform.

Referring now to FIG. 20, a client 2000, which may be the electronic facility 101 of which the embodiment 1938 is one exemplary instance, may communicate with a registry 2002 and a server 2004. The registry 2002 may be the DNS server 1930; a DOI registration agency; an FTP server; a registry of services; and/or any other facility that provides dereferencing, data processing, data storage, data upload, data download, and/or any other service associated with a server in a network.

Applications and transactional service references may be installed into, modified, or removed from the client 2000 by a method that may comprise accessing the server 2004 to receive an install, modification, or removal instruction; a static byte sequence; an executable byte sequence; an interpretable byte sequence; or any other byte sequence. The client 2000 and the server 2004 may rely on the registry 2002 to de-reference or otherwise process data associated with an application or transactional service reference.

Referring now again to FIG. 1, the central computer software may utilize a data format used by a bank or credit card company; store data associated with a transaction; generate a report associated with a transaction; analyze data associated with a transaction; process an account authorization; receive data from the electronic facility 101; maintain a customer database; support a plurality of operator stations 150 (for example, a customer service facility); enable e-commerce functionality; enable connectivity to an electronic facility 101; enable connectivity to a support computer 134; enable connectivity to an external facility 131; enable connectivity to a service institution; and/or perform any other function associated with a transaction.

The central computer software may archive a client password; a code (such as a personal identification code); personal information; or any other information associated with the user or a transaction. The personal information may comprise a street address, a marital status, a name of a spouse, a name of a child, a personal preference (which may comprise a privacy specification and a secrecy specification), a name of an employer, a driver's license, a social security number, a date of birth, a maiden name, a mother's maiden name, a place of birth, a former address, or any other information associated with the user.

The central computer software may additionally, or alternatively, archive financial information such as a bank account number, a credit card number, a number representative of income, information associated with an investment, information associated with an asset, information associated with a payment history, information associated with a credit history, information associated with a loan, or any other information associated with finances.

The central computer software may also, or instead, archive medical information such as a medical history, medical records (including, but not limited to, radiological images, EKGs, EEGs, immunization records), a name of a physician, information associated with an emergency contact, an indication of an allergy, an indication of an ailment, an indication of a treatment, and indication of a medication, a hereditary condition, a family history, a prescription, a list of current medications, or any other information associated with the user's health or associated with the maintenance of the user's health. Medical information may also include information associated with a health care plan or other health insurance or health care providers, such as a plan number, benefits description, account number, deductible information, and so forth.

The central computer software may also, or instead, archive organizational information, which may comprise an appointment, an address book, a memo, a note, a to-do list, a calendar, or any other information associated with the day-to-day organization of the user.

The central computer software may also, or instead, archive information associated with an insurance provider, an emergency contact, a membership in a club, a membership in a trade association, or any other information associated with the user's affiliation with an entity.

Moreover, the central computer software may archive information associated with travel, which may comprise information associated with a discount or travel voucher, a hospitality company, a transportation company, a car rental company, or any other information associated with the travel and lodging of the user. Other travel information may include, for example, passport and visa information, travel itineraries, reservations for rooms, cars, airplanes, and so forth, currency conversion information, time zone information, and the like.

The main service facility 142 may also have the capability of supporting transactional methods described herein, which are the subject of the present invention.

The electronic facility 101 may have the capability to store the same type of data stored by the central computer software. Indeed, the data stored by the central computer software may comprise an archive of the data stored in the electronic facility 101.

The notable data 148 may be recorded electronically, which may obviate the need for paper receipts either at the electronic facility 101 or at the main service facility 142.

The main service facility 142 may provide online analysis services to the electronic facility 101. These analysis services may include credit verification, transaction analysis, billing, payments, and any other analysis associated with transactional data.

The electronic facility 101 may comprise a universal electronic transaction facility, which may comprise a universal electronic transaction card, such as the card described in Pitroda. The universal electronic transaction card may further comprise a smartcard facility, a microphone with speech recognition, a Bluetooth® facility, a virtual private network facility, a holographic memory facility, a removable RAM facility, a removable ROM facility, a registration facility capable of registering with a central security agency, an activation facility capable of interacting with the service facility, and any other feature, function, or facility of the electronic facility 101 herein described. The electronic facility 101 may comprise a Windows, Linux, or Macintosh computer.

Figure 21:
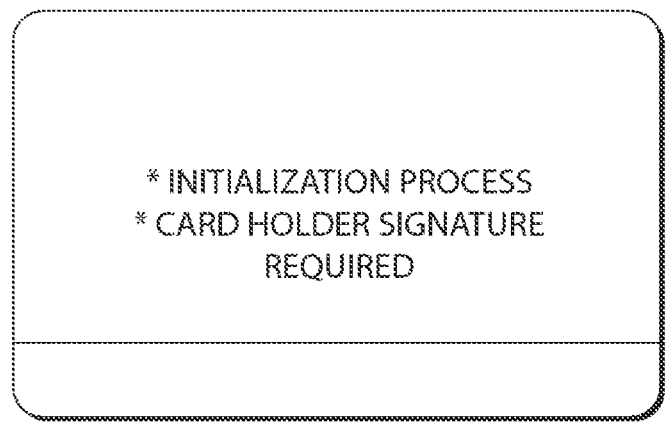
FIG. 21 illustrates various display areas in one embodiment of the electronic facility during an initialization procedure of the present invention.

The electronic facility 101 may require the completion of an initialization procedure prior to use. This initialization may associate the user with the electronic facility 101. As shown in FIG. 21, in one step in the initialization process, the user of the electronic facility 101 may be required to sign in a designated area using, for example, a pen or a stylus and a digitizing pad that converts the user's signature into a bit map or other digital form. This signature may become a permanent record similar to the signature appearing on a driver's license or credit card. This signature may be used for verification, identification, and security purposes. Once entered, the signature may be stored in a nonvolatile RAM 110. The signature may be automatically displayed on a display of the device, such as the touch screen display 100 during a transaction.

Figure 22:
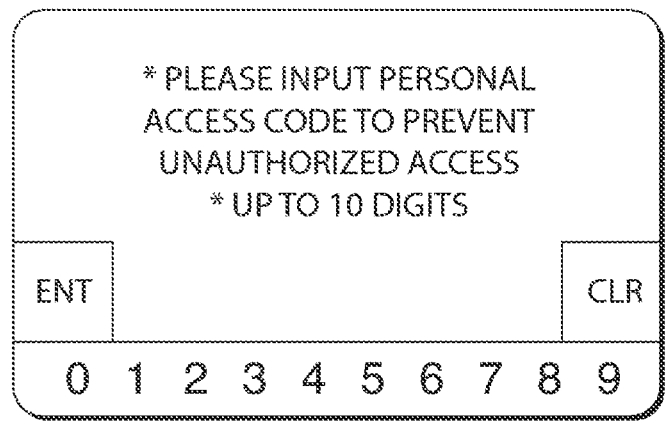
FIG. 22 illustrates various display areas in one embodiment of the electronic facility during an initialization procedure of the present invention.

As shown in FIG. 22, in another step in the initialization process, the user of the electronic facility 101 may be required to provide a code, which may be, any alphanumeric or other code, such as a password, or a numeric code. The code may be maintained by the user in confidence, much like a personal identification number (PIN) used in connection with an ATM card. Later providing the code may be a prerequisite to accessing information stored in the electronic facility 101. Conversely, later failing to provide the code may result in the partial or total disablement of the electronic facility 101. Once the electronic facility 101 is initialized with a signature and a code it may be ready for normal use.

Figure 29:
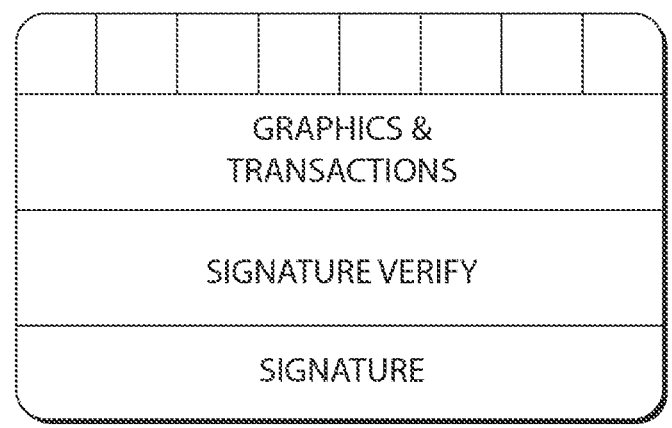
FIG. 29 illustrates various display areas in one potential embodiment of the electronic facility.

As shown in FIG. 29, during standard operation of the electronic facility 101, boxes at the top of the display may appear. These boxes may be associated with commands such as "type", "print", "erase", "security", "shift", or any other command supported by the electronic facility 101. The remaining part of the display may be available for the display and analysis of information associated with transactional methods.

A specific area may be assigned for an original signature that may be entered by the user into the electronic facility 101 during one step in the initialization procedure. The signature may be permanently stored in the electronic facility 101 and may be used for identification purposes. In the same display area, the user of the electronic facility 101 may be required, for the purposes of identification and authorization of the user, to write a signature during the exercise of a transactional method. Instead of or in addition to the signature, the electronic facility 101 may require, again for the purposes of identification and authorization of the user, that the user pose for a photograph, offer a fingerprint, record a voice print, submit to an iris scan, or allow any other digitization of a physical trait likely to identify the user.

In a certain situation, it may be desirable for the electronic facility 101 to display a simulation or simulacrum of a physical entity such as a credit card. In this situation, the original signature sample, which was collected during the initialization process, may be displayed and visually inspected during the exercise of a transactional method by a participant in the transaction other than the user, such as a merchant. The electronic facility 101 may also display basic entity information, which may comprise a name, a card number, a date of issue, an expiration date, and any other information stored within the electronic facility 101. This display of basic card information may take the form of a bar code that may be read by a bar code reader.

Figure 34:
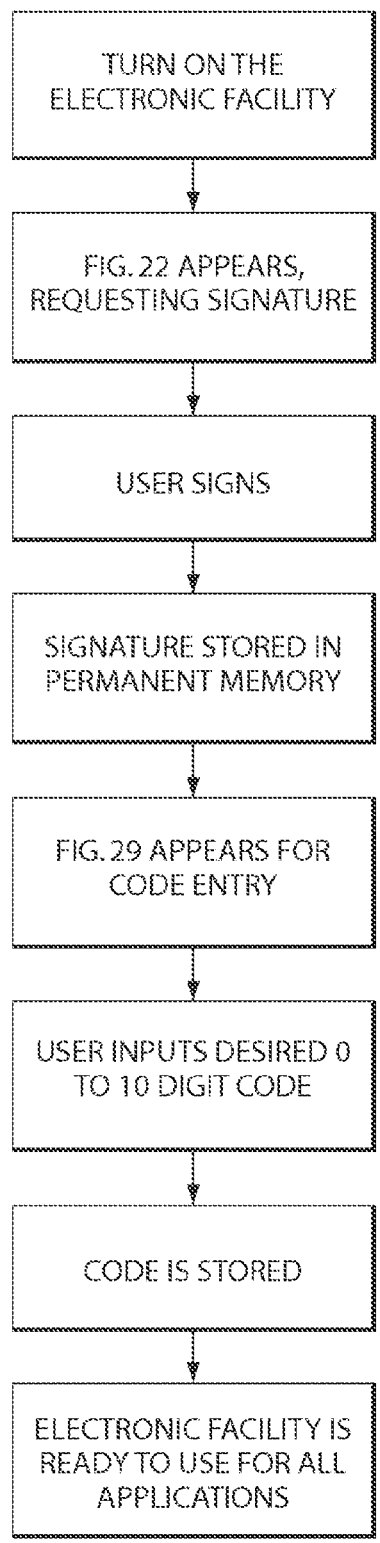
FIG. 34 outlines the initialization process for an electronic facility.

FIG. 34 outlines an initialization process for an electronic facility 101. When the electronic facility 101 is first purchased by the user, it may have a default security code that may be reset by any user. To initialize the electronic facility 101, the user may activate the power on/off switch 114, as shown in FIG. 1. The image shown in FIG. 21 may then appear on the display of the electronic facility 101. The user may write his or her signature on the display in the space indicated. This signature may be stored in nonvolatile RAM 110. Alternatively, the user may provide a personal identification number in lieu of a signature.

Next, the image shown in FIG. 22 will appear on the display of the electronic facility 101, requesting the user to input a code. The user may input a numeric code of any number of digits, such as 10 digits. In an alternate embodiment, the code may be an alphanumeric code and may be more or less than 10 characters. The user may enter the code by touching the numbers (or letters, where alphanumeric capabilities are provided) on the bottom of the display in the desired sequence. The user may use the "CLR" key to erase numbers erroneously entered. When the user is satisfied with the code, the user may use the "ENT" key to input the code into nonvolatile RAM 110. Thereafter, the electronic facility 101, including information stored within the electronic facility 101, may be unusable until the code is reentered. From time to time, the user may have to reenter the code to render usable both the electronic facility 101 and the information therein stored.

As an additional means of security, the service facility may require that the user who purchases or receives an electronic facility 101 register it with a main service facility 142 to receive a personal identification number (PIN). This number may be different from the security code entered by the user into the electronic facility 101 during initialization. Embodiments of security features are described more particularly below.

One purpose of the electronic device 101 is to provide the user with the ability to conduct a transaction with the service facility. The service facility may comprise one or more of a WSC server as defined by Pitroda (included above by reference), a credit card company, a bank, a department store, a travel service company, a gas station, a restaurant, a health service provider, or any other entity with which the user may want to conduct a transaction. A health service provider may comprise a treatment facility, a laboratory, a pharmacy, an emergency room, or any other facility associated with providing health or medical services.

In order to activate the electronic facility 101 for use with the service facility, the user of the electronic facility 101 may complete a normal qualification step required by the service facility. This qualification step may comprise a background check, a credit check, a validation of government-issued documents, or any other step associated with ascertaining the appropriateness of the user to be serviced by the service facility.

After the service facility qualifies the user, it may notify the user of the approval. The user may then connect the electronic facility 101 to an external connector 131, which may dial the number of a main service facility 142, or otherwise establish bi-directional communications with the main service facility 142 using, for example, the Internet or a dedicated private network, that is empowered by the service facility to transmit authorization data enabling the electronic facility 101 to function as a "credit card" or other type of "card" associated with the service facility.

Next, the service facility may identify the user through a PIN known a priori to both the user and the service facility. Alternatively, the service facility may identify the user through caller identification of the user's phone number. Similarly, identity may be established using, for example, a trusted third party service, such as provided by Verisign, Inc., authenticate each participant, and optionally establish secure communications among the participants.

Once the service facility has identified the user, it may transmit information to the electronic facility 101 via the external connector 131. This information may comprise a category in which the service facility is classified, a date of issuance, a date of expiration, a credit limit, a card number, a name of the service facility, and an image associated with institution.

The service facility may also receive information from the electronic facility 101 via the external connector 131. This information may be associated with the user, may be associated with the electronic facility 101, and may comprise a unique serial number of the electronic facility 101 and the encoded signature of the user of the electronic facility 101.

When the user is desirous of utilizing the electronic facility 101 to exercise a transactional method, the following sequence may take place: First, the user may turn on the power of the electronic facility 101. Optionally, the user may be prompted to enter the security code.

The electronic facility 101 may permit the user a fixed and limited number of attempts at entering the security code. When the user fails to enter the security code within the fixed and limited number of attempts, the card may deactivate itself in a manner that renders it unusable without reauthorization from the service facility. On the other hand, when the user enters the security code within the fixed and limited number of attempts, the display shown in FIG. 4 may appear. At this point, the user may select an option from a menu of choices that may comprise a credit card transaction, a bank card transaction, a retail credit transactions, a medical transaction, an insurance transaction, an action associated personal identification, an action associated with travel, an action associated with telephony, an action associated with coupon redemption, an action associated with a person-to-person financial transfer, an action associated with browsing merchandise, an action associated with paying a bill, and any other action associated with the service facility with which the electronic facility 101 be been activated for use.

The action associated with browsing merchandise may be one of checking for a bargain, checking for a discount, checking for a related product, and receiving promotional information. Any action selected by the user may invoke, exercise, or contribute to the completion of a transactional method.

One step in the transactional method may comprise receiving authorization from the service facility. This authorization may be generated by main service facility 142 on behalf of the service facility. The authorization may be contingent upon the verification of a signature, a code, or an approval. The authorization may be received at electronic facility 101 or support computer 134 via external connector 131.

Following the completion of a transactional method the electronic facility 101 may perform an action associated with account reconciliation.

Figure 45:
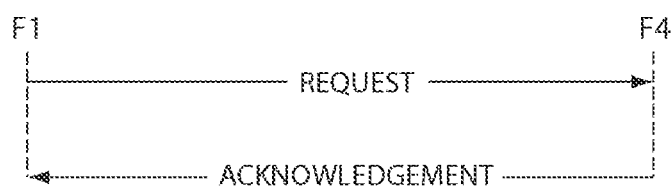
FIG. 45 depicts the steps in one transactional method according to the present invention.

Referring to FIG. 45, high-level steps are presented for a general transactional method in which a user may use an electronic facility 101 to conduct a transaction with another transaction participant. In this method, the user may initiate the transaction. This transactional method may involve two facilities, a first facility F1 and a fourth facility F4. In this transactional method, a request from the first facility F1 may be received by the fourth facility F4. The fourth facility may then transmit an acknowledgement to the first facility F1. Generally, the first facility F1 may comprise an electronic facility 101 and, thus, may be referred to as "the client facility." Generally, the fourth facility F4 may be the main service facility 142, which may be the service facility, which may be a transaction service facility, a "wallet service center", a financial service provider, and/or a bank. Security facilities for handling requests are described more particularly below.

This transactional method may be a method for providing to the first facility F1 a financial transaction service, wherein the request from the first facility F1 is a transaction request. This transactional method may further comprise a communication between the first facility F1 and the fourth facility F4.

Figure 46:
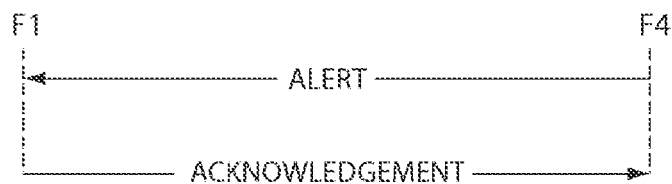
FIG. 46 depicts the steps in one transactional method according to the present invention.

Referring to FIG. 46, high-level steps are presented for another general transactional method in which a user can use an electronic facility 101 to conduct a transaction with another transaction participant (referred to in this paragraph as "the other participant"). In this method, the other participant may initiate the transaction. This transactional method may involve two facilities, the first facility F1 and the fourth facility F4. First, an alert may be transmitted from the fourth facility F4 to the first facility F1. Then, the fourth facility F4 may receive an acknowledgement from the first facility F1. In embodiments the alert may include a secure communication according to the security protocols and facilities described more particularly below.

Figure 6:
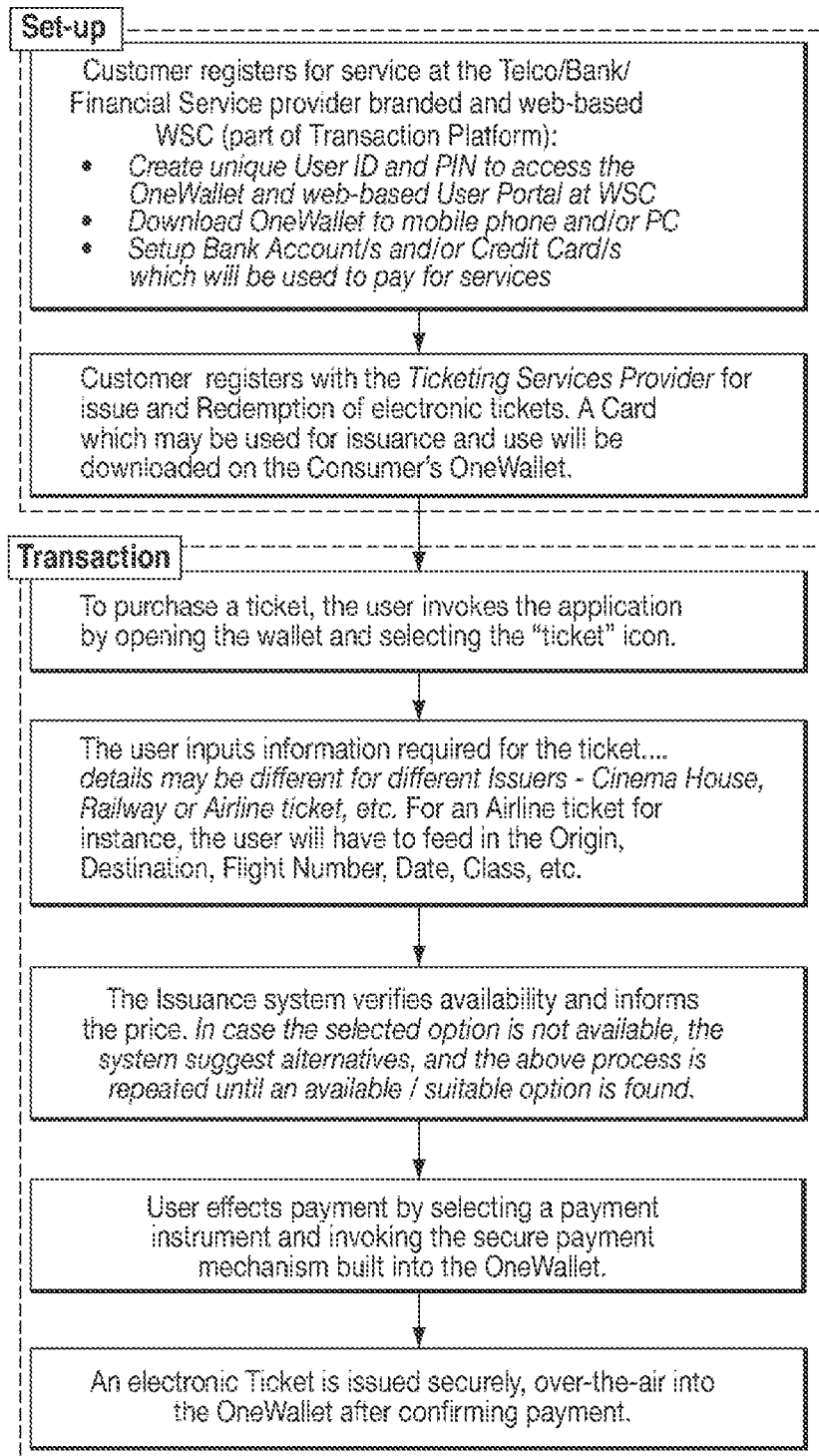
FIG. 6 is a generalized flow diagram illustrating the methodology for a ticket issuance process.

There are many types of business processes that can be supported by a system that has an electronic transactions facility 101. For example, FIG. 6 depicts a ticket issuance process where a user, perhaps in association with the client device 162, the merchant systems 170, and/or the main service facility 142, may be issued a ticket.

Figure 7:
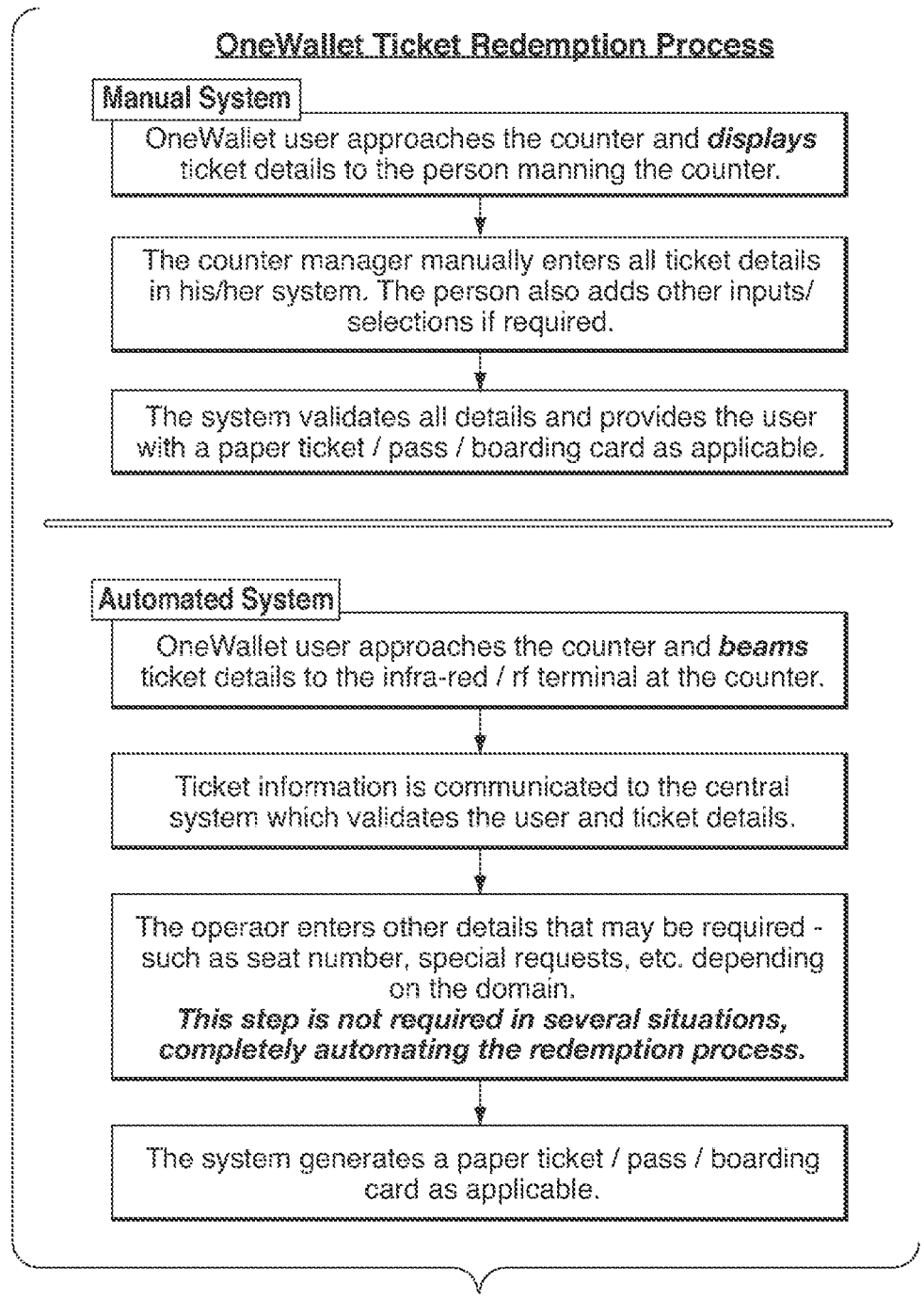
FIG. 7 is a generalized flow diagram illustrating the methodology for one potential exemplary embodiment of a ticket redemption process.

FIG. 7 depicts a ticket redemption process whereby a user, perhaps in association with the client device 162, the merchant system 170, and/or the main service facility 142, may redeem a ticket.

Figure 8:
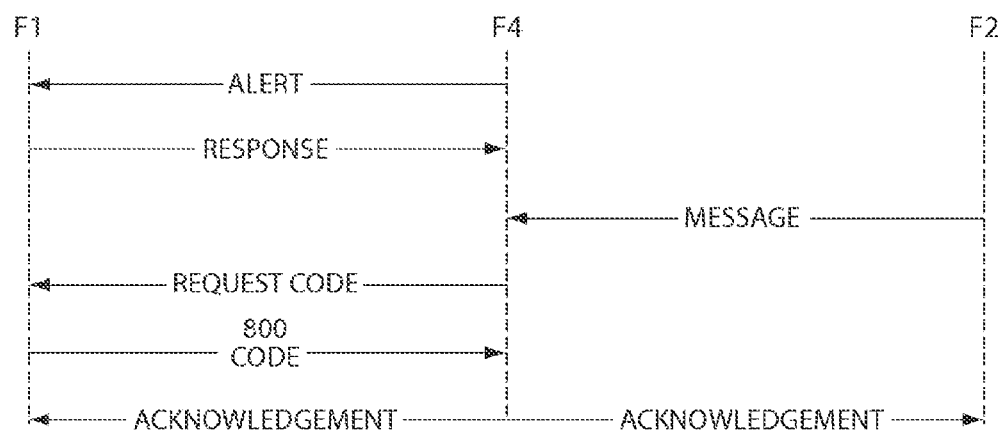
FIG. 8 depicts the steps in one transactional method according to one potential exemplary embodiment of the present invention.

Referring to FIG. 8, high-level steps are presented for a transaction in which a user can use an electronic facility 101 to conduct a transaction with another facility, wherein the transaction may involve the first step of bill presentment. This method may involve three facilities, the first facility F1, a second facility F2, and the fourth facility F4. In this transactional method, an alert associated with a pending transaction may be transmitted by the fourth facility F4 to the first facility F1. The fourth facility F4 may then receive a response from the first facility F1, wherein the response may be a request for direct settlement of the pending transaction associated. Next, the fourth facility F4 may receive a message from the second facility F2, wherein the message may comprise information pertaining to the transaction. Following that, the fourth facility F4 may send a request for a code to the first facility F1. Later, the fourth facility F4 may receive a code 800 from the first facility F1. The fourth facility F4 may determine the validity of the code 800. Finally, the fourth facility F4 may transmit an acknowledgement of the pending transaction being settled to both the first facility F1 and the second facility F2. In embodiments the communications include secure packets according to the security protocols and facilities described more particularly below.

In this context, the second facility F2 may be a merchant facility, or a transaction facility of any other seller, reseller, or other agent for the sale of goods, services, or combinations thereof that might financially transact with the user. The message received from the second facility F2 by the fourth facility F4 may further comprise an identifier that is unique to the second facility F2.

This method may be a method for providing the first facility F1 with the capability of transacting with the second facility F2. This method may be a method for providing the second facility F2 with the capability of first sending a bill to the first facility F1 and then receiving payment of the bill from the first facility F1.

In one example, the alert associated with a pending transaction may include a bill. In embodiments, this bill will include a detailed listing of all charges, taxes, service fees as well as a grand total. In some embodiments, the bill will be dynamic allowing a user to change the service fee to reflect the level of satisfaction with the service. In embodiments, the bill be presented as a graphical depiction of an actual entity. The code 800 may be a personal identifier, a password, a personal identification number, or any other confidential data known to the user and not generally known to other users.

Any of the steps of this transaction may be comprise the transmission of data (or a payload). The data may be without limitation the alert, the response, the message, the request for a code, the code, or the acknowledgement. The data may be transmitted in a secure fashion, such as via SSL, XML Encryption, SSH, and so forth. The bill may be a graphical replica of a physical bill, which may comprise branding, images, and information required to complete the transaction. The first facility F1 may securely store, such as in a smart card, a plurality of bills and may from time to time alert the user, such as with an audible alarm, when an attribute of the bill matches a preset criterion. In embodiments, the attribute may without limitation comprise the time of issuance of the bill, a specified number of days prior to the due date of the bill, the due date of the bill, the amount of the bill, the time of provision of the product or service associated with the bill, and so forth. The criterion may without limitation comprise a Boolean value indicating a user preference to receive an alert when the time of issuance of the bill matches the present time, a Boolean value indicating a user preference to receive an alert when the specified number of days prior to the due date of a bill matches the present day, a Boolean value indicating a user preference to receive an alert when the due date of the bill matches the present day, a Boolean value indicating a user preference to receive an alert when the amount of the bill is less than, equal to, or greater than a preset value, a Boolean value indicating a user preference to receive an alert when the time of provision of the product or service associated with the bill matches a preset time. The user may securely pay a bill using the client facility in real-time with on-line or off-line settlement, using a preferred mode of payment, at a preferred time and from a preferred location. The acknowledgement of the pending transaction may comprise a receipt or a replica of the bill with a "PAID" stamp. The client facility may securely store and/or archive the bill, such as by writing the bill to a smart card. Alternatively, a Web-based personalized portal may securely store and/or archive the bill, such as by encrypting the bill and storing it in an RDBMS. In some embodiments, a profile-driven value added service associated with the bill may be transmitted to the user by the personalized portal, such as a coupon offer for a competitive service related to a service for which the user just paid.

Figure 9:
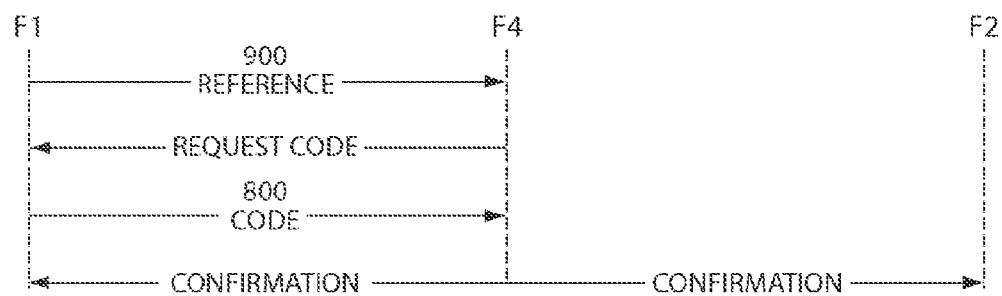
FIG. 9 depicts the steps in one transactional method according one potential exemplary embodiment of to the present invention.

Referring now to FIG. 9, high-level steps are presented for a transactional method in which a user can use an electronic facility 101 to conduct a transaction with another transaction participant, wherein the transaction may be a peer-to-peer asset transfer. This transactional method may involve three facilities, the first facility F1, a second facility F2, and fourth facility F4. In this transactional method, the fourth facility F4 may receive a reference 900 to the second facility F2 from the first facility F1. Then, the fourth facility F4 may send a request for a code to the first facility F1. Later, the fourth facility F4 may receive a code 800 from the first facility F1. The fourth facility F4 may determine the validity of the code 800. Following that, the fourth facility F4 may settle a transaction between the first facility F1 and the second facility F2. The fourth facility F4 may send a confirmation of the transaction to both the first facility F1 and the second facility F2. The communications of alerts and other information may be secure in accordance with the security facilities described more particularly below.

This method may be a method for providing a person-to-person asset transfer from first facility F1 to second facility F2. Within the context of this method, the second facility F2 may be an electronic facility 101. The reference 900 to a second facility may be an identifier, which may be a unique identifier. More generally, a number of variations, additions, and omissions to the above method will be readily apparent, and are intended to fall within the scope of the methods and systems described herein.

Figure 18:
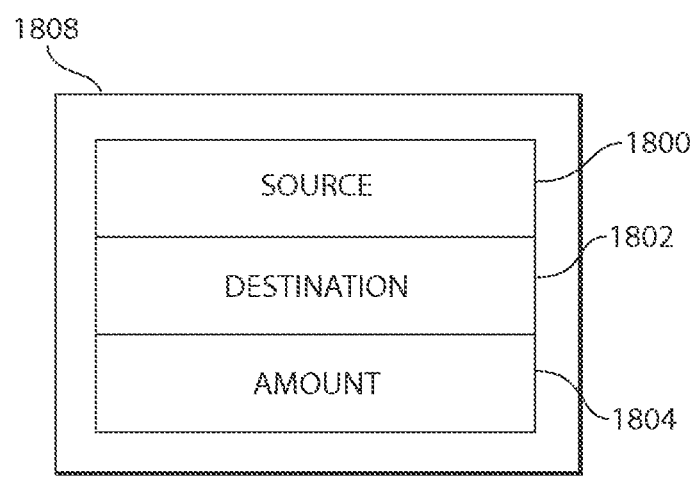
FIG. 18 depicts a data representative structure of one potential exemplary embodiment of a request for funds transfer.

Some transactional methods effect the transfer of funds between two facilities. Referring now to FIG. 18, a common element in these methods may be a funds transfer request data structure 1808. A funds transfer request 1808 may comprise a reference to a source facility 1800, a reference to destination facility 1802, and a transfer amount 1804. The references 1808 and 1802 may be identical in type to reference 900. The data structure 1808 may also include a header to identify the type of data contained within the packet. Embodiments of such data structures are described more particularly below.

Returning to FIG. 9 and subsequent figures, in embodiments, the fourth facility F4 may securely issue a payment token, which may comprise an electronic replica of a payment such as an image of a payment stub, directly to the client facility. This payment token may comprise branding, images, and other information required to complete a transaction. The request for a code that is sent to the first facility F1 may comprise this payment token. In all, this transactional method may enable the user of the client facility, which may be first facility F1, to pay another user of a similar client facility, which may be second facility F2. This payment may or may not comprise a proximity transaction. In any case, the client facility and/or the similar client facility may send and/or receive from the fourth facility F4 via an over-the-air facility, such as IEEE 802.11, IEEE 802.16, and so forth. This transactional method may securely settle a transaction in real time with on-line or off-line settlement by securely debiting a financial account associated with the first facility F1 and by securely crediting a financial account associated with the second facility F2. This debiting and/or crediting may be conducted by the forth facility F4. The confirmation of the transaction may comprise a receipt and/or an electronic replica of a transaction summary statement, such as that commonly printed on a slip of paper by an automated teller machine (ATM) and provided by the ATM to the user of the ATM at the conclusion of a transaction. The confirmation of the transaction may be sent securely and/or may comprise a "PAID" stamp. The client facility may securely store and/or archive the confirmation of the transaction, such as by writing the confirmation to a smart card. Alternatively, a Web-based personalized portal may securely store and/or archive the confirmation, such as by encrypting the bill and storing it in a RDBMS. In some embodiments, a profile-driven value added service associated with the confirmation of the transaction may be transmitted to the user via the personalized portal, such as a promotional offer targeted to the demographic of the user.

Figure 10:
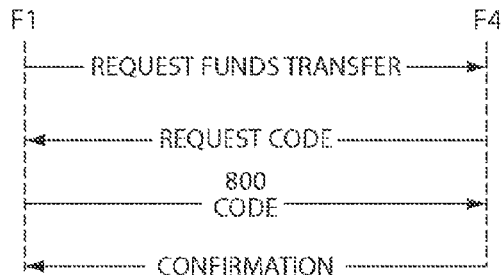
FIG. 10 depicts the steps in one transactional method according to one potential exemplary embodiment of the present invention.

Referring now to FIG. 10, high-level steps are presented for a transactional method in which a user can use an electronic facility 101 to conduct a transaction with another transaction participant, wherein the transaction may be a transfer of assets from one facility to another such as a funds transfer from one bank account to another. This transactional method may involve two facilities, the first facility F1 and the fourth facility F4. In this transactional method, the fourth facility F4 may receive a request for funds transfer from a first facility F1. Then, the fourth facility F4 may send a request for a code to the first facility F1. Later, the fourth facility F4 may receive a code 800 from the first facility F1. The fourth facility F4 may determine the validity of the code 800. Following that, the fourth facility F4 may initiate a funds transfer from first facility F1 to another facility. The fourth facility F4 may send a confirmation of the transaction to the first facility F1.

This method may be a method for providing a funds transfer from one financial account to another. The request for funds transfer may comprise a funds transfer request data structure 1808. In this context, the reference to a source facility 1800 may be a reference to first facility F1 and the reference to a destination facility 1802 may be a reference to another facility.

In embodiments, the fourth facility F4 may securely issue an electronic replica of a money transfer token, which may comprise necessary branding, images, and/or information required to complete the transaction. The request for a code that is sent to the first facility F1 may comprise the electronic replica of a money transfer token. The first facility F1 may securely initiate the transaction by securely sending the funds transfer request over the air. The fourth facility F4 may validate the user and the request, such as by requesting, receiving, and validating the code. The funds transfer from the first facility F1 may be to another facility that may be hosted by a different financial service provider, bank, wallet service center, or transaction service facility. The fourth facility F4 may request (not shown) that the different financial service provider complete the funds transfer through a particular settlement and/or acquisition network. The confirmation of the transaction may comprise an electronic replica of a transaction summary statement, which may comprise a "PAID" stamp and/or receipt. As previously described, the client facility may securely store and/or archive the confirmation of the transaction, or a Web-based personalized portal may securely store and/or archive the confirmation. In some embodiments, also as described above, a profile-driven value added service associated with the confirmation of the transaction may be transmitted to the user via the personalized portal. The recipient of the funds transfer, described above as "another facility", may comprise an electronic facility 101 and may be able to use the funds transferred by the user of the first facility F1. For example, in a subsequent transaction, the "another facility" may be the first facility F1 and may participate in the subsequent transaction according to one of the transactional methods of the present invention.

Figure 11:
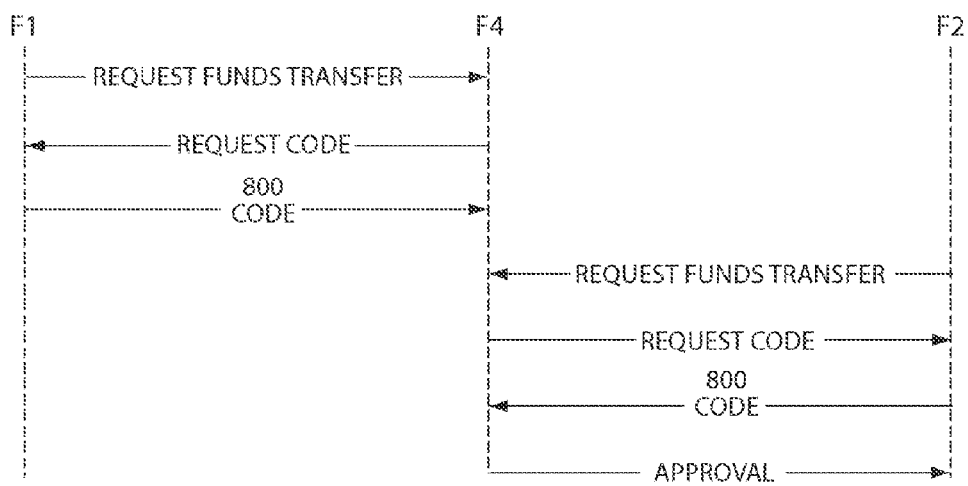
FIG. 11 depicts the steps in one transactional method according to one potential exemplary embodiment of the present invention.

Referring now to FIG. 11, high-level steps are presented for a transactional method in which a user can use an electronic facility 101 to conduct a transaction with another transaction participant, wherein the transaction may comprise the transmission of a money order. This transactional method may involve three facilities, the first facility F1, a second facility F2, and the fourth facility F4. In this transactional method, the fourth facility F4 may receive a request for funds transfer from the first facility F1. Then, the fourth facility F4 may send a request for a code to the first facility F1. Later, the fourth facility F4 may receive a code 800 from the first facility F1. The fourth facility F4 may then receive a request for funds transfer from a second facility F2. Then, the fourth facility F4 may send a request for a code to the second facility F2. Later, the fourth facility F4 may receive a code 800 from the second facility F2. Finally, the fourth facility F4 may send an approval to the second facility F2. At any time after receiving a code 800 but prior to sending the approval, the fourth facility F4 may determine the validity of the code 800.

This method may be a method for transmitting a money order or conducting a wire transfer. Both the request for funds transfer received from the first facility F1 and the request for funds transfer received from the second facility F2 may comprise a funds transfer request data structure 1808. In this context, the reference to a source facility 1800 may be a reference to first facility F1 and the reference to a destination facility 1802 may be a reference to second facility F2.

The approval may be an approval to release funds. The first facility F1 may be a sender facility, which may be a merchant. In this context, the second facility F2 may be a destination facility, which may also be a merchant, and may comprise an electronic facility 101.

In embodiments, the fourth facility F4 may securely issue an electronic replica of a money order, which may comprise necessary branding, images, and/or information required to complete the transaction. The request for a code that is sent to the first facility F1 may comprise the electronic replica of a money transfer token. The first facility F1 may securely initiate the transaction by securely sending the funds transfer request over the air. The fourth facility F4 may validate the user and the request, such as by requesting, receiving, and validating the code. The funds transfer from the first facility F1 may be to another facility that may be hosted by a different financial service provider, bank, wallet service center, or transaction service facility. The fourth facility F4 may request that the different financial service provider complete the funds transfer through a particular settlement and/or acquisition network. The confirmation of the transaction may comprise an electronic replica of a transaction summary statement, which may comprise a "PAID" stamp and/or receipt. As previously described, the client facility may securely store and/or archive the confirmation of the transaction, or a Web-based personalized portal may securely store and/or archive the confirmation. In some embodiments, also as described above, a profile-driven value added service associated with the confirmation of the transaction may be transmitted to the user via the personalized portal. The recipient of the funds transfer, described above as "another facility", may comprise an electronic facility 101 and may be able to use the funds transferred by the user of the first facility F1. For example, in a subsequent transaction, the "another facility" may be the first facility F1 and may participate in the subsequent transaction according to one of the transactional methods of the present invention.

It will be appreciated that transactions described herein, including the financial transactions described above, as well as health care transactions, information transfers, and so on, may be compliant with standards-based transaction protocols. For example, certain financial transactions may be conducted in whole or in part using the XML-based SWIFT protocol. Similarly, by law certain health care information must be handled in a manner compliant with the requirements of the Health Insurance Portability and Accountability Act ("HIPAA"), which handling may be applied as a protocol to transactions described herein that involve health care information among parties covered by HIPAA.

Figure 12:
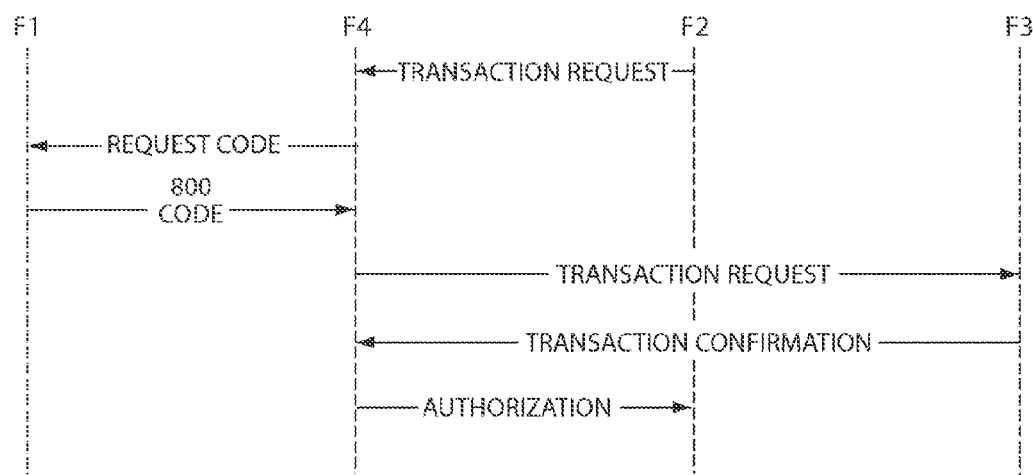
FIG. 12 depicts the steps in one transactional method according to one potential exemplary embodiment of the present invention.

Referring now to FIG. 12, high-level steps are presented for a transactional method in which a user can use an electronic facility 101 to conduct a transaction with another transaction participant, wherein the transaction may be a method for conducting a purchase, which may be an activation of a prepaid shopping card, a recharge of a prepaid shopping card, a top-up of a prepaid cell phone, or any other transaction resulting in the transfer of money or credits into or out of a debit facility associated with consumption. This transactional method may involve four facilities, the first facility F1, a second facility F2, a third facility F3, and the fourth facility F4. In this transactional method, the fourth facility F4 may receive a transaction request from the second facility F2. Then, the fourth facility F4 may send a request for a code to the first facility F1. Later, the fourth facility F4 may receive a code 800 from the first facility F1. The fourth facility F4 may determine the validity of the code 800. Next, the fourth facility F4 may transmit a transaction request to the third facility F3. Subsequently, the fourth facility F4 may receive a transaction confirmation from the third facility F3. Finally, the fourth facility F4 may transmit a transaction authorization to the second facility F2.

The transaction request received from the second facility F2 may be associated with the first facility F1 and the third facility F3. In this context, the second facility F2 may be a merchant facility, the user of the first facility F1 may be a customer, and the third facility F3 may be a supplier facility.

The second facility F2 or the third facility F3 may securely issue an electronic replica of a prepaid airtime token directly to the client facility, which as has been mentioned may be the first facility F1. The replica may comprise branding, images, and/or information required to complete the transaction. The request for the code may comprise the electronic replica. The user of the client facility may securely top-up and/or replenish an airtime account by selecting a preconfigured time/amount package, such as a 100-minute plan offered at $10. Alternatively, the user may specify a desired time/amount, such as by touching a combination of numbers displayed on the LCD/touchpad. In any case, the user may select a preferred mode of payment, such as a credit card associated with the client facility. The fourth facility F4 may validate the user such as by determining the validity of the code 800 received from the first facility F1. Upon the completion of the transaction, minutes or an amount may be credited to an account associated with the user. A telephone company, which may comprise the third facility F3, may host this account. Moreover, the same minutes or amount may be debited from an account associated with the second facility F2. This account may be an account that the merchant facility (the second facility F2) has with the supplier facility/Telco (the third facility F3). Any or all of the sending, receiving, or transmitting of this method may be secure. This transactional method may comprise the transmission of an electronic replica of a transaction summary statement, which, as in previously described transactional methods, may comprise a "PAID" stamp and/or receipt. As previously described, the client facility may securely store and/or archive the confirmation of the transaction, or a Web-based personalized portal may securely store and/or archive the confirmation. In some embodiments, also as described above, a profile-driven value added service associated with the confirmation of the transaction may be transmitted to the user via the personalized portal.

Figure 13:
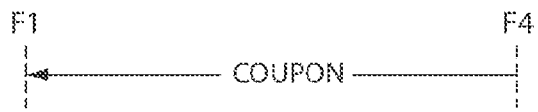
FIG. 13 depicts the steps in one transactional method according to one potential exemplary embodiment of the present invention.

Referring now to FIG. 13, high-level steps are presented for a transactional method in which a user can use an electronic facility 101 to conduct a transaction with another transaction participant, wherein the transaction may comprise the transmission of a coupon, loyalty card, or promotion to the electronic facility 101. This transactional method may involve two facilities, the first facility F1, which may without limitation comprise the user's client facility, and the fourth facility F4, which may without limitation comprise the merchant, service provider, or Telco. The fourth facility F4 may transmit a coupon to the first facility F1. This transmission may or may not be secure. This transmission may be broadcast to all electronic facilities, to all electronic facilities associated with a particular geographic region, to all electronic facilities that have stored a particular type of credit card or have conducted a particular type of transaction. The coupon, loyalty card, or promotion may be an electronic replica of the same and may comprise necessary branding, images, or information required to procure relevant services from the merchant, service provider, or Telco. The first facility F1 may securely store and/or archive the coupon, loyalty card, or promotion. The first facility F1 may from time to time alert, such as with an audible alarm, the user based upon when an attribute of the coupon, loyalty card, or promotion matches a preset criterion. The criterion may without limitation comprise a Boolean value indicating a user preference to receive an alert when the time of issuance of the coupon, loyalty card, or promotion matches the present time, a Boolean value indicating a user preference to receive an alert when the specified number of days prior to the expiration date of a coupon, loyalty card, or promotion matches the present day, a Boolean value indicating a user preference to receive an alert when the expiration date of the coupon, loyalty card, or promotion matches the present day, and so forth. The user of the first facility F1 may securely redeem the coupon, loyalty card, or promotion that may be stored in the first facility F1 via a proximity medium, such as without limitation IrDA, or an over the air medium, such as without limitation IEEE 802.16. The fourth facility F4 may securely issue an electronic replica of a loyalty statement, such as a transaction summary, that may comprise a "PAID" stamp and/or receipt, directly to the first facility F1. The first facility F1 may securely store and/or archive, such as by writing to a smart card, an electronic replica of a statement, such as a transaction summary. Alternatively, as described above, a Web-based personalized portal may securely store and/or archive the statement. In some embodiments, also as described above, a profile-driven value added service associated with the statement may be transmitted to the user via the personalized portal.

Figure 14:
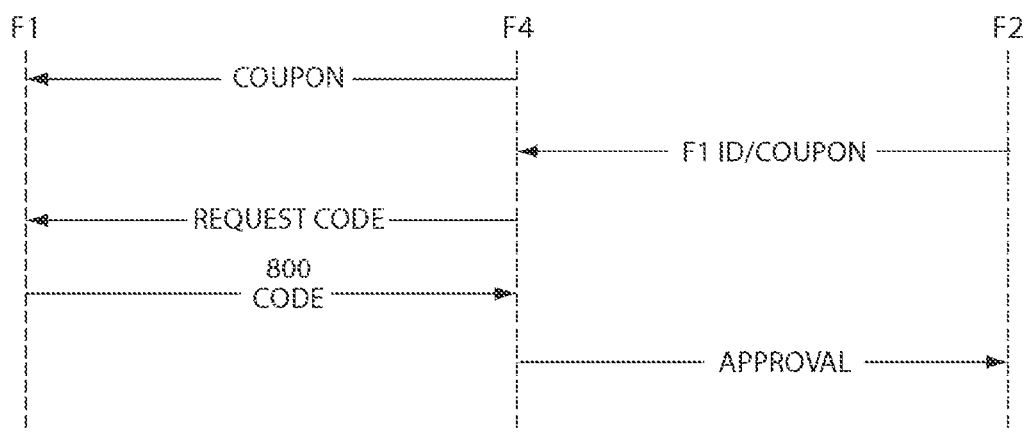
FIG. 14 depicts the steps in one transactional method according to one potential exemplary embodiment of the present invention.

Referring now to FIG. 14, high-level steps are presented for a transactional method in which a user can use an electronic facility 101 to conduct a transaction with another transaction participant, wherein the transaction may comprise the redemption of a coupon. This transactional method may involve three facilities, the first facility F1, a second facility F2, and the fourth facility F4. In this transactional method, a fourth facility F4 (such as the facility of a merchant offering a coupon) may transmit a coupon to the first facility F1 (such as the facility of a customer who wishes to have the coupon). Then, the fourth facility F4 may receive a message from the second facility F2 (such as a wallet service center), the message comprising an identifier of or reference to the first facility F1 and information associated with the coupon, such as a unique identifier associated with the coupon/user combination. The fourth facility F4 may then send a request for a code (such as a security code, identifier, or password) to the first facility F1, and the first facility F1 may return a suitable code 800 to the fourth facility F4. The fourth facility F4 may determine the validity of the code 800. Finally, a coupon redemption approval is transmitted by the fourth facility F4 to the second facility F2, at which point the second facility may redeem the coupon, such as by applying it toward a transaction that is supported by the second facility F2 and that is executed by the user of the first facility F1.

In this context, the second facility F2 may be a merchant facility, which may comprise a facility for recognizing coupons, which may be one of a barcode scanner, an RFID reader, a magnetic stripe reader, an IrDA facility, a Bluetooth® facility, or any other wired wireless, optical, electro-magnetic, or other facility suitable for use in coupon recognition. The information associated with the coupon may be an identifier, which may be a unique identifier.

Figure 15:
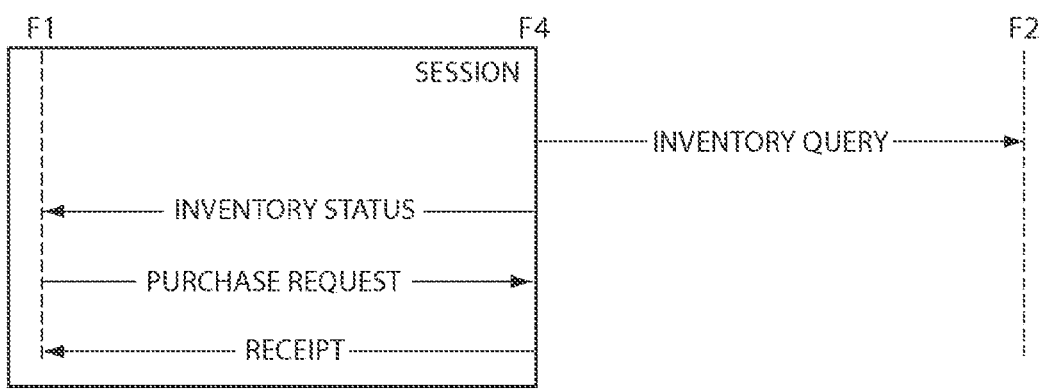
FIG. 15 depicts the steps in one transactional method according to one potential exemplary embodiment of the present invention.

Referring now to FIG. 15, high-level steps are presented for a transactional method in which a user can use an electronic facility 101 to conduct a transaction with another transaction participant, wherein the transaction may comprise the purchase of a ticket by the user. This transactional method may involve three facilities, the first facility F1, a second facility F2, and the fourth facility F4. In this transactional method, the fourth facility F4 may establish a session with a first facility F1. Then, the fourth facility F4 queries the inventory of the second facility F2. This query results in the fourth facility F4 being privy to certain details of the inventory of the second facility F2. The fourth facility F4 transmits an inventory status report to a first facility F1. The inventory status report may comprise certain details of the inventory of the second facility F2. The fourth facility F4 then receives a purchase request from the first facility F1. The fourth facility F4 may act to effect this purchase. Finally, the fourth facility F4 may transmit a receipt to the first facility F1.

In this context, the first facility F1 may be a consumer facility and the second facility F2 may be a supplier facility, which may be a ticket issuing facility. The method may further comprise the step of issuing a ticket to the first facility F1. The purchase request may be a ticket order. The inventory status report may comprise a ticket availability report. The session may be a secure session.

In embodiments, the ticket issuing facility may securely issue the ticket, which may comprise an electronic replica of a ticket. The ticket may comprise branding, images, or information required to procure associated services from the ticket issuing facility. The first facility F1 may securely store, such as by writing to a smart card, the ticket. The first facility F1 may from time to tile alert, such as with an audible alarm, the user based upon when an attribute of the ticket matches a preset criterion. The criterion may without limitation comprise a Boolean value indicating a user preference to receive an alert when the time of issuance of the ticket matches the present time, a Boolean value indicating a user preference to receive an alert when the specified number of days prior to an event date of an event associated with the ticket, such as the date of a live performance to which the ticket may allow admittance, matches the present day, a Boolean value indicating a user preference to receive an alert when the event date of an event associated with the ticket matches the present day, and so forth. The user may securely redeem the ticket that may be stored in the first facility F1 at a point of transaction, such as a turnstile at the entrance to the event, via a proximity medium or an over-the-air medium. The ticket issuing facility may securely issue a transaction summary statement, which may comprise a "PAID" stamp, and/or a receipt to the consumer facility. The first facility F1 may securely store and/or archive, such as by writing to a smart card, the transaction summary statement and/or receipt. Alternatively, as described above, a Web-based personalized portal may securely store and/or archive the transaction summary statement and/or receipt. In some embodiments, also as described above, a profile-driven value added service associated with the statement may be transmitted to the user via the personalized portal.

Figure 16:
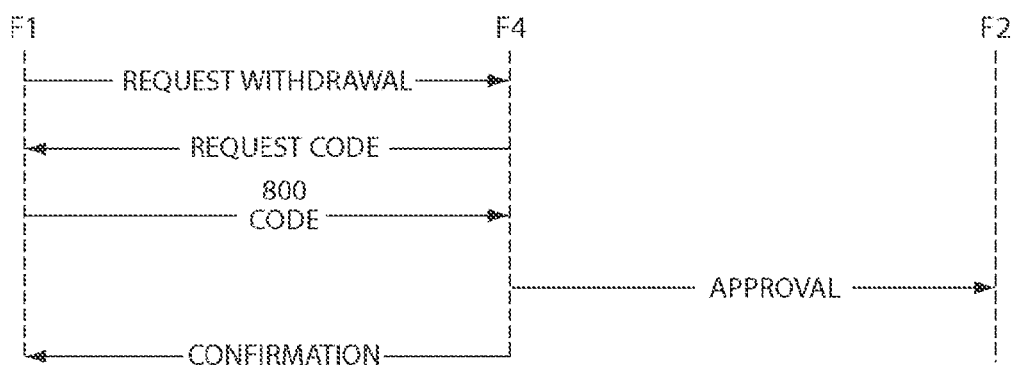
FIG. 16 depicts the steps in one transactional method according to one potential exemplary embodiment of the present invention.

Referring now to FIG. 16, high-level steps are presented for a transactional method in which a user can use an electronic facility 101 to conduct a transaction with another transaction participant, wherein the transaction may comprise the withdrawal of funds from an account. The transactional method may involve three facilities, the first facility F1, a second facility F2, and the fourth facility F4. In this transactional method, the fourth facility F4 receives a request for withdrawal from an account associated with the first facility F1. The fourth facility F4 may then send a request for a code to the first facility F1. Later, the fourth facility F4 may receive a code 800 from the first facility F1. The fourth facility F4 may determine the validity of the code

800. The fourth facility F4 may effect a withdrawal of funds from an account associated with the first facility F1. Then, the fourth facility F4 may transmit to the second facility F2 an approval. Finally, the fourth facility F4 may transmit a confirmation to the first facility F1.

The method may be a method for withdrawing money from an account. The approval may be an approval to accept funds that are associated with the first facility F1. The confirmation may be a confirmation of withdrawal. The request for withdrawal may comprise a funds transfer request data structure 1808. In this context, the reference to a source facility 1800 may be first facility F1 and the reference to a destination facility 1802 may be a reference to second facility F2. The second facility F2 may be a merchant facility.

Figure 17:
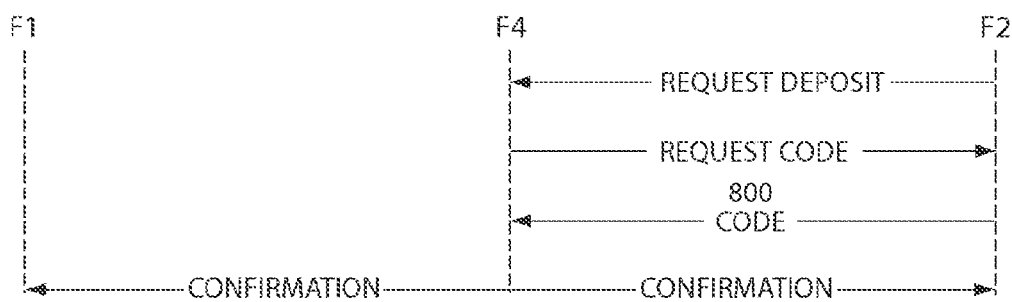
FIG. 17 depicts the steps in one transactional method according to one potential exemplary embodiment of the present invention.

Referring now to FIG. 17, high-level steps are presented for a transactional method in which a user can use electronic facility 101 to conduct a transaction with another transaction participant, wherein the transaction may comprise a deposit of funds into an account. The transactional method may involve three facilities, the first facility F1, a second facility F2, and the fourth facility F4. In this transactional method, the fourth facility F4 receives a request to deposit funds into an account associated with the first facility F1. The fourth facility F4 may then send a request for a code to the second facility F2. Later, the fourth facility F4 may receive a code 800 from the second facility F2. The fourth facility F4 determine the validity of the code 800. Next, the fourth facility may effect a deposit of funds associated with the second facility F2 into an account associated with the first facility F1. Finally, the fourth facility F4 may send a confirmation of the deposit to both the first facility F1 and the second facility F2.

The request to deposit funds may comprise a funds transfer request data structure 1808. In this context, the reference to a source facility 1800 may be a reference to second facility F2 and the reference to a destination facility 1802 may be a reference to first facility F1. In this context, the second facility F2 may be a merchant facility. This method may be a method for depositing money into an account.

Generally, the transactional methods herein described, in particular those described above in FIGS. 6, 7, 8, 9, 10, 11, 12, 13, 14, 15, 16, 17, and 18, may be embodied as a transactional service such as and without limitation, a driver's license service, a lottery service, a voting service, a health service, a travel service, an infotainment service, a personal information management service, and so forth.

Figure 23:
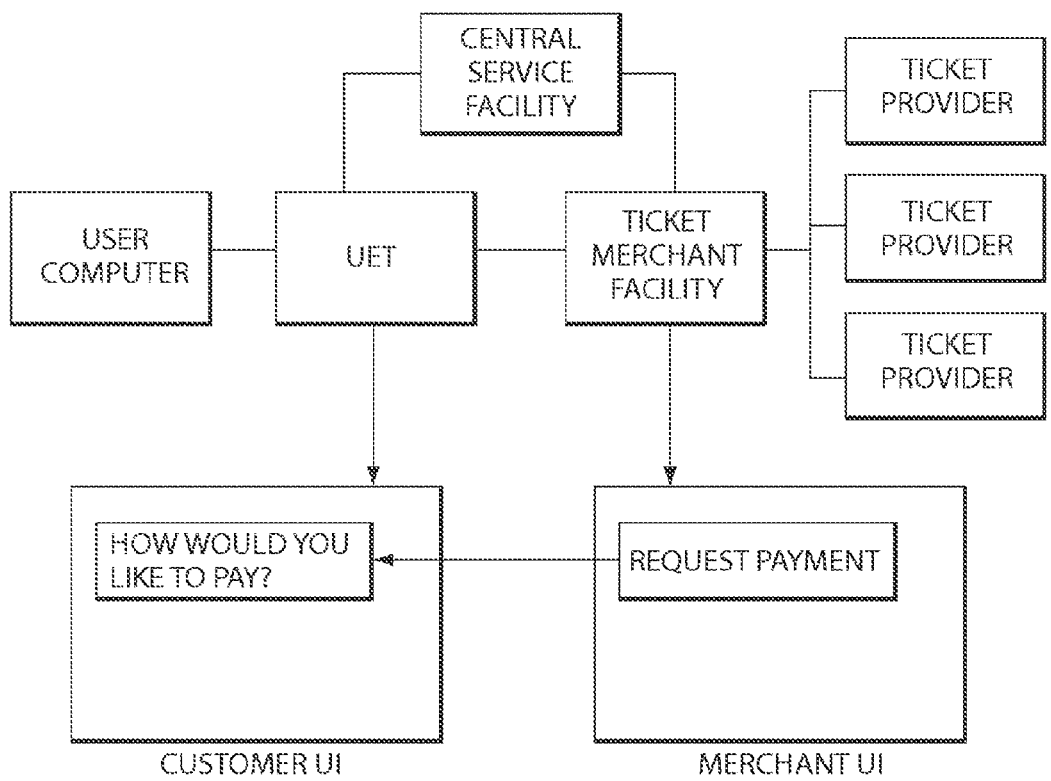
FIG. 23 depicts one potential exemplary embodiment of a ticketing service deployed using the electronic transaction platform.

FIG. 23 shows one potential exemplary embodiment of a ticketing service deployed using the systems described herein. A ticketing service system may include a universal electronic transaction facility ("UET") including a customer user interface, a central service facility, a ticket merchant facility including a merchant user interface, a user computer, and a plurality of ticket providers. As illustrated in FIG. 23, the system may be used to conduct a ticket purchase including a request for payment from the merchant and a payment authorization by the customer. However, it will be readily appreciated that the system may be used for any ticket-related service including related financial transactions, reservation requests, purchases, reservation changes, travel itinerary tracking and revisions, scheduling, and so forth. All such related transactions and transaction types are intended to fall within the scope of ticketing services as described herein.

The UET may contain data for a ticketing service. For example, the UET may store travel preferences related to reservation requests, such as a preference for non-stop versus least expensive tickets, meal preferences, seating preferences, or a default request for a rental car or limousine at a travel destination. As another example, the UET may store money in digital form, or credit card account and authorization for payment-based ticketing transactions. As another example, the UET may store tickets and or reservations for a user of the UET.

The customer user interface may be rendered on or by the UET. In the example of the figure, the UET may use financial information to respond to the request for payment from the ticket merchant facility. In general the customer user interface may include any features associated with an interface, such as text fields, buttons, drop down lists, check boxes, and the like, for navigation and use by the user. The user interface may be dynamically generated in response to information received from the ticket merchant facility, such as a drop down list of available flights, or seats available at an event.

The ticket merchant facility may operate at a point of sale, such as entry into a concert, or may be near a point of sale, such as an information or ticket counter at an airport, or may be a stand alone ticket-ordering location. The ticket merchant facility may be associated with a specific venue or business, or may be an agent or reseller for a plurality of ticket providers. Where other ticket providers issue tickets, these ticket providers may communicate with the ticket merchant facility to provide scheduling and availability information, and to provide back-end processing and ticket issuance for tickets that have been purchased.

In the example of the figure, the ticket merchant facility may provide a user interface to an employee of the merchant (or other authorized user), who may operate the user interface to conduct a ticketing transaction with the user of the UET. The merchant user interface may be rendered on a device that includes the ticket merchant facility, or a related or peripheral device. In one embodiment, the merchant user interface is rendered on a desktop computer, and may be, for example, a browser-based user interface. In general the merchant user interface may include any features associated with an interface, such as text fields, buttons, drop down lists, check boxes, and the like, for navigation and use by the employee. In an embodiment, where the UET is running on a cellular telephone, the system and method may further comprise establishing an audio communication between the user's cellular telephone and the merchant's telephone to facilitate the transaction between the merchant employee and the user.

The central service facility coordinates transactions between the UET and the ticket merchant facility as described generally above, and may provide or support any related authentication, authorization, security, financial, or other functions associated with the ticketing transaction.

The user computer may optionally participate in the ticketing service, and may be used by the user to program or provide data to the UET. The user computer may also independently connect through a network such as the PSTN or the Internet to the central service facility, the ticket merchant facility, and/or the ticket providers to conduct network-based transactions. This includes transactions relating to the ticketing service such as, for example, adding cash or credit pre-approval to the UET for anticipated ticket purchases. Tickets may also be purchased online, and then transferred to the UET for subsequent use by the customer at a related venue.

In general, the ticketing service described herein may be used for tickets of any form, such as tickets for traveling on a train, bus, airplane, boat, or other transportation medium, as well as tickets to a movie, a theater performance, a sporting event, a concert, a trade show, a conference, and so on.

Figure 24:
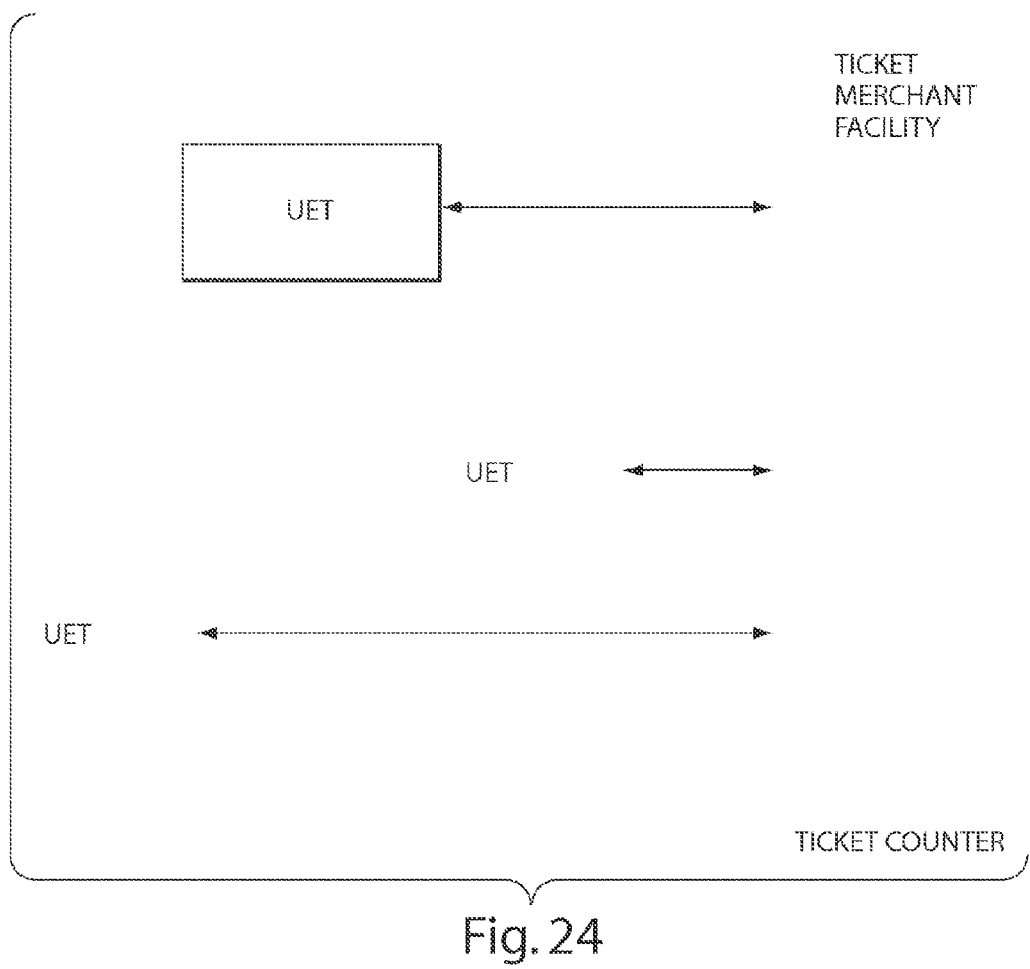
FIG. 24 depicts one potential exemplary embodiment of a ticketing service environment including a number of universal electronic transaction facilities.

FIG. 24 depicts a ticketing service environment including a number of universal electronic transaction facilities. The system may include a plurality of universal electronic transaction facilities ("UETs") and a ticket counter including at least one ticket merchant facility. Each UET may be carried, for example, by an individual holding and/or wishing to acquire one or more tickets or reservations.

This system may be employed for a number of ticketing services. In one embodiment, the ticketing service is an airline ticketing service. In this embodiment, the UET and ticket merchant facility may cooperate to render related services, such as check-in, baggage checking, and passenger seating. The UET may also coordinate authentication of the customer's identity at various times (i.e., during check-in and/or boarding). The customer's ticket may be resident on the UET, and may transferred to an airline at some time during the travel activity, such as while boarding the airplane. Or the ticket may be retrieved by the airline at check-in, and replaced by a boarding pass identifying a particular seat on a particular flight at a particular gate in an airport. The UET may also be used to provide payment for ticketing services, including travel tickets as well as change fees, seat upgrades, and so on. Through the customer user interface, a traveler may make additional travel plans, such as reservations for a rental car, a hotel, and/or a restaurant, either in communication with the ticket merchant facility, or a kiosk or other location including another merchant facility.

More generally, a travel service may include the ticketing service described above and/or a number of related travel services. For example, flight status, destination weather conditions, departure times, and gate information may be wirelessly communicated to a customer's UET when a ticket is purchased, or when a customer checks in for a flight, and may be periodically updated when the UET has wireless access to the ticket merchant facility or a related network, such as a wireless local area network offered throughout an airport, or at specific locations within an airport. As another example, reservations for cars, hotel rooms, meals, entertainment may be arranged while a customer is checking in, or may be entered by a customer into the customer's UET and then transmitted or negotiated when wireless service is available. Traveling companions such as a family, a group of friends on a vacation, or a group of professionals on a business trip, may also maintain a buddy list of co-travels for which travel, location, itinerary, and status information are shared. This information may also be shared among a group of UETs in a peer network, or when a wireless network connection is available to one or more of the UETs. Buddy-list information such as travel information may also, or instead, be maintained at the central service facility (not shown) for access by buddy list members.

In another embodiment, the ticketing service may be a sports event ticketing service. In this embodiment, a user may reserve one or more seats to a sporting event at a kiosk, or at the ticket counter of an associated venue. At the ticket counter, the UET may also be employed to convert a reservation, which may be stored on the UET or uniquely identified by data on the UET, into a ticket for entry into the event.

In a peer-to-peer embodiment of a ticketing service system, a number of UETs of individual customers may cooperate in a ticket acquisition. For example, one customer may purchase a group of tickets, which may then be distributed to individual UETs through a peer network. Similarly, a customer at one UET may distribute reservations and/or cash to other UETs through a peer network, enabling each customer to convert the reservation and cash into a ticket independently at the ticket counter or other location.

While the ticket counter may be a conventional ticket counter including a ticket window with a teller or other employee, the ticket counter may also, or instead, include a virtual ticket counter. This may be a designated and/or market space within an entrance area of a venue, or may be embedded into entranceways so that ticketing and/or check-in events occur automatically when UET holders cross a physical threshold during passage into the venue. This may, for example, advantageously decrease bottlenecks at certain entry points into venues such as sports stadiums or concert halls.

Figure 25:
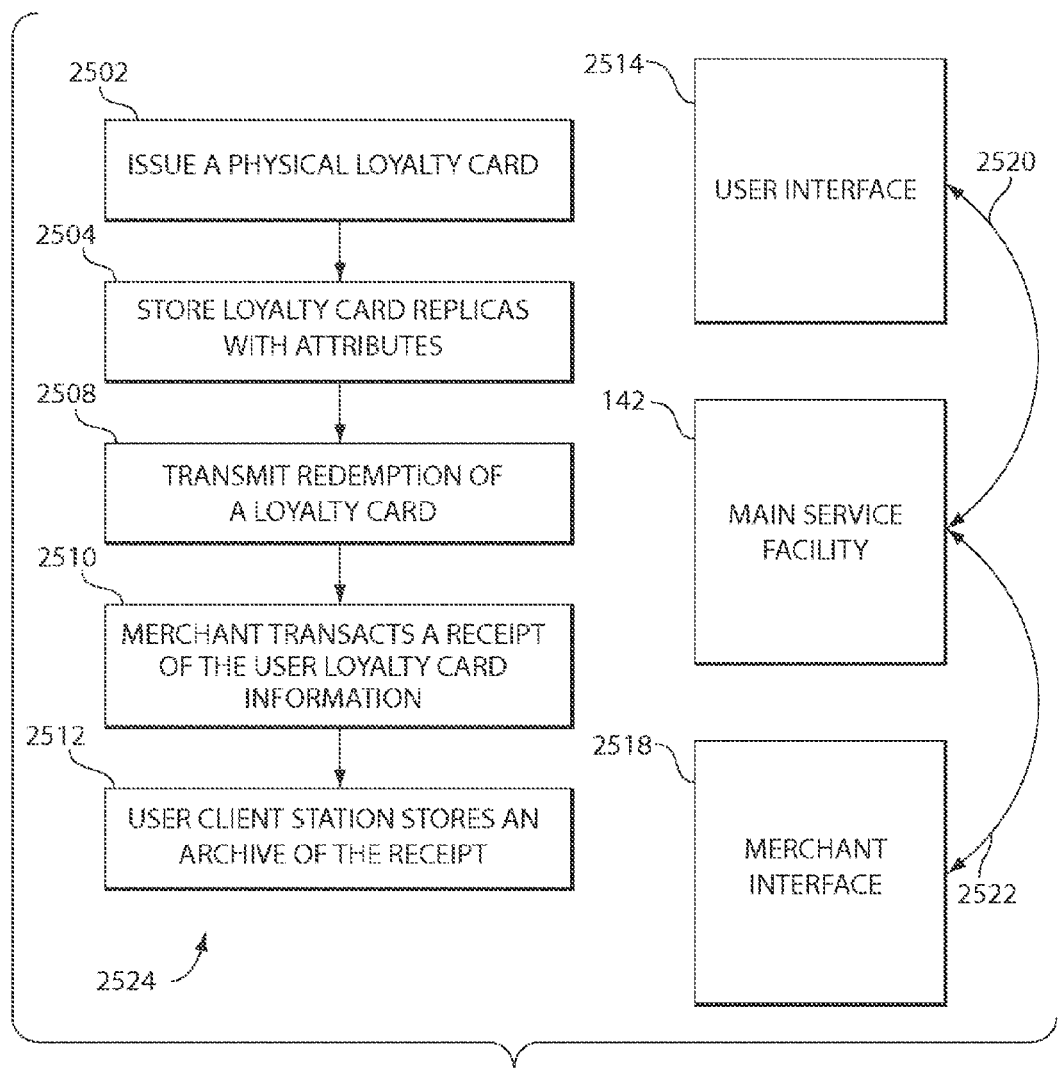
FIG. 25 depicts an embodiment of an issuance of one potential exemplary embodiment of a loyalty card to a user.

In an embodiment, a user may be signed up for a loyalty reward program for an airline, rail line, hotel/motel, store, business, or other business that may provide rewards for loyalty to their company. Referring to FIG. 25, an embodiment of an actual issuance of a loyalty card to a user is shown. For example, a user may receive an actual loyalty reward card 2502 from a business. In an embodiment, the loyalty reward card may be a facsimile of the reward card that may contain information such as amount of the reward, the effective date, when the reward can be redeemed, the ending date of the reward, the name of the person, or other information relevant to the loyalty card. In an embodiment, the user may then be able to store the loyalty card 2504 on a client facility. For example, the client facility may be a cell phone, PDA, Pocket PC, home computer, or other device capable of data storage. The client facility may be able to store at least one loyalty card for a business and may be able to store loyalty cards for at least one business.

In embodiments, the user may be able to select from the stored loyalty cards to determine which loyalty card to redeem. For example, after a user selects a loyalty card to be used, the user may transmit the redemption of the loyalty card 2508. The user may be able to redeem the loyalty card from a remote location, as an example from home, or while at the location of the business. If at the business location, the user may be able to use a portable computing device to transmit the redemption 2508 to the business. In embodiments the user may also be able to check for new loyalty rewards upon entering a business location that the user has a loyalty account.

In embodiments, after a user redeems loyalty rewards the business may transmit a receipt of the loyalty reward 2510 back to the user's client. For example, the loyalty reward receipt may be an actual facsimile of a receipt with an acknowledgement of redemption such as "paid," "redeemed," or other acknowledgement.

In embodiments, the user may be able to store the loyalty reward receipt 2512 on the user client. For example, the user may be able to store the receipt in an archive with other received receipts. The user may be able to store the receipts in at least one category that may contain loyalty reward receipts from similar businesses or the categories may be by business.

In an embodiment of the communication between the user client 2514, the main service facility 142, and the business client 2518 is shown. In an embodiment, either the user client 2514 or the business client may begin the exchange of information on loyalty rewards. For example, a user client 2514 may request a loyalty reward update from certain or all businesses that may be available. A business client may broadcast to a select number or all users of its loyalty rewards an update to the loyalty rewards.

In an embodiment, a user client 2514 may start a transaction by choosing a loyalty reward to redeem and transmitting the redemption 2520. For example, the request may be sent 2520 to the main service facility 142. The main service facility 142 may match the redemption request to a business client and transmit the request 2522 to the business client 2518. The business client 2518 may verify the validity of the redemption, credit the loyalty reward against the users account, and send a receipt 2522 to the main service facility 142. The main service facility 142 may match the receipt to a user client 2514 and forward the receipt 2520 to the user client 2514. The user client 2514 may then archive the receipt.

Figure 26:
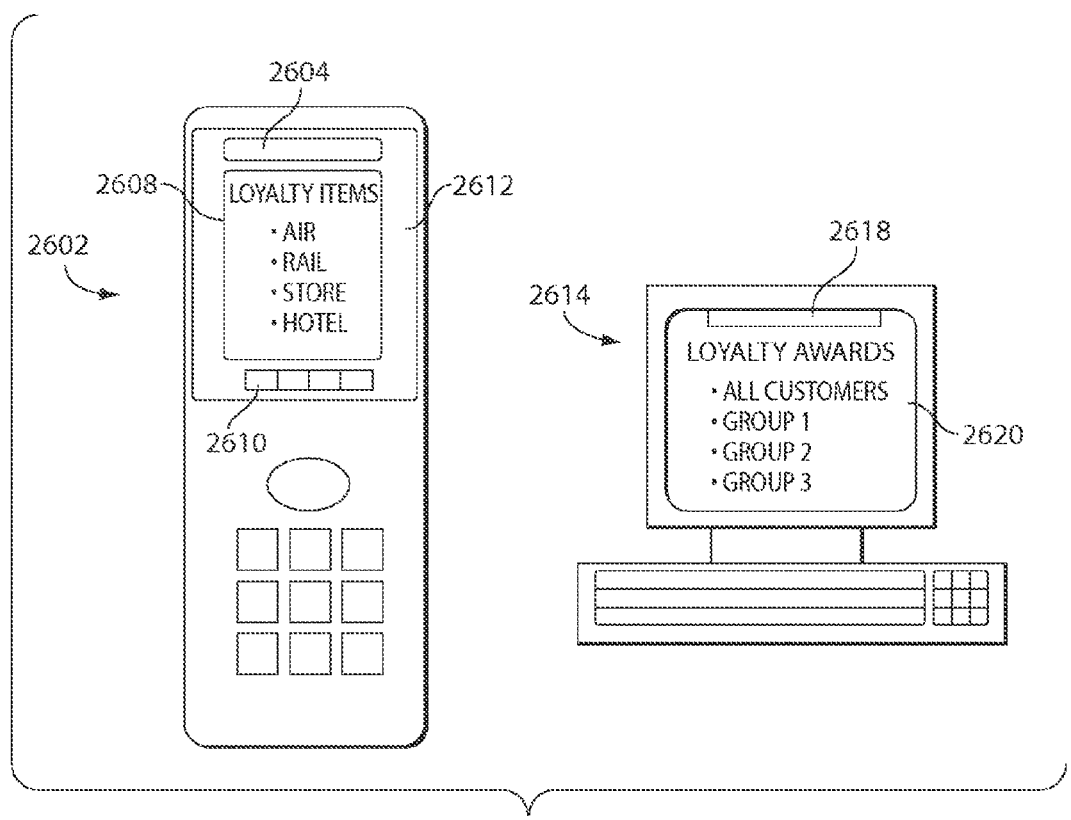
FIG. 26 depicts an embodiment of a portal user device for viewing a user interface to the electronic loyalty card.

Referring to FIG. 26, an embodiment of a portable user device 2602 for viewing a user interface 2612 is shown. For example, a portable computer device may be a cell phone, PDA, Pocket PC, tablet PC, or other similar computer device. In embodiments, the user interface 2612 may contain a menu 2604, buttons 2610, a window for selecting actions 2608, or other method of navigating the user interface 2612. In embodiments, the menu 2604 may contain categories of actions. For example, the menu may contain file, search, retrieve, quit, or other option associated with managing loyalty card rewards. In embodiments, the user interface may also have buttons 2610 that may be shortcuts to options available on the menu 2604.

In embodiments, selecting a user interface 2612 option, either through the menu 2604 or buttons 2610, may open a window with related options. For example, a user may select an option to view the categories of loyalty rewards available on the client. A listing may be presented on in the window 2608. The listing displayed in the window 2608 may be selected to perform additional actions.

In an embodiment of a business user interface 2614 is shown. In embodiments, the user interface 2614 may contain a menu 2618, a window for selecting actions 2620, or other method of navigating the user interface 2614. In embodiments, the menu 2618 may contain categories of actions. For example, the menu may contain file, search, retrieve, quit, or other option associated with managing loyalty card rewards.

In embodiments, selecting a user interface 2614 option through the menu 2618 may open a window with related options. For example, a business may select an option to view the categories of loyalty reward accounts available on the client. A listing may be presented on in the window 2620. The listing displayed in the window 2620 may be selected to perform additional actions.

Figure 27:
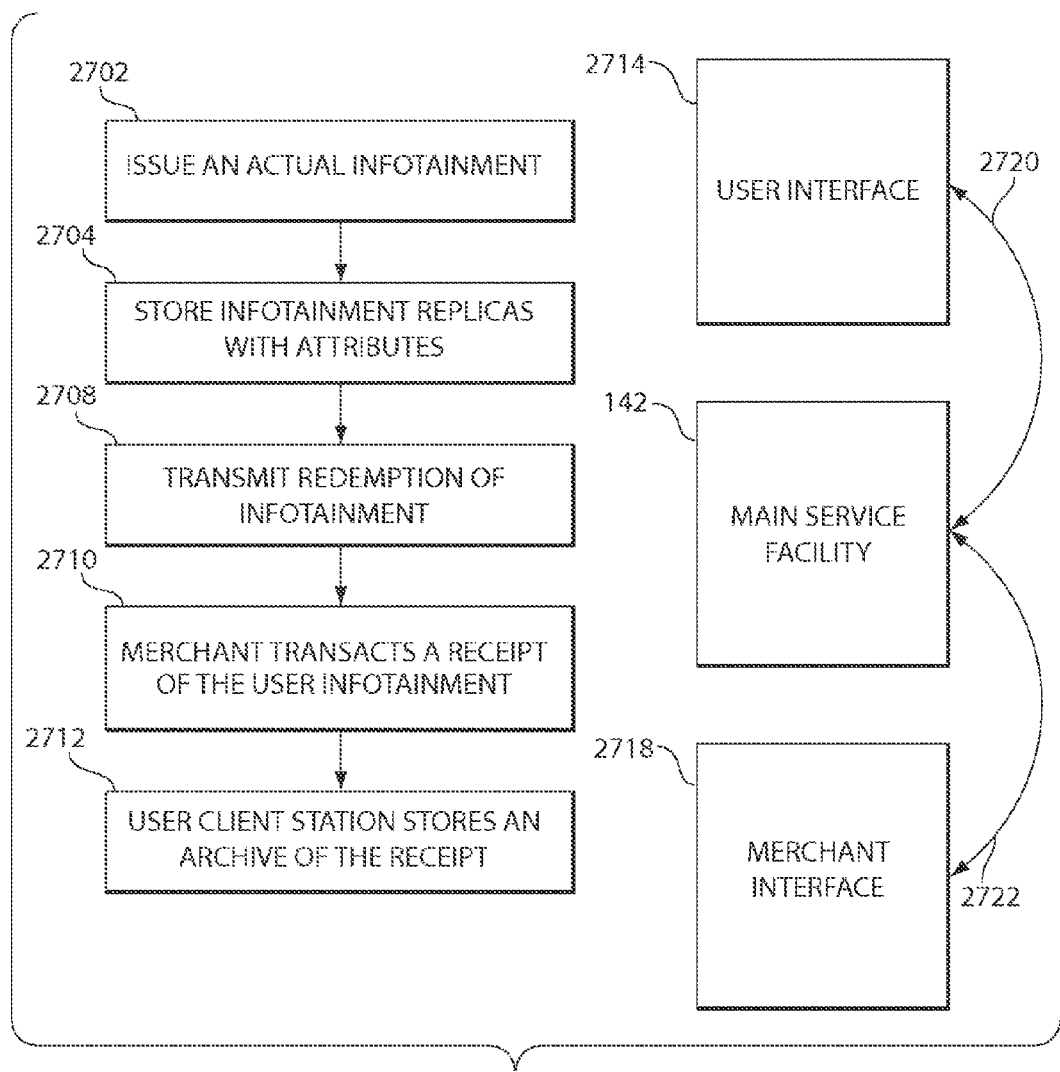
FIG. 27 depicts a flow chart representative of an embodiment of the process to download the infotainment.

In an embodiment, a user may download music, video, movies, games, or other infotainment to a user client for entertainment. Referring to FIG. 27, a flow chart shows an embodiment of the process to download the infotainment. For example, a user may receive downloaded music, video, movies, games, or other infotainment to a user client computer. The user may receive the actual infotainment file 2702 to reside on the user client computer. The user may store the actual infotainment 2704 on the user client computer, the infotainment may also contain additional information such the viewing/playing protocol, gaming databases, play list, movie chapter lists, or other information that would be useful for the playing of the infotainment. The user client may also receive the infotainment license for the downloaded infotainment.

In an embodiment, once the user receives the infotainment the user client computer may transmit payment for the infotainment 2708. For example, the payment may be taken from a predetermined bank account or charged to a credit/debit card. In an embodiment, the user may be able to receive infotainment and make payment either remotely using a home computer or at a local business where the transaction may take place within the business. For example, a user could use a portable computing device to purchase and download music within a retail music store. The user may select the desired music, perform an electronic payment from the user client to the merchant client, and then download the music to the user client.

In embodiments, after a user transmits payment, the business may transmit a receipt of the payment 2710 back to the user client. For example, the infotainment payment receipt may be an actual facsimile of a receipt with an acknowledgement of payment such as "paid", "redeemed", or other acknowledgement of receiving payment.

In embodiments, the user may be able to store the infotainment payment receipt 2712 on the user client. For example, the user may be able to store the receipt in an archive with other received receipts. The user may be able to store the receipts in at least one category that may contain infotainment receipts from similar sources/types or the categories may be viewed by sources/types.

In an embodiment of the communication between the user client 2714, the main service facility 142, and the business client 2718 is shown. In an embodiment, either the user client 2714 or the business client may begin the exchange of information on infotainment. For example, a user client 2714 may request a download of music from a music store or service. A music store or service client may broadcast to a select number or all users of its latest available downloads.

In an embodiment, the user client 2714 may request an infotainment download from an infotainment merchant. In an embodiment, the user client may transmit the download request 2720 to the main service facility 142. The main service facility 142 may match the download request to an infotainment merchant and transmit the request for a download 2722.

In an embodiment, an infotainment merchant client 2718 may receive the download request and may transmit back 2718 to the main service facility 142 the payment request for the download. The main service facility 142 may match the payment request back to the user client 2714 and transmit the payment request 2720.

In an embodiment, the user client 2714 may authorize a method of payment, for example a bank account, credit card, debit card, or other electronic payment method. The payment may be transmitted 2720 to the main service facility 142. The main service facility 142 may match up the payment to the infotainment merchant client 2718 and transmit 2722 the payment.

In an embodiment, once the merchant client 2718 receives the infotainment payment the merchant client may transmit the download file and a payment receipt 2722 to the main service facility 142. The main service facility 142 may match the download and receipt to the user client 2714 and transmit the download and receipt 2720 to the user client 2714. The user client 2714 may store the receipt.

Figure 28:
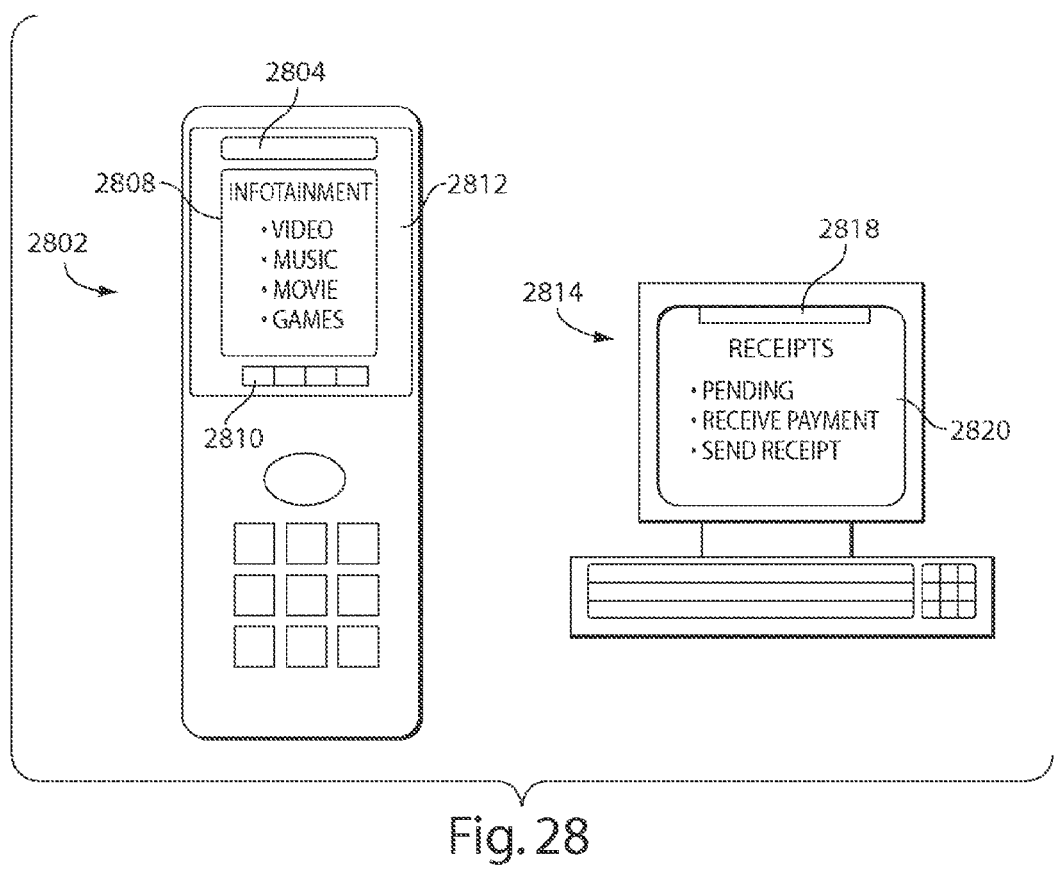
FIG. 28 depicts an embodiment of a portable user device for viewing a user interface to the infotainment.

Referring to FIG. 28, an embodiment of a portable user device 2802 for viewing a user interface 2812 is shown. For example, a portable computer device may be a cell phone, PDA, Pocket PC, tablet PC, or other similar computer device. In embodiments, the user interface 2812 may contain a menu 2804, buttons 2810, a window for selecting actions 2808, or other method of navigating the user interface 2812. In embodiments, the menu 2804 may contain categories of actions. For example, the menu may contain file, search, retrieve, quit, or other option associated with managing loyalty card rewards. In embodiments, the user interface may also have buttons 2810 that may be shortcuts to options available on the menu 2804.

In embodiments, selecting a user interface 2812 option, either through the menu 2804 or buttons 2810, may open a window with related options. For example, a user may select an option to view the categories of types of infotainment available on the client. A listing may be presented in the window 2808. The listing displayed in the window 2808 may be selected to perform additional actions, for example viewing a list of the infotainment in each category.

In an embodiment of a business user interface 2814 is shown. In embodiments, the user interface 2814 may contain a menu 2818, a window for selecting actions 2820, or other method of navigating the user interface 2814. In embodiments, the menu 2818 may contain categories of actions. For example, the menu may contain file, search, retrieve, quit, or other option associated with managing infotainment files.

In embodiments, selecting a user interface 2814 option through the menu 2818 may open a window with related options. For example, a business may select an option to view the categories of purchaser accounts available on the client. A listing may be presented on in the window 2820. The listing displayed in the window 2820 may be selected to perform additional actions.

Generally speaking, nearly every household pays several bills each month. Embodiments of the present invention relate to systems and methods for receiving and or paying bills received on a periodic basis, such as a mortgage, rent, electric, gas, oil, phone, cell phone, cable, dish, dsl, internet provider, tuition, medical, dental, taxes, and or other periodically occurring bills. Embodiments of the present invention relate to receiving and paying bills on a non-periodic basis for the purchase of goods and services, such as for groceries, gas, repairs, improvements, tuition, cars, tickets, homes, airline tickets, transportation, and other non-recurring or non-periodic bills. In embodiments, the bill pay systems and methods may include bill issuers that traditionally print bills, mail them to customers, and then collect and process physical paper checks for every billing period. In embodiments, online or Internet based Electronic Bill Presentment and Payment (EBPP) services may be employed as part of the overall process according to principles of the present invention; however, the systems and methods may eliminate many of the cumbersome aspects generally encountered when using such systems.

An aspect of the present invention describes a unique solution to the problems associated with paying bills. In embodiments, a bill issuer may electronically, wirelessly, and securely issue a bill or invoice directly to the electronic facility 101, which may be associated with a user/customer of the bill issuer. In embodiments, a customer may be provided with the ability to pay a bill in real-time and or directly through the client facility. In embodiments, the user may be presented with the additional flexibility of using any one of a plurality of pre-registered bank, credit card, or other transactional accounts. In embodiments, the transactional account may include tokens (personalized or non-personalized), to settle the bill or invoice. In embodiments, the bill issuer may use the system and methods described herein to collect a bill electronically and or in real-time through a trusted retail establishment. This may result in increased convenience along with a significant reduction in cost and settlement periods.

Generally, the present invention may provide for issuing, securely and electronically, a token (personalized or not) with all necessary images, branding, and/or data for conducting a transaction, directly to the user, through a wired and/or wireless medium, to an electronic facility 101. The token may without limitation be associated with a service or application such as a credit card, a bank account, a frequent flyer card, a stored value card, a loyalty card, an insurance card, a driver's license, a bill, or a coupon. The electronic facility 101 may render a token, securely and electronically, the token so that it is visible to the user. This rendering may comprise branding and other images along with necessary data for conducting a transaction. The token may be procured from one of a plurality of domains, through any wired or wireless medium, and may be used during the initiation or completion of a transaction. The token may be encrypted, such as with 3DES or AES, when issued and/or when stored in the electronic facility 101. The token, the service, or the application may or may not be personalized and may be provisioned with a high level of throughput, efficiency, or fault tolerance to the client facility. This personalization or provisioning may be conducted in whole or in part may an expert system associated with the client facility that may determine the appropriate personalization or provisioning based upon observation and/or analysis of the user's behavior, usage patters, transaction history, other external inputs such as time-of-day, and so forth.

Figure 30:
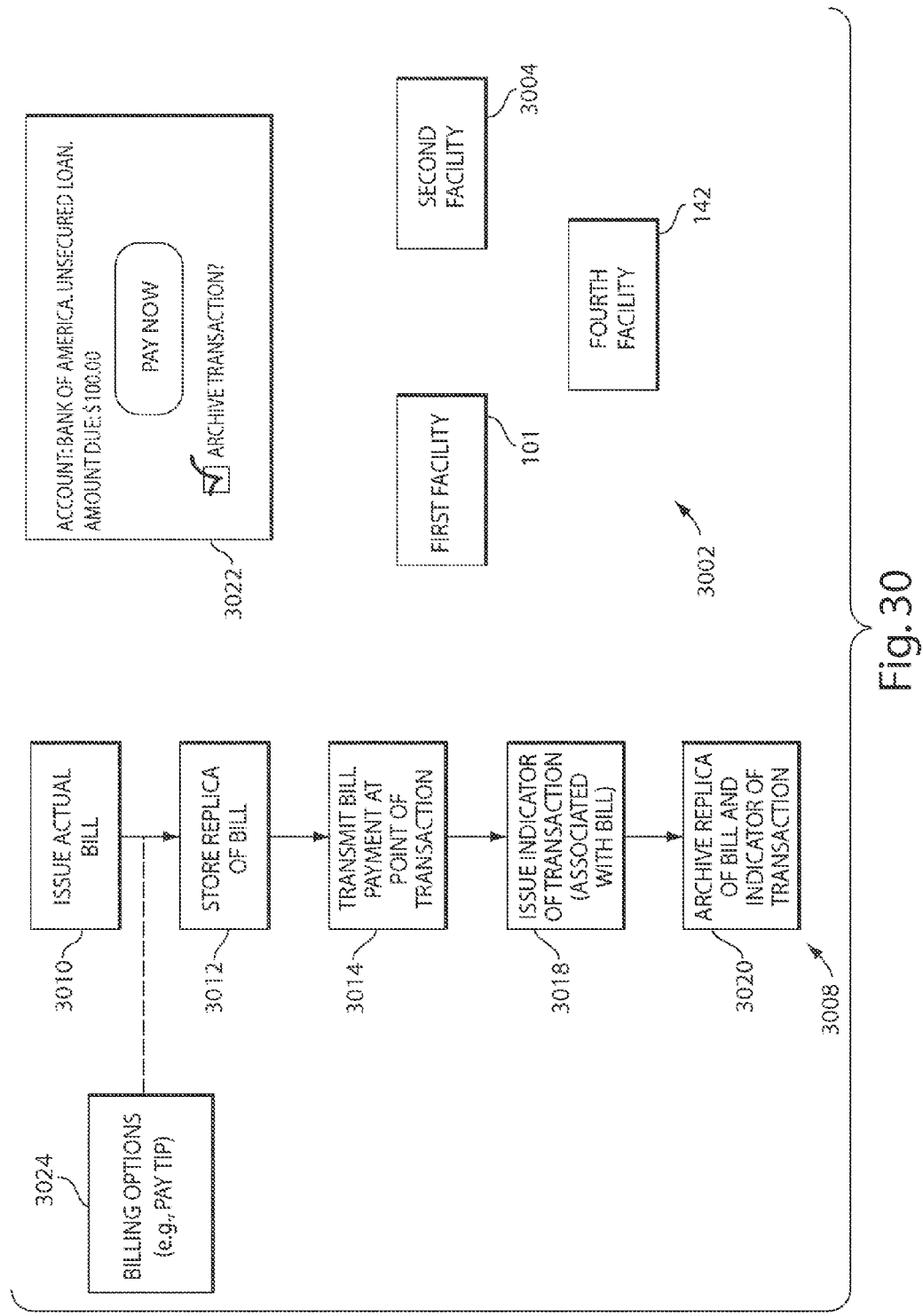
FIG. 30 depicts a high-level block diagram of one aspect of a potential exemplary transaction.

FIG. 30 depicts a high-level block diagram of one aspect of a transaction 3002, such as a bill presentment and payment transaction, according to the principles of the present invention. In this embodiment, the electronic transaction facility 101 may be associated with a client facility as described herein. The electronic transaction facility 101 may also be associated with a merchant facility, a retail facility, a public utility billing facility, a service facility, or any other facility 3004 involved in a transaction with the user of the electronic transaction facility 101. The electronic transaction facility 101 may also be associated with a main service facility 142 as described herein. In embodiments, the associations between the electronic transaction facility 101 and the other facilities may involve wired and or wireless communications and the communications may be directed at downloading bill information and or uploading payment information.

FIG. 30 also depicts the high-level steps of a bill payment transaction 3008 according to the present invention. In the first step 3110, an actual bill is issued from a bill issuing facility to the electronic transaction facility 101. For example, the bill may be a request for payment, which may be issued by service provider, product provider or other establishment for which a debt may be due. In embodiments, a bank may be used as an intermediary to facilitate the issuance or collection of the bill. In embodiments, the actual bill, or representation thereof, may be encoded using a three-dimensional authentication scheme, described elsewhere herein, such as authenticating the transaction based on the user, the device and the domain. In the second step 3012, upon receipt of the actual bill, or representation thereof, the electronic facility 101 may store a replica of the actual bill. The replica, in certain embodiments, may comprise a bit-for-bit copy of the data that comprises the actual bill.

In the third step 3014, the user may transmit a payment in response to a received bill and the payment may be made at the point of purchase. In some cases, the point of purchase may be in the virtual world, such as with an on-line retail Web site, public utility, such as an electric company, bank, web service provider or other provider through a computer network. In other cases, the point of purchase may be in the real world, such as at a local convenience store, department store, gas station, grocery store, mall, food market, food service provider, restaurant, or other provider of goods and or services in the real world. In embodiments, the user may pay such bills, whether on-line, in the real world or otherwise, through his electronic transaction facility 101.

In the fourth step 3018, an acknowledgement, receipt, or other indication of the transaction may be issued by bill issuing company in response to an acceptable payment. This acknowledgement may include a receipt, a confirmation, an updated account statement, or other indication of the acceptable outcome of the transaction.

In the fifth step 3020, the original bill and/or the acknowledgement, either of which may include notable data 148, may be archived. As is described elsewhere herein, the main service facility software may be capable of archiving notable data 148. Also as is described elsewhere herein, the electronic facility 101 may be capable of archiving the original bill and/or acknowledgement. In this step, the original bill and/or acknowledgement may be archived by the main service facility software and or the electronic facility 101.

FIG. 30 also illustrates, a user interface 3022 that may be presented on the client facility. The user interface 3022 may include a message indicative of an account; a message indicative of an amount due; an operative element such as a Pay Now button; an option providing for the archival of the transaction and or other information or action buttons. In embodiments, the transaction is initiated when the user affects the operative element in a predefined way, such as by selecting the button with a finger press on the LCD and touch screen display 100. In embodiments, the user interface may be associated with an application on the client facility. The user interface and/or the application may be configured based upon a preference of the user, which may be stored in or associated with the client facility. The storage or association of the preference of the user may be permanent, in the case of an electronic transaction facility 101 generally associated with a particular user, or temporary, such as in the case of client facility that is generally available for public use but that, at a given instant, may be dedicated to the personal use of one user. The user may manually enter the preference, such as by selecting the preference with a finger press on the LCD and touch screen display 100. Alternatively, an expert system associated with the client facility may discern the preference based upon observation and/or analysis of the user's behavior, usage patters, transaction history, other external inputs such as time-of-day, and so forth.

In embodiments, a value-added service may be provided and associated with the transaction, such as overdraft protection, bill alerts, customer feedback and the like. For example, the electronic transaction facility 101 may be used to engage in a transaction with the second facility 3004 for which the electronic transaction facility 101 does not have sufficient funds. Under usual circumstances, this may result in a rejected transaction. With overdraft protection, however, the fourth facility 142 may clear the transaction and charge an account associated with an overdraft protection facility, as opposed to deducting an amount from the funds associated with the first facility 101, which would be the normal course of action.

Generally, a customer may be anybody that utilizes a fourth facility 142. The customer may utilize the fourth facility 142 via a user interface, which may comprise a customer-side Web-based interface, an interaction between an autonomous agent associated with the customer and the fourth facility 142, a scripted interaction between the second facility 3004 and the fourth facility 142, a scheduled interaction between the second facility 3004 and the fourth facility 142, an event-driven interaction between the second facility 3004 and the fourth facility 142, or any other practicable interaction between the second facility 3004 and the fourth facility 142.

In general people make several transaction between one another each month. In embodiments, systems and methods are presented that improve person to person transactions. In embodiments, the transactions may include economic transactions and relate to payment of rent, household utility bills like electricity, gas, cable and telephone, repaying a friend who put a restaurant bill entirely on a credit card, for example. In embodiments, the transactions may be non-economic in nature, such as showing and or sending another person a government-issued identification card, health insurance card, atm card, credit card (e.g. for identification), for example. In embodiments, the transaction is completed through the exchange of a physical object, for example and without limitation, a personal check (such as for rent); cash at a later date (such as for later paying back a friend for a restaurant meal); and handing a driver's license to a bartender (such as for allowing the bartender to check the age of the person associated with the driver's license).

In embodiments, a first person may directly, electronically, wirelessly, and or securely conduct a transaction with a second person. In embodiments, the transaction may involve direct communication from a first electronic facility 101, which may be associated with the first person, to a second electronic facility 101, which may be associated with the other person. Embodiments, may allow the second person to accept in real-time or quasi-real-time, directly through the second electronic facility 101, an object of the transaction, such as for example, money or information associated with the first person. In embodiments, the second person may use the systems and methods described herein to collect the object of the transaction in real-time through a trusted public digital facility. This may result in increased convenience and a significant reduction in inefficiency.

Figure 31:
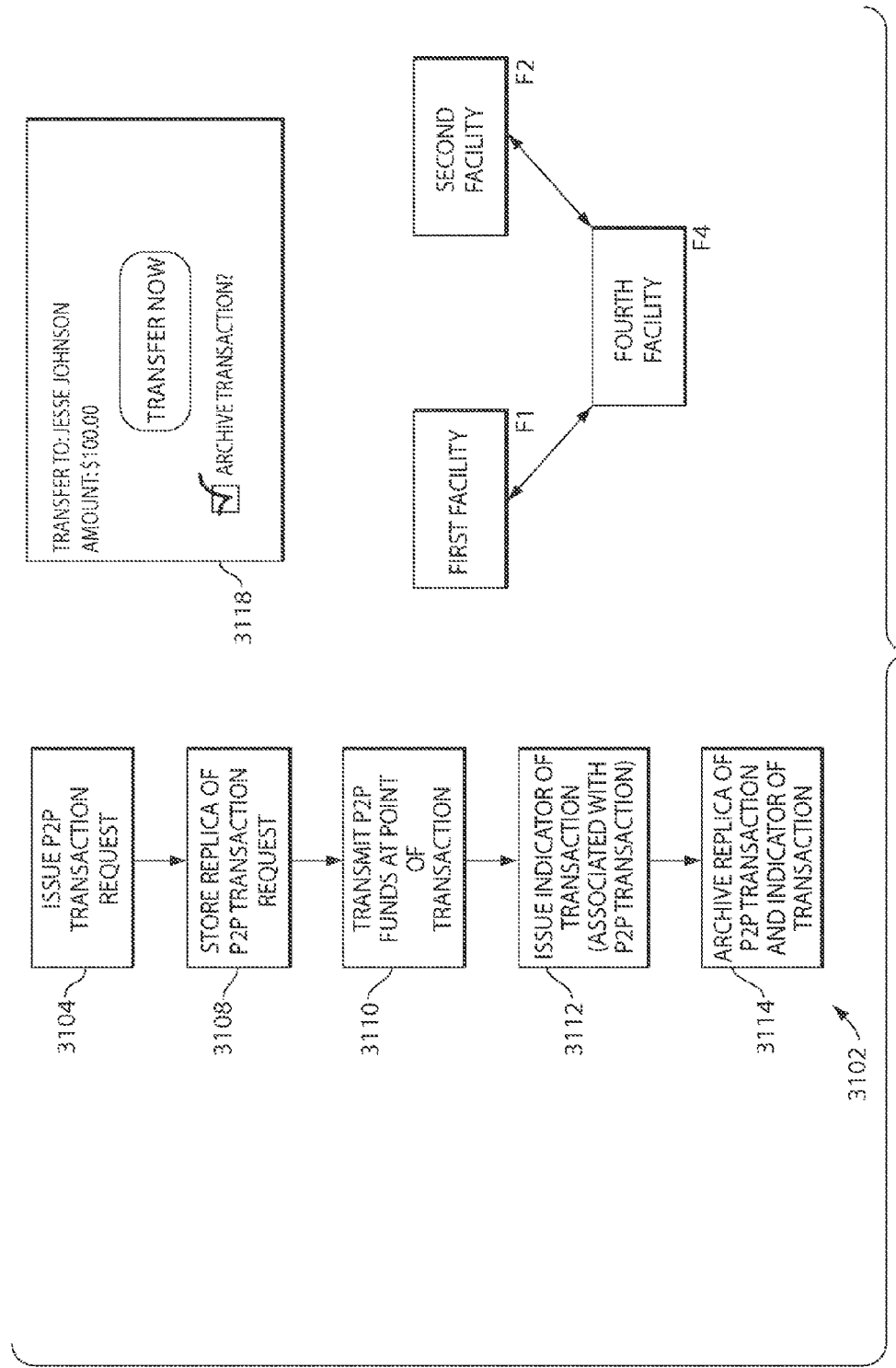
FIG. 31 depicts a high-level block diagram of one aspect of a potential exemplary transaction according to the principles of the present invention.

FIG. 31 depicts a high-level block diagram of one aspect of a transaction according to the principles of the present invention. In this embodiment, a P2P transaction is presented. Each of the elements may correspond to the elements of FIG. 9, described elsewhere herein. The first facility F1 may comprise the first electronic facility 101 and may be associated with the first person. The second facility F2 may comprise the second electronic facility 101. F4 may comprise the main service facility 142.

FIG. 31 depicts the high-level steps of a transaction flow diagram 3102 according to the principles of the present invention. In the first step 3104, an actual transaction request is issued. For example and without limitation, the actual transaction request may be a request for acceptance of cash offered from the first person to the second person, a request for acceptance of information offered from the first person to the second person, and so forth. The actual transaction request may be encoded using a three-dimensional authentication scheme, described elsewhere herein.

In the second step 3108, upon receipt of the actual transaction request the second electronic facility 101 may store a replica of the actual transaction request. This replica, in some embodiments, may comprise a bit-for-bit copy of the data that comprises the actual transaction request.

In the third step 3110, the second person may accept the object of the transaction at the point of transaction. In some cases, the point of transaction may be in the virtual world, such as electronically over long distances. In other cases, the point of transaction may be in the real world, such as the first person being in proximity of the second person and "beaming" the actual transaction request to the second person, such as and without limitation via IrDA or other means described elsewhere herein. In any case, either person may have access to a client facility. Either person's interaction with the client facility may affect the first facility F1 and/or the second facility F2 to engage in transactional steps, which may involve the fourth facility F4 and may comprise the transactional steps detailed in the description of FIG. 9.

In the fourth step 3112, an indicator of the transaction may be issued by the fourth facility F4 to the first facility F1 and/or the second facility F2, such as the confirmation in FIG. 9. This confirmation may comprise a receipt, an acknowledgement, an updated account statement, or any other indication of the outcome of the transaction.

In the fifth step 3114, the replica and/or the confirmation, either of which may comprise notable data 148, may be archived. As is described elsewhere herein, the main service facility software may be capable of archiving notable data 148. Also as is described elsewhere herein, the electronic facility 101 may be capable of archiving the replica and/or acknowledgement. In this step, the replica and/or acknowledgement may be archived by the main service facility software, the first electronic facility 101, and/or the second electronic facility 101.

FIG. 31 also illustrates a user interface 3118 according to the principles of the present invention. The user interface 3118 that is presented here is for the purposes of example, not limitation. The user interface 3118 may include a message indicative of an intended recipient; a message indicative of an amount to be transferred from the sender (such as the first person) to the recipient (such as the second person); an operative element such as a "Transfer Now" button; an option providing for the archival of the transaction and or other features relevant to the p2p transaction. In embodiments, the transaction is initiated when the first person affects the operative element in a predefined way, such as by selecting the button with a finger press on the LCD and touch screen display 100.

In embodiments, an additional value-added service may be provided, such as an overdraft protection associated with the transaction. For example, the first facility F1 may be used to engage in a transaction with the second facility F2 for which the first facility F1 does not have sufficient funds associated with it. Under usual circumstances, this may result in a rejected transaction. With overdraft protection, however, the fourth facility F4 may clear the transaction and charge an account associated with an overdraft protection facility, as opposed to deducting an amount from the funds associated with the first facility F1, which would be the normal course of action.

In embodiments, a customer may be any person that utilizes the fourth facility F4. The customer may utilize the fourth facility F4 via a user interface, which may comprise a customer-side Web-based interface, an interaction between an autonomous agent associated with the customer and the fourth facility F4, a scripted interaction between the second facility F2 and the fourth facility F4, a scheduled interaction between the second facility F2 and the fourth facility F4, an event-driven interaction between the second facility F2 and the fourth facility F4, or any other practicable interaction between the second facility F2 and the fourth facility F4.

Many consumers utilize prepaid facilities, for example and without limitation a prepaid cellular telephone. These facilities, in many embodiments allow for what is commonly known as "top up", which is the addition of funds to a prepaid facility. This is convenient as prepaid facilities eventually become depleted over time and/or with use.

This invention describes a unique solution, whereby a consumer may directly, electronically, wirelessly, and securely conduct a top up transaction via a merchant facility and with a supplier facility, directly from a first electronic facility 101. The unique solution also allows the merchant facility to act in real-time as a retail agent of the supplier facility. This may result in increased convenience and reduced transactional cost.

Figure 32:
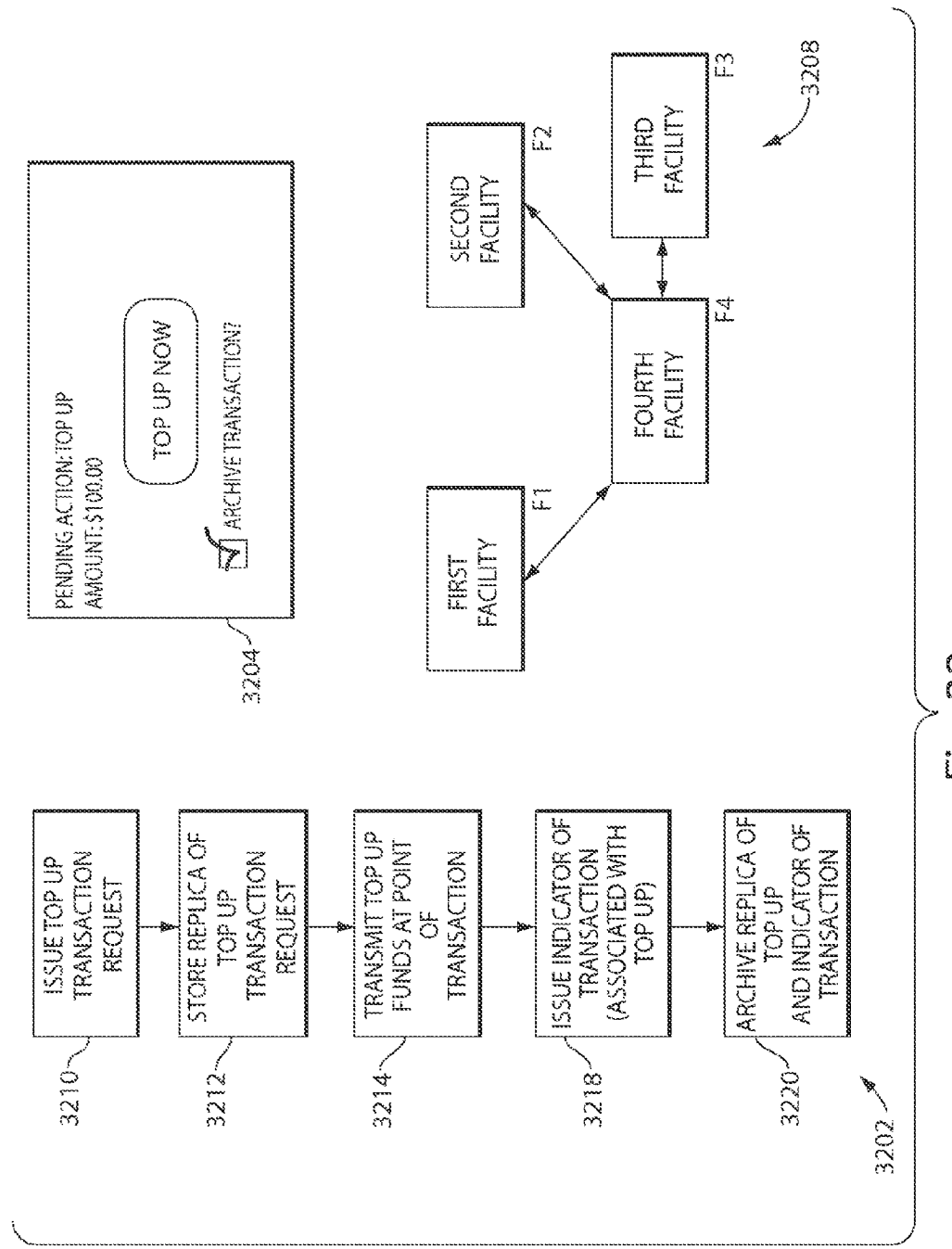
FIG. 32 depicts a high-level block diagram of one aspect of a potential exemplary transaction.

FIG. 32 depicts a high-level block diagram of one aspect of a transaction 3208, such as a top up transaction, according to the principles of the present invention. Each of the elements may correspond to the elements of FIG. 12, described elsewhere herein. The first facility F1 may comprise the electronic facility 101 and may be associated with the consumer. The second facility F2 may comprise the supplier facility, such as a cellular telephone service provider facility. F3 may comprise a merchant facility. F4 may comprise the main service facility 142.

FIG. 32 also depicts the high-level steps of a transaction 3202 according to the principles of the present invention. In the first step 3210, an actual transaction request is issued. For example and without limitation, the actual transaction request may be a request for a top up transaction issued from the merchant facility (presumably at the behest of the consumer) to the main service facility 142. The actual transaction request may be forwarded, altered or unaltered, by the main service facility 142 to the supplier facility and/or the electronic facility 101. The actual transaction request may be encoded using a three-dimensional authentication scheme, described elsewhere herein.

In the second step 3212, upon receipt of the actual transaction request the main service facility 142, the supplier facility, and or the electronic facility 101 may store a replica of the actual transaction request. The replica, in some embodiments, may comprise a bit-for-bit copy of the data that comprises the actual transaction request.

In the third step 3214, the funds may be transferred, at the point of transaction, from an account associated with the consumer to an account associated with the electronic facility 101. In embodiments, the point of transaction may be in the virtual world, such as a top up via a Web site. In embodiments, the point of transaction may be in the real world, such as the first person being on the merchant's premises. In embodiments, the consumer may have access to a client facility. The consumer's interaction with the client facility may affect the second facility F2 to initiate transactional steps associate with a top up transaction, which may involve the fourth facility F4, may involve the second facility F2 and the third facility F3, and may comprise the transactional steps detailed in the description of FIG. 12.

In the fourth step 3218, an indicator of the transaction may be issued by the fourth facility F4 to the second facility F2 and/or the third facility F3, such as the transaction confirmation and/or the authorization in FIG. 12. The confirmation and/or authorization may comprise a receipt, an acknowledgement, an updated account statement, or any other indication of the outcome of the transaction.

In the fifth step 3220, the replica and/or the confirmation and/or authorization, any of which may comprise notable data 148, may be archived. As is described elsewhere herein, the main service facility software may be capable of archiving notable data 148. Also as is described elsewhere herein, the electronic facility 101 may be capable of archiving the replica. In this step, the replica and/or confirmation and/or acknowledgement may be archived by the main service facility software, the merchant facility, and/or the supplier facility.

FIG. 32 also represents a user interface 3204 according to the principles of the present invention. In embodiments, the user interface 3204 may be presented on the client facility. The user interface that is presented here is for the purposes of example, not limitation. The user interface may include a message indicative of an pending transaction, such as a pending top up; a message indicative of pending magnitude of the top up; an operative element such as a Top Up Now button; an option providing for the archival of the transaction and or other information relating to the transaction. In embodiments, the transaction may be initiated by the merchant at the behest of the consumer. In embodiments, the transaction may be completed after consumer interacts with the operative element in a predefined way, such as by selecting the button with a finger press on the LCD and touch screen display 100.

In embodiments, an additional value-added service may be provided, such as an overdraft protection associated with the transaction. For example, the first facility F1 may be used to engage in a transaction with the second facility F2 for which the first facility F1 does not have sufficient funds associated with it. Under usual circumstances, this may result in a rejected transaction. With overdraft protection, however, the fourth facility F4 may clear the transaction and charge an account associated with an overdraft protection facility, as opposed to deducting an amount from the funds associated with the first facility F1, which would be the normal course of action.

In embodiments, a customer may be any person that utilizes the fourth facility F4. The customer may utilize the fourth facility F4 via a user interface, which may comprise a customer-side Web-based interface, an interaction between an autonomous agent associated with the customer and the fourth facility F4, a scripted interaction between the second facility F2 and the fourth facility F4, a scheduled interaction between the second facility F2 and the fourth facility F4, an event-driven interaction between the second facility F2 and the fourth facility F4, or any other practicable interaction between the second facility F2 and the fourth facility F4. In embodiments, the interaction between the third facility F3 and the fourth facility F4 may be manual or automated and may be event-driven, such as being initiated by the event of the consumer requesting that a merchant initiate a top up transaction.

An aspect of the present invention relates to providing heath care services, products, identifications, medical records and other materials, products and services through electronic transaction facilities. In embodiments, the transactions may be economic in nature and or non-economic in nature.

Figure 33:
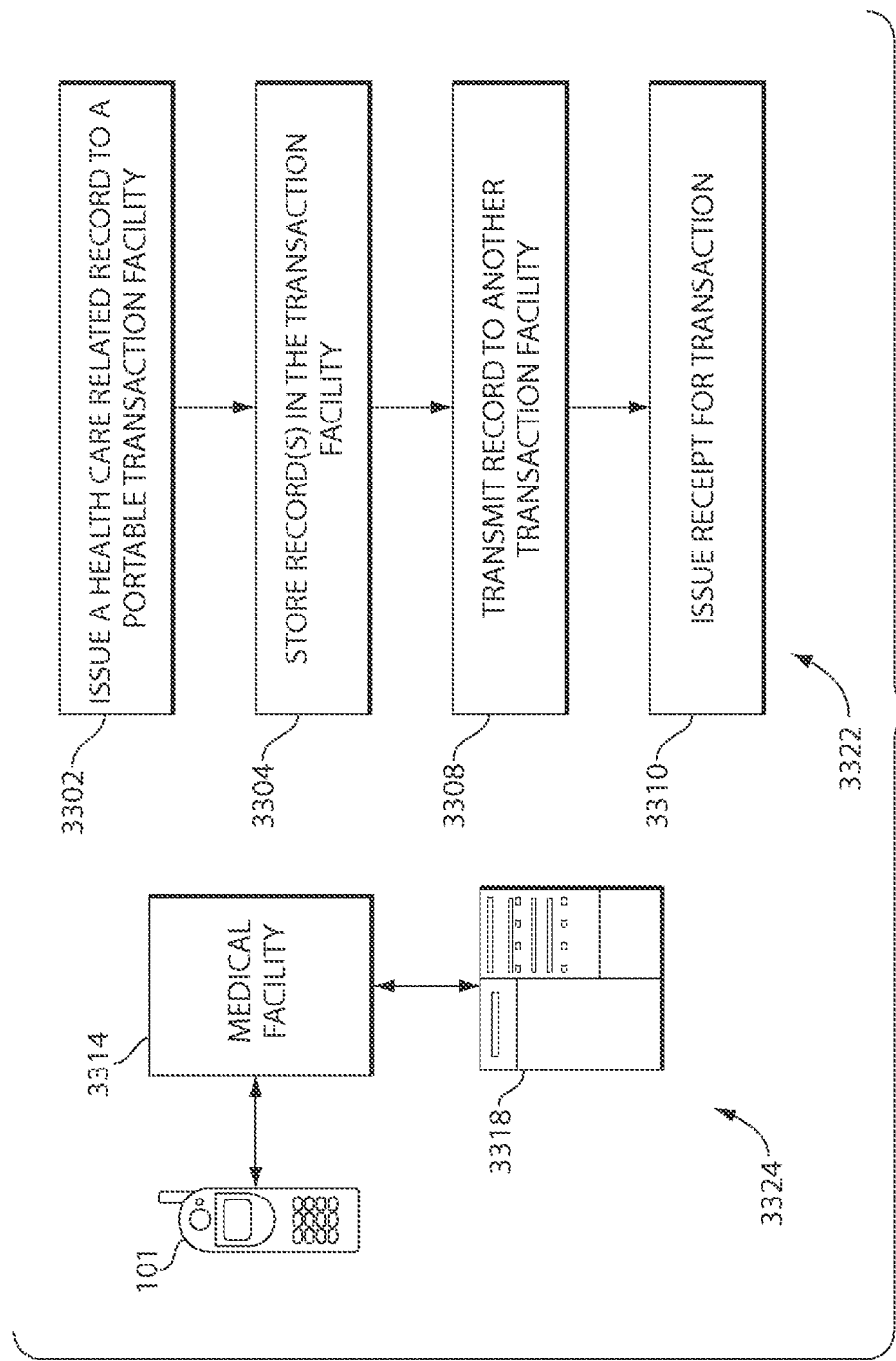
FIG. 33 illustrates a medical transaction process according to the principles of the present invention.

FIG. 33 illustrates a medical transaction process 3322 according to the principles of the present invention. In embodiments, the process involves the issuance of a health care related record to an electronic transaction facility 3302. In embodiments, the electronic transaction facility may be an electronic transaction facility as described herein. Following the transmission of the medical record to the electronic transaction facility, the record may be stored in memory associated with the electronic transaction facility 3304. In embodiments, the record may then be transmitted to another electronic transaction facility 3308. In embodiments, a receipt of the transaction(s) may be communicated back to the electronic transaction facility. FIG. 33 also illustrates a medical transaction 3324. In embodiments, the electronic transaction facility 101 may be used to retrieve and or send a medical record to a medical facility 3314. The medical facility 3314 may be associated with a computer, computer network or other such facility used for the storage of such medical records.

In embodiments, a user of an electronic transaction facility may have personal medical records from a health care provider from whom the user receives medical care stored in an electronic format. For example, a user may receive an electronic medical record from a physician's office, hospital or other medical facility. In embodiments, the electronic medical record may be an electronic facsimile of medical record stored at the physician's office that may contain information such as the patient's address, phone number, email address, emergency contact information, primary care physician, age, height, weight, blood type, medical conditions (e.g., disease, blood pressure, cholesterol levels), currently prescribed medications, allergies, previous surgeries, previous health care providers, current health insurance provider and policy number, and or other information relevant to the user's medical history or and treatment. In embodiments, the user may then be able to store the electronic medical record on a client facility. For example, the client facility may be a cell phone, PDA, Pocket PC, home computer, or other device capable of data storage. The client facility may be able to store electronic medical records from one health care provider and may be able to store the electronic medical records for at least one health care provider. In embodiments, the issuer of the medical information may issue a receipt of the transaction to the user's transaction facility. In embodiments, the user may issue a receipt to the issuer of the medical records through his electronic transaction facility.

In embodiments, the user may be able to select from stored personal health care information relevant to an interaction with a health care provider. For example, after a user accesses the electronic medical record, the user may transmit the health insurance information necessary for the health care provider to receive reimbursement for the user's visit to the health care provider. The user may be able to update health insurance information from a remote location, as an example from home, or while at the location of the business. If at the location of the health care provider, the user may be able to use a portable computing device to transmit the health insurance information to the health care provider's place of business. In embodiments, the recipient of the transmitted information may transmit a receipt of the transaction.

In embodiments, a user in need of urgent medical care while traveling may have his electronic medical record transmitted from his remote health care provider directly to his device, such as a cell phone or PDA, in order to make the record available to health care providers with whom the user has no treatment history. During treatment at the remote health care provider facility, the user's electronic medical record may be updated, enabling the user to integrate the new treatment record obtained at a distant facility with that of the primary health care provider and to share this new treatment information with the primary health care provider.

In embodiments, a user may have health insurance information from at least one insurer from whom the user receives health care policy information in electronic format as an electronic health insurance policy card. For example, a user may receive an electronic health insurance policy card directly from a health insurer. In embodiments, the electronic health insurance policy card may be an electronic facsimile of health insurance policy covering the user's medical care that may contain the user's name, address, health insurance policy number, contact information for the health insurance provider, coverage initiation and expiration dates, the user's primary care physician, and or other information relevant to the user's health insurance coverage. In embodiments, the user may then be able to store the electronic health insurance policy card on a client facility. For example, the client facility may be a cell phone, PDA, Pocket PC, home computer, or other device capable of data storage. The client facility may be able to store at least one electronic health insurance policy card from one health insurance provider.

In embodiments, the user may be able to select from stored electronic health insurance policy cards relevant to an interaction with a health care provider, pharmacy, or other health care entities for which the user carries a health insurance policy. For example, upon admission to a health care provider's facility, the user may transmit the health insurance information necessary for the health care provider to receive reimbursement for the user's visit to the health care provider. The user may be able to update health insurance information from a remote location, as an example from home, or while at the location of the business. If at the location of the health care provider, the user may be able to use a portable computing device to transmit the health insurance information to the health care provider's place of business. Additionally, the health insurance provider may be able to update the user's health insurance policy information remotely by transmitting the new information directly to the user's device. If the user has health insurance providing coverage for prescription medications, the user could present the electronic health insurance policy card at the pharmacy at the point of sale for prescription medication. In embodiments, the cards are transmitted and stored as a representation of an actual card as disclosed herein.

In embodiments, a user may be able to request, obtain, and transmit a health care referral that is required by a health insurance provider from a user's health provider to the appropriate health insurance provider.

In embodiments, a physician may transmit a drug prescription for a user directly to the user's device. In embodiments, the electronic drug prescription may be an electronic facsimile of the physician's DEA-sanctioned drug prescription form including the physician's name and contact information, the patient's name, the drug prescribed, the correct dosage and the amount prescribed, the date of the prescription, or other information relevant to the user's drug prescription. In embodiments, the user may then be able to store the electronic drug prescription on a client facility. For example, the client facility may be a cell phone, PDA, Pocket PC, home computer, or other device capable of data storage. The client facility may be able to store at least one electronic drug prescription from one health care provider.

In embodiments, the user may be able to transmit the electronic drug prescription at the point of sale with a pharmacist. For example, upon entry to the pharmacy a user may transmit the electronic drug prescription directly from the user's device to the electronic network of the pharmacy. To assist the pharmacy in verifying the authenticity of the electronic drug prescription, the prescription may be bound to an electronic watermark or other security encryption device. In embodiments, the pharmacist may transmit a receipt in accordance with the principles of the present invention.

In embodiments, drug manufacturers may provide direct-to-consumer marketing for specific drugs of relevance to the user's current medical needs. This direct-to-consumer marketing may take place at the time point of the physician transmitting the prescription to the user's device, at the time point of the user transmitting the prescription from the user device to the pharmacy network, or both. Pharmacy information, such as price, inventory, hours of operation, or other information, for pharmacies in the current locale of the user could also be transmitted to the user's device in a manner similar to the drug manufacturer's direct-to-consumer marketing.

In embodiments, the user may be able to transmit an electronic informed consent form to a health care provider. For example, upon admission to a hospital emergency department, a user may transmit an electronic informed consent for treatment from a user device to the electronic network of the hospital. Similarly, a user eligible for participation in a clinical research trial may transmit an informed consent form to participate in the research trial directly from a user device to a health care provider network.

In embodiments, a user may store electronic emergency medical information and medical contact persons directly to the user's device. In an embodiment, the electronic emergency medical information may summarize the user's name, address, phone, location of medical records, allergies to medications, list of current medications person is taking, blood type, disease, wishes for organ donation, or other information relevant to the user's drug prescription. In an embodiment, the user may then be able to store the electronic drug prescription on a client facility. For example, the client facility may be a cell phone, PDA, Pocket PC, home computer, or other device capable of data storage. The client facility may be able to store at least one emergency medical record from one user.

In an embodiment, a user may store personal information on an electronic transaction facility according to aspects of the present invention. For example, a user may store information such as phone numbers, addresses, email addresses, social security cards, driver license, credit card accounts, debit card accounts, business card information, address book, email address book, or other personal identification. In embodiments, the personal information may be information that is necessary for transactions, such as a driver license, social security card, personal ID, or for communicating with acquaintances with email, messages, or phoning. A user may need to communicate personal information for a monetary transaction as proof of identification; the identification may include name, address, images, bar codes or other information for positive identification with the business. In an embodiment, the user may communicate with other users to exchange personal information. For example, a user may communicate with an acquaintance that may be near by to make an appointment. In an embodiment, a user may also be able to exchange electronic business cards at a meeting; wherein the electronic business card may be a facsimile of the business card.

In an embodiment, there may be a personal identification manager that may review all transmissions from the user client. For example, the manager may review the distribution list of an email to determine if a group of email addresses may be associated and a new email with some of these email addresses the personal information manager may query if the user wants to include the related addresses on the email. The personal identification manager may also track when a user is traveling and establish a subset of acquaintances that were made. Upon the next visit to the same location, the personal identification manager may query if the user wants to contact the other associated acquaintances. In an embodiment, the personal identification manager may be able to interface with an available location detection facility of the user client computer to determine a location. For example, the personal identification manager may determine that the user is at a location that matches addresses in the address book and suggest communication may be appropriate with a person in the address book.

In an embodiment, the personal information manager may track personal bill payments and may make suggestions for changes in personal finances. For example, the personal information manager may determine that a user is using a credit card with a higher interest rate than another available card. The personal information manager may suggest that the user take advantage of the lower interest credit card.

FIG. 34 illustrates a process flow chart for the exchange of personal information between users 3422 according to principles of the present invention. For example, the process may involve the exchange of business cards at a meeting. In an embodiment, a user may store a business card facsimile 3402 on a user client computer (e.g. an electronic transaction facility as described herein). The business card facsimile may contain associated attributes such as name, address, business name, business icon, personal image, or other information associated with a business card. In an embodiment, a first user may transmit a business card to a second user 3404.

In an embodiment, after the second user receives the business card from the first user a reply 3408 may be sent. For example, the reply 3408 may be an acknowledgment that the business card was received and may be a facsimile of the first user's business card with an indication that the first user's business card was received. In an embodiment, the second user may reply 3408 by transmitting a facsimile of the second user's business card. The reply with a facsimile of the second user's business card may be the reply 3408 to the first user's transmission.

In an embodiment, the first user may be able to store the facsimile reply 3410 in an archive. For example, the facsimile business card may be archived 3410 in at least one category on the user client computer. The client computer may be able to archive the facsimile business card in categories by business, name, address, or other category.

In an embodiment of the communication between a user client facility 3412, main service facility 142, and a second user client facility 34148 is shown. Using the same business card example a user 3412 may want to transmit a facsimile of the user's business card to a second user 3414. In an embodiment, the user 3412 may initiate the transmission of the business card facsimile 3418. In an embodiment, the user client computer 3412 may be a home PC, a kiosk PC, cell phone, PDA, Pocket PC, or other similar computer device. The transmission may be sent 3418 to a main service facility 142. The main service facility 142 may match the user's transmission 3412 to the intended recipient, the second user 3414. In an embodiment, the main service facility 142 may transmit the business card facsimile 3420 to the second user 3414. In an embodiment, the second user client computer 3414 may be a home PC, a kiosk PC, cell phone, PDA, Pocket PC, or other similar computer device.

In an embodiment, the second user 3414 may receive the business card facsimile. In an embodiment, the second user 3414 may transmit a reply 3420 to the first user 3412 with a facsimile of the second user's 3414 business card or with an acknowledgment of the first user's business card facsimile. In an embodiment, the main service facility 142 may match the reply to the first user 3412 and transmit 3418 the second user's 3414 business card or acknowledgment to the first user 3412. After receiving the reply, the first user 3412 may archive the reply as previously described.

In an embodiment, the communication between the user client 3412 and the second user 3414 may take place remotely, with the users in different locations, or with the users being at the same location.

Figure 35:
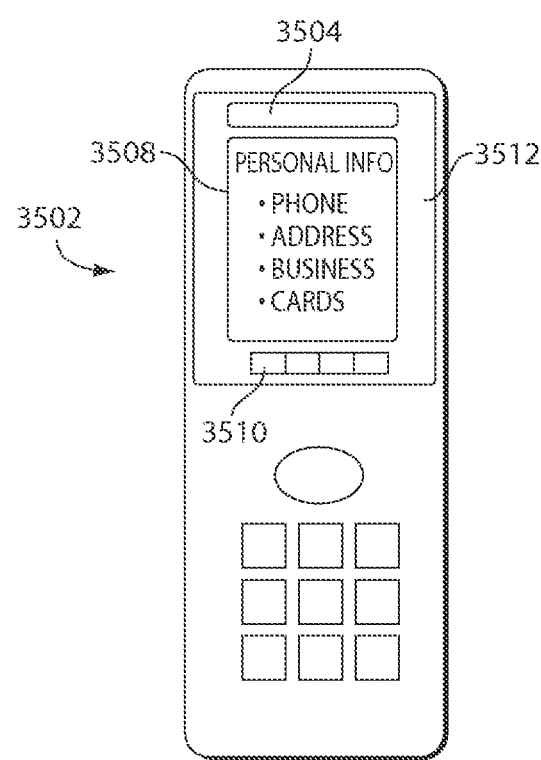
FIG. 35 depicts an embodiment of a user client portable computer device.

Referring to FIG. 35, an embodiment of a user client portable computer device 3504 is shown. For example, a portable computer device may be a cell phone, PDA, Pocket PC, tablet PC, or other similar computer device. In an embodiment, a client computer 3504 may have a user interface 3512 for personal information management. The user interface 3512 may have at least one method of navigation. For example, the user interface 3512 may have a menu 3504, navigation buttons 3510, action window 3508, or other navigation method. The menu 3504 may comprise action headings file, search, category, quit, or other needed action grouping. Within each of these menu 3504 action groupings there may be individual actions. The user interface 3512 may also have short cut buttons 3510 that may perform the function of the menu 3504 action items. After selecting an action, from either the menu 3504 or buttons 3510, an action window 3508 may be accessed to display actions that may be associated to the selected action. For example, in response to an action for display of Personal Action, the action window may display the available actions such as phone, address, business, or cards. The available actions may be selected to begin other actions.

In an embodiment, a user may purchase lottery tickets with a user client computer device. In an embodiment, the user client computer device may be a home computer, a public kiosk computer, cell phone, PDA, Pocket PC, tablet PC, or other computing device capable of communication according to aspects of the present invention. In an embodiment, a user may initiate the purchase of a lottery ticket from a gaming facility. A gaming facility may be any facility that is authorized and capable of issuing lottery tickets for a gaming organization. For example, the user may purchase a ticket from any government operated or legal business gaming operations (e.g. gaming casinos). In embodiments, a user may be able to select a personal lottery number, have the user client facility pick a random number, and or request the gaming facility to pick a random number. The user may transmit the lottery ticket purchase information to the gaming facility either wired or wireless. In an embodiment, the user may purchase the lottery ticket from a location other then the gaming facility or locally at the gaming facility. For example, the user may purchase the lottery tickets over the internet, through a public café, or other transaction center dealing with the exchange of lottery tickets.

Figure 36:
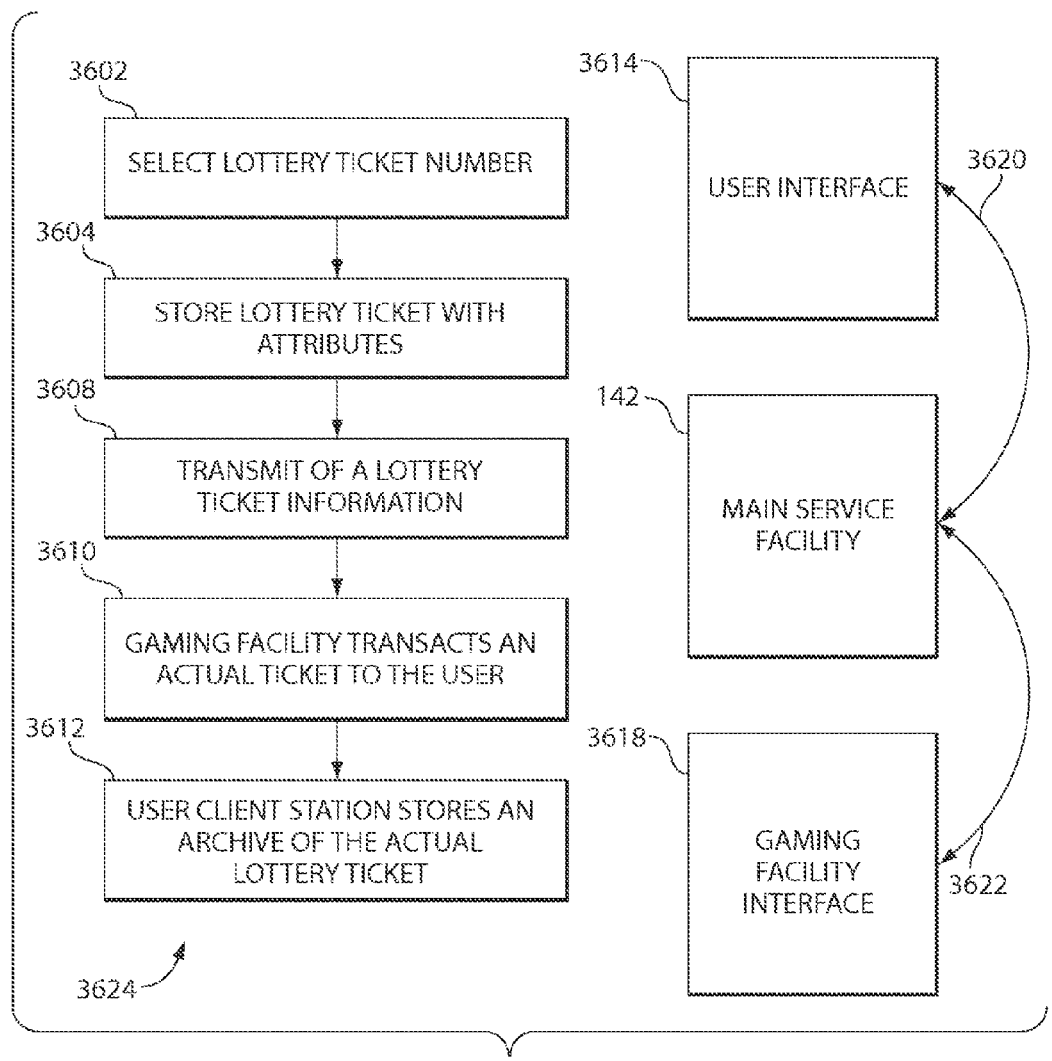
FIG. 36 illustrates a flow chart for the purchase of lottery tickets according to the principles of the present invention.

FIG. 36 illustrates a flow chart for the purchase of lottery tickets 3624 according to the principles of the present invention. In an embodiment, a user may select a lottery number 3602 to play at a gaming facility. The number may be selected by the user, randomly selected by the user's client computer, or the user may request the gaming facility to randomly select the lottery number. The user may then be able to store the lottery ticket number and or other attributes 3604 on the user client facility. The other attributes may be the users gaming identification number, name, phone number, or other information to identify the user as the lottery ticket purchaser. In an embodiment, the use may transmit the lottery ticket purchase to a gaming facility with the attributes 3608.

In an embodiment, the gaming facility may receive the lottery ticket purchase request from the user and then may transact the purchase of the ticket. For example, the gaming facility may transact payment of the lottery ticket before issuing the ticket to the user. The payment information may have been received with the lottery ticket request from the user. After verification of payment, the gaming facility may issue an actual facsimile of the lottery ticket 3610 to the user as a receipt of the purchase of the lottery ticket. The actual facsimile of the lottery ticket may be marked with an acknowledgement of payment for the lottery ticket, for example with the words "paid". The gaming facility may also issue a facsimile of the lottery ticket and a receipt indicating the payment for the lottery ticket.

Once the user receives a copy of the lottery ticket facsimile from a gaming facility, the user may store the facsimile in an archive 3612. The archives may be cataloged by gaming type, drawing date, date purchased, or other catalog chosen by the user.

Continuing with FIG. 36, an embodiment of the communication flow between the user client facility 3614, main service facility 142, and the gaming facility client 3618 is shown. In an embodiment, the user client 3614 may initiate communication to the gaming facility client 3618. The user client 3614 may transmit 3620 the lottery ticket request with the associated attributes to the main service facility 142. In embodiments, the attributes may be the number of tickets, the ticket number information, the users ID, the method of payment, and other information required for the purchase of the lottery ticket. The main service facility 142 may match the ticket request with the requested gaming facility 3618 and transmit all of the information 3622.

In an embodiment, the gaming facility client 3618 may receive the ticket request information from the main service facility 142. The gaming facility may process the payment from the user and then issue a facsimile of the lottery ticket to the user client 3614. The lottery ticket facsimile may have a marking acknowledging payment for the lottery ticket or the lottery ticket facsimile may be transmitted with a receipt indicating payment of the lottery ticket. The gaming facility 3618 may transmit 3622 the lottery ticket facsimile along with attributes that may be the purchase date, lottery drawing date, or other lottery information.

In an embodiment, the main service facility 142 may receive the lottery ticket facsimile and attributes and match them with the user 3614. The main service may then transmit 3620 the lottery ticket facsimile and attributes to the user 3614. The user 3614 may store the facsimile as previously described.

In an embodiment, either the user 3614 or the gaming facility 3618 may initiate the communication for notification for lottery winnings. In an embodiment, using the communication method described, the user 3614 may request from the gaming facility if at least one lottery ticket number has won. In an embodiment, after a lottery ticket drawing, the gaming facility may transmit to all winners' notification a lottery ticket has won. After notification of winning, the gaming facility may credit the winning amount to a user indicated bank account, credit account, debt account, or other designated account.

Figure 37:
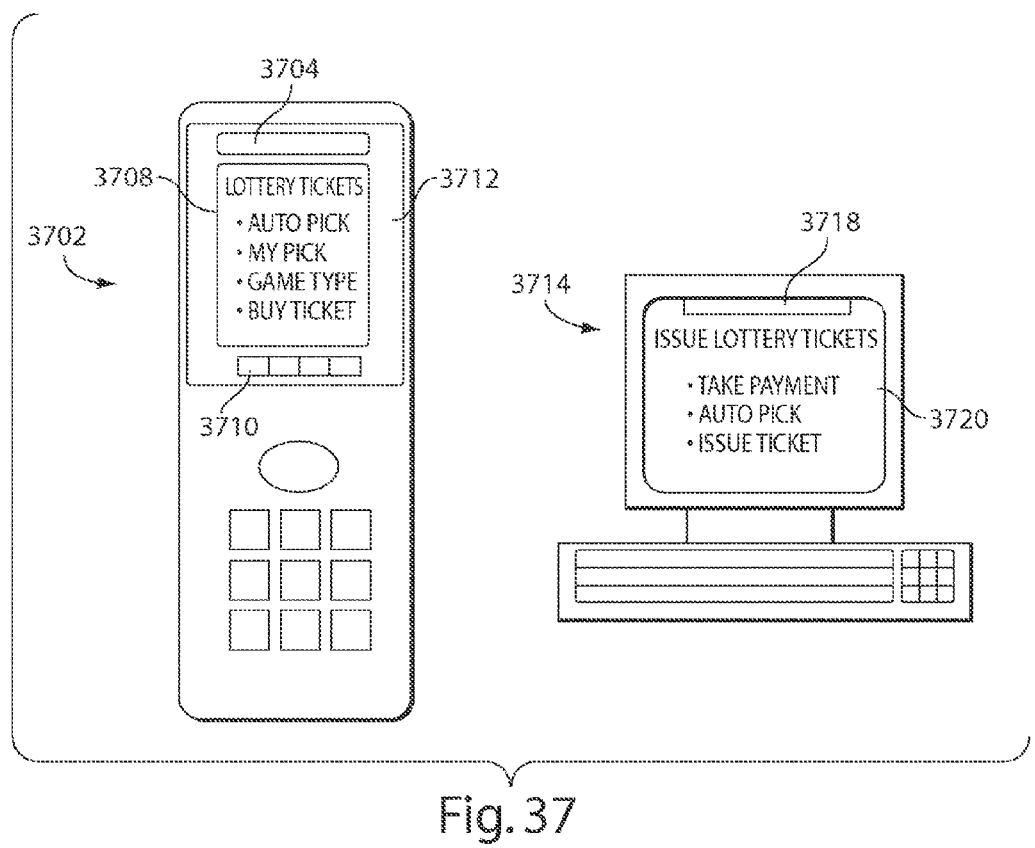
FIG. 37 depicts an embodiment of a user client portable computer device.

Referring to FIG. 37, an embodiment of a user client portable computer device 3704 is shown. For example, a portable computer device may be a cell phone, PDA, Pocket PC, tablet PC, or other similar computer device. In an embodiment, a client computer 3704 may have a user interface 3712 for purchase of lottery tickets. The user interface 3712 may have at least one method of navigation. For example, the user interface 3712 may have a menu 3704, navigation buttons 3710, action window 3708, or other navigation method. The menu 3704 may comprise action headings file, search, category, quit, or other needed action grouping. Within each of these menu 3704 action groupings there may be individual actions. The user interface 3712 may also have short cut buttons 3710 that may perform the function of the menu 3704 action items. After selecting an action, from either the menu 3704 or buttons 3710, an action window 3708 may be accessed to display actions that may be associated to the selected action. For example, in response to an action for Lottery Tickets, the action window may display the available actions such as Auto Pick, My Pick, Game Type, and Buy Tickets. The available actions may be selected to begin other actions.

In an embodiment of a gaming facility user interface 3714 is shown. In embodiments, the user interface 3714 may contain a menu 3718, a window for selecting actions 3720, or other method of navigating the user interface 3714. In embodiments, the menu 3718 may contain categories of actions. For example, the menu may contain file, search, retrieve, quit, or other option associated with managing lottery ticket distribution.

In embodiments, selecting a user interface 3714 option through the menu 3718 may open a window with related options. For example, a gaming facility may select an option to view the categories of options for issuing lottery tickets available on the client. A listing may be presented on in the window 3720. The listing displayed in the window 3720 may be selected to perform additional actions.

In an embodiment, a user may vote from a user client facility in place of using paper ballots at a dedicated polling place. For example, a user device may be used for corporate voting (e.g. vote for directors, shareholders, proxies, tender offers), public election voting (e.g. political candidates, unsafe area voting, local, municipal, county, state, federal), party elections, intra-party elections, selecting candidates, voting on certain bills and other legislation. A user may receive an actual facsimile of the ballot and may vote remotely or at a polling location. In an embodiment, remote voting may take place anywhere the user can communicate with a network. In an embodiment, a vote may take place within a certain distance within a polling location. In an embodiment, a vote may be registered by the polling location to prevent more than one vote to be cast by the same user.

In an embodiment, a user may vote for a television program (e.g. a game show) and the television operations may poll the audience. For example, polling may allow an entire population or anyone with a voting enabled electronic transaction facility to vote. In an embodiment, the audience may vote to determine what happens in an alternate ending of a television program.

In an embodiment, a vote may be based on or relate to advertising. For example, a user of an electronic vote transaction facility may see, hear or otherwise interact with an advertisement and he may vote for, or elect a preference, based on the advertisement.

In an embodiment, a user may store a ballot on an electronic vote transaction facility and the ballot may include attributes such as the date of the election, the type of election, and or past election results. In embodiments, the ballot may be stored and or transmitted in a format that represents an actual ballot containing ballot information.

In an embodiment, a user client facility may create a notification if a user misses the deadline for a certain election. For example, the device may inform the user as the deadline approaches, after the deadline and or when the next election of that type is taking place. Such vote reminders may be tailored to the users preferences. For example, the user client facility may be sensitive to a location (e.g. through a GPS facility, or through a proximity detection facility) and present ballot(s) for elections taking place in an area in close proximity to the user. In embodiments, such notifications may be based, at least in part, on the user's qualifications to vote in the election.

Figure 38:
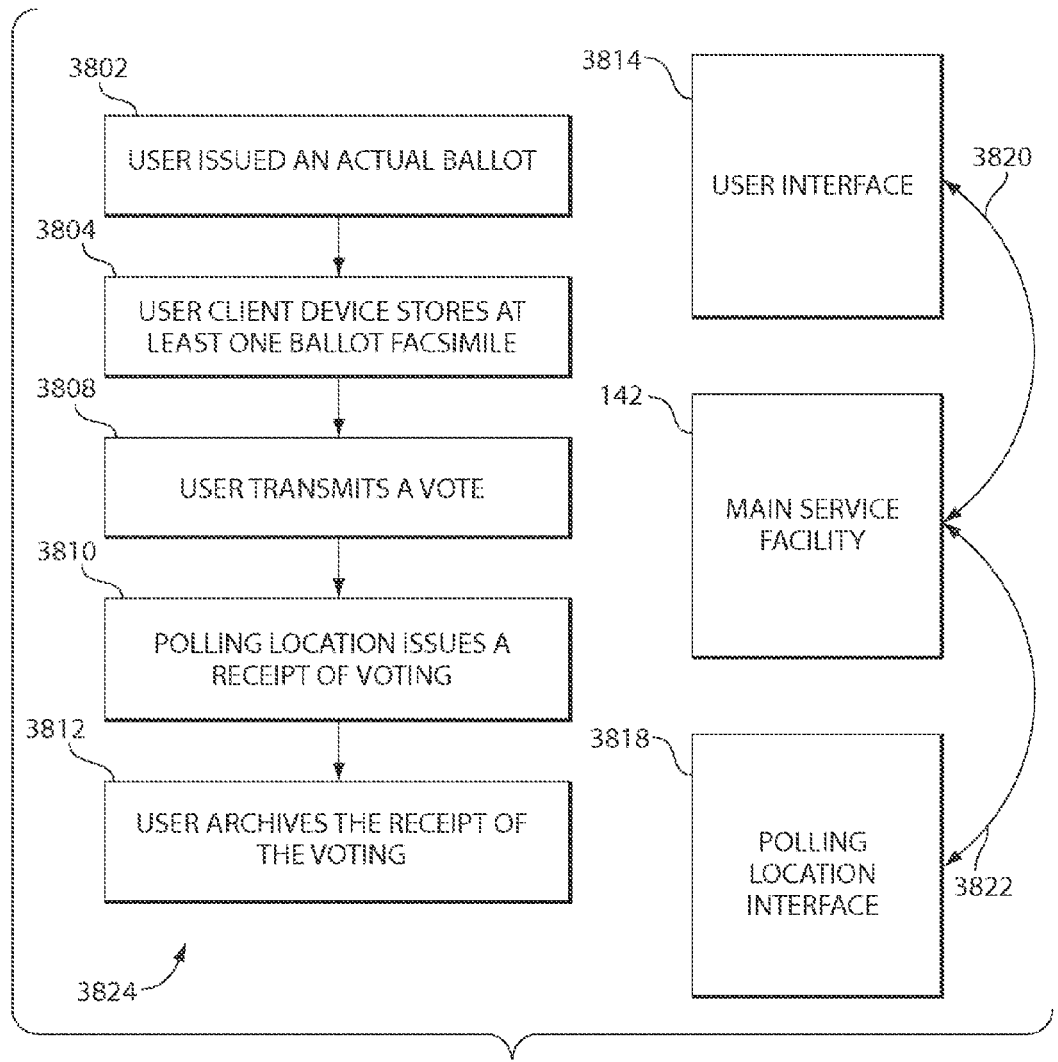
FIG. 38 illustrates a voting process flow according to the principles of the present invention.

FIG. 38 illustrates a voting process flow 3824 according to the principles of the present invention. In an embodiment, a user may be issued an actual ballot 3802 by a polling place. The ballot may be an actual facsimile of a ballot that the user may mark a vote. The user may store one or more facsimile ballots on a user client facility 3804. The ballots may be stored by ballot type, vote date, vote location, or other storage category.

In an embodiment, on an election day, a user may select a ballot from the stored ballots on the user client facility 3814 that will be used for voting. In an embodiment, there may be at least one ballot for an election. After the user has selected a ballot the user may mark the ballot for the users vote preferences. In an embodiment, with the ballot marked, the user may transmit the ballot 3808 to a polling location.

In an embodiment, a polling location may receive the user's marked facsimile ballot and may apply the users vote. In an embodiment, the users identification may be marked as voted to prevent the user from voting more than once. The user may be marked on a paper poll listing or a poll database to indicate that the user has voted. In an embodiment, after the users vote is recorded, the polling place may issue a receipt of the voting to the user 3810. For example, the receipt may be a facsimile of the ballot marked with an acknowledgement that the vote was recorded. The receipt may also be a facsimile of a document indicating that the users vote has been recorded.

In an embodiment, the user may receive the polling place receipt and archive it on the user client facility 3812. In an embodiment, the receipt from the polling place may be a facsimile of the ballot or a facsimile of a receipt document indicating the vote has been recorded. The user may archive the receipt in a category based on election date, election type, or other archive the user chooses.

Continuing to refer to FIG. 38, an embodiment of the communication between the user client 3814, main service facility 142, and the polling location 3818 is shown. A user may choose a ballot from the available ballots and transmit 3820 the ballot to the polling place. The facsimile of the ballot may be transmitted 3820 to the main service facility 142. The main service facility 142, may determine the correct polling location to transmit the facsimile ballot and transmit 3822 the facsimile ballot to the polling location 3818.

In an embodiment, the polling location 3818 may receive the facsimile ballot from the main service facility 142 and record the vote. In recording the users vote the polling location may mark the user's identification as having voted to prevent the user from voting more than once. In an embodiment, the polling place may transmit a receipt back to the user acknowledging that the ballot has been recorded. The polling location 3818 may transmit the receipt 3822 back to the main service facility 142. In an embodiment, the receipt may be a facsimile of the ballot with an indication that the vote has been recorded or the receipt may be a facsimile of a document indicating the vote was recorded.

In an embodiment, the main service facility 142 may match the ballot receipt to the voting user and transmit the voting receipt 3820 to the user 3814. In an embodiment, once the user has received the ballot receipt, the user may archive the receipt as described previously.

Figure 39:
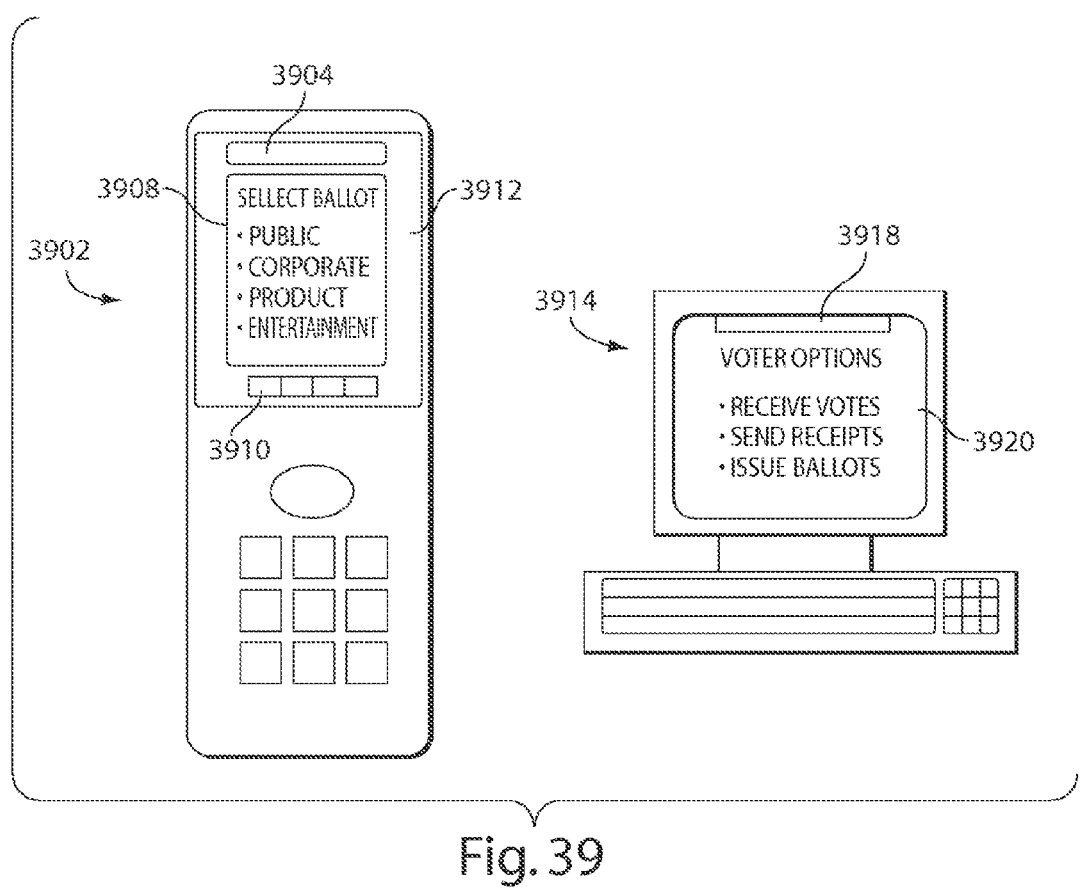
FIG. 39 depicts an embodiment of a user client portable computer device.

Referring to FIG. 39, an embodiment of a user client portable computer device 3904 is shown. For example, a portable computer device may be a cell phone, PDA, Pocket PC, tablet PC, or other similar computer device. In an embodiment, a client computer 3904 may have a user interface 3912 for voting using a facsimile ballot. The user interface 3912 may have at least one method of navigation. For example, the user interface 3912 may have a menu 3904, navigation buttons 3910, action window 3908, or other navigation method. The menu 3904 may comprise action headings file, search, category, quit, or other needed action grouping. Within each of these menu 3904 action groupings there may be individual actions. The user interface 3912 may also have short cut buttons 3910 that may perform the function of the menu 3904 action items. After selecting an action, from either the menu 3904 or buttons 3910, an action window 3908 may be accessed to display actions that may be associated to the selected action. For example, in response to an action for Select Ballot, the action window may display the available actions such as Public, Corporate, Product, or Entertainment. The available actions may be selected to begin other actions.

A voting transaction facility according to the principles of the present invention may include a user interface 3914 as illustrated in FIG. 39. In embodiments, the user interface 3914 may contain a menu 3918, a window for selecting actions 3920, or other method of navigating the user interface 3914. In embodiments, the menu 3918 may contain categories of actions. For example, the menu may contain file, search, retrieve, quit, or other option associated with managing the polling location ballots.

In embodiments, selecting a user interface 3914 option through the menu 3918 may open a window with related options. For example, a polling location may select an option to view the categories of options for handling ballots available on the client. A listing may be presented on in the window 3920. The listing displayed in the window 3920 may be selected to perform additional actions.

Certain embodiments of the present invention involve communicating, storing, printing and otherwise manipulating representations of particular transaction medium, such as when a representation of a check or money order is communicated and stored by an electronic transaction facility. It should be understood that there are many systems and methods adapted for communicating, storing and or retrieving representations of transaction mediums envisioned by the applicants of the present invention and such systems and methods are encompassed by the present invention. For example, the representation or facsimile may be presented in the form of a computer file associated with XML programming language in such a way that many transaction facilities (e.g. a pda, cell phone, laptop, or point of purchase transaction facility) may be able to read, view, store or otherwise manipulate the file. In embodiments, communicating a universal representation of a particular transaction medium may be used to facilitate a transaction, such as check cashing, where the receiver of the representation can visually see a representation that is familiar in nature.

An aspect of the present invention relates to making check payments through an electronic transaction facility. In embodiments, a portable transaction facility stores a facsimile of the check itself and or information relating to the check. The facsimile may be transmitted along with or in addition to check, personal, identification or other information. The transmission of the check facsimile may provide for the presentation of a check, as opposed to simply providing information pertaining to the check, tracking of the check, printing of the check and or otherwise processing of the check itself. In embodiments, the check may be transmitted or otherwise presented by itself. In other embodiments, the check may be accompanied by related check information, such as an account number, check number, routing number, account information, magnetic ink character recognition (MICR) number, name, address, phone, driver's license number, form of identification, form of identification verification, credit card information, other check information, signature, signature information, signature facsimile, security feature information or other information that may be useful in the transaction.

In embodiments, a bank or other financial institution may issue a customer checks in a form to be stored on the customers electronic transaction facility. For example, the bank may provide checks to a customer in a form to be stored on the customer's cell phone, pda, combination pda cell phone, desktop computer, laptop computer, hand held computer, or other transaction facility (e.g. those described herein). In embodiments, the customer may purchase or otherwise retrieve the checks and or related check information, remote from the bank, such as through the internet, local area network, personal area network, secure network, unsecure network, and or through other wired and or wireless communication facilities. The actual checks, check facsimiles, check replications, check images, and or other forms of check reproduction may be stored in the customer's transaction facility. Once the customer receives the checks and or other related information, the customer may be ready to use the checks and or other related information to perform transactions. For example, the customer may then go to a store or other location where he would like to pay for goods and or services by check and he may make the transaction through his portable transaction facility. During the transaction, the merchant in the transaction may have a transaction facility compatible with the customer's portable transaction facility to enable the transaction. The merchant's transaction facility may be capable of receiving the check, check information and or other forms of payment (e.g. credit cards, atm cards, paper checks and the like).

Figure 40:
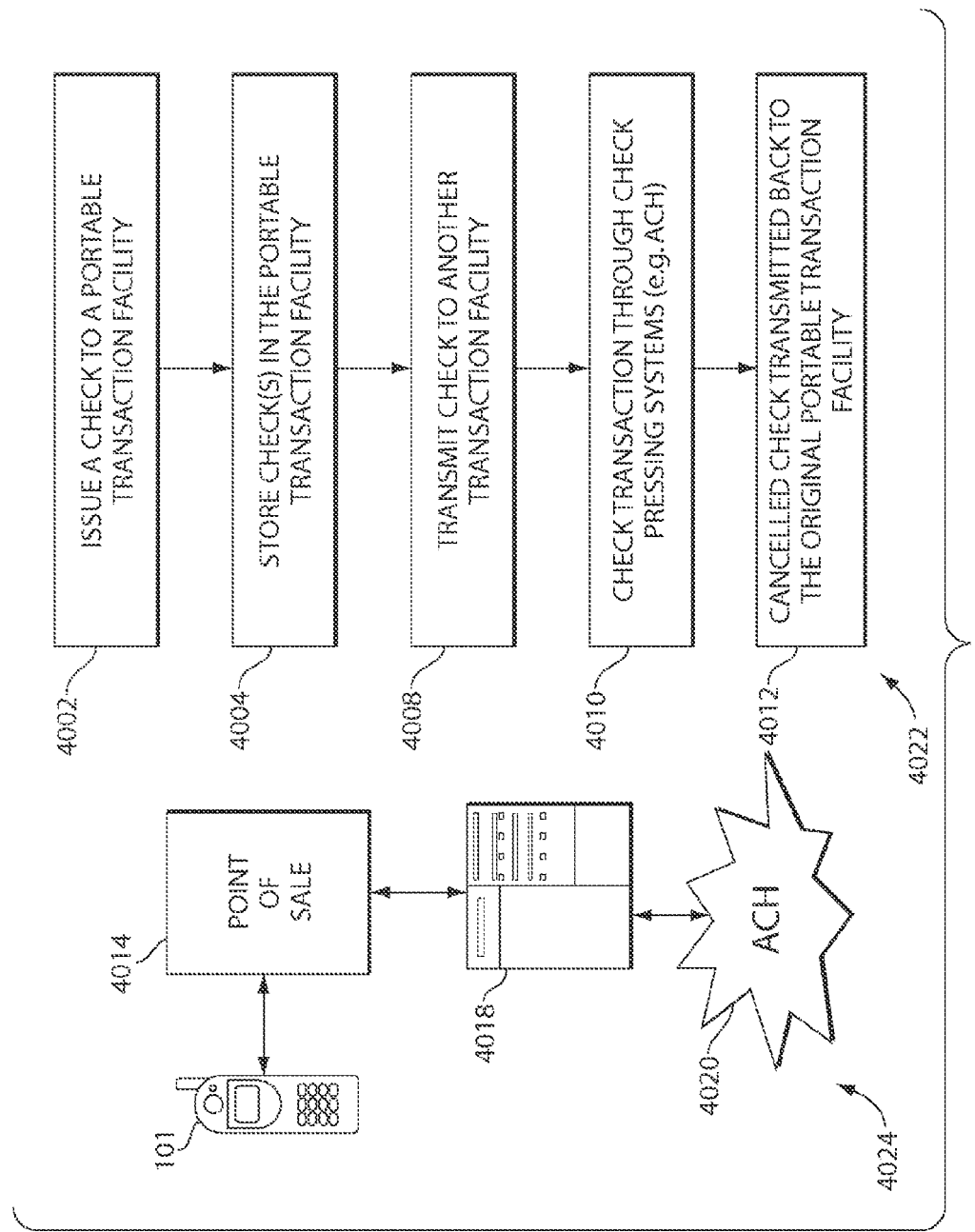
FIG. 40 illustrates a process for making a check transaction according to the principles of the present invention.

FIG. 40 illustrates a process for making a check transaction 4022 according to the principles of the present invention. For example, a check, and or related information, may be issued to a portable, or other, transaction facility through a financial institution (e.g. bank, credit union, or agent) in step 4002 of the process flow diagram. Then, the checks, and or related information, may be stored in memory in the transaction facility in step 4004. Then, a person in possession of the portable, or other, transaction facility may make a check transaction by communicating the check and or related information to another transaction facility 4008. In embodiments, the other transaction facility may be a dedicated check transaction facility or it may be a multi-functional transaction facility capable of making several types of economic transactions (e.g. credit card, atm card, printed check and the like). In embodiments, the other transaction facility may be a printer adapted to receive the check and print it for further transaction processing and or providing a receipt of the transaction. Once the merchant's transaction facility receives the check and or other related information, the merchant's transaction facility may communicate the check and or related information to a financial institution and or other check processing facility. For example, the check and or related information may be transmitted into an Automated Clearing House (ACH) processing system or other third party system designed to process the check and retrieve funds from the issuing financial institution 4010. Following an accepted transaction, a cancelled check and or related information may be communicated back to the customer's transaction facility where it may be stored, viewed, manipulated, re-communicated or otherwise handled 4012.

FIG. 40 also illustrates an electronic check transaction 4024 according to the principles of the present invention. In embodiments, a portable check transaction facility 101 may be used to make a check transaction for the purchase of goods, services, or to make other financial transfers. For example, the portable transaction facility 101 may be used to communicate with a point of purchase transaction facility 4014. The point of purchase transaction facility 4014 may receive a check and or check information from the portable transaction facility and communicate the check and or check information to a computer server, computer facility, computer network or other facility adapted to facilitate the check transaction 4018. For example, the computer facility 4018 may facilitate the check transaction through ACH processing centers, other third party processing centers, with a financial institution, bank, or other institution adapted to facilitate the check transaction 4020. In embodiments, once the check has been cleared, money has been transferred, money has been allocated or the transaction has otherwise been approved, a cancelled check, or other indication of a completed transaction, may be communicated back to the portable transaction facility 101. In embodiments, the point of purchase facility 4014 may facilitate the communication of the cancelled check and or receipt. In embodiments, an external facility (e.g. wireless cell phone provider, wireless network provider) may facilitate the communication of the cancelled check and or receipt.

Figure 41:
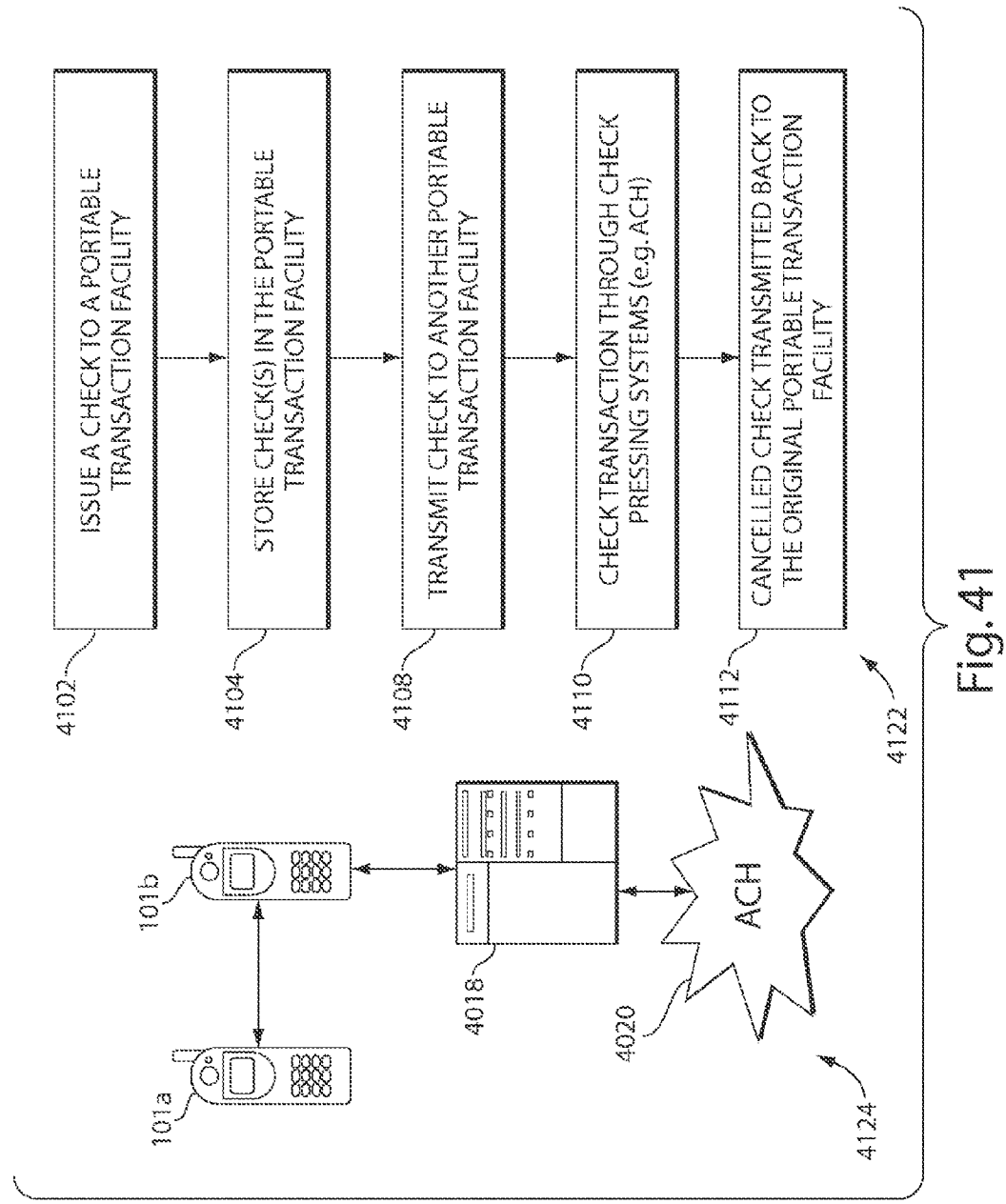
FIG. 41 illustrates a process for making a check transaction according to the principles of the present invention.

FIG. 41 illustrates a process for making a check transaction 4122 according to the principles of the present invention. For example, a check, and or related information, may be issued to a portable, or other, transaction facility through a financial institution (e.g. bank, credit union, or agent) in step 4102 of the process flow diagram. Then, the checks, and or related information, may be stored in memory in the transaction facility in step 4104. Then, a person in possession of the portable, or other, transaction facility may make a check transaction by communicating the check and or related information to another portable transaction facility 4108. Once the second portable transaction facility receives the check and or other related information, the second transaction facility may communicate the check and or related information to a financial institution and or other check processing facility. For example, the check and or related information may be transmitted into an Automated Clearing House (ACH) processing system or other third party system designed to process the check and retrieve funds from the issuing financial institution 4110. Following an accepted transaction, a cancelled check and or related information may be communicated back to the originator's transaction facility where it may be stored, viewed, manipulated, re-communicated or otherwise handled 4112.

FIG. 40 also illustrates an electronic check transaction 4124 according to the principles of the present invention. In embodiments, a portable check transaction facility 101*a* may be used to make a check transaction for the purchase of goods, services, or to make other financial transfers. For example, the portable transaction facility 101*a* may be used to communicate with portable transaction facility 101*b*. The second transaction facility 101*b* may receive a check and or check information from the portable transaction facility and communicate the check and or check information to a computer server, computer facility, computer network or other facility adapted to facilitate the check transaction 4018. For example, the computer facility 4018 may facilitate the check transaction through ACH processing centers, other third party processing centers, with a financial institution, bank, or other institution adapted to facilitate the check transaction 4020. In embodiments, once the check has been cleared, money has been transferred, money has been allocated or the transaction has otherwise been approved, a cancelled check, or other indication of a completed transaction, may be communicated back to the portable transaction facility 101*a*. In embodiments, the second transaction facility 101*b* may facilitate the communication of the cancelled check and or receipt. In embodiments, an external facility (e.g. wireless cell phone provider, wireless network provider) may facilitate the communication of the cancelled check and or receipt.

An aspect of the present invention relates to making money order transactions through electronic transaction facilities. In embodiments, a portable transaction facility stores a facsimile of the money order itself and or information related to the money order. The facsimile may be transmitted along with or in addition to money order, personal, identification or other information. The transmission of the money order facsimile may provide for the presentation of a money, as opposed to simply providing information pertaining to the money order, tracking of the money order, printing of the money order and or otherwise processing of the money order itself. In embodiments, the money order may be transmitted or otherwise presented by itself. In other embodiments, the money order may be accompanied by related money order information, such as an account number, check number, routing number, account information, magnetic ink character recognition (MICR) number, name, address, phone, driver's license number, form of identification, form of identification verification, credit card information, other check information, signature, signature information, signature facsimile, security feature information or other information that may be useful in the transaction.

In embodiments, a bank or other financial institution may issue a customer a money order in a form to be stored on the customer's electronic transaction facility. For example, the bank may provide a money order to a customer in a form to be stored on the customer's cell phone, pda, combination pda cell phone, desktop computer, laptop computer, hand held computer, or other transaction facility (e.g. those described herein). In embodiments, the customer may purchase or otherwise retrieve the a money order and or related money order information, remote from the bank, such as through the internet, local area network, personal area network, secure network, unsecure network, and or through other wired and or wireless communication facilities. The actual money order, money order facsimile, money order replication, money order image, and or other forms of money order reproduction may be stored in the customer's transaction facility. Once the customer receives the money order and or other related information, the customer may be ready to use the money order and or other related information to perform transactions. For example, the customer may then go to a store or other location where he would like to pay for goods and or services by money order and he may make the transaction through his portable transaction facility. During the transaction, the merchant in the transaction may have a transaction facility compatible with the customer's portable transaction facility to enable the transaction. The merchant's transaction facility may be capable of receiving the money order, money order information and or other forms of payment (e.g. credit cards, atm cards, paper checks and the like).

Figure 42:
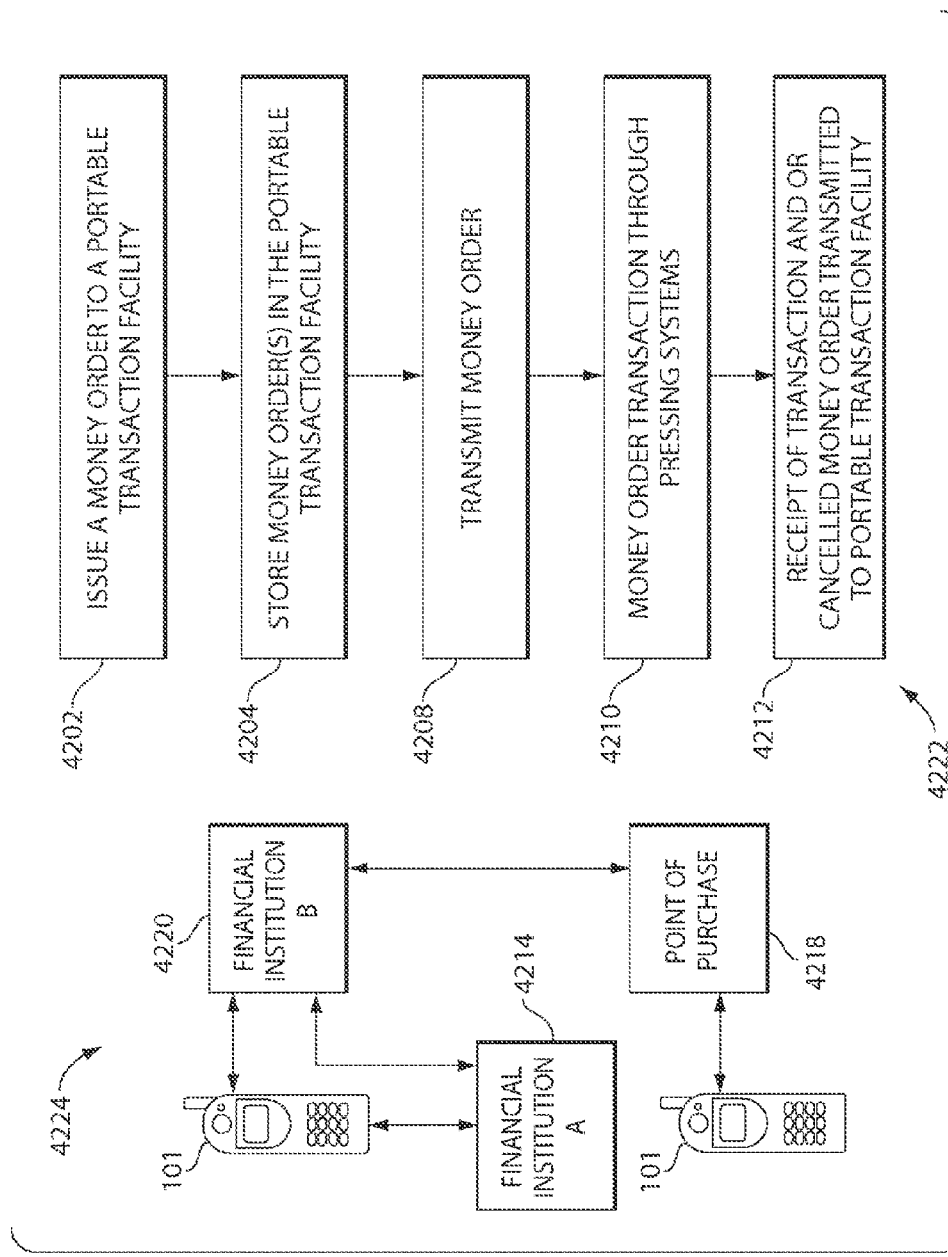
FIG. 42 illustrates an electronic money order transaction process according to the principles of the present invention.

FIG. 42 illustrates an electronic money order transaction process 4222 according to the principles of the present invention. In embodiments, the money order transaction process involves issuing a money order and or associated information to an electronic transaction facility (e.g. a cell phone, pda, laptop computer or other electronic transaction facility described herein) 4202. The money order and or associated information may be stored in memory in the electronic transaction facility 4204. In embodiments, it may be a representation of the actual money order that is communicated and or stored. For example, a money order facsimile or other representation may be stored in the memory of the electronic transaction facility to be later retrieved and or manipulated. To continue the process of performing a money order transaction through an electronic transaction facility, the process may involve transmitting the money order to another transaction facility 4210. The money order may then be processed through normal financial institutions 4210. Following an accepted transaction, a receipt of the transaction may be communicated back to the issuer's transaction facility 4212.

FIG. 42 also illustrates an electronic transaction 4224 according to the principles of the present invention. In embodiments, a transaction facility 101 may be used to purchase a money order from financial institution B 4220. For example, the transaction facility 101 may be used to communicate with financial institution B 4220 to request a money order purchase. The financial institution B 4220 may request payment for the money order from and or through the transaction facility 101 or the transaction facility 101 may direct financial institution B 4220 to withdraw the funds from another financial institution, financial institution A 4214. Once issuing financial institution B 4220 is paid or receives sufficient indication that it will be paid, it may issue the money order and or other associated information to the transactional facility 101. Then, possibly at a later time, the transaction facility 101 may be used to communicate the money order, representation of the money order and or other related information, to another transaction facility (e.g. at a point of purchase 4218). The transaction facility associated with the point of purchase may then communicate with financial institution B, or through an intermediate financial institution or exchange, to collect the money.

Figure 43:
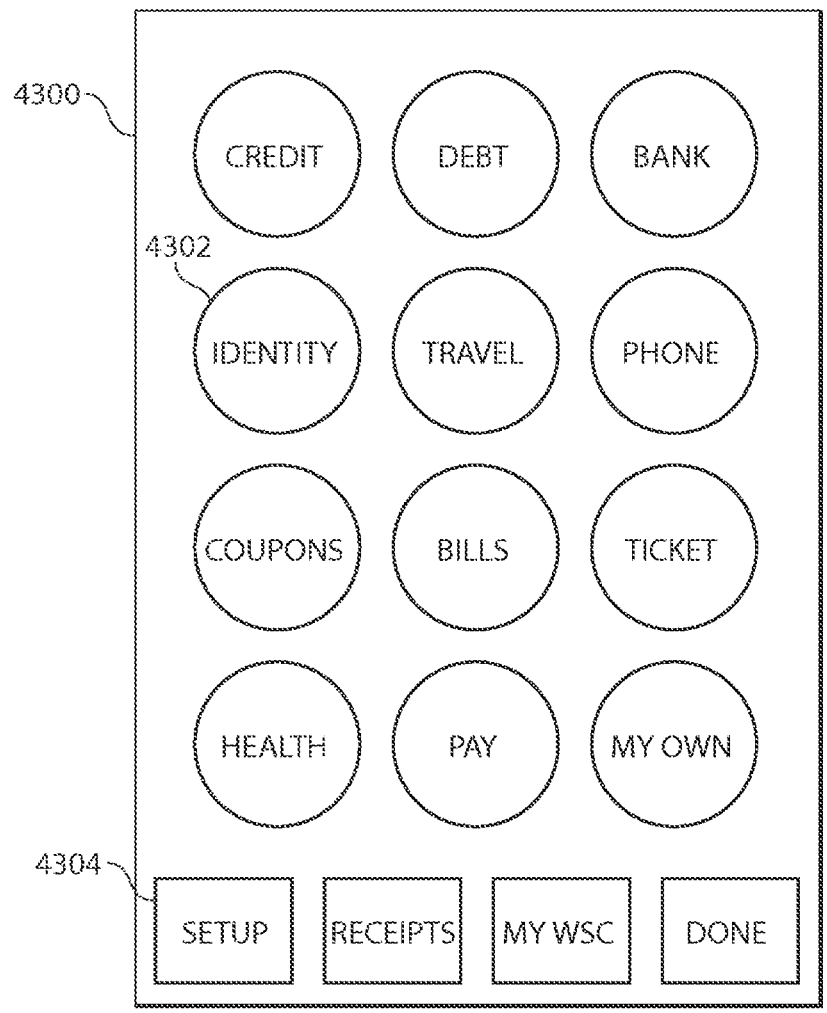
FIG. 43 depicts a potential user interface representative of a portal.

Referring now to FIG. 43, a user interface representative of a portal 4300 is depicted. In embodiments, the portal 4300 may be displayed on the display 100 of the electronic facility 101, on the local computer 160, on the support computer 134, or on any other display facility that may be operatively coupled to the main service facility 142. Within the portal 4300 may appear a user interface element representative of a service 4302. The service 4302 may be the service provided to the user by the electronic facility 101, including without limitation a service associated with credit, debit, banking, identity, travel, phone, a coupon, a bill, a ticket, a health-related service, and/or a payment, or, in other embodiments, any of the other services described herein and in the documents incorporated by reference herein. Alternatively or additionally, the service 4302 may be personalized and/or customized to the user, depicted in the figure as the service 4302 labeled "MY OWN." The portal may further comprise a binary user interface input element 4304, such as a button, checkbox, and/or link. The input element 4304 may allow the user to select a function associated with or related to the service. In this figure, for example, the portal 4300 presents the function to "SETUP" a service, to view one or more "RECEIPTS" from one or more prior transactions performed by the service, to view the user's wallet service center, or to indicate that the user has completed the current portal session. In any case, the portal 4300 provides for a single interface through which the user may access multiple services 4302, which may be offered by a plurality of service partners. Service partners have been described above and, in any case, may comprise without limitation a telecommunications company, an Internet service provider, an Internet content and/or services aggregator, a game publisher, an application service provider, or any of the other service providers described herein. The portal 4300 may serve as the user's view of his electronic wallet and/or as a functional point of contact between the service partners and the user. The portal 4300 may specialize in providing particular value added services that are related to a particular topic, such as game-related services, merchant-related services, airline-related services, government-related services, enterprise-related services, health-related services, fitness-related services, religion-related services, sports-related services, insurance-related services, university-related services, party-related services, pharma-exchange-related services, commodity-exchange-related services, secure payment services, secure transaction services, or any other services, including without limitation the services described herein. The portal 4300 may provide a particular service only to a registered user. This particular service may be personalized version of a value added service.

Figure 44:
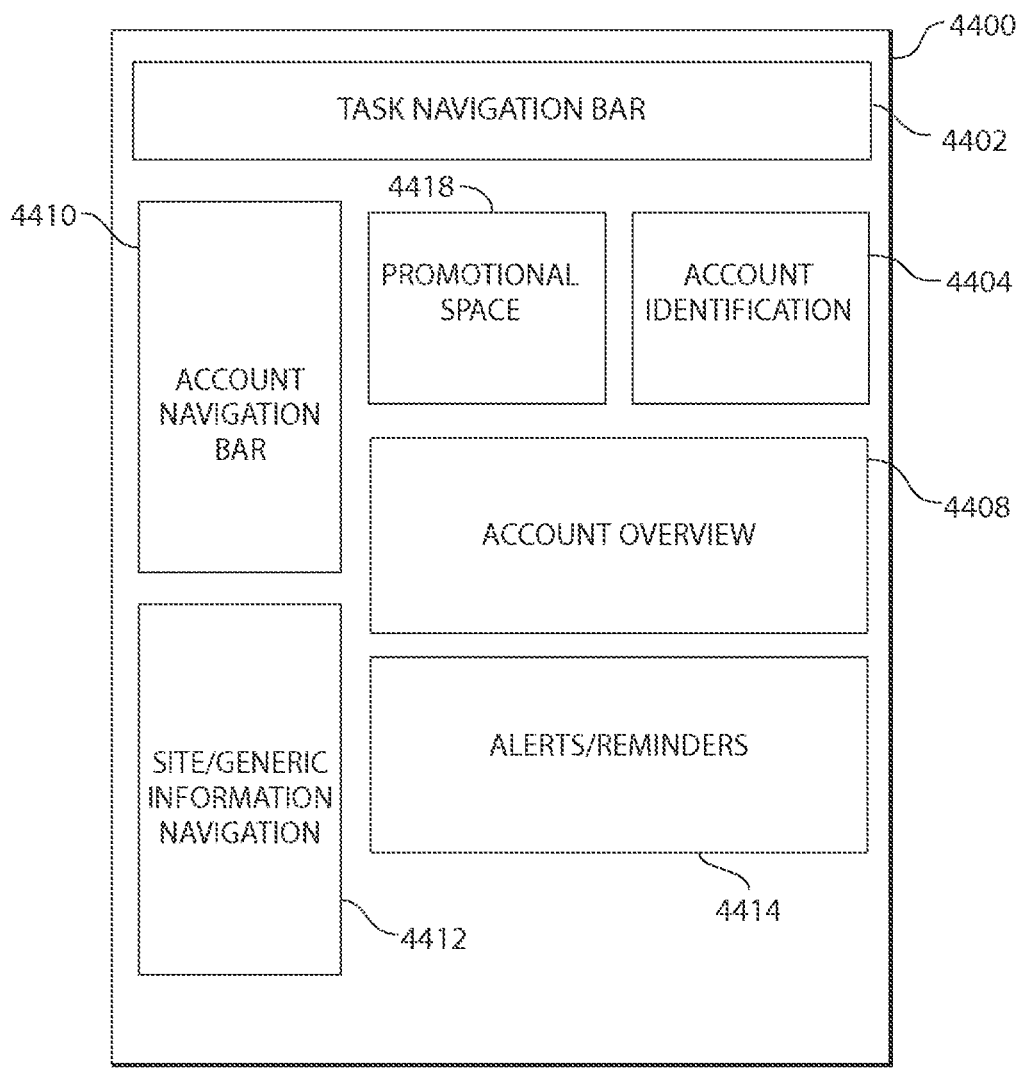
FIG. 44 depicts another potential user interface representative of a portal.

Referring now to FIG. 44, a Web-based user interface representative of a portal 4400 is depicted. In embodiments, the portal 4300 may be displayed on the display 100 of the electronic facility 101, on the local computer 160, on the support computer 134, or on any other display facility that may be operatively coupled to the main service facility 142. The task navigation bar 4402 may include navigational elements such as drop-down menus, tabs, buttons, links, and so forth. The tasks associated with the elements may relate to any of the services provided by the electronic transaction platform 100. The account navigation bar 4410 may include navigational elements such as drop-down menus, tabs, buttons, links, and so forth. The accounts associated with the elements may be any of the accounts supported by the electronic transaction platform 100, many of which are described herein and others of which will be apparent from the present disclosure and/or from the references included herein. The site/generic information navigation 4412 may include navigational elements akin to those of the task navigation bar 4402 and/or the account navigation bar 4410. The information associated with these elements of the site/generic information navigation area 4412 may be associated with a privacy policy; an item of contact information such as and without limitation an address, an e-mail address, a phone number, a fax number, a URL, a URI, and so forth; investor relations; a shopping cart; an account; an item; a press release; a solicitation for employment; a condition of use; a copyright notice; and so forth. The promotional space 4418 may include informational elements associated with promotion of a product and/or service. Such informational elements may, without limitation, comprise an advertisement, an image, a multimedia clip, an interactive application, text, a Google advertisement, and so forth. The account identification area 4404 may contain information pertaining to an account of a user. This information may include an account name, a user name, a field in which a user name may be entered, a field in which a password may be entered, a link to a feature that may remind the user of a password, and so forth. The account overview area 4408 may include information associated with an account to which the user is logged in. This information may be associated with a type of the account or a type of good and/or service that may be associated with the account. Many types of accounts, goods, and services are disclosed herein and many more will be apparent from the present disclosure and the references included herein. The alerts/reminders area 4414 may contain alerts and/or reminders that may be associated with the type of the account and/or with the type of a good/and or service that may be associated with the account. For example and without limitation, these alerts and/or reminders may comprise a birthday reminder; a scheduled payment reminder; an item pickup reminder; a renewal reminder; a low-balance alert; a buy alert; a sell alert; a voting reminder; and so forth.

Figure 47:
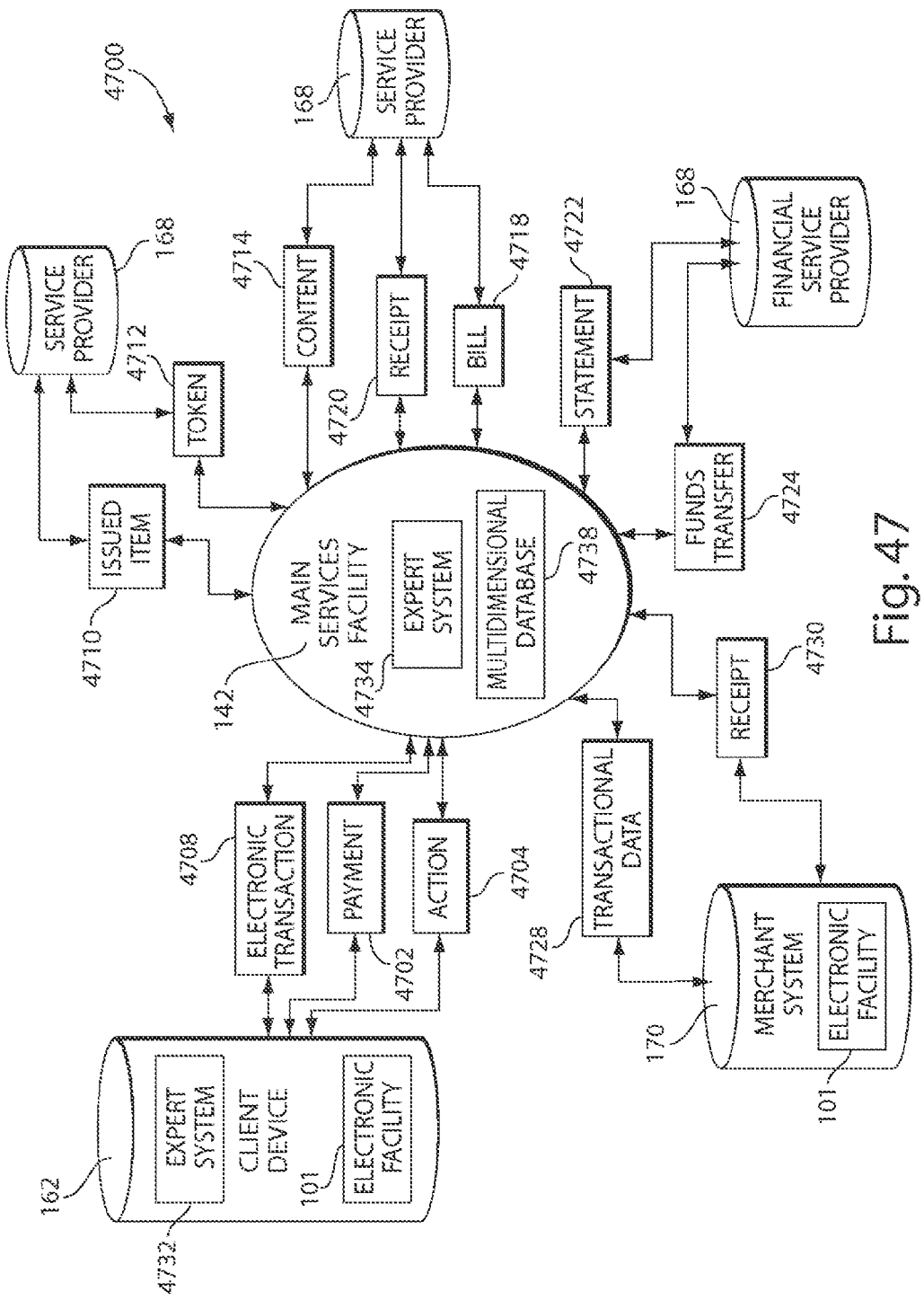
FIG. 47 depicts a platform according to the present invention.

Referring to FIG. 47, a platform 4700 having the components and attributes described herein may include a client device 162 with an electronic transaction facility 101, a merchant system 170, also with an electronic transaction facility 101, and a main services facility 142, which may be associated with various service providers 168, one of which may be a financial service provider 168. The platform 4700 may have the attributes described elsewhere herein. These include the attributes described in connection with the platform 100 of FIGS. 1 through 5, such as secure transaction capability, optionally using a client device 162 and supported by a secure distributed web-based platform, such as the main service facility 142. In embodiments, the transaction capability may be provided with or without a wallet-based metaphor, for payment or non-payment transactions. For example, a client device may initiate a payment 4702, initiate another form of electronic transaction 4708 (such as making an offer for an item in an auction, naming a price in a reverse auction, or the like), or initiate another action 4702, in each case optionally engaging device-level and user-level security features of the client device 162. In embodiments, the platform 4700 also provides the ability to issue, securely and electronically, an entire transaction token 4712 (which may be personalized or non-personalized) with all necessary images, branding, and/or data for conducting transactions, directly to a user, through a wired and/or wireless medium, to a personal client device 162. In embodiments the client device 162 may be a public device that is taken over for temporary personal use, such as a kiosk, public access computer, ATM, billboard, sign, appliance, or other public device equipped with computing capabilities. A transaction token 4712 may be any facility for enabling or embodying a transaction, including, but not limited to, credit cards, bank account cards, frequent flyer cards, stored value cards, loyalty cards, insurance cards, drivers licenses and other licenses, bills, invoices and similar instruments, coupons, tickets, promotional flyers, and a wide range of other tokens. A platform 4700 may also provide the ability to reproduce, securely and electronically, multiple existing card, account, and vendor information, or similar information, with branding and/or images, with necessary data for conducting transactions, on client device of choice (including a personal device or a public device taken for temporary personal use). Thus, a service provider may issue an item 4710, such as any of the foregoing, through the main services facility 142. A platform 100 may also provide the ability to conduct secure transactions n the physical world using proximity communication systems, such as infrared, RF, scanners, bar code readers, ultra-wide-band network facilities, Bluetooth facilities, 802.11x facilities, Wifi facilities and the like with any client device 162 and with any merchant system 170. In embodiments such transactions may include use of biometric parameters.

The platform 4700, like the platform 100 described above, may further include the ability to securely access personalized web-based user interface facilities for accessing various value added services from the service providers 168. A platform 4700 may also include payment related services, such as funds transfers 4724 or issuance of statements 4722 from a financial services provider 168. The platform 4700 may also include the ability to issue to, and reproduce on, a client device 162 (which may be a personal device or public device for temporary personal use), securely and electronically, a receipt 4720 or acknowledgement related to transactions conducted in the real world and/or virtual world. A platform 4700 may also provide the ability to store and archive electronic replica of receipts on a client device 162 and/or on a personalized web-based portal. In embodiments such receipts may be stored with a merchant acknowledgment of a transaction, such as a "PAID" stamp. In embodiments a platform 100 may enable the ability to securely and electronically interact with multiple domains, through any wired and/or wireless medium, to procure personalized tokens, initiate and complete transactions, receive receipt or acknowledgement of transaction, directly from client device of choice (a personal device or public device for temporary personal use).

A platform 4700 like a platform 100 as described herein also enables the ability to secure proximity and over-the-air transactions, including issuance of tokens and receipts, using multidimensional authentication, verifying the identity of, for example, the user of a client device 162, merchant system 170 or other device, verifying the identity of the device itself, and verifying the identity of the domain for one or more transactions, in each case using appropriate cryptography tools and an appropriate strength of encryption, optionally with the ability to customize the nature of the Public/Private Key Infrastructure on a per user, per device and per domain basis. A platform 4700 also provides the ability to securely encrypt tokens and receipts, not only when they are issued, but also when they are stored on the client device. A platform 100 as described herein also includes the ability to configure the user-Interface and various personalized and/or non-personalized applications on the client device 162 (which may be a personal device or a public device taken for temporary personal use) based on the user's preferences and/or through the support of an Expert system 4732 capable of learning over a period of time based on the user's behavior, usage patterns, transaction history and qualified external inputs. An expert system 4734 may also reside on the main services facility 142 (which may comprise one or more servers). A platform 4700 may also enable the ability to provision multiple tokens, multiple services and multiple personalized and/or non-personalized applications, with a high level of throughput, efficiency, and fault tolerance, to the user's client device 162 (which may be a personal device or a public device taken for temporary personal use) based on the user's preferences and/or through the support of an expert system capable of learning over a period of time based on the user's behavior, usage patterns, transaction history and qualified external inputs. In embodiments, the platform 4700 has a distributed infrastructure, so that the various attributes described herein can be embodied on a client device 162, merchant system 170, main service facility 142 or other device or system, such as a service provider system. In embodiments a multidimensional database 4738 may be used to store attributes related to clients, client devices 162, services, service providers 168, merchants, merchant systems 170, transactions, payments, tokens, receipts, and other items. The database may store such information in more than one dimension, so that it can be accessed by different applications or for different purposes.

Figure 48:
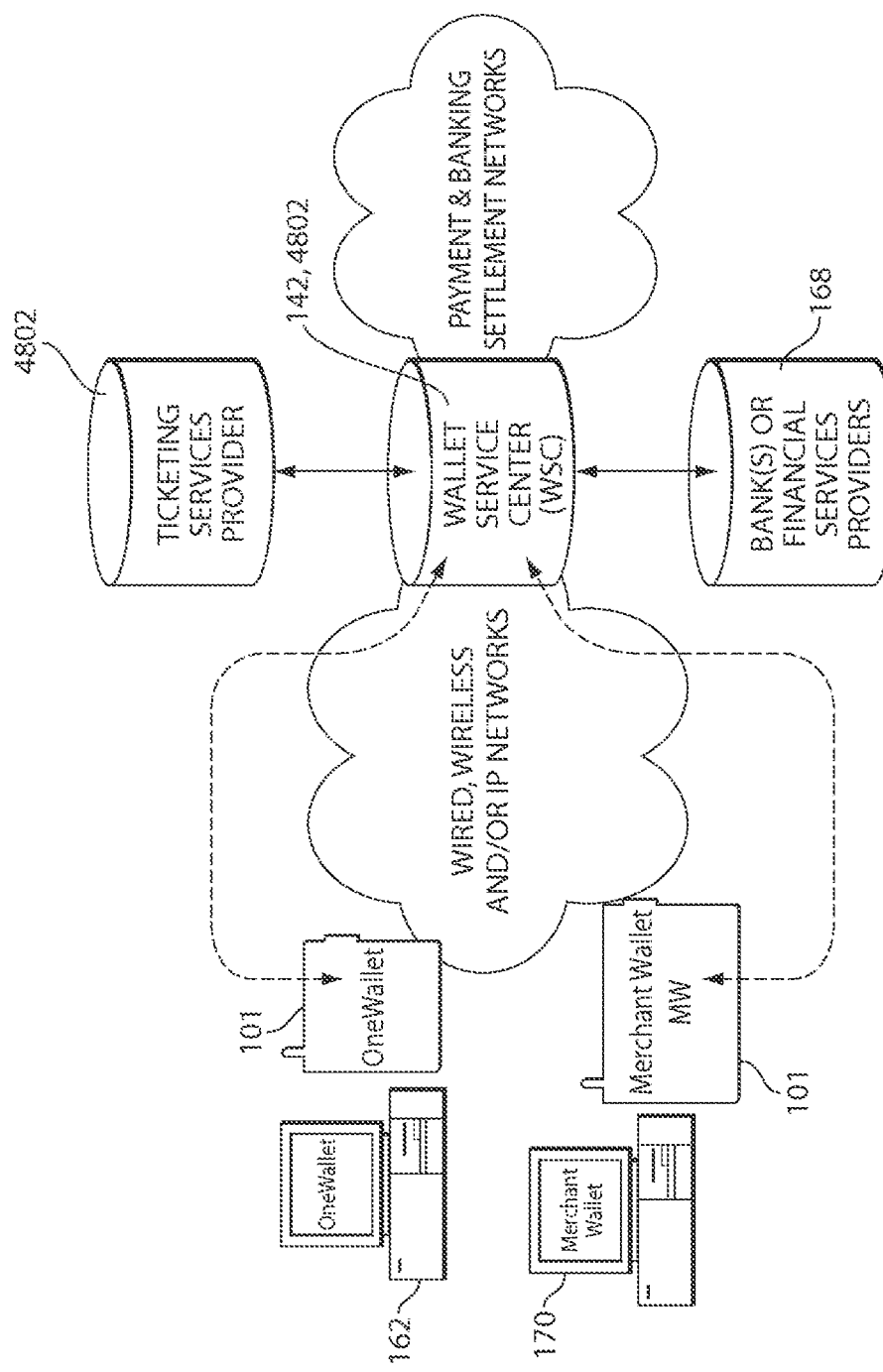
FIG. 48 is a high-level schematic diagram depicting features of a ticketing process using a platform.

Referring to FIG. 48, a high-level schematic diagram depicts features of a ticketing process, using a platform 100 that includes an electronic facility 101 and one or more main service facilities 142. The electronic facility 101 is referred to as the "OneWallet," in this figure, and the main service facility 142 is referred to as the wallet service center (WSC) 4808. In embodiments, a user invokes the universal electronic facility 101, such as invoking a "OneWallet" application, and inputs details of the ticket to be purchased, which might be any kind of ticket. The ticketing system 4802 of a ticketing services provider validates the request and confirms the availability of the ticket, optionally providing pricing data or other data, such as prompting the user to select among other options, such as a class of ticket, a seat location, or the like. The user may select a payment instrument from the electronic facility 101 and initiate a secure electronic payment process, such as a process that results in payment from a bank or financial service provider 168. The service provider 168 may receive a credit confirmation, after which an electronic ticket is sent securely and electronically, over-the-air, through the main service facility 142 to the electronic facility 101 on the client device 162. In embodiments the platform 100 may also include an electronic transaction facility 101 suitable to run as an application on a merchant system 170, such as the merchant wallet 4804. A merchant, through the merchant wallet 4804, may use the wallet 4804 on a merchant system 170, such as a machine at a merchant location, such as a retail location or the like. The merchant may interact with the main service facility 142, in this case the wallet service center 4808, capturing and sending a customer's request for a ticket to the ticketing system. The ticketing system can validate the request and confirm availability, communicating pricing to the electronic facility 101 (a "merchant wallet") on the merchant system 170. On confirmation, payment details may be sent securely and electronically through the wallet service center 4808 (or similar main service facility 142). The merchant may accept payment from the customer. On payment, the ticketing system issues a ticket to the electronic facility 101 of the merchant system 170. In embodiments the merchant may print out the ticket and hand it to the customer.

Figure 49:
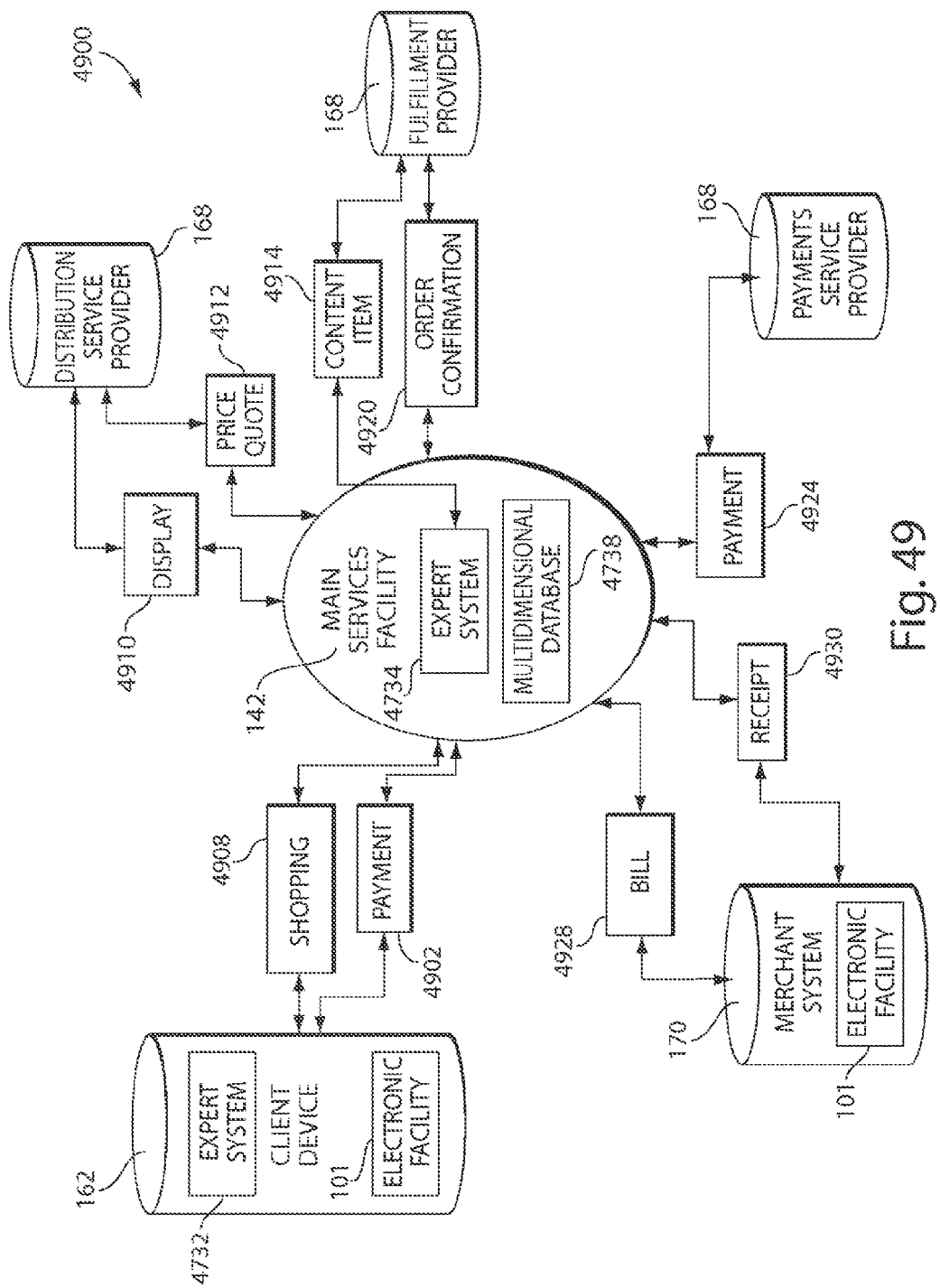
FIG. 49 depicts a platform through which a merchant using a merchant system make enable various features and attributes according to the present invention.

FIG. 49 shows a platform 4900 through which a merchant using a merchant system 170 can enable the various features and attributes described herein, such as in connection with the platforms 100 and 4700 described above. A merchant may be any merchant, such as a telecommunications company, bank, internet service provider, or vendor of goods or services. The merchant can set up a web-based platform using a main services facility 142, which may have a secure transaction interface with the merchant system 170 in the form of an electronic transaction facility 101 with the attributes described herein, which may interface with various backend systems such as a supply chain management system, an inventory database, and the like of the merchant. The merchant may also set up payment systems using the main service facility 142, in conjunction with a payments services provider 168, such as a bank, paypal or a similar service, so that the payments service provider 168 can provide secure payments 4924 to the merchant through the platform of a main services facility 142. The merchant may also set up relationships with manufacturers, vendors, service providers, sales representatives, distributors and other parties, each of whom may access the main service facility 142 to provide various value added services relating to the selling of the merchant's goods or services, including services such as distribution, fulfillment and secure payment services. For example, a distribution service provider 168 may display goods 4910 with a price quote 4912, such as on a web site or by an email that can be accessed through the main services facility 142 by a client device 162. In some cases goods may include content items 4914 that can be fulfilled by a fulfillment provider directly to the client device 162. The goods may be physical goods that are shipped by the fulfillment provider after receiving a payment 4924 from a payments service provider 168, or may be electronic goods, such as tickets, music, entertainment content, games, or the like, which in embodiments are fulfilled with branding, logos or the like. The fulfillment provider may provide order confirmation 4920 through the main services facility 142. In each case, the main services facility 142 can provide the features described above, including providing multilevel security related to the domain, user and device, as well as capturing multidimensional data about the goods, services, customers, transactions and the like supported by the merchant in the multidimensional database 4738. The merchant may have a physical retail location or may be an entirely online merchant.

The platform 4900 can use client devices of a merchant (which might be a personal device or a public device such as a sign or vending machine taken for temporary personal use). This may include mobile phones, PCs, point-of-sale terminals, kiosks, etc., to conduct various secure transactions, which include but are not limited to accepting payments, conducting payments on behalf of other service providers, procuring goods and/or services, and distributing goods and/or services, using existing payment instruments, which include but are not limited to cash, credit cards, debit cards, electronic checks, prepaid and stored value accounts, etc. Merchants can use the platform 4900 to offer consumers the ability to conduct various secure personalized transactions, including but not limited to, buying goods and/or services, or redeeming personalized coupons and promotions, or paying their bills, or transferring funds, or topping up airtime, or purchasing and procuring tickets (travel or entertainment), or conducting mobile banking transactions, or buying/redeeming lotteries, or voting (for Government and/or private Enterprise), etc., utilizing their own infrastructure (physical and virtual) as well as the secure transaction abilities of the platform 4900.

Merchants can use the platform 4900 to procure goods and services from distributors and manufacturers, for the purposes of re-selling to consumers and/or other retailers and/or other distributors, by placing orders for such goods and/or services and making payments securely and electronically in real time, using the secure transaction capabilities of the platform 4900. Merchants can use the platform 4900 to enable distributors and fulfillment service providers to distribute and fulfill the merchants' own goods and services. The platform 4900 can support various value added services for merchants, such as the capability to securely store transaction records, capability to mine and analyze the data, and capability to avail various analytical, quantitative and value added services for increasing overall profitability.

The merchant using a merchant system 170 may be an entity in the real world and/or a virtual world. The provider of the platform 4900 may without limitation be a Telco, Internet service provider, Internet content and/or service aggregator, game publisher, third-party application service provider, or any other service provider 168. The capability may be comprise the setup and provision of a Web-based platform.

The platform 4900 may specialize in providing a value added service related to the selling of goods and/or services; the procurement of goods and/or services; and/or the distribution of goods and/or services. The value added service may comprise a secure payment and transaction service, which may be described elsewhere in this disclosure. In particular, the platform 4900 may have a secure transaction interface with the merchant's existing backend system, a financial services provider, a payment system, a manufacturer, a service provider, a distributor, or with any other system.

The platform 4900 may use an exiting client facility of the merchant or may interface with an electronic facility (portable or otherwise) that acts as a client facility. In any case, the client facility may be a privately available device or a publicly available device. The client facility may be a portable electronic facility, a mobile phone, a personal computer, a point-of-sale terminal, a kiosk, and so forth. The client facility may conduct a secure transaction, which may without limitation comprise accepting a payment, conducting a payment on behalf of a service provider, procuring a good and/or service, distributing a good and/or service, using an existing payment instrument, and so forth. The existing payment instrument may comprise cash, a credit card, a debit card, an electronic check, a prepaid account, a stored value account, and so forth.

The platform 4900 may provide the merchant with the ability to offer a user, who may be a consumer, with the ability to conduct a secure transaction, which may be a personalized transaction, which may without limitation comprise without limitation buying a good and/or service, redeeming a coupon (personalized or otherwise), participating in a promotion (personalized or otherwise), paying a bill, transferring funds, topping up airtime, purchasing and/or procuring a ticket (including without limitation a travel ticket or entertainment ticket), conducting a banking transaction (which may without limitation be a mobile banking transaction), buying a lottery instrument (such as without limitation a lottery ticket), redeeming the lottery instrument, voting (such as without limitation for a governmental election, a corporate election, and so on), and so forth.

Figure 50:
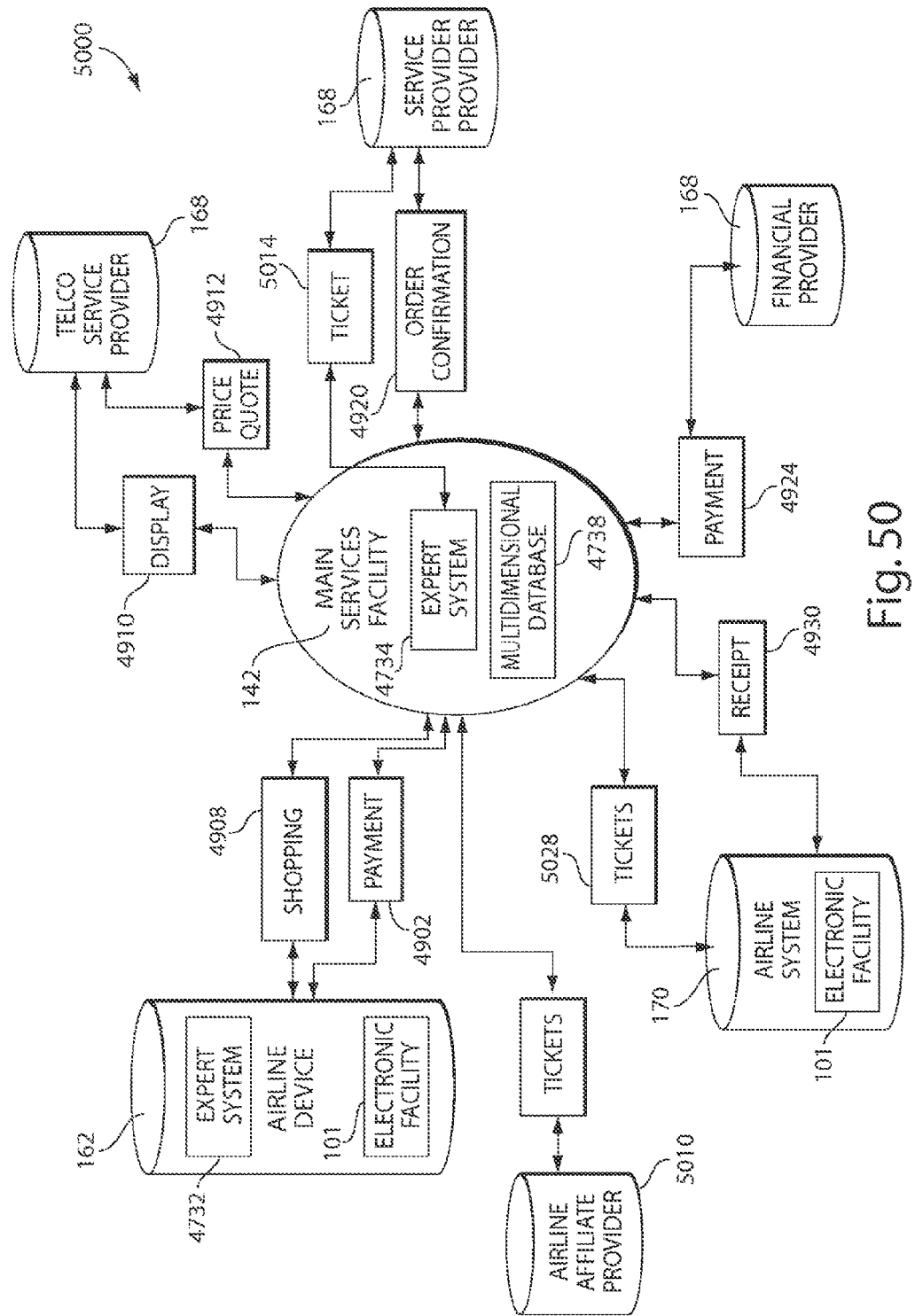
FIG. 50 depicts a platform through which a provider can connect with an airline system or an affiliate to enable various features and attributes according to the present invention.

FIG. 50 shows a platform 5000 through which a service provider, financial provider, telecommunications provider or other provider or entity 168 can connect with an airline system 170 or an affiliate of the airline 5110 which can enable the various feature and attributes described herein, such as in connection with the platforms 100 and 4700 described above. FIG. 50 illustrates a platform where an Airline and/or Telco and/or Bank and/or Service Provider and/or Internet Service Provider and/or Application Service Provider and/or other entity, has the ability to setup a web-based platform through a main service facility 142, which has secure transaction interfaces with Airline's existing back-end systems 170, various financial services providers, payment systems, service providers, and third-party ticketing systems (e.g. providing third party tickets 5014), where such platform 5000 specializes in providing various value added services related to the selling and distribution of tickets (such as airline tickets 5028) and related services (e.g. for their own Airline, as well as other partners or affiliates 5110 which may include other Airlines, Hotels, Car-rentals, Restaurants, Banks, etc.), selling and distribution of loyalty based products and services (e.g. for their own Airline, as well as other partners or affiliates 5110 which may include other Airlines, Hotels, Car-rentals, Restaurants, Banks, etc.), distribution of coupons and promotions (e.g. for their own Airline, as well as other partners which may include other Airlines, Hotels, Car-rentals, Restaurants, Banks, etc.), and overall management of employee's time and resources, and including various secure payment and transaction services; with a focus on increasing efficiency, user convenience, customer and partner support, and overall profitability.

The airline connectivity platform 5000 may also provide Customers, Employees, Distributors and Agents, with client devices 162 or alternately use their existing client devices 162 (in either case, the client device could be a personal device or public device for temporary personal use), which include but are not limited to mobile phones, PCs, point-of-sale terminals, kiosks, etc., to conduct various secure transactions, which includes but are not limited to accepting payments for goods and services, distribution of goods and services, distribution of information with our without preferences, and conducting payments on behalf of other service providers, using existing payment instruments, which include but are not limited to cash, credit cards, debit cards, electronic checks, prepaid and stored value accounts, etc.

The airplane connectivity platform 5000 may also provide Customers with the ability to securely book travel and other related services from the Airline or any of its partners, purchase tickets and related services from the Airline or any of its partners, securely download the tickets and related information/services from the Airline or any of its partners, securely download loyalty cards/co-branded cards/payment cards/coupons/promotions, etc. from the Airline or any of its partners, redeem tickets/cards/coupons, etc. at a point of transaction, and avail various related profile driven and personalized value added services, such as managing travel and loyalty information, archiving transaction records, etc. For example, a customer may make such transaction(s) thorough the use of a client device or airline device similar to that described in connection with Airline device 162 and other such devices described herein.

The airline connectivity platform 5000 may also enable the Airline to better manage its Employees and usage of various goods and resources, with a focus on increasing overall profitability, for example, by allowing Employees to access their individual flight scheduling information, or by allowing Employees to schedule the delivery of various goods and services to the aircraft, etc., all done remotely, securely and in real-time through client devices, airline device 162 or other such devices as described herein.

The airline connectivity platform 5000 may also enable the Airline to sell tickets, issue tickets and other related services directly to their customers, without using agents and their networks.

The airline connectivity platform 5000 may also enable the Airline's Agents to issue tickets and other related services (of the Airline as well as their participating partners), to customers.

Figure 51:
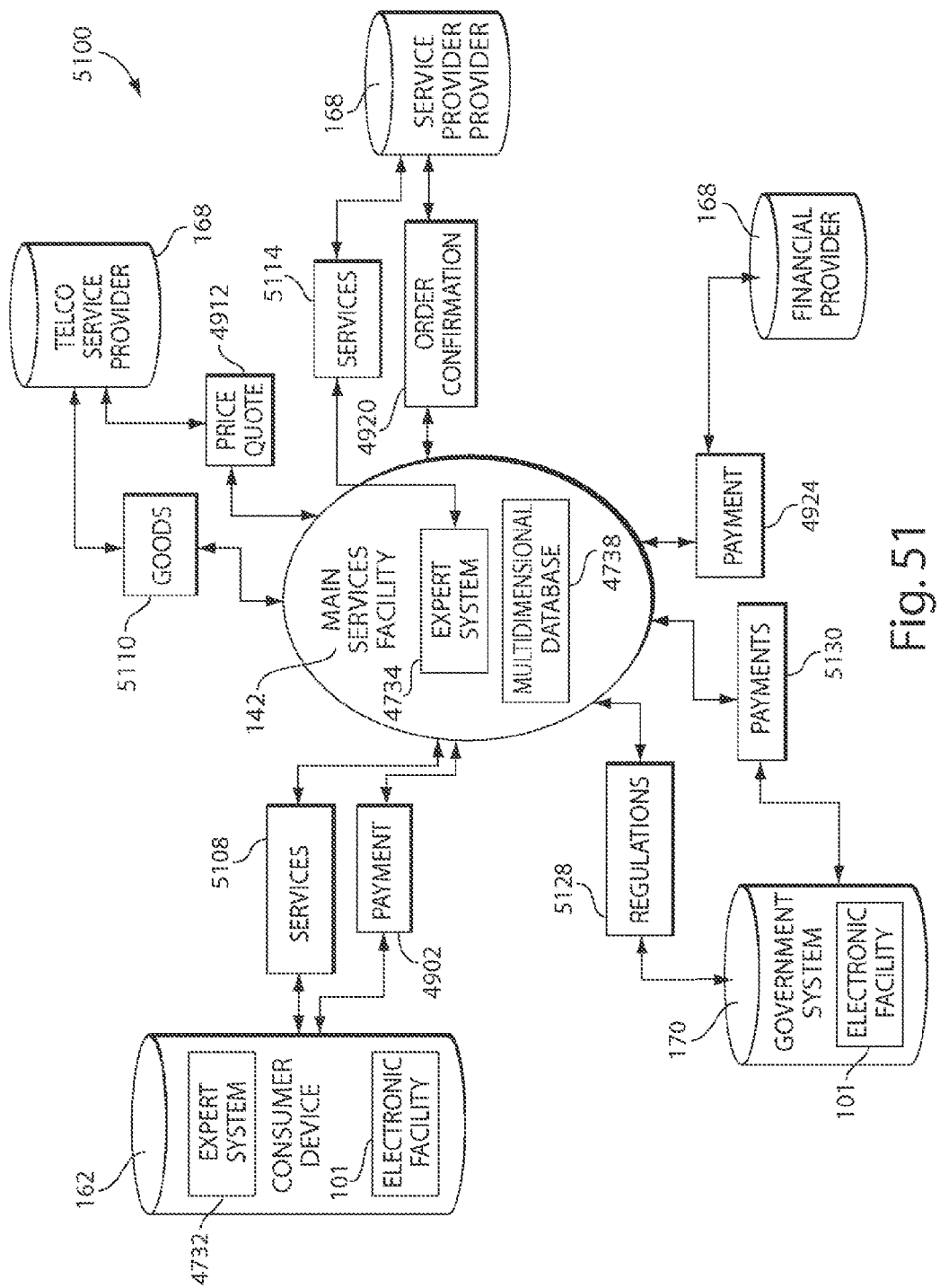
FIG. 51 depicts a platform through which a government entity using a government entity system can enable various features and attributes according to the present invention.

FIG. 51 shows a platform 5100 through which a government entity using a government entity system 170 can enable the various feature and attributes described herein, such as in connection with the platforms 100 and 4700 described above. FIG. 51 illustrates a government connectivity platform 5100 where a Government and/or Telco and/or Bank and/or Service Provider and/or Internet Service Provider and/or Application Service Provider and/or other entity, has the ability to setup a web-based platform through a main services facility 142, which has secure transaction interfaces with Government's existing back-end systems 170, various financial services providers, payment systems, utility and service providers, where such Portal specializes in providing value added services related to the selling and distribution of various government run/managed goods 5110 and services directly to citizens, as well as other government organizations, and private enterprises (G2C, G2G, G2B, etc.), and including various secure payment and transaction services (which may be associated with payments 5130); in association and/or accordance with governmental regulations 5128; in the process increasing overall efficiency, convenience for citizens and employees, and profitability.

The government connectivity platform 5100 may provide Employees, Commission Agents, Enterprises and Citizens, with client devices or alternately use their existing client devices (in either case, the client device could be a personal device or public device for temporary personal use), which include but are not limited to mobile phones, PCs, point-of-sale terminals, kiosks, etc., to conduct various secure transactions, which includes but are not limited to accepting payments for goods and services, distribution of goods and services, distribution of information with our without preferences, and conducting payments on behalf of other service providers, using existing payment instruments, which include but are not limited to cash, credit cards, debit cards, electronic checks, prepaid and stored value accounts, etc. For example, a government service provider 168 may provide services through the government entity (e.g. such as providing services 5114 and issuing order confirmations 4920) on behalf of the government entity. As another example, a service provider 168 may provide services or goods 5110 to the government entity along with price quotes 4912 and the like. A citizen (or non-citizen) may connect to the government system 170 through the main facility 142 to obtain services 5108, provide payment 4902, receive payment 4902 or obtain another form or product or service from the government system 170.

The government connectivity platform 5100 may also allow Citizens to securely access information related to various Government managed services and programs, to securely procure various Government managed goods and services, to securely pay for various Government managed goods and services in real-time, in other than real-time, and or securely receive a receipt of payment on successful delivery of goods and services, where all such transaction can be conducted either by the Consumer through his/her own client device 162, or through a client device housed in a merchant/retail/community location and equipped with the ability to enable such secure transactions 162.

The government connectivity platform 5100 may also allow Employees and other Government organizations to conduct secure transactions, related to the procurement, distribution and payment of various goods and services, using either the client devices 162 provided by the Government, or their own client devices, or client devices housed in a merchant/retail/community location, wherein the client device is equipped to conduct secure transactions with such a platform (e.g. through the main services facility 142).

The government connectivity platform 5100 may also allow Government Employees and other Government organizations to conduct secure transactions with private Enterprises (e.g. service provider 168), related to the procurement, distribution and payment of various goods and services, using either the client devices provided by the Government, or their own client devices, or client devices housed in a merchant/retail/community location, wherein the client device is equipped to conduct secure transactions with such a platform (e.g. through the main services facility 142).

Figure 52:
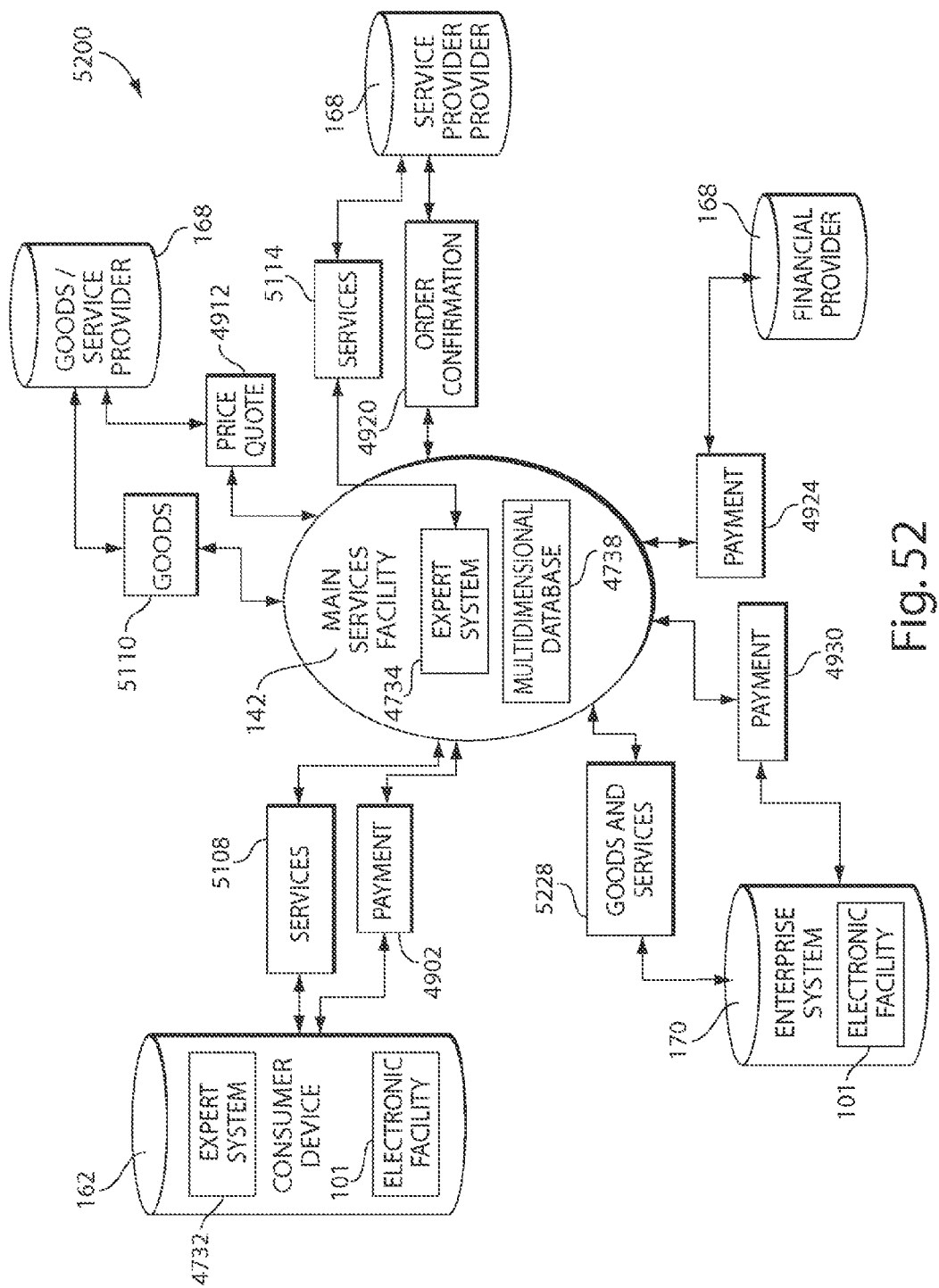
FIG. 52 depicts a platform through which an enterprise entity using an enterprise entity system can enable various features and attributes according to the present invention.

FIG. 52 shows a platform 5200 through which an enterprise entity using a enterprise entity system 170 can enable the various feature and attributes described herein, such as in connection with the platforms 100 and 4700 described above. FIG. 52 illustrates a enterprise connectivity platform 5200 where an Enterprise and/or Telco and/or Bank and/or Service Provider and/or Internet Service Provider and/or Application Service Provider and/or other entity, has the ability to setup a web-based platform through a main services facility 142, which has secure transaction interfaces with Enterprise's existing back-end systems, various financial services providers, payment systems, and service providers, where such Portal specializes in providing value added services with a focus on increasing the overall profitability of the organization, by enabling their employees to conduct various secure payment and transaction services. For example, a service provider 168 may receive an order for services 5114 from an enterprise system 170 through a main services facility 142 and the service provider 168 may send confirmation of the order 4920 to the enterprise system. The service may be a service for the enterprise or a customer of the enterprise for example. Where the service is for a customer, interactions may be directed to the customer through the main services facility 142. As another example, a service provider 168 may deliver goods 5110 and/or goods and services 5228 to the enterprise system 170 (or customer of the enterprise) and the transaction for the goods may be facilitated through the main services facility 142.

The enterprise connectivity platform 5200 may provide the enterprise's own Employees and their partners Employees with client devices 162 or alternately use their existing client devices (in either case, the client device could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The enterprise connectivity platform 5200 may enable the Enterprise's Employees (or partner's Employees) to conduct secure transactions, including payment and financial transactions, either related to procuring and paying for goods and services for the Enterprise and/or related to procuring and paying for goods and services for their own personal use, where such transactions can be conducted in the real world or the virtual world (including Bill Payments, Money Transfers, etc.), and additionally enabling the Employee to file expense reports and collecting reimbursements.

The enterprise connectivity platform 5200 may enable the Enterprise's Employees (or partner's Employees) to conduct secure transactions, which may include instances where an Employee or Employees can securely and electronically send a summary of the tasks performed and time/resources spent to perform such tasks, to their immediate supervisors, where the tasks may be related to an internal project and/or an external customer.

The enterprise connectivity platform 5200 may enable the Enterprise's Employees (or partner's Employees) to conduct secure transactions, which may include instances where a staff member can remotely send sensitive and personalized data to another Employee or Employees, in relation to the Enterprises internal dealings (disaster recovery, etc.) or dealings related to their Customers, Partners, etc. (e.g. quotations, invoices, etc.).

The enterprise connectivity platform 5200 may integrate employees' payroll, and allow employees to use their payroll for settling personal payment transactions conducted using the client devices supported by the Portal, related to the procurement of goods and services.

Figure 53:
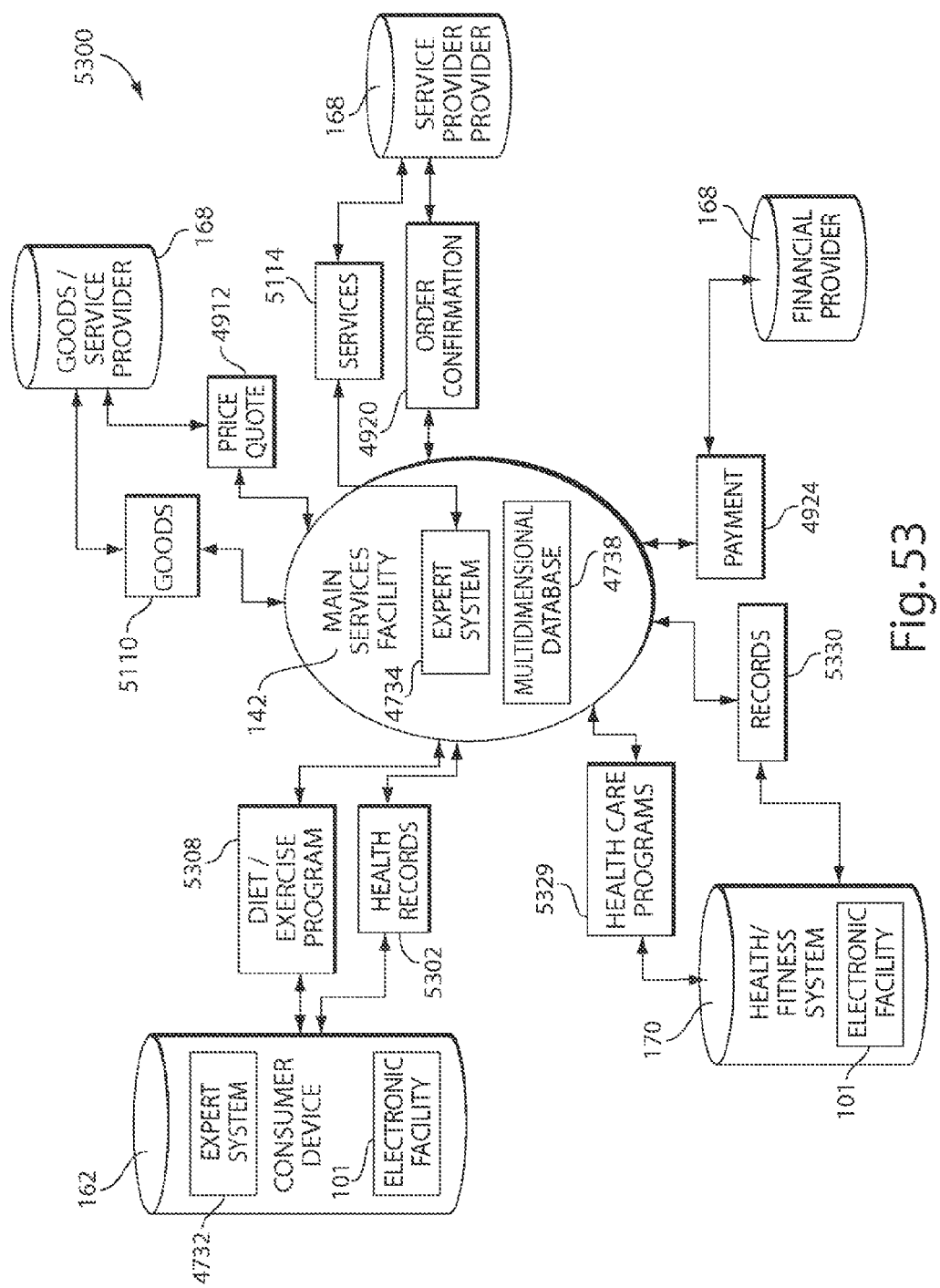
FIG. 53 depicts a platform through which a heath/fitness entity using a health/fitness entity system can enable various features and attributes according to the present invention.

FIG. 53 shows a platform 5300 through which a health/fitness entity using a health/fitness entity system 170 can enable the various feature and attributes described herein, such as in connection with the platforms 100 and 4700 described above. FIG. 53 illustrates a health/fitness connectivity platform 5200 where a Health/Fitness institution and/or Telco and/or Bank and/or Service Provider and/or Internet Service Provider and/or Application Service Provider and/or other entity, has the ability to setup a web-based platform through a main services facility 142, which has secure transaction interfaces with Health/Fitness institution's existing back-end systems, potentially other Health Information Systems hosted by Hospitals, Laboratories, Pharmacies, etc., various financial services providers, payment systems, and service providers, where such Portal specializes in providing value added services to their customers, with a focus on increasing the overall efficiency, user convenience, customer support, and profitability of the organization, by enabling their customers to conduct various secure payment and transaction services. For example, a service provider 168 may provide transactions associated with goods 5110 and or services 5114 to a consumer through a consumer device 162 through a main services facility 142. The main services facility may include security features to maintain the security of the information being transferred between various providers 168, consumers 162 and the health/fitness organization system 170.

The health/fitness connectivity platform 5300 may provide their customers with client devices or alternately use their existing client devices (in either case, the client device could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The health/fitness connectivity platform 5300 may enable customers to pay for various goods and services.

The health/fitness connectivity platform 5300 may personalize goods and services (including, but not limited to health/fitness programs 5329, diet/exercise programs 5308, diets, dietary supplements, etc.) for customers, perhaps in association with the contents health records 5302 or other records 5330, which may comprise the health records 5302.

The health/fitness connectivity platform 5300 may securely distribute personalized content, services and messages directly to the customer, through their client devices, including but not limited to fitness programs, dietary instructions, alerts based on time or other relevant criteria, etc.

The health/fitness connectivity platform 5300 may allow customers to feed information back into their personalized account at the Portal, using their client devices, with the purpose of archiving and updating their records to avail various profile driven value added services, including but not limited to performance reports, update reports, revised training programs, revised dietary programs, etc.

The health/fitness connectivity platform 5300 may interface with other Health Information Systems (hosted by Hospitals, etc), including personal health monitors, and update the customer's profile, further customizing various personalized goods and services offered by the Portal.

Figure 54:
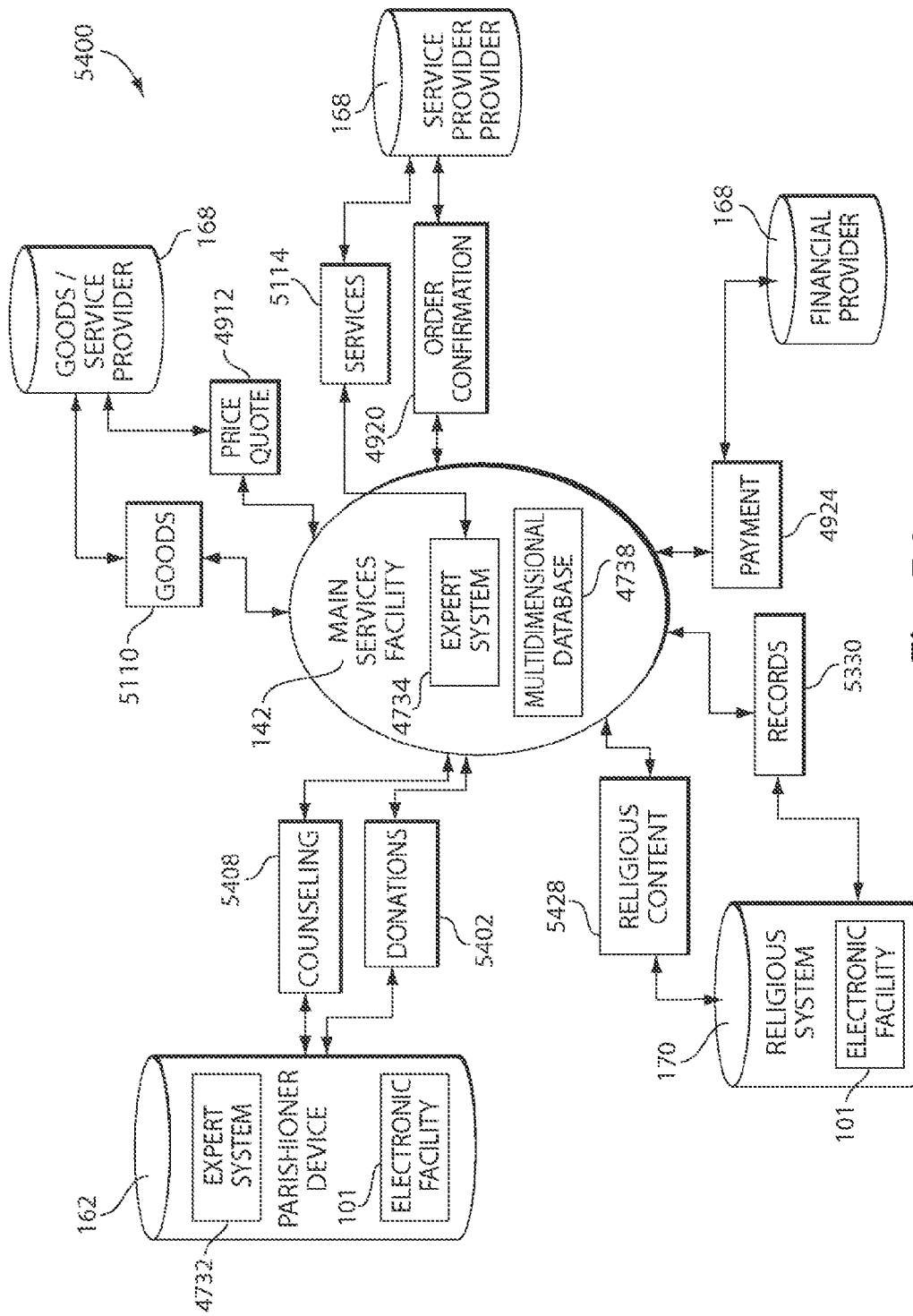
FIG. 54 depicts a platform through which a religious entity using a religious entity system can enable various features and attributes according to the present invention.

FIG. 54 shows a platform 5400 through which a religious entity using a religious entity system 170 can enable the various feature and attributes described herein, such as in connection with the platforms 100 and 4700 described above. FIG. 54 illustrates a religious connectivity platform 5400 where a Religious institution and/or Telco and/or Bank and/or Service Provider and/or Internet Service Provider and/or Application Service Provider and/or other entity, has the ability to setup a web-based platform through a main services facility 142, which has secure transaction interfaces with Religious institution's existing back-end systems, various financial services providers, payment systems, and service providers, where such platform specializes in providing value added services to their customers or followers, with a focus on offering personalized value added services, enabling customers to conduct various secure payment and transaction services. For example, a religious organization may connect its services with its parishioner's or other followers through a parishioner device 162 through the main services facility 142. The religious organization may also connect service provider(s) 168 with its own organization, affiliates, followers, other of its service providers and the like through the main services facility.

The religious connectivity platform 5400 may provide their customers with client devices or alternately use their existing client devices (in either case, the client device 162 could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The religious connectivity platform 5400 may provide for customized services or counseling 5408 (such as religious messages, blessings, etc.), which may comprise religious content 5428, and securely send them directly to the customer or follower's client device 162, where such services can in turn be dictated by various criteria, such as time, location, auspicious periods, etc.; additionally, where similar messages can be broadcasted to a larger group of followers.

The religious connectivity platform 5400 may allow customer or follower's to securely transmit the donations 5402 to the Religious organization, using existing payment instruments and systems, in real time, and receive an acknowledgement in the form of a receipt in real time from the platform; additionally, where such funds may be donated by a group of followers, and where such funds may be donated on a periodic basis by an individual follower or a group of followers, based on certain pre-set conditions, such as the time of the month, anniversaries, etc.

The religious connectivity platform 5400 may customers or followers to securely procure and pay for various goods and services sold by the Religious organization or its partners.

Figure 55:
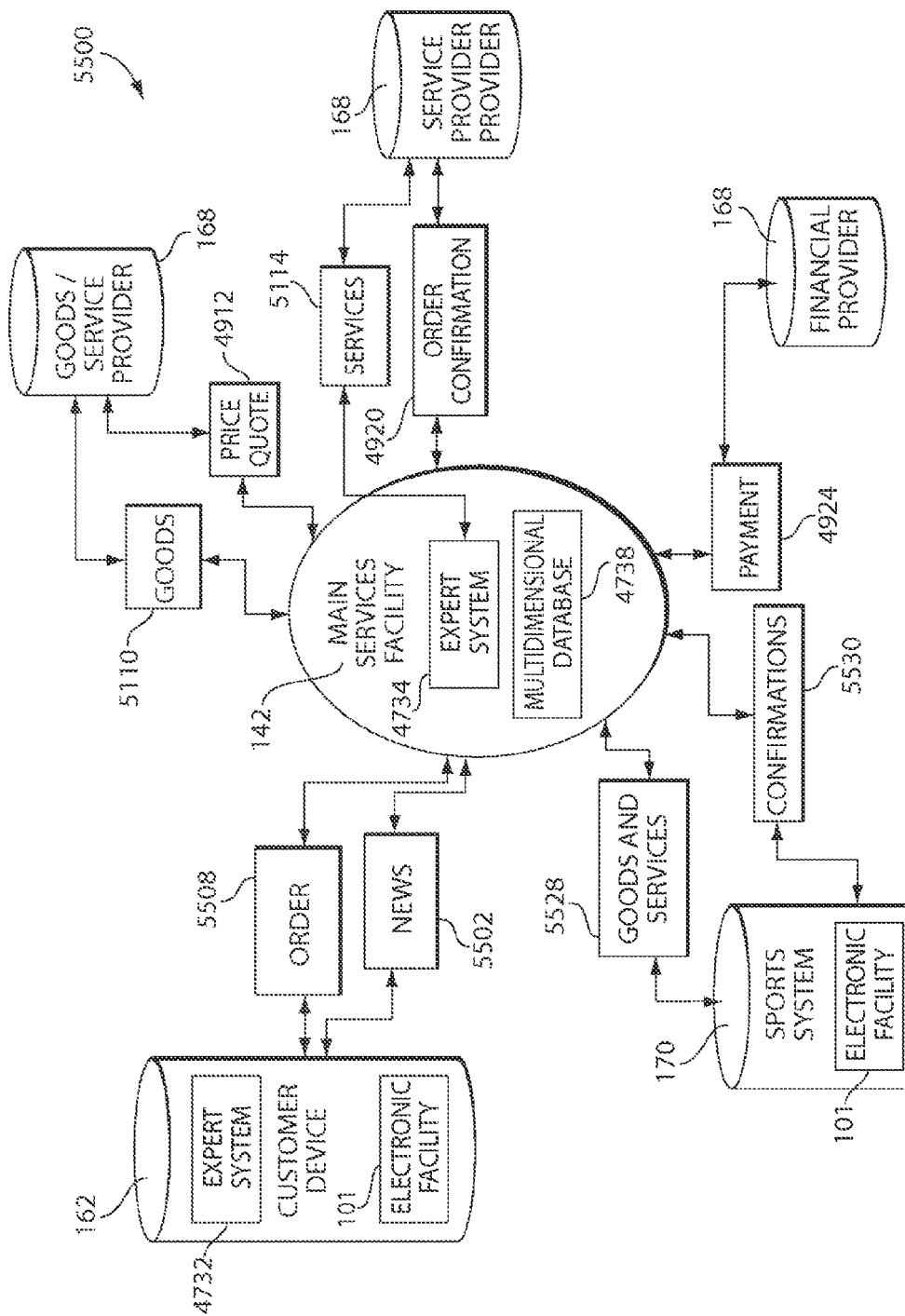
FIG. 55 depicts a platform through which a sports entity using a sports entity system can enable various features and attributes according to the present invention.

FIG. 55 shows a platform 5500 through which a sports entity using a sports entity system 170 can enable the various feature and attributes described herein, such as in connection with the platforms 100 and 4700 described above. FIG. 55 illustrates a religious connectivity platform 5500 where a Sports institution and/or Telco and/or Bank and/or Service Provider and/or Internet Service Provider and/or Application Service Provider and/or other entity, has the ability to setup a web-based platform through the use of a main services facility 142, which has secure transaction interfaces with the Sports institution's existing back-end systems, gambling organizations, casinos, various financial services providers, payment systems, and service providers, where such platform specializes in providing value added services to their customers or fans, with a focus on offering personalized value added services, enabling customers to conduct various secure payment and transaction services.

The sports connectivity platform 5500 provide their customers or fans with client devices or alternately use their existing client devices (in either case, the client device could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The sports connectivity platform 5500 may provide the ability to customize various content and services for customers or fans (such as news 5502, which may comprise scores, statistics, etc.) and securely send such personalized content and services to their respective client devices.

The sports connectivity platform 5500 may enable customers or fans to place wagers and bets (which may be embodied as an order 5508) on live sporting events, on a P2P basis (i.e. with other customers of fans), or on a tournament basis (against a group of customers or fans), or against the "house" or the Portal and/or its participating partners. The placement of wagers and bets may be verified through the transmission of a confirmation 5330 associated with the wagers and bets.

The sports connectivity platform 5500 may customers or fans to procure and pay for various goods and services 5528 sold by the Sports organization or its participating partners.

Figure 56:
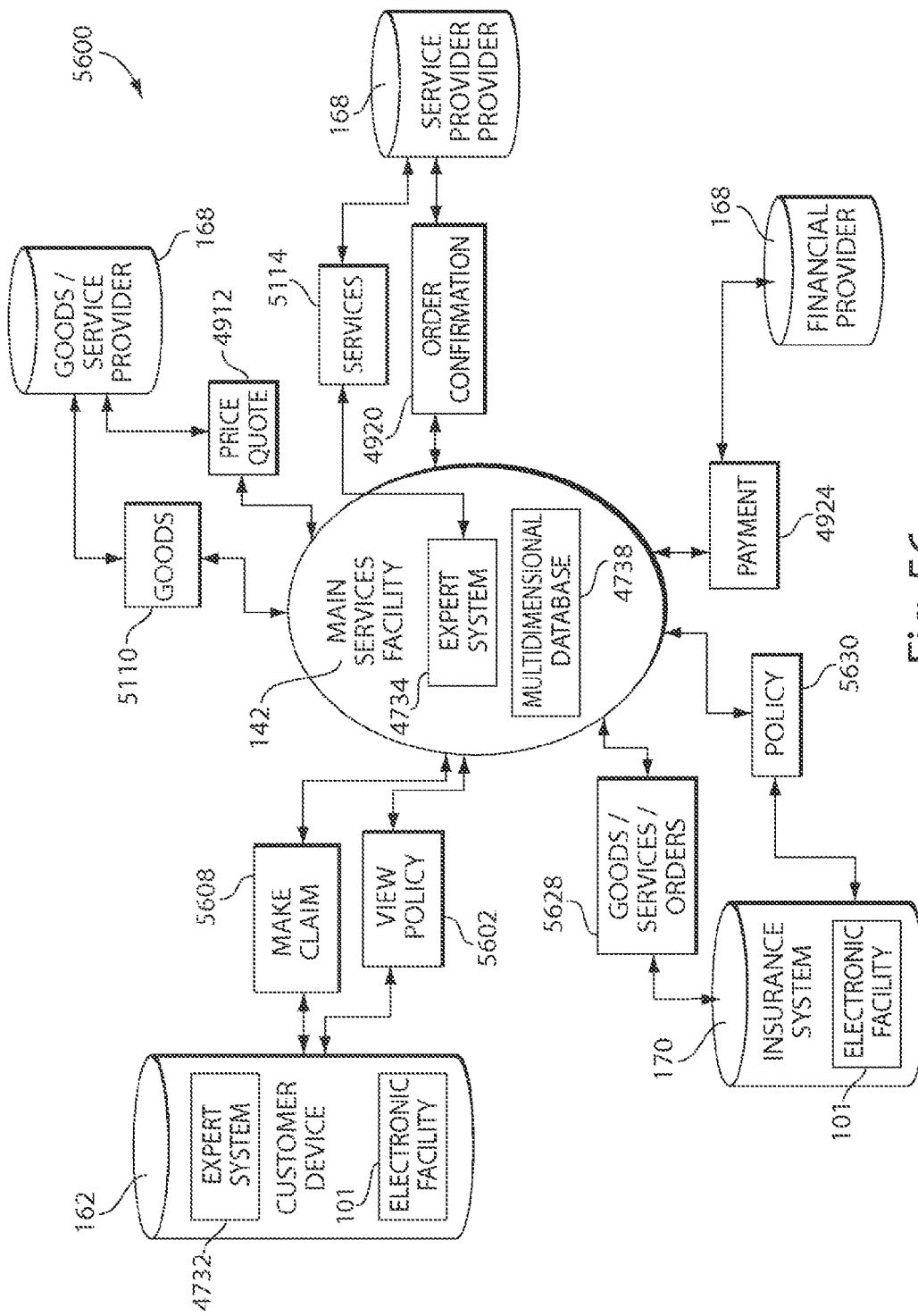
FIG. 56 depicts a platform through which an insurance entity using an insurance entity system can enable various features and attributes according to the present invention.

FIG. 56 shows a platform 5600 through which an insurance entity using an insurance entity system 170 can enable the various feature and attributes described herein, such as in connection with the platforms 100 and 4700 described above. FIG. 56 illustrates an insurance connectivity platform 5500 where an Insurance Company and/or Telco and/or Bank and/or Service Provider and/or Internet Service Provider and/or Application Service Provider and/or other entity, may have the ability to setup a web-based platform through a main services facility 142, which has secure transaction interfaces with the Insurance Company's existing back-end systems, various financial services providers, payment systems, and service providers, where such Portal specializes in providing value added services to their customers—individuals or entities—with a focus on offering personalized value added services, increasing efficiency, increasing convenience for customers, providing better customer support and increasing overall profitability, enabling customers to conduct various secure payment and transaction services. For example, a customer may use a customer device 162 to access an insurance policy 5630 or make a claim 5608. The customer device 162 may interact with the insurance system 170, one of the insurance entities affiliates and or service providers 168 through the main services facility 142. The insurance system may provide goods, services, or instructions 5628 to its customer or service providers 168. For example, the insurance system may issue an instruction or approval that may be associated with a claim 5608 to one of its service providers 168 and it service provider 168 may then communicate with the customer through the customer device.

The insurance connectivity platform 5600 may provide the insurance company's customers with client devices or alternately use their existing client devices (in either case, the client device could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The insurance connectivity platform 5600 may allow employees to securely send sensitive messages (including quotations, sales figures, etc.) to other employees or their managers, etc.

The insurance connectivity platform 5600 may allow employees to submit information related to claims, securely and electronically, possibly from a remote location.

The insurance connectivity platform 5600 may allow employees to view an insurance policy 5602, securely and electronically, possibly from a remote location.

The insurance connectivity platform 5600 may enable employees to process payments related to claims or other services, for customers, where claims have been approved (on-line or off-line), where if the customer also has capable client device the payment or funds can be transferred from the employees client device to the customers device in real-time.

The insurance connectivity platform 5600 may enable customers to securely send information to the Insurance Company, and also procure and pay for various goods and services in real-time.

Figure 57:
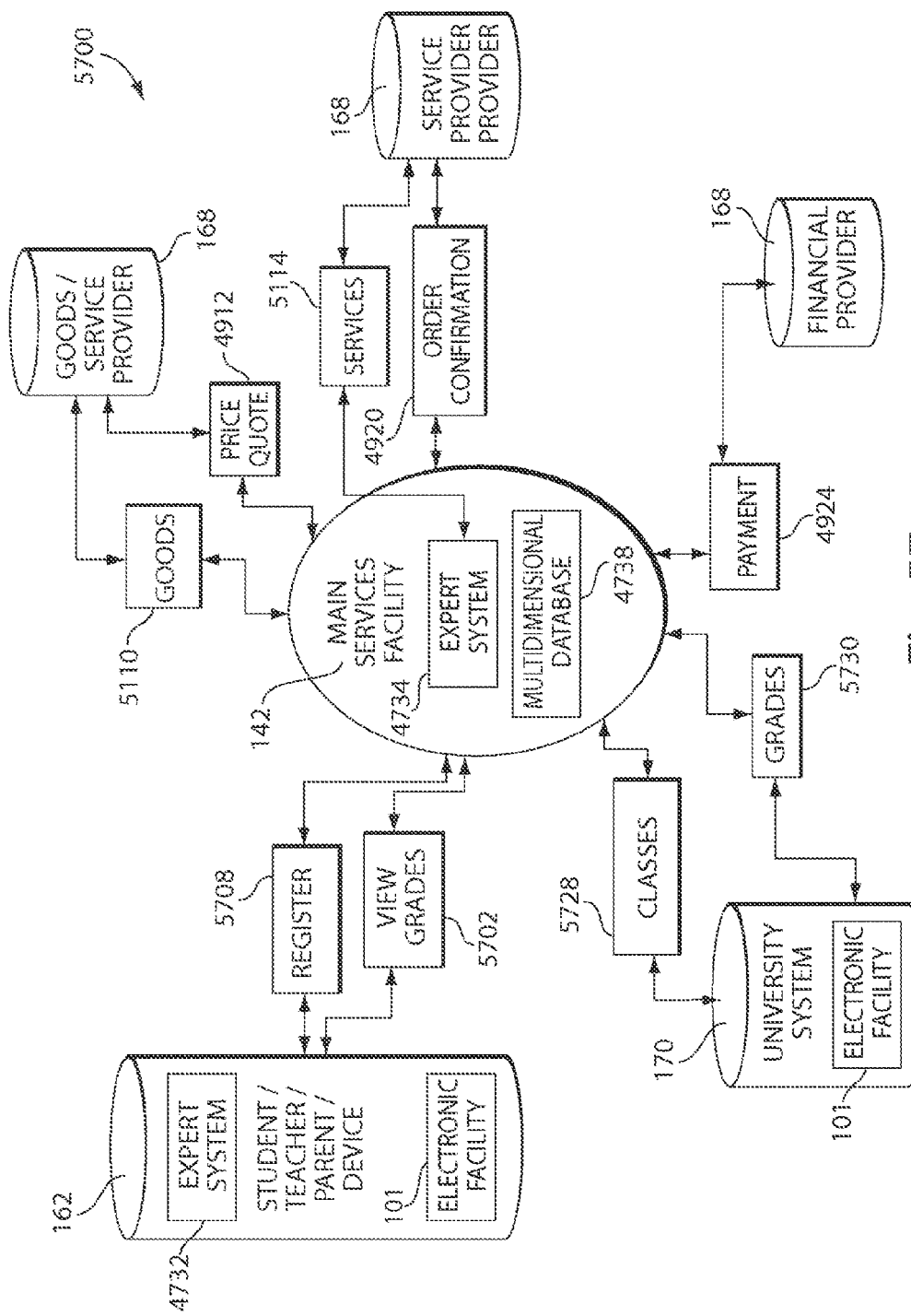
FIG. 57 depicts a platform through which a university using a university entity system can enable various features and attributes according to the present invention.

FIG. 57 shows a platform 5700 through which a university entity using an university entity system 170 can enable the various feature and attributes described herein, such as in connection with the platforms 100 and 4700 described above. FIG. 57 illustrates a university connectivity platform 5700 where a University and/or Telco and/or Bank and/or Service Provider and/or Internet Service Provider and/or Application Service Provider and/or other entity, may be able to setup a web-based platform through the main services facility 142, which has secure transaction interfaces with the University's existing back-end systems, various financial services providers, payment systems, and service providers, where such platform specializes in providing value added services to the University's students and employees, with a focus on increasing convenience, efficiency, support, and overall profitability, offering personalized value added services, and enabling students and employees to conduct various secure payment and transaction services.

The university connectivity platform 5700 the university's students and employees with client devices or alternately use their existing client devices (in either case, the client device could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The university connectivity platform 5700 may enable students to conduct secure and personalized transactions with the University, as well as with other students and employees, which may include but are not limited to browsing through, selecting and registering for courses, any of which may be associated with an act of registering 5708; accessing various University resources including libraries, laboratories, etc.; viewing grades 5702; procuring various goods and services, including loyalty based services, coupons, etc. from the University and its affiliates/partners on or off-campus (including stores, cafeteria, restaurants, cinemas, book-stores, etc.) and paying for such goods and services.

The university connectivity platform 5700 may enable employees to conduct secure transactions, with other employees, with students and with the University or its affiliates/partners, which may include but are not limited to procurement of goods and services, scheduling and/or re-scheduling of classes 5728, seminars, etc., collaboration with other employees and students and the secure exchange of sensitive information such as and without limitation grades 5730, with the overall goal of increasing efficiency and profitability.

The university connectivity platform 5700 may enable the University to customize and offer various personalized distance learning packages to students and customers.

Figure 58:
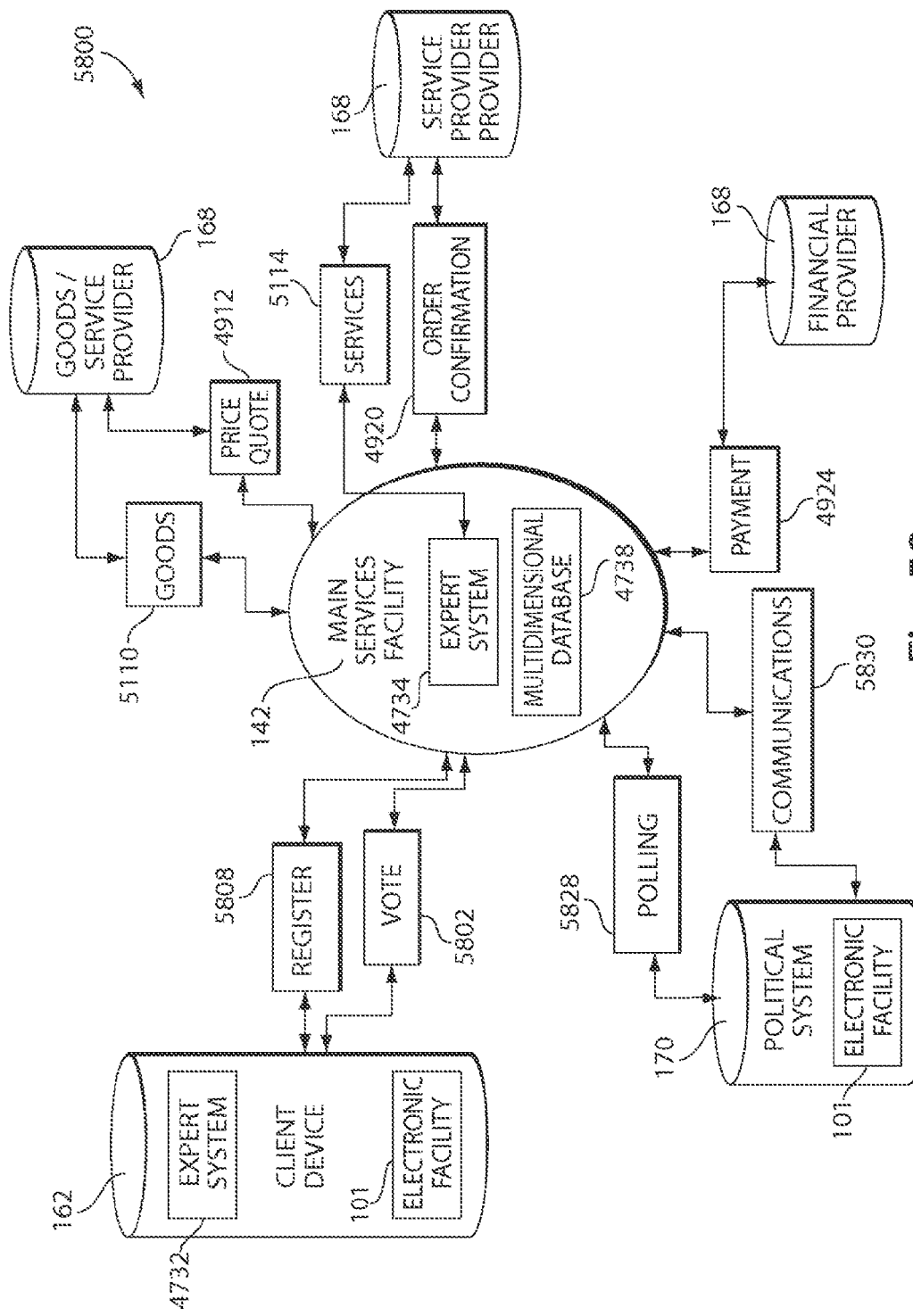
FIG. 58 depicts a platform through which a political entity using a political entity system can enable various features and attributes according to the present invention.

FIG. 58 shows a platform 5800 through which a political entity (e.g. political party) using an political entity system 170 can enable the various feature and attributes described herein, such as in connection with the platforms 100 and 4700 described above. FIG. 58 illustrates a political connectivity platform 5800 where a Party and/or Government and/or Telco and/or Bank and/or Service Provider and/or Internet Service Provider and/or Application Service Provider or other entity, may have the ability to setup a web-based a platform through the main services facility 142, which has secure transaction interfaces with the Government's existing back-end systems, various financial services providers, payment systems, and service providers, where such platform specializes in providing value added services to their members, employees and citizens, with a focus on increasing convenience, efficiency, customer support, and overall profitability, offering personalized value added services, and including the ability to conduct various secure payment and transaction services. For example, a person may use a client device 162 to interact with the political system 170, its affiliates, service providers 168 and the like to register 5708, vote 5802, interact with poling 5828, communicate with the political party 5830, make payments 4924 and the like.

The political connectivity system 5800 may provide party-members, employees and citizens with client devices or alternately use their existing client devices (in either case, the client device could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The political connectivity system 5800 may be adapted to enroll various individuals as party members and workers, capturing their personal and professional profile, and also issuing them personalized tokens of registration, which may include but are not limited to plastic cards that may additionally capture some form of bio-metric identification and/or photographs, where the same information could also be issued in the form of a virtual card onto the individual's client device, etc.

The political connectivity system 5800 may allow designated and pre-authorized party-member/s (including but not limited to Party's Member in Parliament or House of Representative, Party Leader, etc.) to populate, review and consequently update the platform, with information related to party-members or workers, or information related to the status of various projects in the party-member's constituency, or other related information, etc.

The political connectivity system 5800 may allow citizens (which includes party members, party workers and employees) of the state and/or country, to access certain areas of the platform, and view information related to the status of projects, view information related to the activities undertaken by their elected representatives, as well as the progress (or lack) of initiatives in their own, and other, constituencies.

The political connectivity system 5800 may allow citizens to express their opinions in the form of votes, on particular party-member/s/worker/s, on the progress (or lack off) of various initiatives, on a formal and/or informal basis.

The political connectivity system 5800 may enable pre-authorized party workers to utilize the secure transaction capabilities of the platform to securely send messages or sensitive information, either directly to other party-members and/or groups of party-members.

The political connectivity system 5800 may enable citizens or party workers or employees to procure various good and services, and if required pay for various goods and services.

Figure 59:
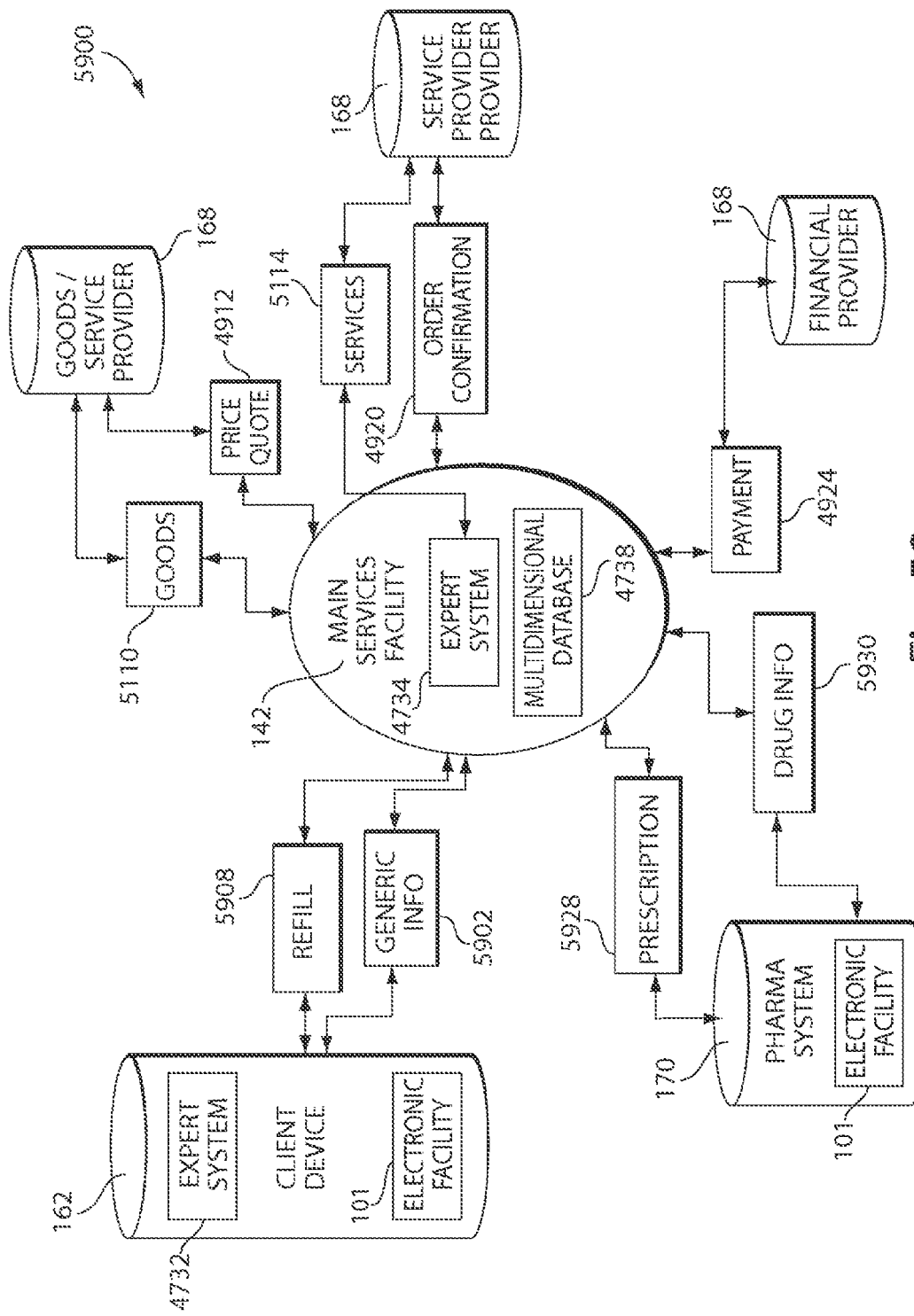
FIG. 59 depicts a platform through which a pharmaceutical entity using a pharmaceutical system can enable various features and attributes according to the present invention.

FIG. 59 shows a pharmaceutical connectivity platform 5900 through which a pharmaceutical entity using an pharmaceutical system 170 can enable the various feature and attributes described herein, such as in connection with the platforms 100 and 4700 described above. FIG. 59 illustrates a pharmaceutical connectivity platform 5900 where a Pharmaceutical Company or Companies and/or Telco and/or Bank and/or Service Provider and/or Internet Service Provider and/or Application Service Provider or other entity, may have the ability to setup a web-based Portal, which has secure transaction interfaces with the Pharmaceutical Company's or Companies' existing back-end systems, manufacturers/distributors/retailers back-end systems, various financial services providers, payment systems, and service providers, where such platform specializes in providing value added services to their registered users and customers, with a focus on increasing convenience, efficiency, customer support, and overall profitability, offering personalized value added services, and enabling registered users and customers to conduct various secure payment and transaction services. For example, the client device 162 may be used to interact with the pharma system 170, its affiliates, service providers 168 or other entities to order refills 5908, obtain information on generic drugs 5902, order prescriptions 5928, receive drug information 5930 (e.g. drug interaction information, drug overdose information, drug warning information), make payments 168 and the like.

The pharmaceutical connectivity platform 5900 may provide registered users and customers with client devices or alternately use their existing client devices (in either case, the client device could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The pharmaceutical connectivity platform 5900 may enable registered users, which includes but is not limited to pharmaceutical companies, manufacturers, distributors, retailers, healthcare providers, government organizations, etc., to securely access the platform and populate or post information on goods and/or services they would like to trade, where trading includes but is not limited to selling, bartering or buying, from other interested and relevant entities, where such goods may include but are not limited to generic drugs, patented drugs, alternative medication, etc.

The pharmaceutical connectivity platform 5900 may enable registered users, which includes but is not limited to pharmaceutical companies, manufacturers, distributors, retailers, healthcare providers, government organizations, etc., to securely access the platform, procure and pay for various goods and services, including goods and services from other registered users of the Portal, where such goods may include but are not limited to generic drugs, patented drugs, alternative medication, etc.

The pharmaceutical connectivity platform 5900 may facilitate on-line bidding, and enable registered users to place goods and services for bidding, as well as enable registered users to place bids for goods and services.

The pharmaceutical connectivity platform 5900 may enable registered users to procure and pay for goods and services.

The pharmaceutical connectivity platform 5900 may facilitate between registered users, communication of secure messages and sensitive information; where such communication may be conducted between two registered users or groups of registered users.

Figure 60:
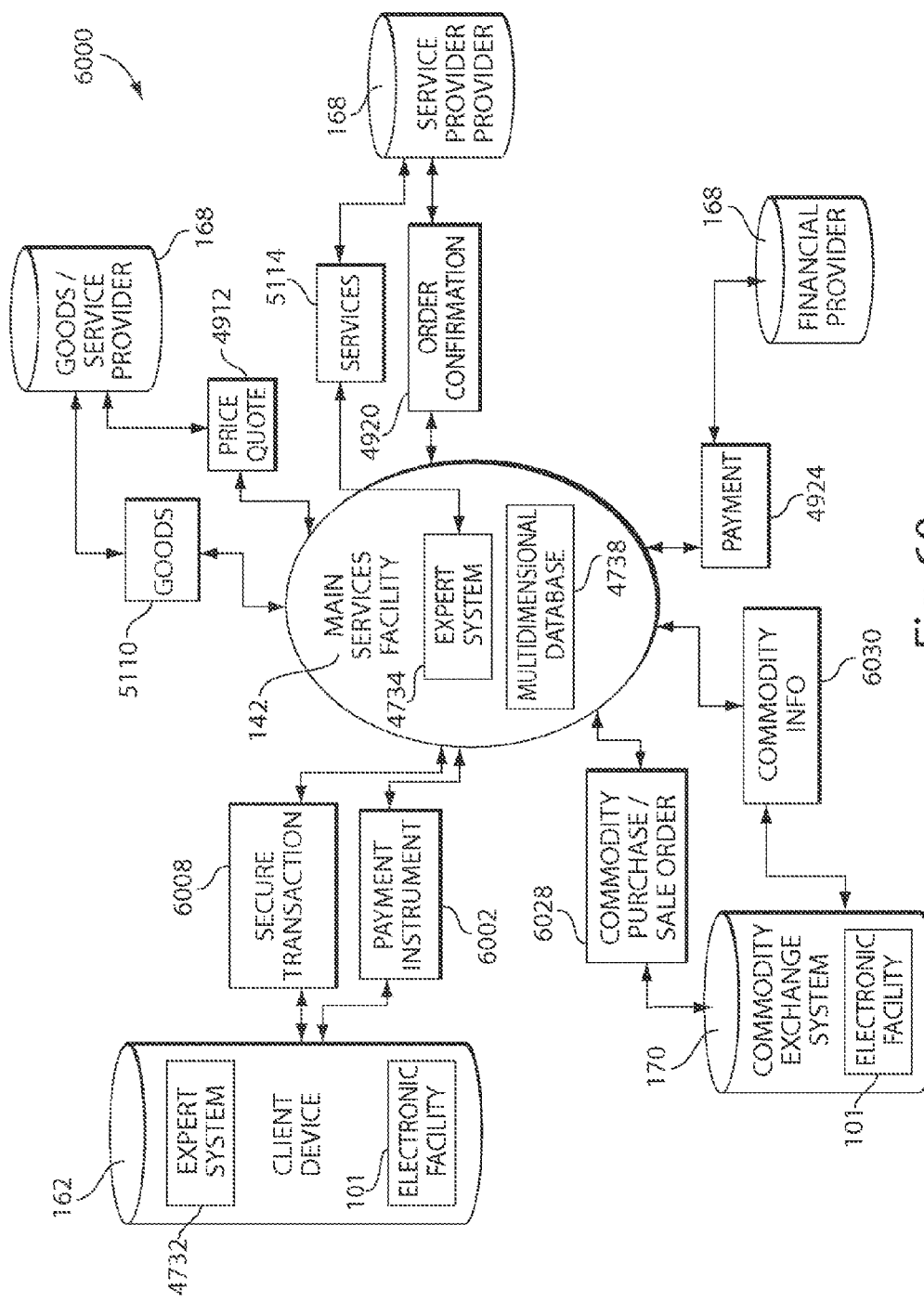
FIG. 60 depicts a platform through which a commodity exchange entity using a commodity system can enable various features and attributes according to the present invention.

FIG. 60 shows a commodity exchange platform 6000 through which a commodity entity using a commodity exchange system 170 can enable the various features and attributes described herein, such as in connection with the platforms 100 and 4700 described above. FIG. 60 illustrates a commodity exchange platform 6000 where Commodity Cooperatives (including Cooperatives of Farmers, Mining Companies, etc.) and/or Telco and/or Bank and/or Service Provider and/or Internet Service Provider and/or Application Service Provider, may have the ability to setup a web-based Portal, which has secure transaction interfaces with the Cooperatives' (and/or its members) existing back-end systems, distributor and retailers back-end systems, various financial services providers, payment systems, and service providers, where such Portal specializes in providing value added services to their registered users and customers, with a focus on increasing convenience, efficiency, customer support, and overall profitability, offering personalized value added services, and enabling registered users and customers to conduct various secure payment and transaction services. For example, the client device 162, which may be a personal device or a public device for temporary personal use such as and without limitation a mobile phone or a personal computer, may be used to interact with the commodity exchange system 170, its affiliates, service providers 168 or other entities to conduct various secure transactions 6008, including payment transactions, using existing payment instruments 6002, which include but are not limited to cash, credit cards, debit cards, electronic checks, prepaid and stored value accounts, and so forth.

The commodity exchange platform 6000 may enable pre-authorized users and customers (and in turn their members, e.g. farmers, etc.) to populate and consequently update the information 6030 at the portal, which may include but is not limited to pricing information, availability information, location information, etc.

The commodity exchange platform 6000 may allow pre-authorized users and customers (and in turn their members, e.g. farmers, etc.) to access the Portal, procure various goods and services, and pay for such goods and services, such as and without limitation via a commodity purchase/sale order 6028.

The commodity exchange platform 6000 may facilitate on-line or off-line bidding, enabling registered users and customers (and in turn their members, e.g. farmers, etc.) to place goods and services for bidding, as well as enable registered users to place bids for goods and services, and consequently procure and pay for such goods and services, again such as and without limitation via a commodity purchase/sale order 6028.

Figure 61:
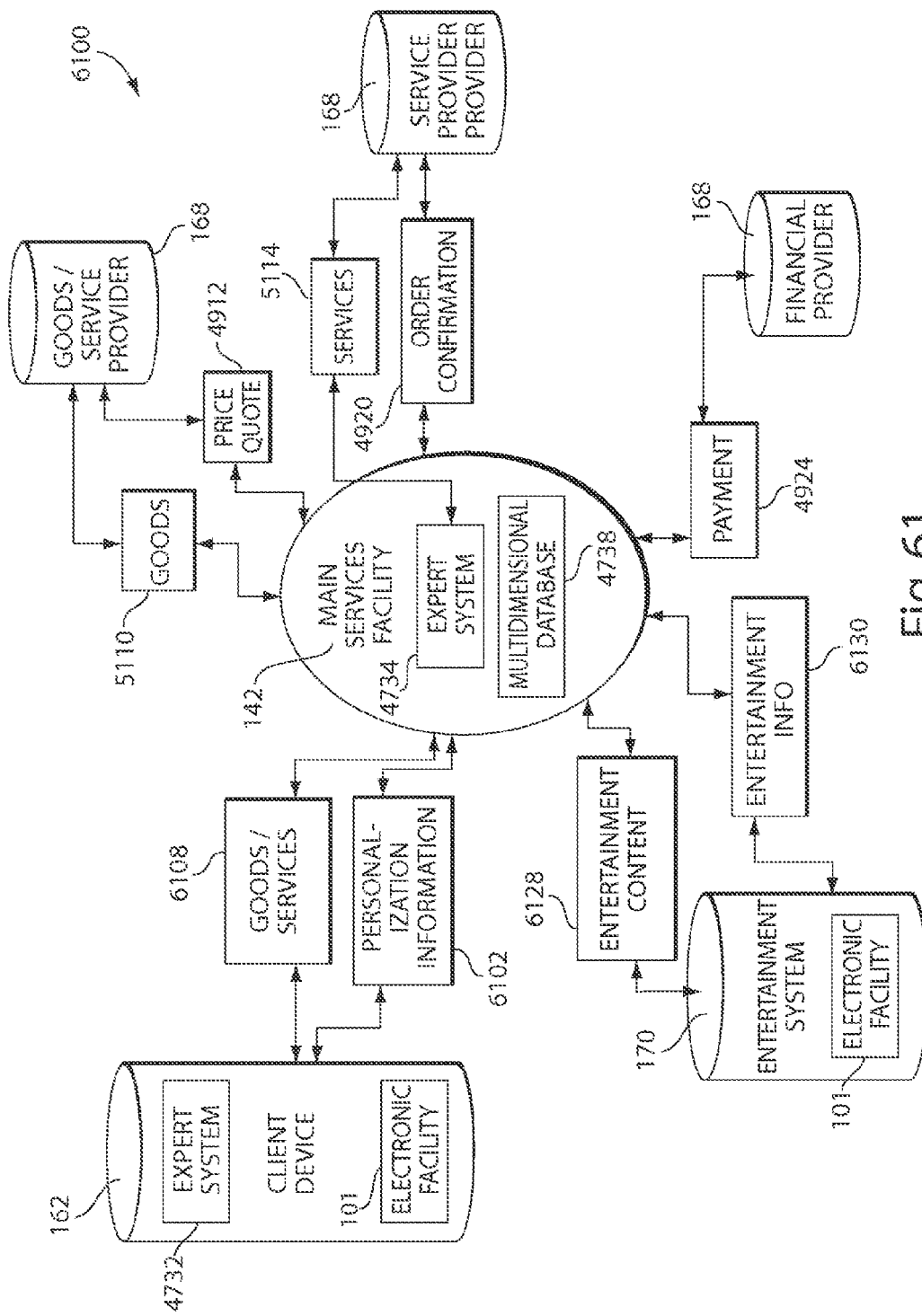
FIG. 61 depicts a platform through which an entertainment entity using an entertainment system can enable various features and attributes according to the present invention.

FIG. 61 shows an entertainment platform 6100 through which an entertainment entity using an entertainment system 170 can enable the various features and attributes described herein, such as in connection with the platforms 100 and 4700 described above. FIG. 61 illustrates an entertainment platform 6100 where an Entertainment Company (including Studios, Producers, Artists, etc.) and/or Telco and/or Bank and/or Service Provider and/or Internet Service Provider and/or Application Service Provider, to setup a web-based Portal, which has secure transaction interfaces with the Entertainment Company's existing back-end systems, various financial services providers, payment systems, and service providers, where such Portal specializes in providing value added services to the Entertainment Company's customers, including but not limited to the end-Consumer, with a focus on increasing convenience, efficiency, support, and overall profitability, offering personalized value added services, and enabling customers to conduct various secure payment and transaction services. For example, the client device 162, which may be a personal device or a public device for temporary personal use such as and without limitation a mobile phone or a personal computer, may be used to interact with the entertainment system 170, its affiliates, service providers 168 or other entities to provide their goods and services 6108 (including programming content, movies, music, video-clips, documentaries, feature shows, etc.), personalizing their delivery, perhaps according to personalization information 6102, for registered users of the Portal, including customers, distributors, end-Consumers, and so forth.

The entertainment platform 6100 may provide registered users and customers with client devices (in either case, the client device could be a personal device or public device for temporary personal use), which include but are not limited to mobile phones, PCs, etc., to conduct various secure transactions, including payment transactions, using existing payment instruments, which include but are not limited to cash, credit cards, debit cards, electronic checks, prepaid and stored value accounts, etc.

The entertainment platform 6100 may enable various Entertainment Companies to provide their goods and services (such as entertainment content 6128, which may without limitation comprise programming content, movies, music, video-clips, documentaries, feature shows, etc.), personalizing their delivery for registered users of the Portal, including customers, distributors, end-Consumers, and so forth. The entertainment content 6128 may be associated with entertainment information 6130, which may include price, length, type of content, title, director name, actor name, performer name, musician name, genre, and any other relevant information.

The entertainment platform 6100 may enable registered users of the Portal, including customers, distributors, end-Consumers, etc., to setup preferences for delivery of goods and services based on various criteria, including but not limited to time, location, client device, and so forth.

In embodiments the entertainment platform 6100 may be a web-based gaming platform. Embodiments of the present invention furnish a gaming provider 170 with a capability. The gaming provider 170 may without limitation be a telecommunications company, Internet service provider, Internet content and/or service aggregator, game publisher, third-party application service provider, or any other service provider. The capability may be comprise the setup and provision of a Web-based platform 6100.

The platform 6100 may specialize in providing a value added service related to online or offline games, including a secure payment and transaction service, which may be described elsewhere in this disclosure. In particular, the platform 6100 may have a secure transaction interface with the game publisher, with a game developer, with an online game host's back-end system, with an offline game host's back-end system, or with any other system.

The platform 6100 may provide a mobile phone user, a PC user, and/or a game console user, or the user of any electronic facility (portable or otherwise) the ability to download a game and/or a personalized service. The platform 6100 may, alternatively or additionally, provide the user with an ability to pay for the game and/or personalized service. In one embodiment, the user may be able to place a bet on the outcome of a game. In another embodiment, the user may collect a payment for playing a game. The platform 6100 may, alternatively or additionally, provide the user with an ability to pay for a service on a subscription (that is, recurring) and/or per-transaction basis, using a payment instrument offered by an existing financial services provider, including without limitation a credit card, a debit card, an electronic check, a prepaid account, a stored value account, and so forth.

The platform 6100 may enable the user to play the game in real time against another user, where both users may or may not be known to each other. One or both users may be able to place a bet, via the platform 6100 and on a person-to-person basis, on the outcome of the game. In an alternate embodiment, one or both users may be able to put a predetermined amount of funds into a common pot at a predetermined time, such as before and/or after the start of the game. In this case, the platform 6100 may distribute a portion or the entirety of the contents of the pot (minus, perhaps, a commission) to the winner of the game. In yet another alternate embodiment, the platform 6100 may enable the user to play the game in real time against a computer facility operated by the platform 6100 provider. In this case, the platform 6100 may enable the user to place a bet against the platform 6100 provider. This bet may be based upon predetermined conditions, predetermined milestones, or outcomes, any of which may apply to a particular gaming session and/or multiple gaming sessions. For example, in a first-person shoot'em up game, the user may bet that he can kill 100 monsters within 10 minutes. Or, the user may bet that he can kill 10,000 monsters within 8 hours of cumulative game play, which may span multiple gaming sessions played at different times by the user. In still yet another embodiment, the platform 6100 may enable a non-participant, such as a platform 6100 user who is not playing the game, to place a bet on the user. In any case, the game may be a game of skill and/or luck and the outcome of the game may be a function of skill and/or luck.

The platform 6100 may enable the user to resell games to a second user, which may allow the second user to download the game as described above. This reselling of a game may comprise a person-to-person transaction or a wholesale transaction. The platform 6100 may capture a commission associated with the transaction.

It should be clear to one of ordinary skill in the art that aspects of the platform 6100 may be applied to other items and/or events such as commodities, weather, and so forth. For example, instead of providing for the downloading and playing of games, the platform 6100 may provide for the downloading and playing/rendering of ring tones, music, songs, videos, films, books, articles, reports, and so forth.

Figure 63:
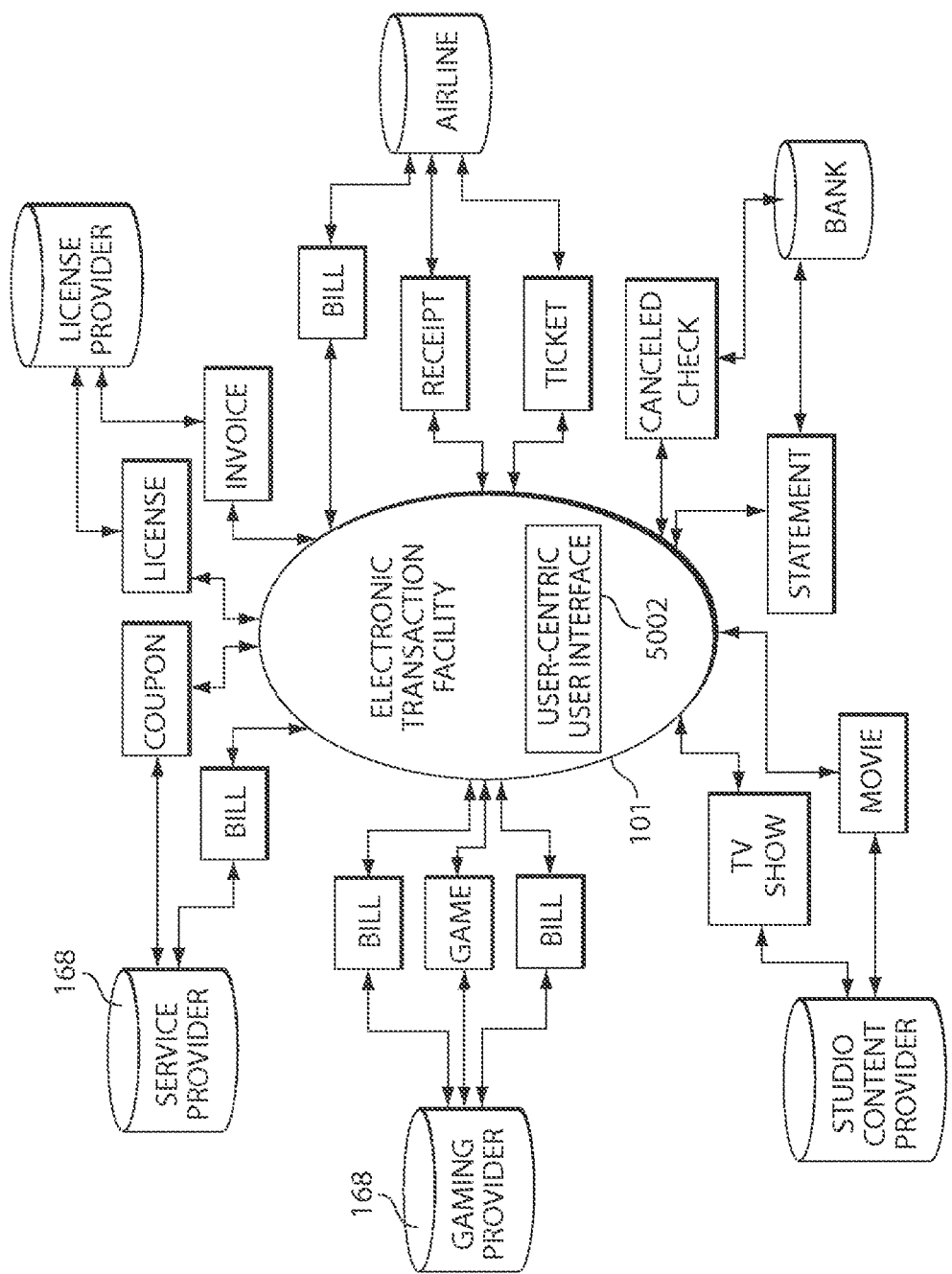
FIG. 63 depicts a user-centric set of services deployed using systems according to the present invention.

FIG. 63 shows a user-centric set of services deployed using the systems described herein. For a given user, a set of services from various service providers 168 may be may be enabled by an system that includes a universal electronic transaction facility ("UET") 101 on a client device 162, including a user interface 5002, and main service facilities 142 (not shown). Various main services facilities 142 can support, for example, gaming services, licensing services, airline ticket services, content services, banking services, and other services. Each of those services may be represented by the user-centric user interface 5002, which allows a user to initiate the various services from a client device 162, such as any of those described herein. The client may thus interact with multiple services, each of which includes the features and attributes described herein, such as device, domain and user-level security facilities, such as security features relating to each service provider's 168 own system, as well as a user password and device password for each service of the user. Various services may be represented as icons (optionally with branding elements and security features that make the services the actual item (e.g., a credit card) as opposed to a mere representation of the item. An example of a user interface 2002 can be seen in FIG. 43, which is one of many possible examples.

In other embodiments, a UET 101 may contain data for a licensing or registration item. For example, the UET may store personal information, such as address information, social security number, license number, registration number, driving history, past licenses, compliance data, and the like. As another example, the UET may store money in digital form, or credit card account and authorization for payment-based licensing transactions. As another example, the UET may store licenses or registrations for a user of the UET. In an embodiment, the UET stores and actual license or registration, optionally including a unique identifier that identifies it as such or permits verification of the license or registration. Thus, the UET may contain, for example, a driver's license, including graphical representations of the items that appear on the license, such as the photo of the driver, the signature of the driver, the state seal, a watermark or similar mark to prevent falsification of the document, and other features. The UET system, by enabling multiple distinct layers of security, can facilitate the storing of the actual license on the UET, with a user being able to access the license to enable transactions, and the issuer being able to verify the issuance and use of the license.

Licenses that can be issued and supported by the UET system may include a driver's license, a fishing license, a hunting license, a medical license, a professional license, a bar registration, an attorney license, a dental license, a CPA certification, a degree or evidence of professional membership or attainment, evidence of a membership in an organization, a license to a seat in a sporting venue, a license to use a premises or venue, a license to enter a venue, a vehicle registration, a commercial license, a license to transport goods, an import license, an export license, a license to disclose information, a license to access information, a license to use a product, a license to receive a service, and any other kind of license, permission, registration, an immigration visa, a passport, a travel visa, a foreign filing license, a building permit, an occupancy license, an occupancy permit, a business license, a foreign qualification, a good standing certificate, a corporate license, a government decree or issuance, a GSA license, a government procurement license, or the like.

A customer user interface may be rendered on or by the UET to support a license service. In general the customer user interface may include any features associated with an interface, such as text fields, buttons, drop down lists, check boxes, and the like, for navigation and use by the user. The user interface may be dynamically generated in response to information received from the license issuer, such as a drop down list of available license types, fields that indicate prices for licenses, and the like.

The issuer facility may operate at a central location, such as a license issuer facility, such as a government entity, department of motor vehicles, organization headquarters, or the like, and at a point of transaction, such as an office for issuing licenses, or a location where a license is presented. The issuer facility may support functions and features described in connection with various issuer and merchant facilities described elsewhere herein. A license issuer facility may include modules for storing, retrieving, manipulating and analyzing data and events that relate to issuance, maintenance, revocation and modification of licenses and registrations. For example, an issuer facility may include a compliance module for recording transaction events that relate to licenses, such as parking tickets, moving violations, violations of fishing or hunting licenses, suspensions, debarments, and other events. A compliance module can trigger a renewal of a license in the case of expiration of a license that is compliance, or it can revoke a license, either because conditions have not been met for renewal, or because one or more conditions for continued licensing have failed. A license issuer facility may include a financial module for executing secure financial transactions related to licensing, such as receiving a payment from a UET for a license issuance, renewal, or the like, applying payments, storing data related to payments, reporting on financial transactions, or the like.

The license issuer facility may provide a user interface to an employee of the issuer (or other authorized user), who may operate the user interface to conduct a licensing transaction with the user of the UET. The issuer user interface may be rendered on a device that includes the license issuer facility, or a related or peripheral device. In one embodiment, the issuer user interface is rendered on a desktop computer, and may be, for example, a browser-based user interface. In general the license issuer user interface may include any features associated with an interface, such as text fields, buttons, drop down lists, check boxes, and the like, for navigation and use by the employee.

In embodiments, a central service facility as described above coordinates transactions between the UET and the issuer facility as described generally above, and may provide or support any related authentication, issuance, renewal, revocation, authorization, security, financial, or other functions associated with the licensing or registration transaction.

The user computer may optionally participate in the licensing or regisration service, and may be used by the user to program or provide data to the UET. The user computer may also independently connect through a network such as the PSTN or the Internet to the central service facility, the license issuer facility, and/or the license or registration providers to conduct network-based transactions. This includes transactions relating to the licensing or registration service. For example, licenses may be issued online, and then transferred to the UET for subsequent use by the customer at a related point of transaction.

In embodiments, the UET may receive and store evidence of licensing transactions, such as proof that a license or registration has been approved, issued or renewed, similar to the "paid" stamp described in other embodiments herein. The evidence of approval may include a graphical depiction of a stamp, seal, or logo of a license issuer, such as a government seal or evidence of official approval. The evidence may be presented graphically in the UET, such as to indicate approval or certification of the license by the issuer. Thus the UET may store the actual approval or certification, as opposed to merely storing evidence of the same. The UET may track and store a history of such transactions, and/or multiple examples of one or more licenses or transactions. The UET may support different security protocols, such as a security protocol for the transaction, a security protocol for the user of the UET, and a security protocol for the issuer. The UET system may support different security protocols for different issuers of different licenses, including different species of the same type of license, such as licenses to do business issued by different states or provinces.

In a peer-to-peer embodiment of a licensing service, a number of UETs of individual customers may cooperate in a license acquisition. For example, a general contractor may procure a building license, which may be then distributed to various subcontractors with an indication of the authenticity of the license.

In embodiments a license may be used at a point of transaction. For example, a building license may be displayed at a building site, such as to a building inspector, including to a handheld computer interface of the building inspector, such as a UET.

In embodiments the methods and systems described herein enable registered users, including customers, distributors, end-consumers, etc., to procure goods and services from various platforms and pay for them.

Figure 62:
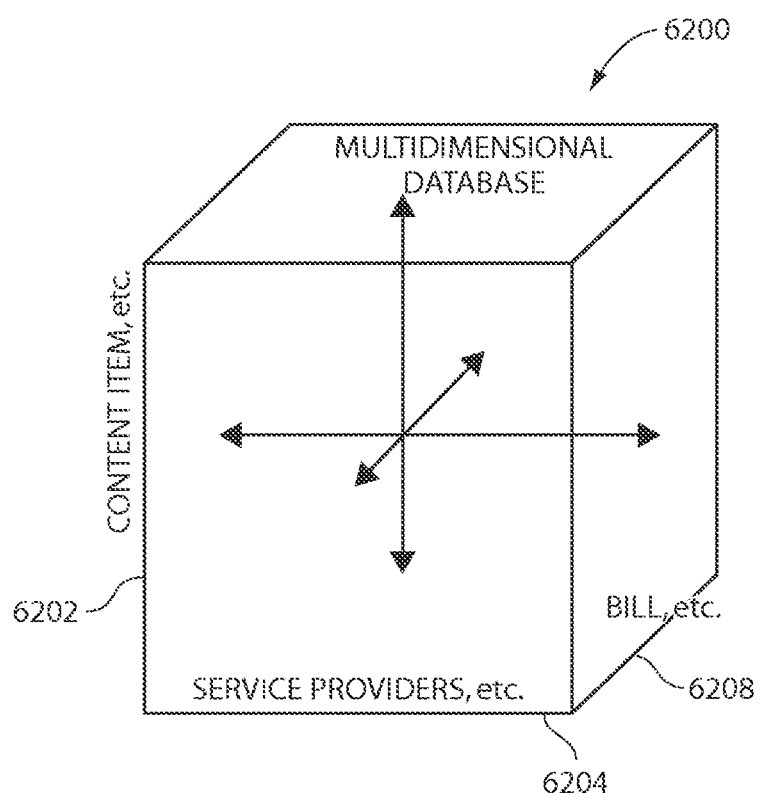
FIG. 62 depicts a conceptual representation of a particular embodiment of a multidimensional database structure.

Referring now to FIG. 62, there is shown a conceptual representation of a particular embodiment the aforementioned multidimensional database structure 6200. While this representation, as shown, is limited to three database dimensions (namely, "service providers, etc." 6202, "content item, etc." 6204, and "bill, etc." 6208), it should be appreciated that in embodiments the number of dimensions may be one, two, three, or any whole number greater than three. In the depicted example, the units of the first dimension 6202 may correspond to an attribute of content items (wherein the content items may, without limitation, comprise items of entertainment content 4928, items of commodity info 4930, items of drug info 4930, votes 4902, grades 4930, policies 4930, orders 4908, records 4930, health records 4902, payments 4930, regulations 4928, tickets 4928, bills 4928, or any other content items herein described, made apparent by this disclosure, or generally known), wherein the attribute may without limitation comprise names of content items, cash values of content items, types of content items, ages of content items, sizes of content items, ratings of content items (such as and without limitation MPAA ratings, personal preference ratings, ratings according to a collaborative filter, Morningstar ratings, and so forth), sources of content items, or any other attribute an item of content items. The units of the second dimension 6204 may correspond to an attribute of the service providers 168, wherein this attribute may without limitation comprise names of the service providers 168, types of the service providers 168, geographic location of the service providers 168, ratings of the service providers 168, and so forth. The units of the third dimension 6208, may correspond to an attribute of bills, wherein this attribute may without limitation comprise amounts of bills, names of payers of bills, name of payees of bills, and so forth. In embodiments, the multidimensional database structure may be associated with the main service facility 142 and, in particular, to the databases associated therewith, as may be described hereinbefore or as may be apparent from the present disclosure and/or included references.

The multidimensional database structure 6200 may support a functional aspect of the electronic transaction platform 100, which may be referred to as a user-centric interface.

The multidimensional database structure 6200 may support another functional aspect of the electronic transaction platform 100, which may be referred to as a user-centric engine.

The multidimensional database structure 6200 may support yet another functional aspect of the electronic transaction platform 100, which may be referred to as security and may relate the client device 162; the transmission 138; and any hardware and/or software infrastructure that may be associated with electronic transaction platform 100.

The multidimensional database structure 6200 may support still yet another functional aspect of the electronic transaction platform 100, which may be referred to as an expert system.

The multidimensional database structure 6200 may support still another functional aspect of the electronic transaction platform 100, which may be referred to as a self-learning and self-scaling system.

The multidimensional database structure 6200 may support another functional aspect of the electronic transaction platform 100, which may be referred to as a multi-dimensional smart-data structure.

The multidimensional database structure 6200 may support yet another functional aspect of the electronic transaction platform 100, which may be referred to as a secure web-services protocol.

The multidimensional database structure 6200 may support another functional aspect of the electronic transaction platform 100, which may be referred to as distributed infrastructure services (billing done directly on the phone—not centralized—distributed infrastructure services).

The multidimensional database structure 6200 may support still another functional aspect of the electronic transaction platform 100, which may be referred to as secure application throughput management (application to manage throughput of applications).

Referring to FIG. 62, a main services facility 142 may include or draw on a multidimensional database 6200, which may be stored on the same system as the main services facility 142 or be stored on a remote machine. The main services facility 142 may be drawing on information from multiple sources, which are populating the database 6200, which may be a very large database. The attributes of the data may be set in multiple dimensions, including relationships among data items across different dimensions. This enables querying data in different ways for different purposes.

For example, the multi-dimensional database 6200 supports the user-centric engine and interface described in connection with FIG. 63, whereby various data relating to various services, service providers, domains, devices and systems are stored to allow a user to access services that use such data. The multidimensional database 6200 allows the system to sift through data more efficiently, employing different dimensions that are optimized for particular retrieval tasks. For example, an element of data may be transaction-related. Another dimension may relate to how data is evaluated. A third element of the data might allow static profiles or entries. A fourth element may allow external entities to enter data associated with the data. Data may include data related to financial transactions such as billings 6208, data related to service providers 6204, data related to content items 6202, or a host of other kinds of data. Storing data in a multidimensional database 6200 may assist with application throughput, as data may be stored in a fashion that allows efficient retrieval of data according to a user's specific needs. For example, a learning algorithm or expert system as described herein may learn which services a user tends to use in which circumstances, and the expert system may push data from the multidimensional database 6200 to, for example, a client device 162 or a relatively local main services facility 162 to improve performance of such services.

A user-centric engine looks at the data and takes advantage of it. For example, if a user flies into London, the platform may be aware of that fact, be aware of past transactions (such as meeting people before), and look at different dimensions of data to propose various transactions. Similarly, the engine may propose multiple transactions to the user, enabled by the data in the multidimensional database.

As the number of applications that use transaction services increase, a problem can arise with application throughput capabilities. Large amounts of data are present, organized in and efficient way in the multidimensional database 6200. Also, engines exist to make applications revolve around a user, growing with the user as the user's history occurs. However, as many data elements come in simultaneously, there is a need for efficient handling of information. This may include many techniques, including an application throughout switch. This may include one or more elements, such as a physical switch that shifts between different physical communication facilities that relate to different services. An expert system may also be used, for example, to intelligently handle data to and from services, such as determining what payments are due, determining which ones are most important, or the like, and then prioritizing data arrival from various services according to the rules of the expert system.

Another example of use of a multidimensional database 6200, a user-centric platform, and application throughput management is for delivery of entertainment services. If the service providers 168 are digital content providers, such as music, television or movie studios, digital content, such as a television show (e.g., a world premier live event), can be delivered to a particular user via the platform 100. The content can be stored in the multidimensional database, and the user-centric interface can allow the user to identify and obtain content desired by the user, such as a particular television show. For the user, a throughput management application may be used to handle digital entertainment content and other data that is sent to the user's electronic transaction facility 101, such as bills, messages, receipts, and other pieces of personalized information. There can be data structures designed to enable better throughput of data for particular services. Also, there can be a physical (e.g., switching) element of application throughput to allow a user to receive such content. Switches can include switching nodes, such as used in digital switching technologies used in telecommunications infrastructure. There can also be an expert system, rules engine, learning engine or the like to manage application throughput to improve the user's access to data. All of these features can enable more effective provision of multiple services to a user.

The platform 100 may have interfaces to various service providers. Each interface may present significant challenges, based on the unique requirements of the service providers. In embodiments, the main service facility 142 may include a secure, self-learning and self-scaling platform 100, such as one that automatically recognizes an interface of a third party service provider and automatically initiates an interface to that service provider. In such embodiments, the platform 100 may include security features as described herein, such as three-dimensional authentication across user, device and domain, as well as the ability to store securely at the client application and the ability to transact securely at the transaction level. One example of a self-learning platform would include an application that would recognize features of an interface and apply preexisting features that are suitable for that interface.

Figure 64:
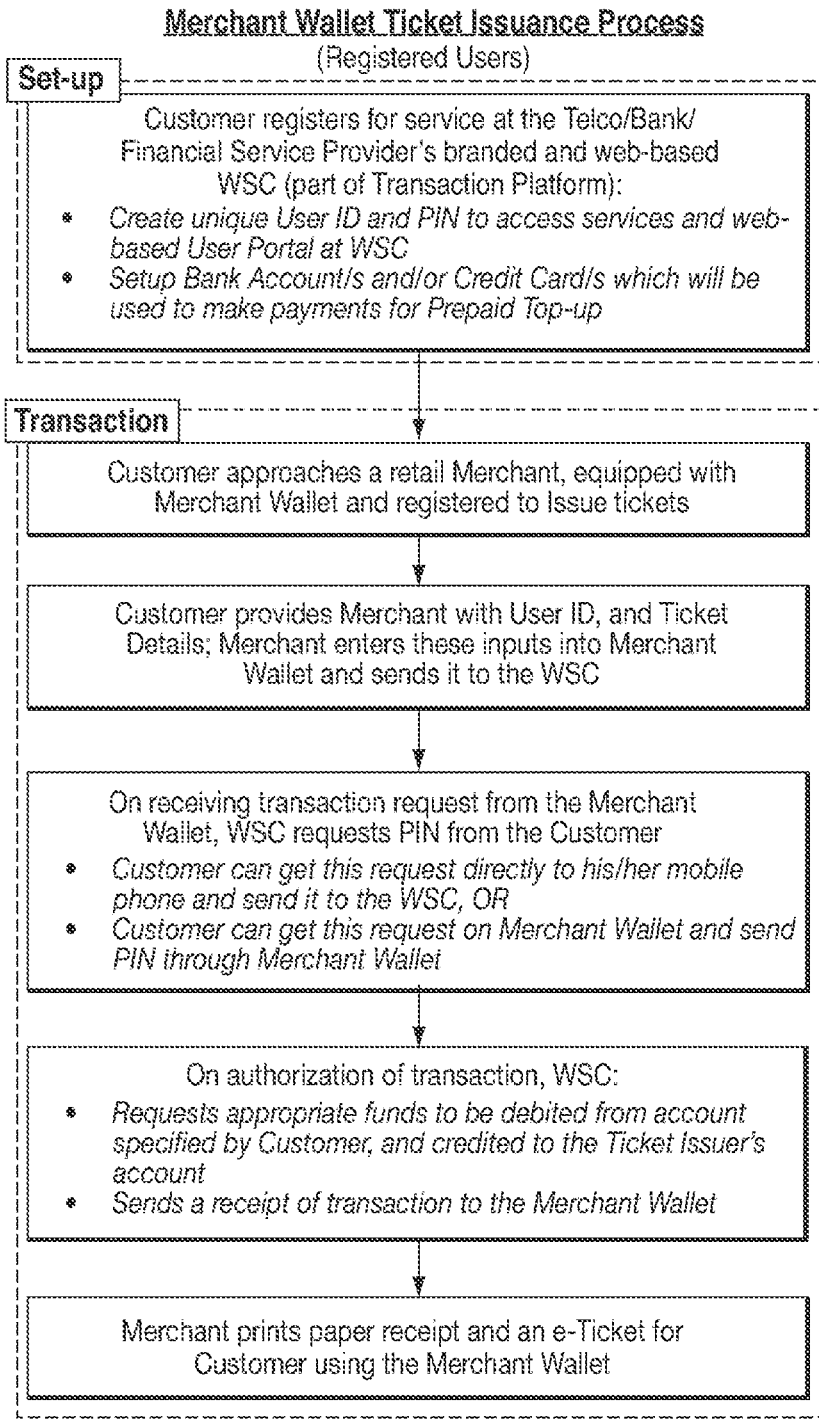
FIG. 64 is a generalized flow diagram illustrating the methodology for a ticket issuance process.

FIG. 64 depicts a ticket issuance process whereby a registered user may, perhaps in association with the client device 162, the merchant systems 170, and/or the main service facility 142, be issued a ticket. During a setup step, a customer registers for a service with a service provider 168, such as a telecommunications company, financial service provider, or the like, optionally through a web-based wallet service center, which may take the form of a main services facility 142 as described herein. The customer may create a unique user identifier and PIN to access services of the web-based platform at the main services facility 142. The customer may set up various services, such as bank accounts, credit cards, or the like that may be used to make payments, such as payments for tickets, top-up or the like. After setup the platform may be used to execute a transaction. For example, a customer may approach a retail merchant, equipped with a merchant wallet, which may be a merchant system 170 equipped with a UET 101 and registered with the main services facility 142 to issue tickets. The customer may provide the merchant with a user ID and ticket details, which the merchant enters into the merchant system 170 and sends to the main services facility 142. On receiving the transaction request from the merchant wallet/merchant system 170, the wallet service center/main services facility 142 requests a PIN from the customer. The customer can get the request directly from a mobile phone and send it to the main services facility 142 or the customer can get the request on the merchant wallet/merchant system 170 and send the PIN through the merchant wallet/merchant system 170. On authorization of the transaction, the main services facility 142 may request appropriate funds to be debited from the account specified by the customer and credited to the ticket issuer's account and may send a receipt of the transaction to the merchant wallet 170. The merchant may print a paper receipt and an e-Ticket for the customer using a merchant wallet/merchant system 170.

Figure 65:
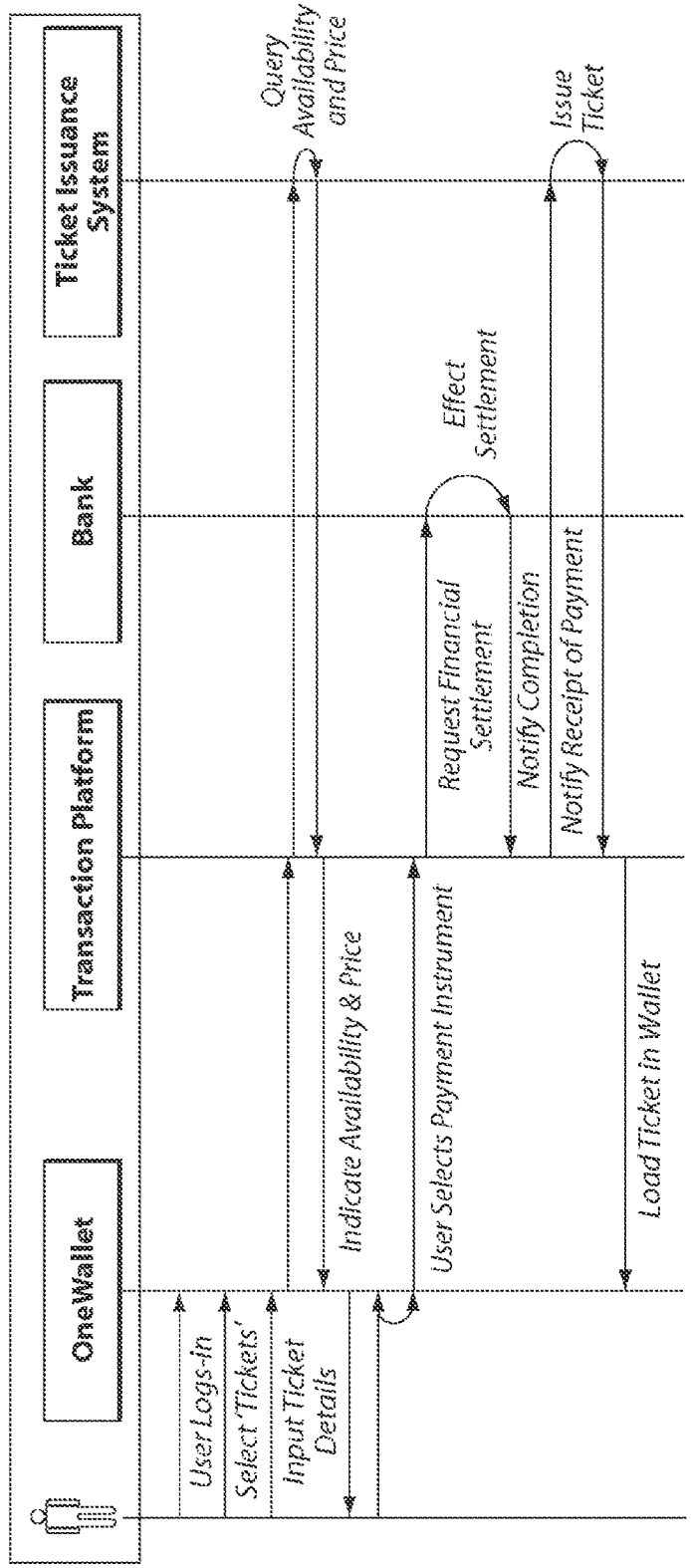
FIG. 65 depicts the steps in one transactional process according to the present invention.

FIG. 65 depicts the steps in another embodiment of the ticket issuance process. A user may log in to the user's client device 162, which may comprise a one-wallet interface. The user may select tickets and input ticket details, then send them to the transaction platform (a main services facility 142), which relays them to a ticket issuance system as a query regarding availability and price. The ticket issuance system returns an indication of availability and price through the main services facility 142 to the client device 162. The user then selects a payment instrument on the client device 162, such as a credit card stored on the client device 162 and passes it through the main services facility 142 to a financial services provider, such as a bank, requesting financial settlement. The bank effects settlement, such as by charging the user's credit card and notifies the main services facility 142 upon settlement completion. The main services facility 142 then notifies the ticket issuance system of receipt of payment, upon which the ticket issuance system issues the ticket to the main services facility 142, which loads the ticket (an actual ticket, not just information about a ticket) on the user's UET 101 on the client device 162.

Figure 66:
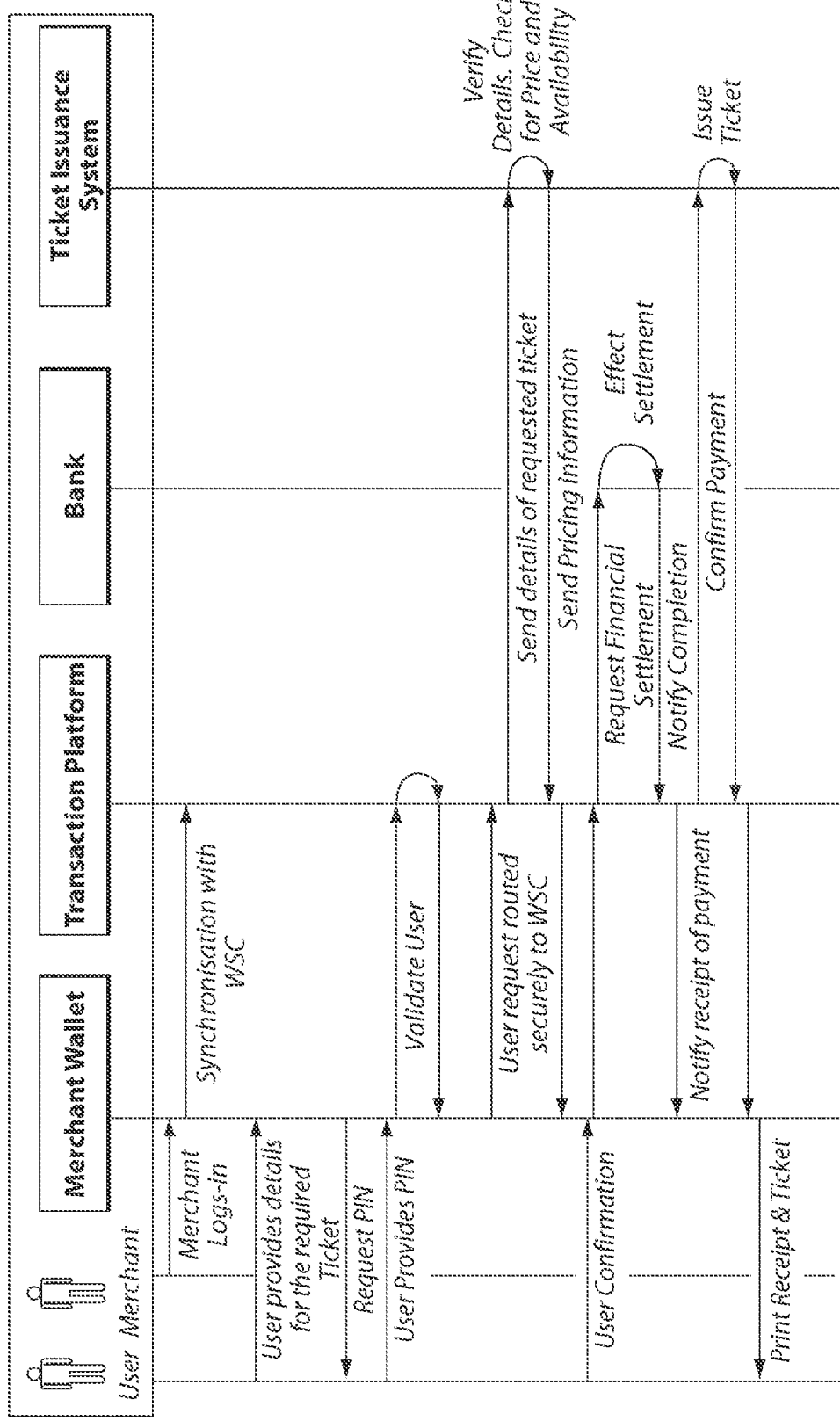
FIG. 66 depicts the steps in one transactional process according to the present invention.

FIG. 66 also depicts the steps in another embodiment of the ticket issuance process, in this case involving interaction with a merchant. A merchant logs in and synchronizes a merchant system 170 with a main services facility 142. A user may provide a merchant with details regarding a ticket that it wishes to have. The merchant system 170 requests and then receives a PIN from the user, at which point the merchant system 170 validates the user using the main services facility 142/transaction platform. The user's request may then be routed securely to the main services facility 142, which sends details of the requested ticket to a ticket issuance system. The ticket issuance system may verify details and check price and availability for the ticket, sending pricing information through the main services facility 142 to the merchant system 170 for discussion with the user. The user may confirm to the merchant a desire to purchase the ticket, at which point the merchant sends a request for financial settlement through the main services facility 142 to a bank, which may effect settlement with the user's account and notify of completion of the settlement process. Upon receiving notice of receipt of payment, the merchant system 170 may confirm payment to the ticket issuance system, which issues the ticket to the merchant system 170, so that the merchant can print the ticket and a receipt.

Figure 67:
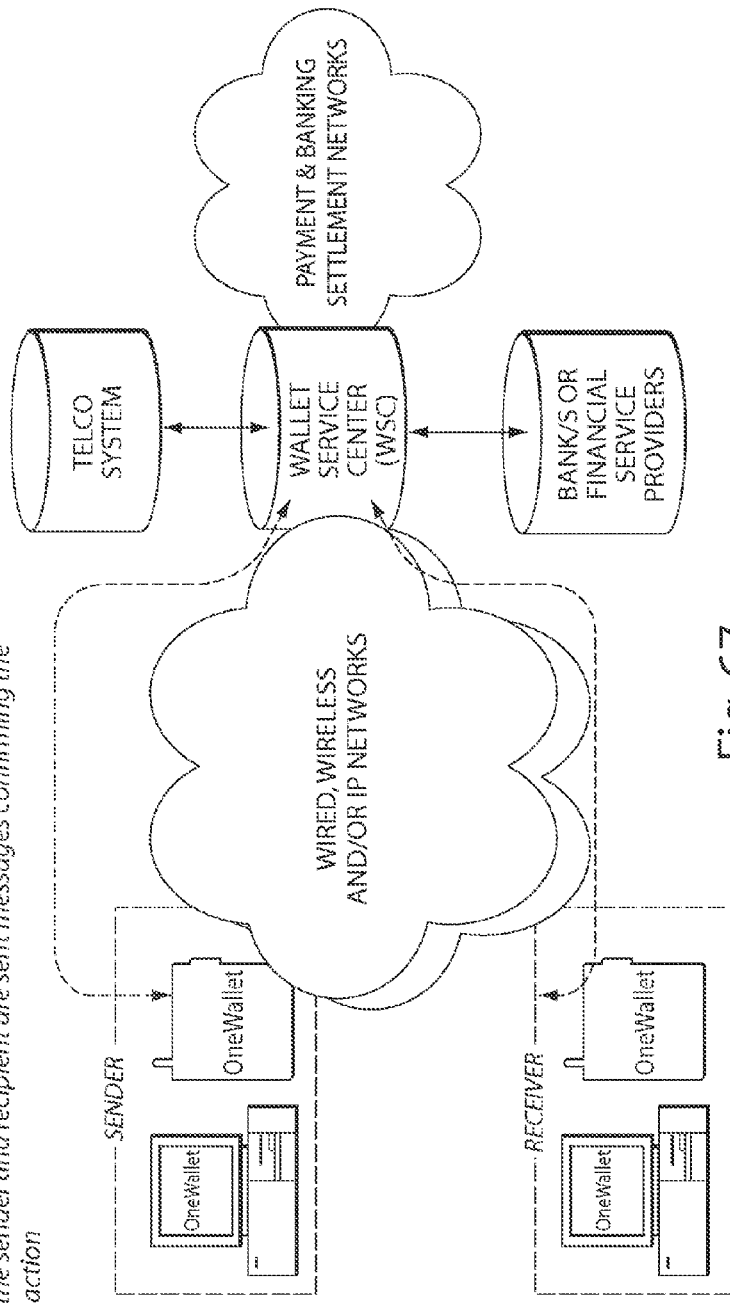
FIG. 67 depicts a system diagram for a P2P service.

FIG. 67 depicts a system having the features and attributes described herein for providing a P2P service. Two users, a sender and receiver, may have client devices 162 equipped with UETs 101. Each of them may interact with a main services facility 142/wallet service center, which may be connected to banks or financial service providers, a telecommunications system and to payment and settlement networks. The sender may open a UET 101 on the client device 162 and select a P2P service. The user may select a payment instrument to be used and type an amount, along with an identifier for the recipient. The main services facility 142 may validate details, including passwords or other security facilities to ensure the security of the transaction. The sender's account may then be debited and the recipient's account credited with the amount indicated by the sender. Both the sender and recipient may receive messages confirming the transaction. In embodiments the sender may send an actual item, such as a content item, ticket, or other item as discussed herein, securely over the main services facility 142 to the recipient, including for a payment as supported by the financial services embodiments described herein, in exchange for another item, or for no consideration.

Figure 68:
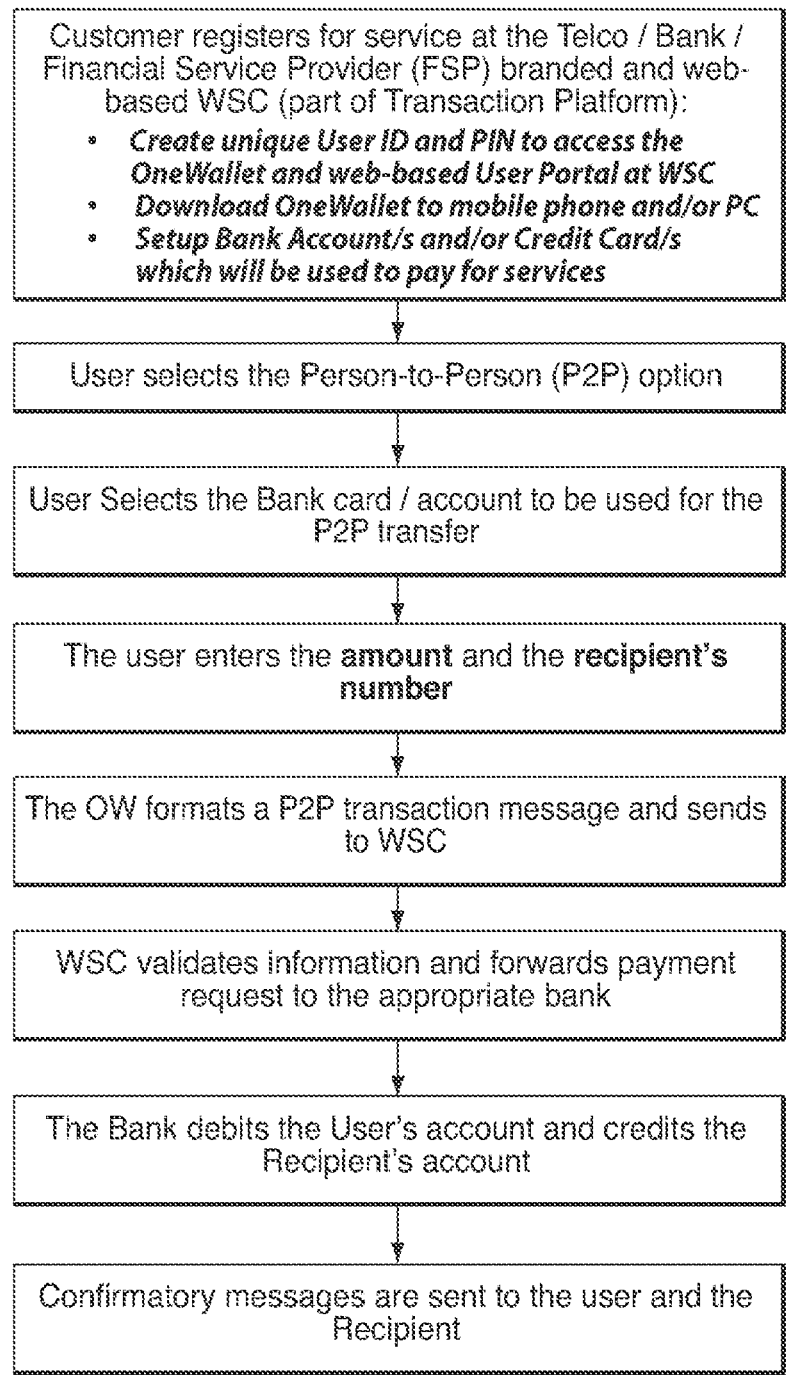
FIG. 68 depicts a generalized flow diagram illustrating the methodology for a P2P service process.

FIG. 68 depicts a P2P service process whereby a user, perhaps in association with the client device 162, the merchant system 170, and/or the main service facility 142, may conduct a P2P payment. First, a customer may register for a service with a service provider, such as a telecommunications service provider, financial services provider, or other provider or host of a main services facility 142, which may be presented as a wallet service center (WSC). The customer may create a unique ID and PIN to access the UET 101 on the customer's client device 162 or to access the main service facility 142. The customer may download the wallet/UET 101 to a mobile phone or other client device 162. The user may set up bank accounts or credit card accounts to be used for P2P transactions. On the UET 101 the user may select the P2P option, then select a bank account or credit card account to be used for the transfer. The user can then enter the amount and the recipient's number. The UET 101 may then format a P2P transaction message and send it to the main services facility 142. The main services facility 142 validates the information and forwards a payment request to the appropriate bank. The bank debits the user's account and credits the recipient's account (optionally including interbank settlement of the transfer). Confirmatory messages may be sent to the user and the recipient.

Figure 69:
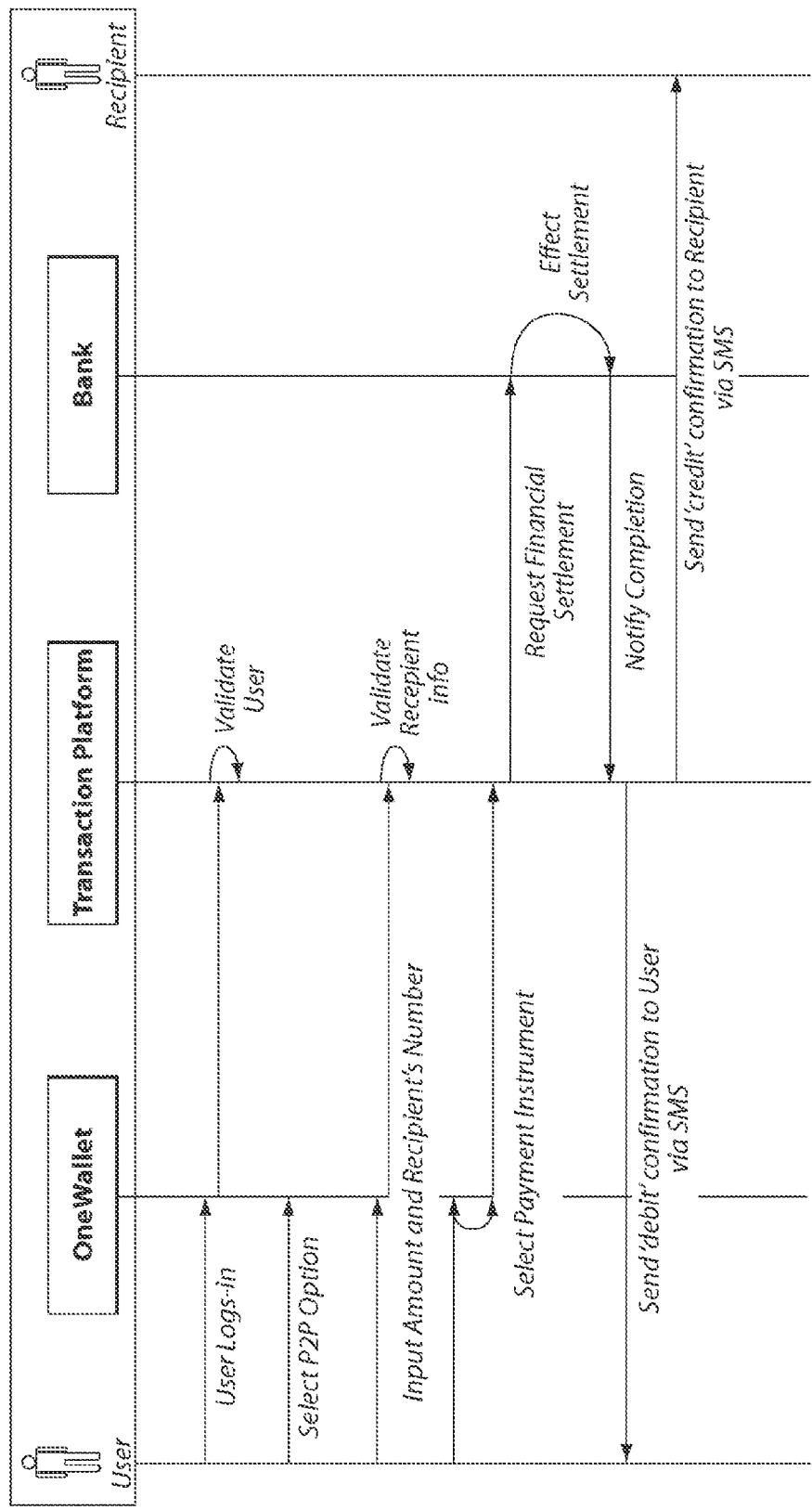
FIG. 69 depicts the steps in one P2P transactional process according to the present invention.

FIG. 69 depicts the steps in an embodiment of the P2P service process. A user logs in and is validated by the main services facility 142, then selects the P2P option. The user inputs an amount and the recipient's number, and the main services facility 142 validates the recipient's information. The user selects a payment instrument through the main services facility 142, which in turn relays a request for settlement to a bank, which effects settlement and notifies the main services facility 142. The main services facility 142 sends a debit confirmation to the user's UET 101 on the client device 162 and relays a credit confirmation to the recipient.

Figure 70:
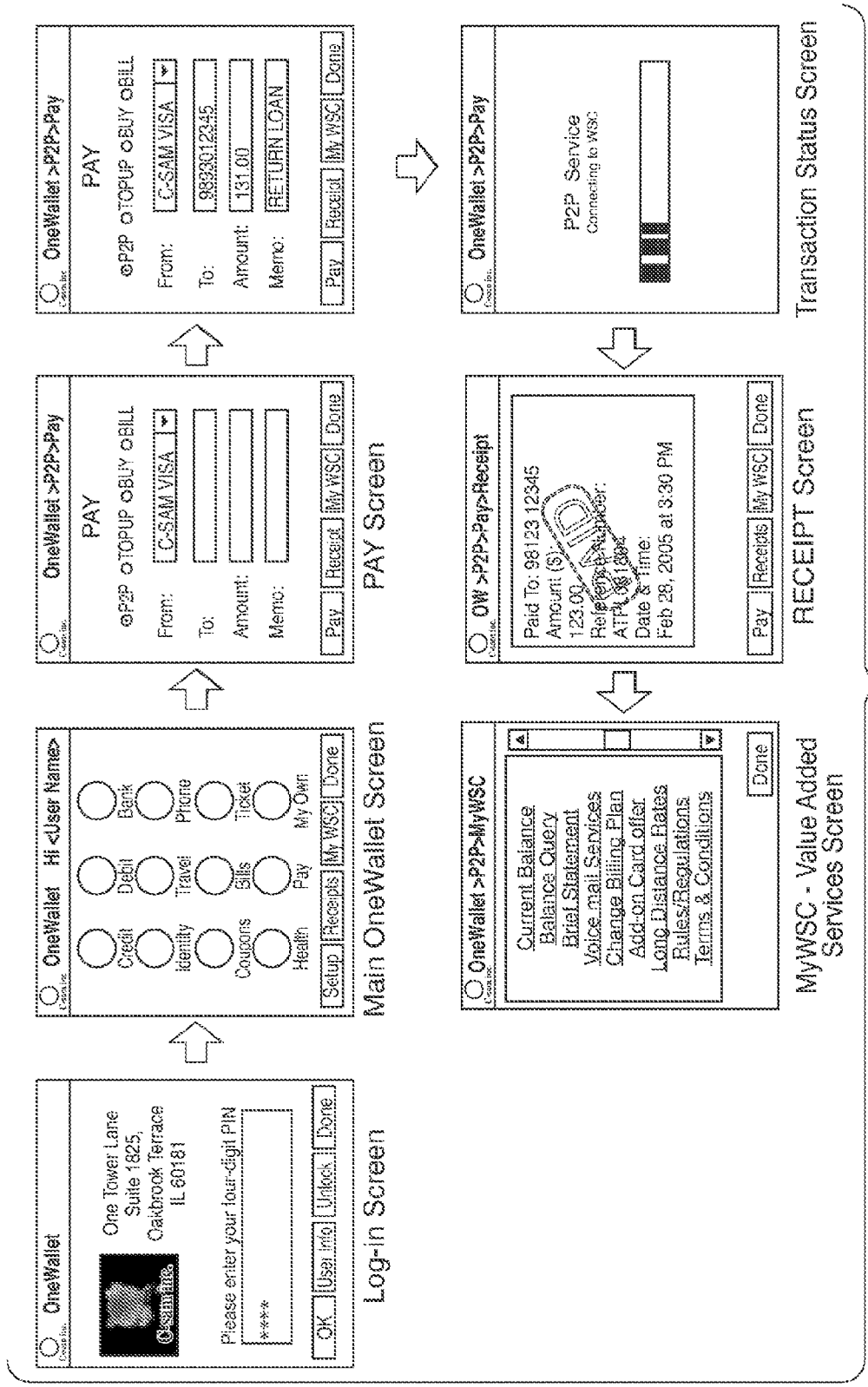
FIG. 70 depicts a representative user interface flow for a P2P service.

FIG. 70 depicts a representative user interface flow for the P2P service process, which may be displayed on the client device 162. A log-in screen prompts a user to enter a PIN, upon which a screen appears showing icons for various services, one of which is PAY screen. When selected, the icon initiates a PAY screen, which allows a user to select a payment instrument (e.g., a credit card) and to enter the recipient, amount and a memo. The interface shows a transaction screen as the transaction steps described in connection with FIGS. 68 and 69 are taken by the main services facility 142 and the financial service provider, after which a receipt screen appears, with a "paid" stamp for the transaction. The user can then return to a value added service screen, such as for services of a financial services provider.

Figure 71:
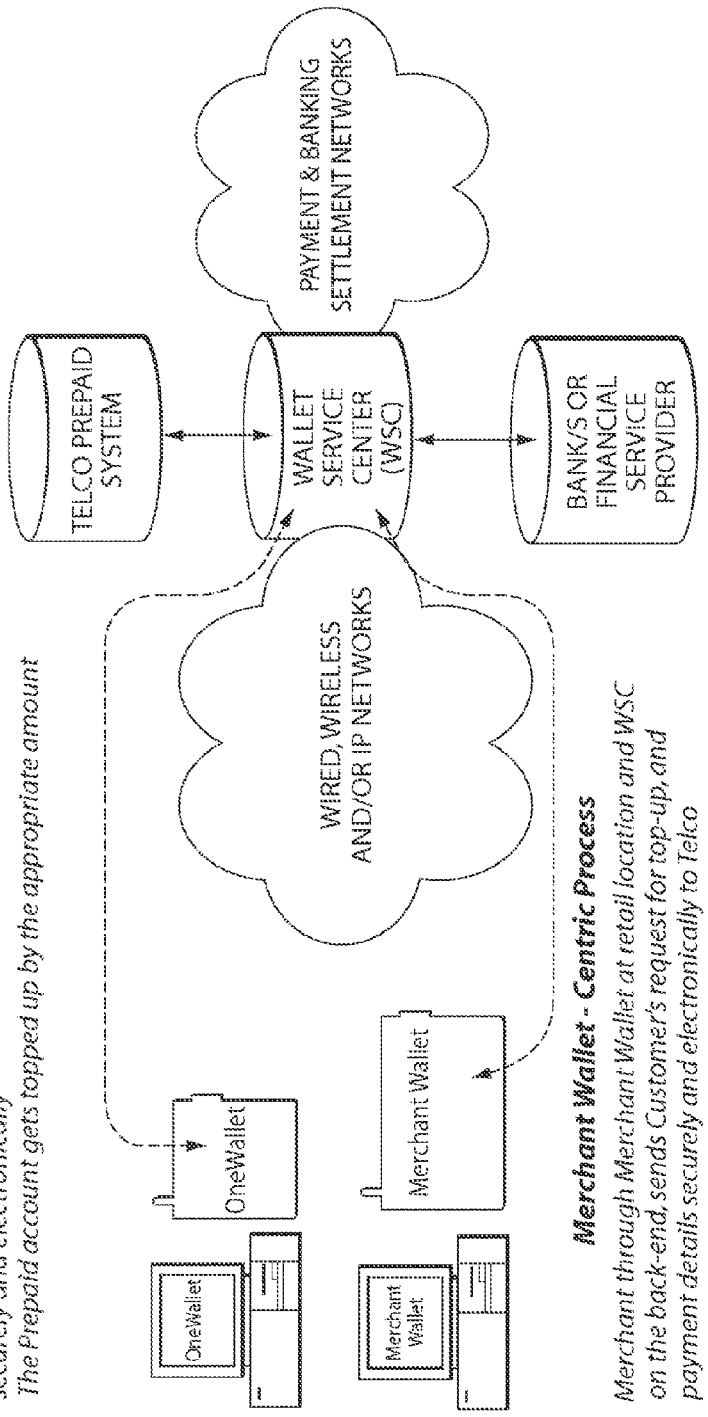
FIG. 71 depicts a system diagram for a prepaid top-up service.

FIG. 71 depicts a platform having the attributes described herein for enabling prepaid top-up services, including a client device 162 (labeled a "one wallet") with a UET 101, a merchant system 170 (labeled a "Merchant Wallet") and a main services facility 142 (labeled a "wallet service center (WSC)). Service providers 168 such as a Telco and a financial services provider interact with the main services facility 142. In embodiments a telecommunications services provider may send a message through the main services facility 142 to a UET 101 on a client device 162, securely and electronically, indicating that a prepaid balance is below a threshold. The customer initiates payment through a UET 101, which is received, securely and electronically, through the main services facility 142. The telecommunications service provider then sends a receipt to the UET 101 of the client device 162, and the prepaid account it topped up. Alternatively, a merchant may use a merchant system 170/merchant wallet at a retail location that is connected at the back end to the main services facility 142. The merchant may send a request for top-up and payment details securely and electronically through the main services facility 142 to the telecommunications service provider. The telecommunications service provider, through the main services facility 142, may complete the transaction and send a receipt for the customer to the merchant system 170 at the retail location.

Figure 72:
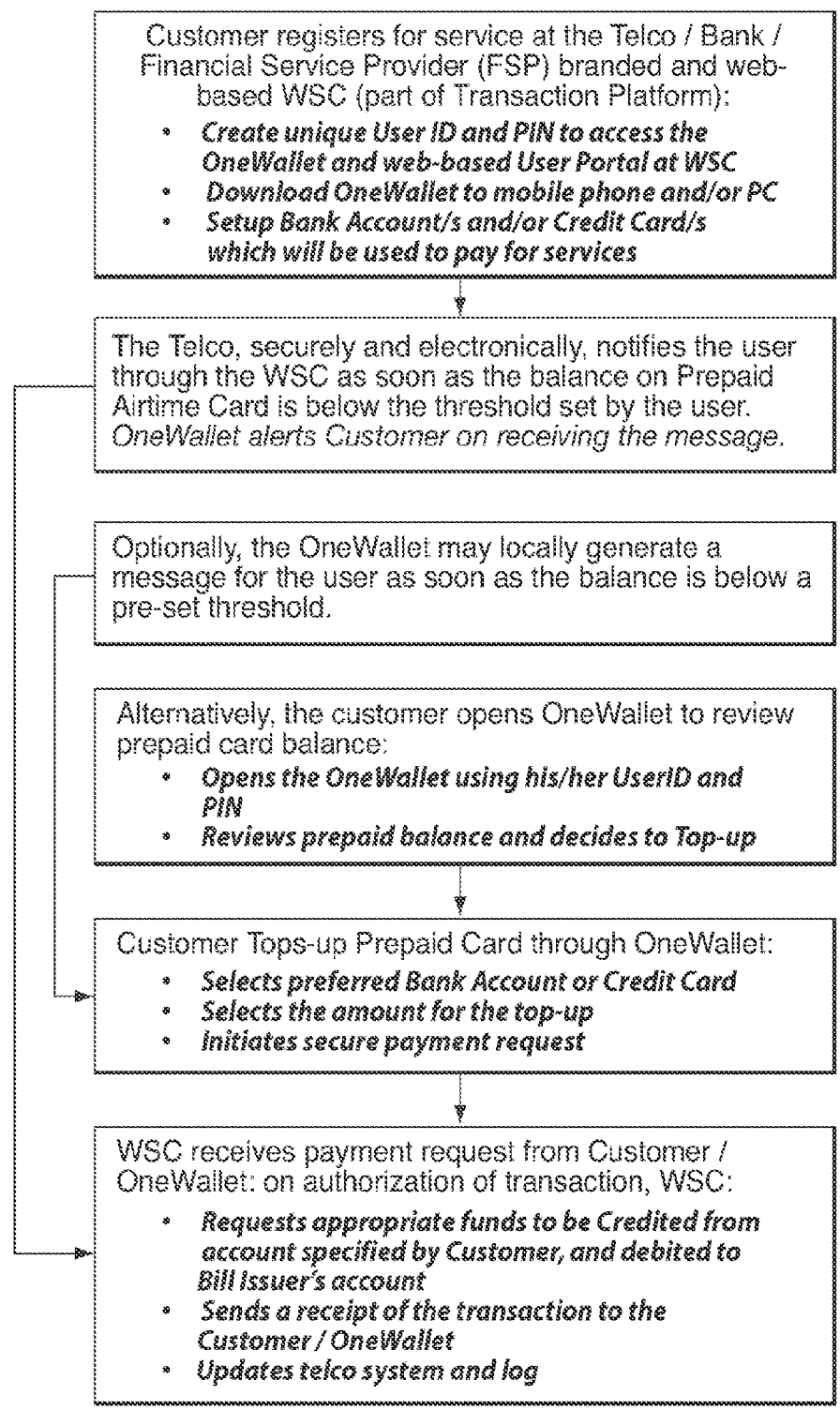
FIG. 72 depicts a generalized flow diagram illustrating the methodology for a prepaid top-up process.

FIG. 72 depicts a prepaid top-up service process whereby a user, perhaps in association with the client device 162, the merchant system 170, and/or the main service facility 142, may top-up a prepaid account. The customer registers for a service with a telecommunications service provider and/or bank, optionally through a branded and web-based main service facility 142. The customer can create a unique ID and PIN to access the UET 101 or a web-based portal of the main service facility 142. the user can download a UET 101 to the user's client device 162. The user can set up bank accounts or credit cards to be used to pay for services. The telecommunications service provider, securely and electronically, notifies the user through the main services facility 142 as soon as the balance on a prepaid airtime card is below a threshold, such as one set by the user. The UET 101 may alert the customer upon receiving the message. Optionally, the UET 101 may locally generate a message for the user as soon as the balance is below a preset threshold. Alternatively, the customer opens the UET 101 to review a prepaid card balance using a user ID and PIN. The customer may top up the prepaid card through the UET by selecting an account or card, selecting an amount and initiating a secure payment request. The main service facility 142 receives the payment request from the customer's UET 101. Upon authorization of the transaction by the telecommunications service provider, the main services facility 142 requests appropriate funds to be debited from the account specified by the customer and sent to the issuer's account, sends a receipt of the transaction to the customer's UET 101 and updates the telecommunications system provider's log.

Figure 73:
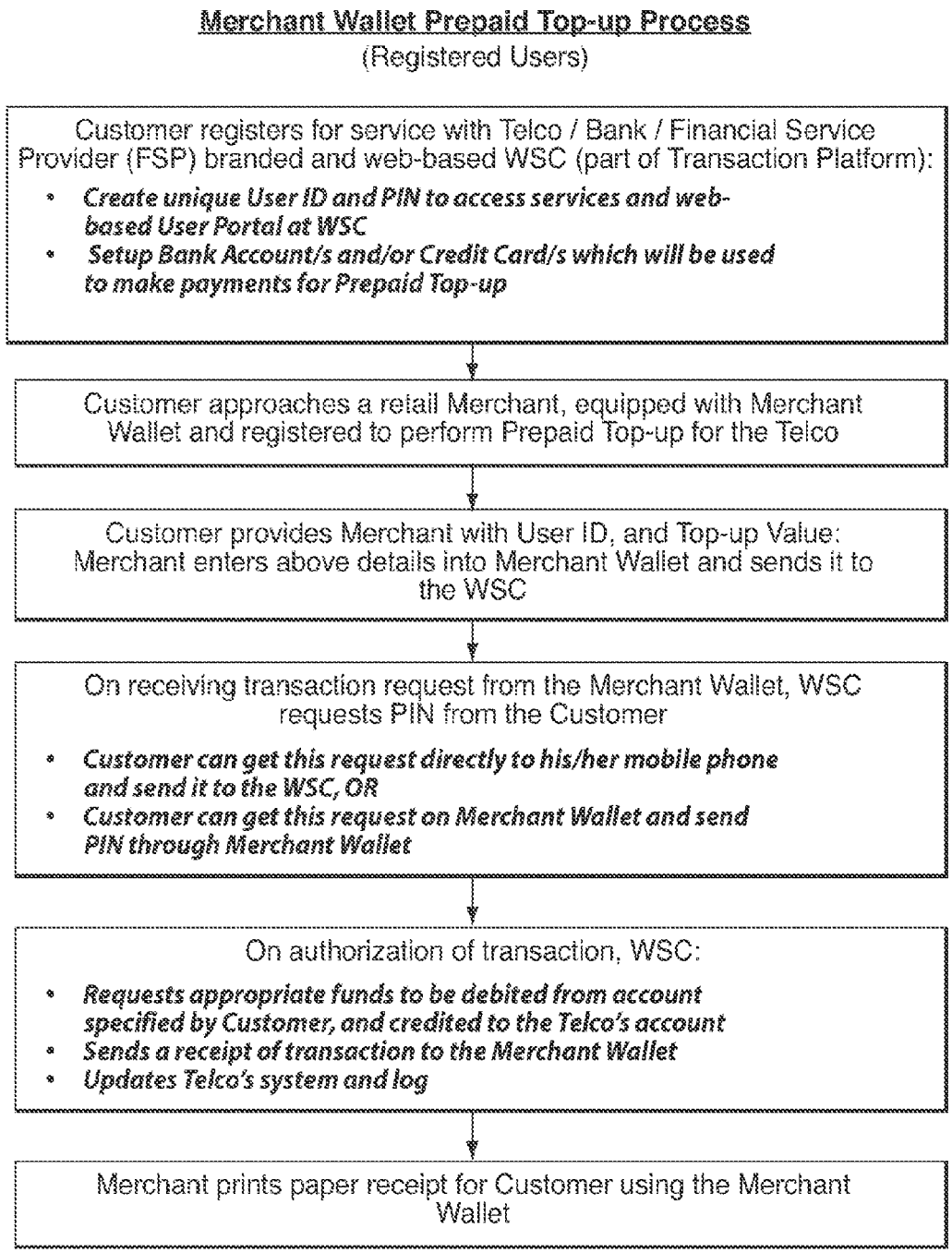
FIG. 73 depicts a generalized flow diagram illustrating the methodology for a prepaid top-up process for registered users.

FIG. 73 depicts a prepaid top-up service process whereby a registered user, perhaps in association with the client device 162, the merchant system 170, and/or the main service facility 142, may top-up a prepaid account. A customer registers with a telecommunications service provider and one or more financial service providers, creating unique PINS and Ids to access services at the main services facility 142. The customer sets up accounts or cards with which to make payments. The customer approaches a retail merchant equipped with a merchant system 170 ("merchant wallet") that is registered to provided prepaid top-up for the telecommunications service provider. The customer provides the merchant with a user ID and a top-up value, which the merchant relays to the telecommunications service provider through the main services facility 142. On receiving the transaction request, the main service facility 142 asks for the PIN, which the customer can enter directly (where the request is sent to the customer's mobile phone or similar client device 162) or the customer can enter through the merchant system 170. On authorization of the transaction, the main services facility 142 requests appropriate funds to be debited from the customer's selected account and credited to the telecommunications service provider's account, sends a receipt to the merchant wallet and updates the telecommunications service provider's system and log. The merchant may print a paper receipt for the customer using the UET 101 of the merchant system 170.

Figure 74:
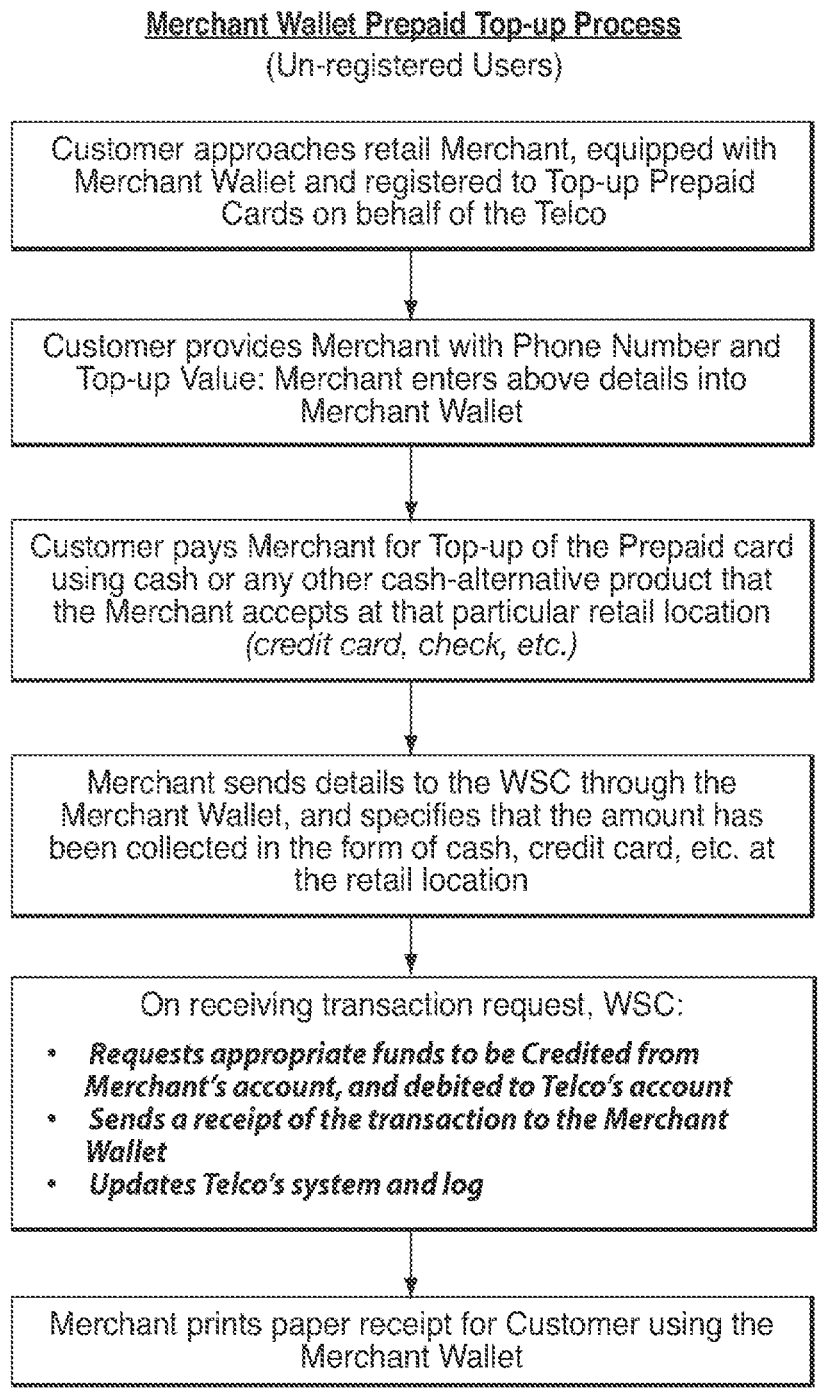
FIG. 74 depicts a generalized flow diagram illustrating the methodology for a prepaid top-up process for unregistered users.

FIG. 74 depicts a prepaid top-up service process whereby an unregistered user, perhaps in association with the client device 162, the merchant system 170, and/or the main service facility 142, may top-up a prepaid account. Here the customer approaches the merchant equipped with a UET 101 (merchant wallet) on a merchant system 170 that is registered to provide top-up services with a telecommunications services provider. The customer provides the merchant with a phone number/prepaid account number and top-up value, which the merchant enters into the merchant wallet/UET 101. The customer pays the merchant for the topup, using any payment form, such as cash. The merchant sends details to the main services facility 142, specifying the amount collected. The main services facility 142 requests that funds be credited from the merchant's account and deposited to the telecommunications service provider's account, sends a receipt and updates the telecommunications service provider's system and log (reflecting top-up of the card). The merchant prints a paper receipt for the customer using the UET 101 of the merchant system 170.

Figure 75:
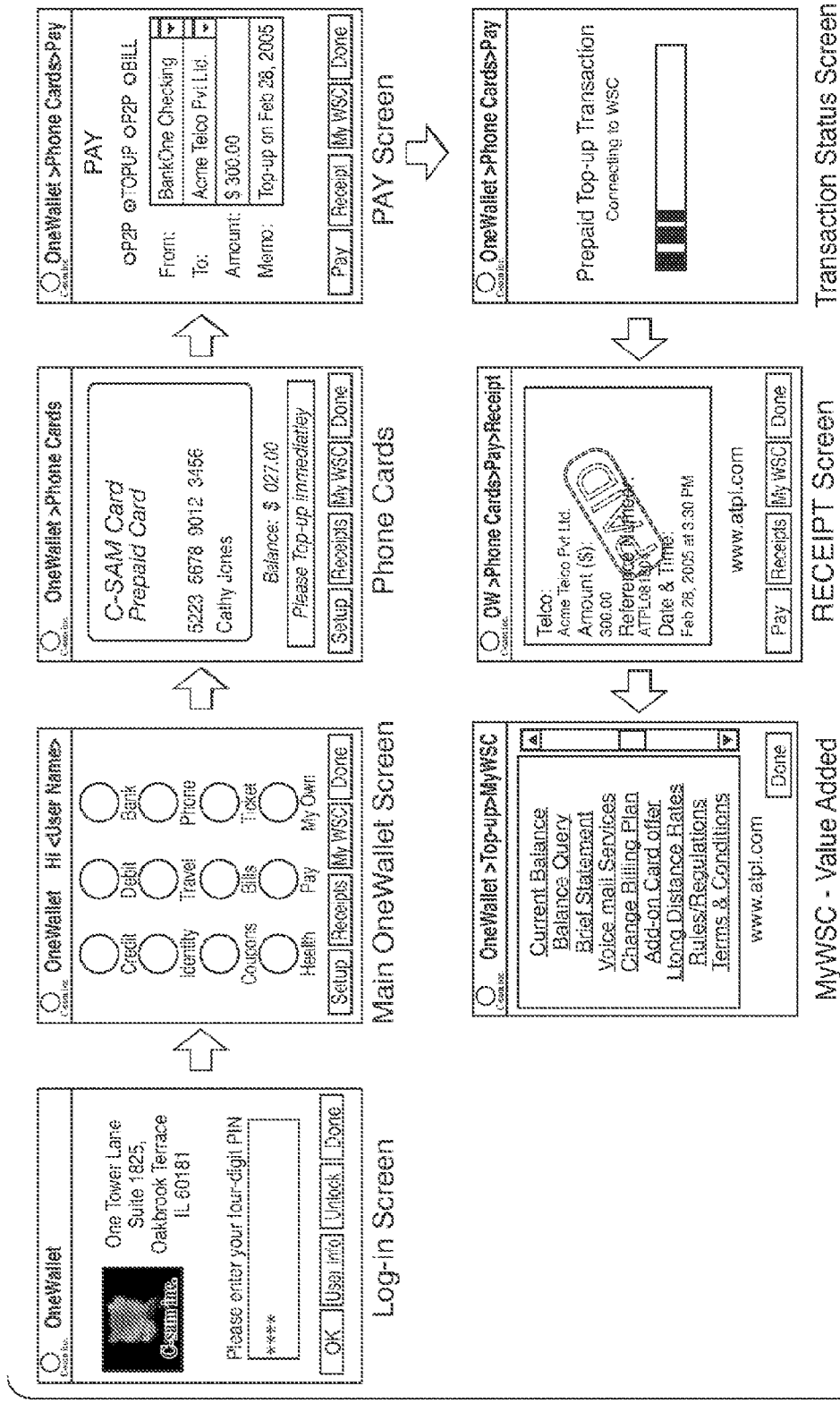
FIG. 75 depicts a representative user interface flow for a prepaid top-up service.

FIG. 75 depicts a representative user interface flow for the prepaid top-up service process, which may be displayed on the client device 162. A user logs in using a PIN and sees a main screen with various services represented as icons. The user selects phone services and is presented with the card (optionally a branded image) and a message to top up the card. The user then is presented a PAY screen at which the user can select an account from which to pay for top-up and an amount. The interface shows a pending transaction as the main services facility 142 completes the steps described in connection with FIGS. 73 and 74. The user's screen then shows the receipt from the main services facility 142 and then shows a menu of other value added services.

Figure 76:
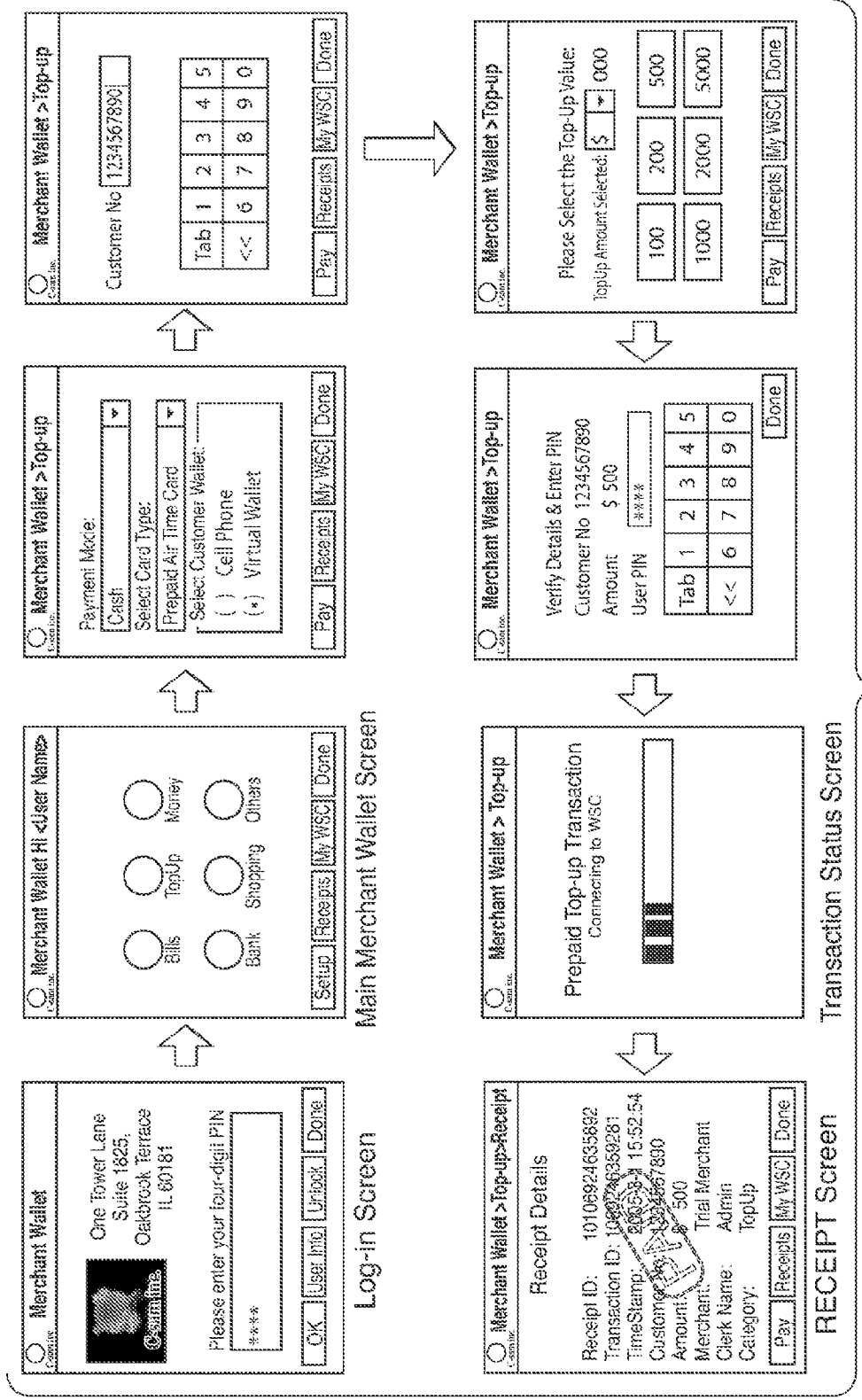
FIG. 76 depicts another representative user interface flow for a prepaid top-up service.

FIG. 76 depicts another representative user interface flow for the prepaid top-up service process, which may be displayed on the client device 162 or any other electronic transaction facility 101. A merchant logs in by entering a PIN and sees icons representing various services of the UET 101. The merchant selects TOPUP and is presented with a prompt to enter a payment mode (e.g., cash) and to select a customer UET 101 type. The merchant is then prompted to enter a customer number (e.g., phone number or account number), after which the merchant is prompted to enter a top-up value. The merchant verifies details and enters a PIN for the transaction, after which a screen indicates that the main services facility 142 is completing the transaction. Upon completion, a receipt appears on the merchant's UET 101, confirming completion.

Figure 77:
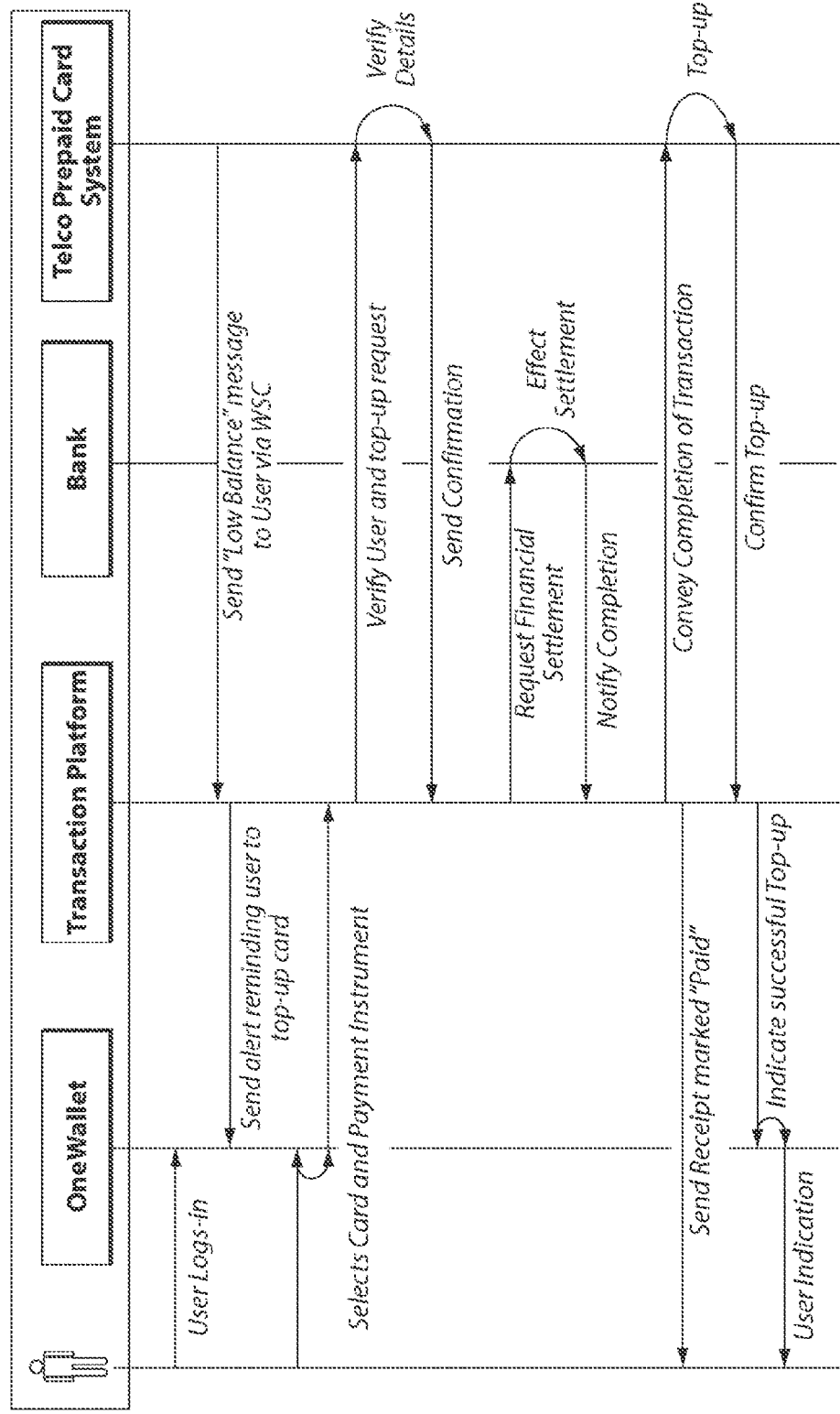
FIG. 77 depicts the steps in one prepaid top-up transaction process according to the present invention.

FIG. 77 depicts the steps in an embodiment of the prepaid top-up service process. A user logs in and receives a reminder from a main services facility 142 to top-up a card, optionally in response to receiving notice of a low balance from a telecommunications services provider. The user selects a payment instrument and amount and sends it through the main services facility 142, which verifies the user and relays a top-up request to the telecommunications services provider. The telecommunications services provider verifies details and sends confirmation to the main services facility 142, which relays the details to a financial services provider, which effects settlement and notifies the main services facility 142. The main services facility 142 sends a receipt marked "paid" to the UET 101 of the user and conveys completion of the transaction to the telecommunications services provider, which tops up the account and sends confirmation through the main services facility 142 to the user's UET 101.

Figure 78:
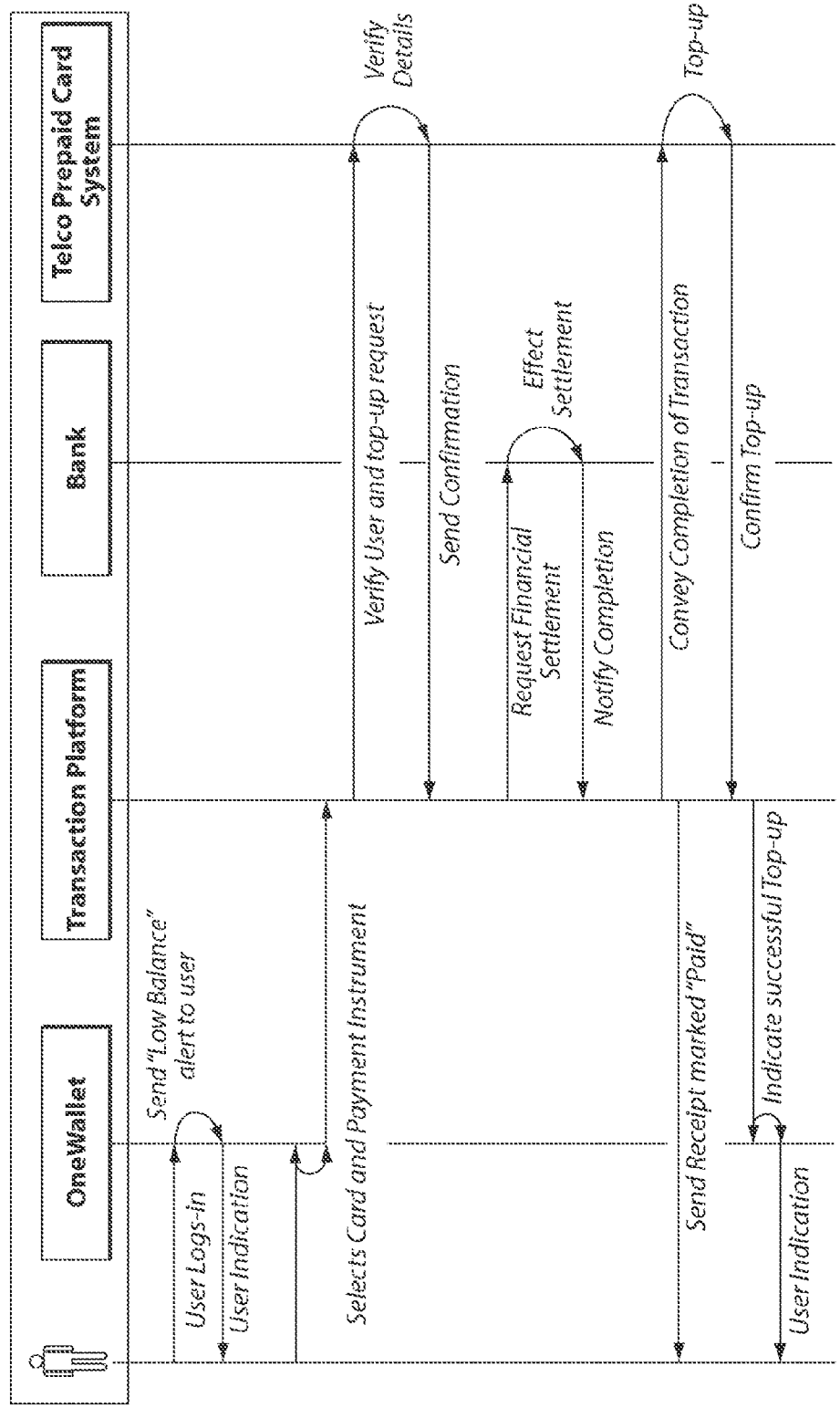
FIG. 78 depicts the steps in another prepaid top-up transaction process according to the present invention.

FIG. 78 depicts the steps in another embodiment of the prepaid top-up service process. Here the steps are the same as in connection with FIG. 77, except that the user's UET 101 tracks usage and automatically sends a low balance alert to the user, without requiring prompting from the main services facility 142.

Figure 79:
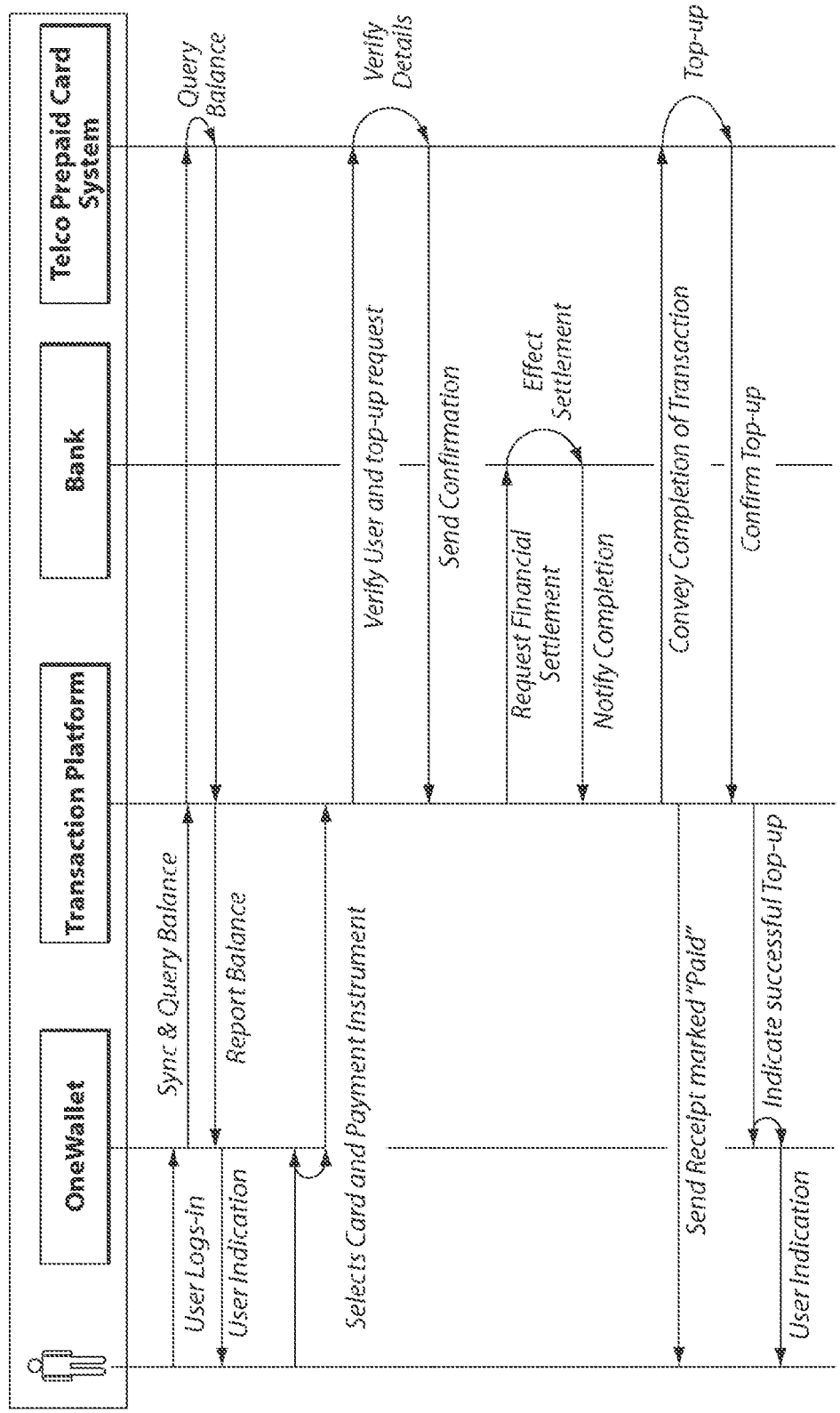
FIG. 79 depicts the steps in yet another prepaid top-up transaction process according to the present invention.

FIG. 79 depicts the steps in yet another an embodiment of the prepaid top-up service process. The steps are similar to those of the processes of FIGS. 77 and 78, except that the UET 101 of the user synchronizes with a main services facility 142 and generates a query about the balance of the user's prepaid account. The telecommunications services provider's system queries the balance and reports it via the main services facility 142 to the UET 101 of the user's client device 162, after which the user completes a top-up transaction as described above.

Figure 80:
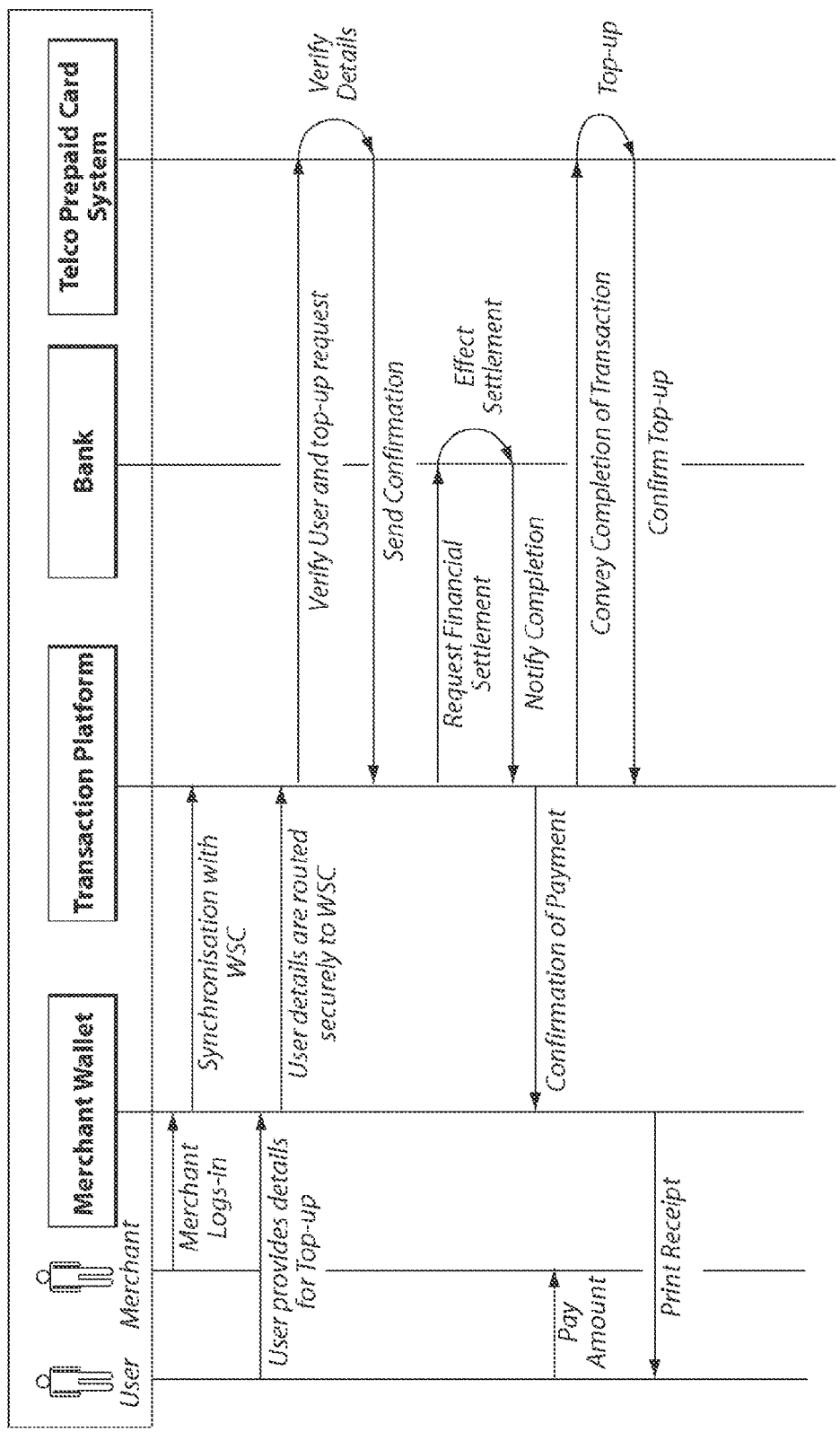
FIG. 80 depicts the steps in still another prepaid top-up transaction process according to the present invention.

FIG. 80 depicts the steps in still another an embodiment of the prepaid top-up service process, in this case using a merchant system 170 ("merchant wallet"). A merchant logs in and synchronizes with a main services facility 142. A user provides a merchant with a top-up request, including phone number/account information, payment instrument/account and a requested top-up amount. The merchant routes those details to the main services facility 142 from the merchant system 170. The request is verified by the telecommunications service provider, which sends a confirmation through the main services facility 142. The main services facility requests financial settlement with a financial services provider, which effects settlement and sends confirmation of payment. The user pays the merchant, which relays confirmation of completion of the transaction to the telecommunications services provider's system. The telecommunications service provider's system then completes top-up, after which the merchant system 170 prints a receipt for the user.

Figure 81:
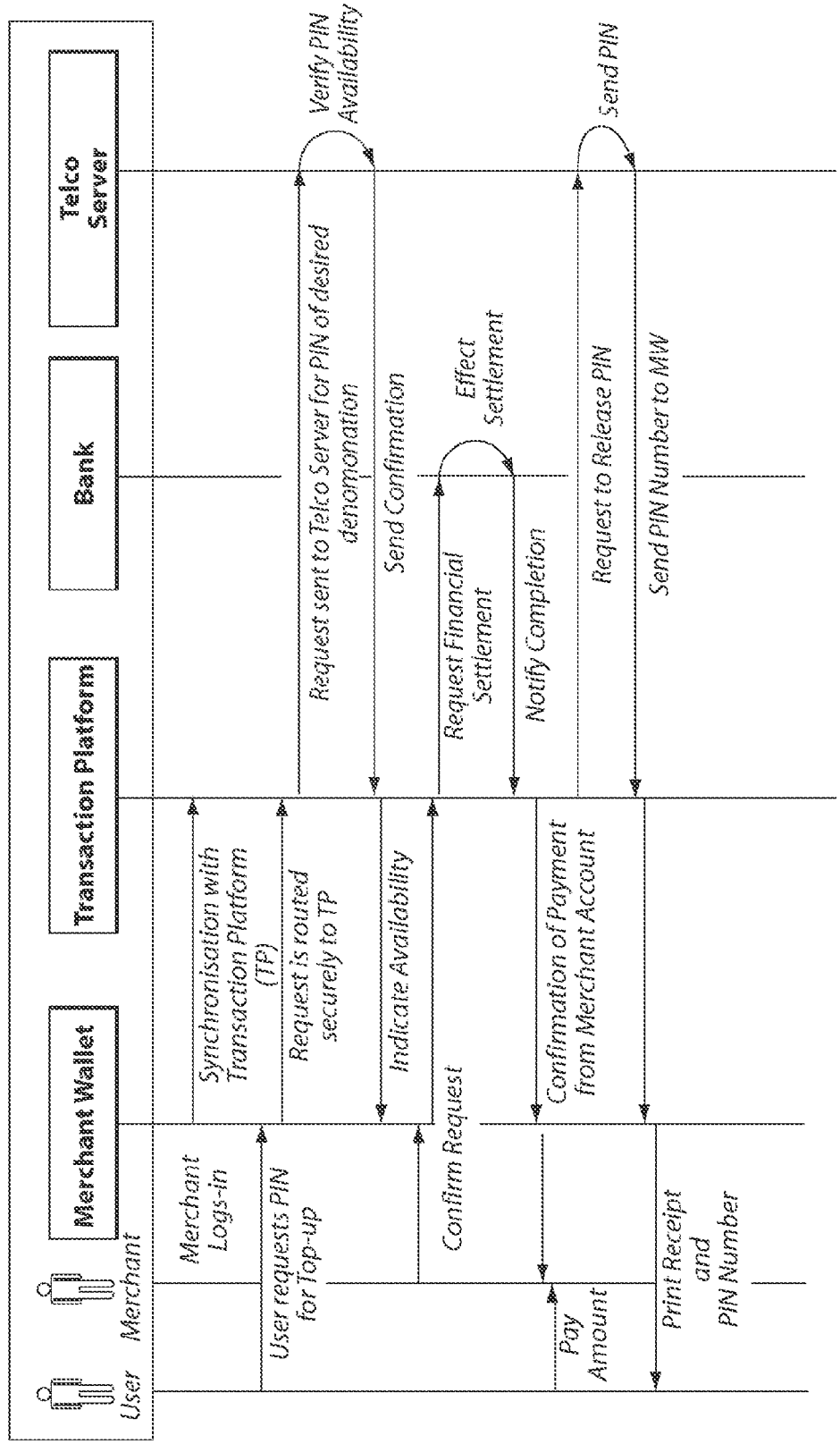
FIG. 81 depicts the steps in still yet another prepaid top-up transaction process according to the present invention.

FIG. 81 depicts the steps in another an embodiment of the prepaid top-up service process. A merchant logs in using a merchant UET 101 (merchant wallet) and synchronizes with the main services facility 142. The user requests a PIN for top-up, which is routed securely to the main services facility 142. The request is then sent to the telecommunications service provider, which verifies availability of topup and sends confirmation through the main services facility 142. The main services facility obtains confirmation of the request from the merchant system 170 and relays a request for financial settlement to a financial services provider, which effects settlement and sends confirmation to the merchant system 170. The customer pays the merchant, which sends a request to release the PIN to the telecommunications service provider. The telecommunications service provider sends the pin to the UET 101 of the merchant system 170, which prints the receipt and the PIN and gives them to the user.

While certain services, such as payments, ticketing and top-up services have been disclosed herein, it should be understood that similar process flows, platforms and user interfaces may support the other types of services and platforms described herein.

Certain embodiments of the secure transaction platform 200 may include various features, protocols, facilities, and the like that will be described in connection with FIGS. 82 through 93. The secure transaction platform 200 optionally enables multi-dimensional security among one or more main service facilities 142, merchant systems 170, electronic transaction facilities 101 and service providers 168, optionally including domain-, user- and device-based security for each of those entities, systems and facilities.

Figure 82:
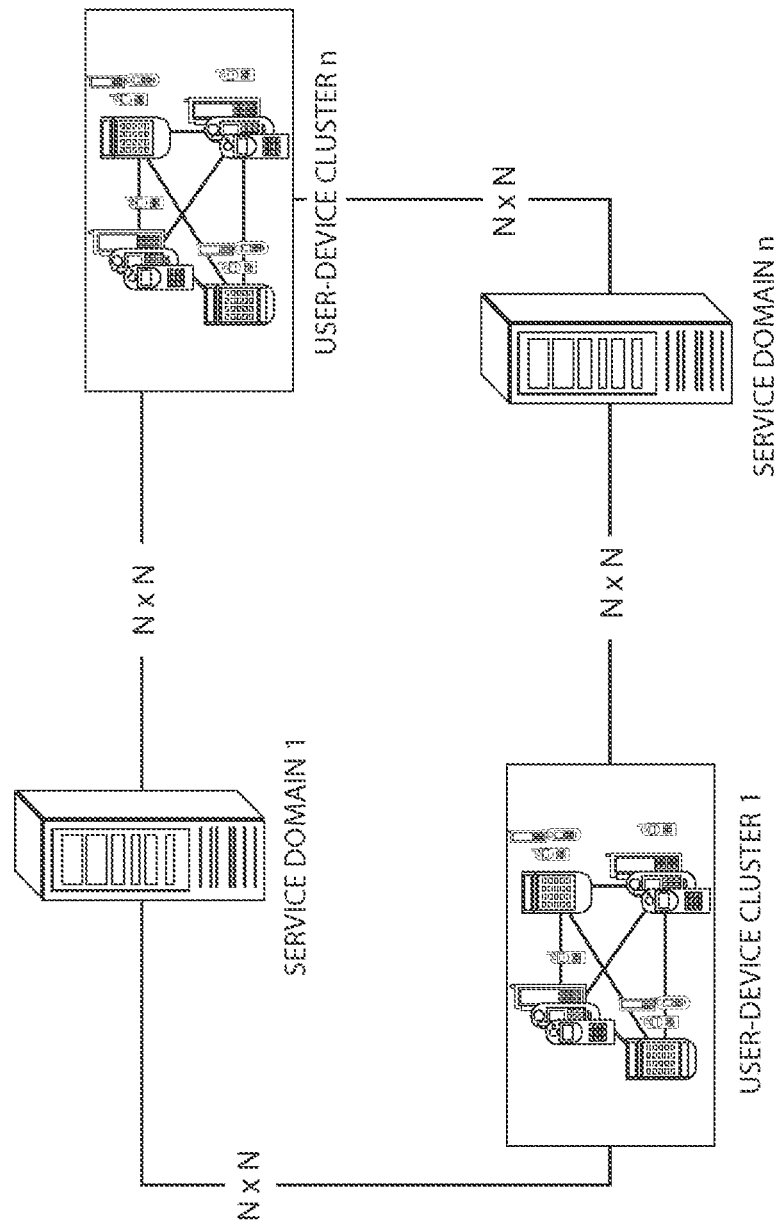
FIG. 82 depicts an overview of the main service facility meeting N×N×N security goals.

The main service facility 142 enables users to avail services from multiple service providers 168, card issuers and/or transaction acquirers. A service may be accessed directly by the user or through one or more electronic transaction facilities 101 (e.g., smart phones, PC, PDA, etc.). A single electronic transaction facility 101 may also be shared by multiple users (e.g., a merchant electronic transaction facility 101 may be operated by multiple clerks). As depicted in FIG. 82, this establishes a N×N cluster of entities (user×electronic transaction facilities 101) that interact with the platform 200. The type of interaction may depend upon the type of service.

The main service facility 142 may be scaled to include multiple service providers 168 (e.g., banking, utility, entertainment, etc.) where the security needs increase to N×(N× N). There may also be multiple electronic transaction facilities 101 (e.g., student, bank, medical) in one device (e.g., cellular phone). For example, a "student facility" containing a student id, library card, copy card, and Citibank-issued college card), and a "bank facility" containing a Citibank issued college card. These two Citibank cards from the student and bank electronic transaction facility 101s may synchronize on the back-end. As another example, within the field of transportation, a truck driver may have one facility containing a gas card, routing, and bill of lading, a second facility with a "scheduler" containing routes, assigned pick-ups, unassigned pick-ups, and a third "distributor" facility containing assigned pick-ups, unassigned pick-ups, and new pick-ups.

To ensure the security and authenticity of the communication taking place between the client (user or electronic transaction facility 101) and service provider 168 entities, the main service facility 142 may support a one-to-one secure relationship between each client (user or electronic transaction facility 101) and entity. Each cluster (user× electronic transaction facility 101) may be introduced into the platform through a primary/home server called the main service facility (MSF) 142. The servers may be configured for individual service providers 168 and suffixed with the nature of the service they provide. For example, a card issuer server is called MSF-I or a transaction acquirer server is called MSF-A. Collectively, these servers are called MSF Family Servers. Each MSF Family Server is equipped with the standard set of components like User Management, Device Management, CA, Authorization, Administration, etc.

There may be two types of clusters interacting with the MSF 142: electronic transaction facilities 101 and other MSF family servers (MSFI, Utilities, etc.). These entities may establish trust in different ways. For electronic transaction facilities 101, the user enrolls for an electronic transaction facility 101 application with the MSF 142. At the time of enrolment, the user may introduce an electronic transaction facility 101 to the MSF 142. The MSF 142 may then authenticate the user through independent channels and delivers the electronic transaction facility 101 software. The electronic transaction facility 101 software is typically downloaded from the MSF 142 or comes pre-installed on the user's physical electronic transaction facility 101 (e.g., phone, PDA, SIM, etc). This software may have the MSF 142 server's public security credentials (e.g. PKI Certificate) built into its code. The electronic transaction facility 101 software may initiate an electronic transaction facility 101 registration process with the server during which the electronic transaction facility 101 generates its own keys that are certified by the MSF 142. From the server's point of view, the MSF 142 may issue an OTAC (One Time Activation Code) to the user for each electronic transaction facility 101. This OTAC may be delivered to the user over a relevant channel (e.g., E-mail, Courier, etc.). The OTAC may be an 8-character strong random generated for the given electronic transaction facility 101 by the server and stored securely on the server for verification. Typically, 128-bit AES key is used to secure the OTAC on the server. Confidentiality of the OTAC may permit a user to be authenticated at the time of establishing the initial trust. The user may enter this OTAC in the electronic transaction facility 101 at the time of electronic transaction facility 101 registration, permitting the MSF 142 to authenticate the electronic transaction facility 101 for the first time and relate the electronic transaction facility 101 to its owner.

The initial trust establishment of the MSF 142 with other MSF Family servers may be done by the administrators of these servers by installing the given server's security certificate as a trusted SSL/HTTPS server's credential or by an inter-server registration process. This allows the inter-server communication among various MSF severs over the HTTPS (with Client Authentication). Alternatively, an OTAC based scheme may also be implemented between two MSF 142 servers. In this case, both the servers need to be enrolled and registered with each other using the server registration process. This may be useful when the inter-server communication has to be done over the C-SAM PKI.

The process of setting up the security and authentication credential with the given MSF 142 server may be referred to as the Device Registration Process. During this process, the electronic transaction facility 101 software may generate the security and authentication keys (e.g. Encryption Keys and Signing Keys) and sends them to the MSF 142. The MSF 142 may then certify these keys with a dedicated CA and store the certificates/public keys in its own database. A sample device registration process for PKI based client may involve the electronic transaction facility 101 encrypting the username & OTAC with the MSF's Public Encryption Key (preinstalled) and sending the data to the MSF 142. The server may verify the OTAC, and respond with its latest encryption and signing keys. The electronic transaction facility 101 may generate an encryption key-pair and a signing key-pair and send a certification request for each to the server. An X.509 certificate may be generated for the electronic transaction facility's 101 keys using its dedicated CA. The electronic transaction facility 101 may then acknowledge the completion of the registration process, and the electronic transaction facility's 101 account activated by the server.

Establishing the initial trust with other MSF 142 servers (e.g., those of service providers 168) may require more than a pre-installed credential. New service providers 168 may join and offer services to the cluster (user×electronic transaction facility 101) that have been enrolled at the MSF 142. These service providers 168 may set up the MSF-I or MSF-A as appropriate. The home MSF 142 server may act as the central gateway for the user to enroll for the services offered by the providers. This may result in the cluster (user×electronic transaction facility 101) having a dynamic relationship with multiple service providers 168, and may, thus, mandate that the initial trust be established dynamically.

As the MSF 142 introduces the service providers 168 and a cluster (user×electronic transaction facilities 101) to each other, the responsibility of dynamic trust establishment between these entities may be best suited for the MSF 142. Since the MSF 142 is typically owned and operated by a service provider 168 (e.g., Mobile Operator, Bank, etc.) that may already have a strong relationship with the client, this introduction may be treated as reliable. When the user opts to avail a service, their home MSF 142 may update the user's electronic transaction facility 101 with the respective service provider's 168 security and authentication credentials (e.g. encryption and signing certificates). This may enable the cluster (user×electronic transaction facility 101) to securely communicate directly with the service provider 168.

When a user opts to avail a service, the MSF 142 may forward the electronic transaction facility's 101 security credentials (e.g. encryption certificate) to the service provider 168. However, the service provider 168 may still need to perform its own authentication and certification of the cluster (user×electronic transaction facility 101). The service provider 168 might not use the electronic transaction facility's 101 MSF 142 authentication credentials (e.g. signing certificate), as the service provider 168 has not issued them. For example, if the MSF 142 forwards the signing certificate of the electronic transaction facility 101 to the MSFI, the MSFI can verify the electronic transaction facility's 101 signature. However, it cannot verify the certificate itself, as it is issued by the MSF's 142 CA and not its own CA. The service provider 168 may issue an OTAC to the user over a relevant channel (e.g. e-mail, courier). When the electronic transaction facility 101 contacts the service provider 168 for the first time, the OTAC may be verified by the service provider 168 for the initial authentication. The service provider 168 may then proceed to certify a unique set of credentials (PKI keys) for the cluster (user×electronic transaction facility 101) relationship with itself.

Different service providers 168 may offer different services to the electronic transaction facility 101 user. This may include services like—downloading of the virtual card to the electronic transaction facility 101 and performing online transactions using such cards. These operations may require a high degree of security and authentication. The cluster (user×electronic transaction facilities 101) may establish a one-to-one relationship directly with the service provider 168 to ensure maximum security and to avoid man-in-the-middle type of attacks.

The electronic transaction facility 101 may encrypt the serviceid and OTAC with the service provider's 168 encryption public key and send the registration/download request directly to the service provider's 168 MSF. The server may then verify the OTAC and respond with its latest encryption and signing keys. The electronic transaction facility 101 may generate a new signing keypair for the given server and send a certification request to the server. The server may issue a signing certificate using its dedicated CA. The server may also send the service data/download response to the electronic transaction facility 101. The electronic transaction facility 101 may then acknowledge the registration/download, and the server may activate the electronic transaction facility's 101 account/services.

The electronic transaction facility 101 application may encapsulate the N×N security credentials in the form of virtual cards. The user may not be required to remember which keys go with which issuer. Instead the user may select the cards to be used for a particular transaction and the appropriate keys may then be selected by the electronic transaction facility 101 application and used for the cryptography.

The electronic transaction facility 101 may allow for a single PIN to unlock the application and retrieve all the individual certificates. Keys and certificates are typically stored using a PKCS#7 symmetric encryption. A PIN may be used to decrypt and retrieve these. Without the electronic transaction facility 101 the user would potentially have N PINS for each relationship. The electronic transaction facility 101 may aggregate the relationships and provide a single access channel to the different business entities. The key pairs may be generated on the electronic transaction facility 101 itself and hence may ensure that the private keys are secure. A secondary approach (for slow electronic transaction facilities 101) may require the key-pairs to be generated on the MSF and delivered securely to the client. The keys may be encrypted with the OTAC, which is delivered securely to the user.

The Electronic transaction facility 101 platform may enable a user to securely store his/her private data on their personal electronic transaction facility 101. The user may access this data using his/her PIN. This imposes a greater level of responsibility on the client side as the single credential i.e. the PIN may be used to retrieve a bulk of private data. The security transaction platform 200 for such systems may need to ensure that the convenience of the single-credential doesn't become the vulnerability point for the system. Furthermore, the Electronic transaction facility 101 may interact with the server over the live/open networks. This communication should be secured as it may carry the user's private data and/or accessibility information to the user's private data.

Figure 83:
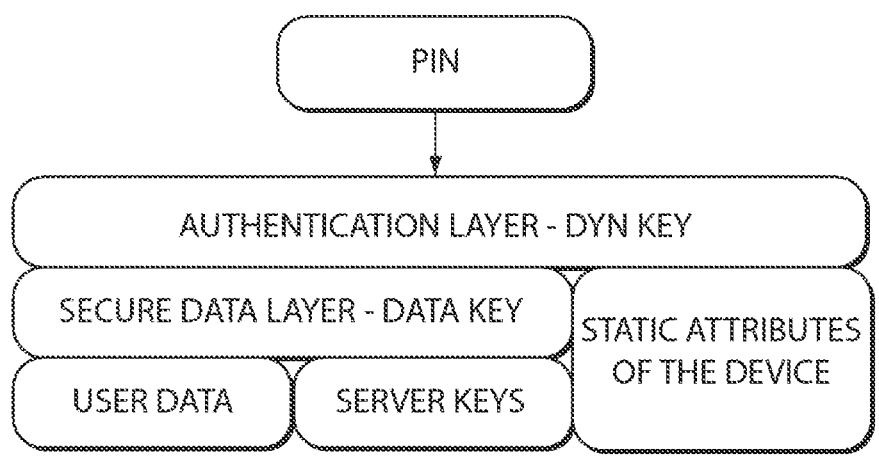
FIG. 83 depicts a multi-layered data security model.

FIG. 83 depicts an electronic transaction facility 101 software implementation of a multi-layered data security model. The electronic transaction facility 101 may use 128-bit AES encryption to store the data in its database. The key used for this may be generated using the PRNG algorithms to ensure the key's effectiveness. This key is called the Data Key. The Data Key may be encrypted with yet another key, called the dynamic key. The dynamic key may be made up of the user's PIN and the physical electronic transaction facility's 101 secret, unique identification attributes. For example, in the case of a phone, the IMSI may be used to bind the user's data with given phone. When a user logs into the Electronic transaction facility 101 system, the system may try to retrieve the Data Key using the PIN supplied by the user. If the Data Key can be retrieved successfully, the user is authenticated. The dynamic key approach has two-fold advantages. First, the dynamic key-to-data key approach may reduce, or eliminate, the need for storing the user's PIN onto the electronic transaction facility 101. This may enhance the PIN's security, as the PIN is never physically stored and resides only in the user's own memory. The static portion of the dynamic key may bind the data to the user's physical electronic transaction facility 101, and therefore may prevent the data to be copied. Data is not decrypted on the file system. The electronic transaction facility 101 application may read the encrypted data, decrypts it in memory and then discards it. Thus, the misuse of the data by another application or user may be reduced.

Figure 84:
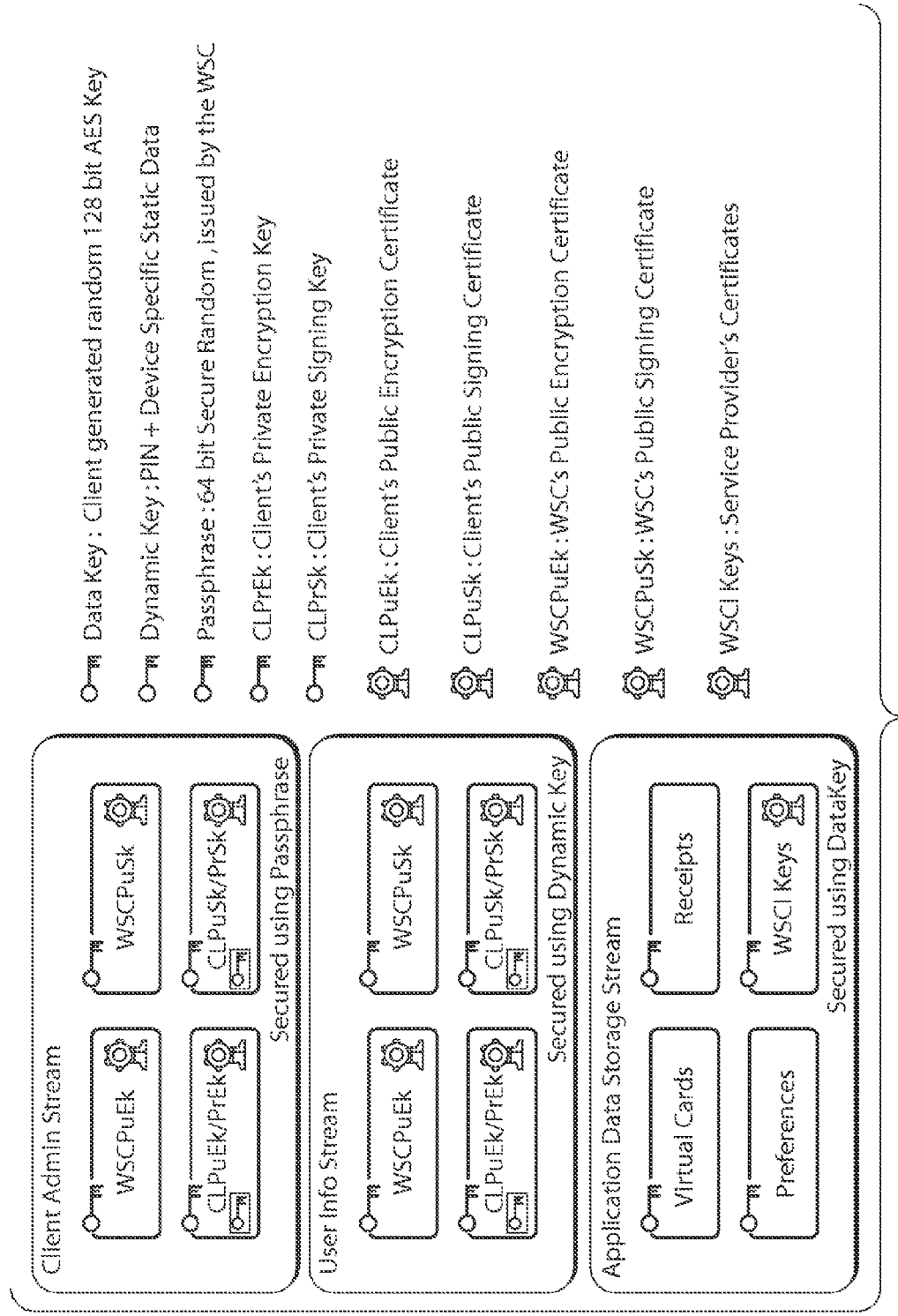
FIG. 84 depicts the use of multiple data streams for grouping data and encrypting with different keys.

FIG. 84 depicts multiple data streams for grouping data and encryption using different keys depending upon business requirements. A user's data stream may include the basic identification and authentication data, along with the data key used to secure the application data. If the user can decrypt the user info with the correct PIN and therefore the correct dynamic key, the electronic transaction facility 101 may provide the application data and various services to the user. If an electronic transaction facility 101 caters to the multiple users, the user info stream may be replicated for each user. This may result in individual authentication for 'n' users, without establishing electronic transaction facility 101-to-server relationship 'n' times.

Figure 85:
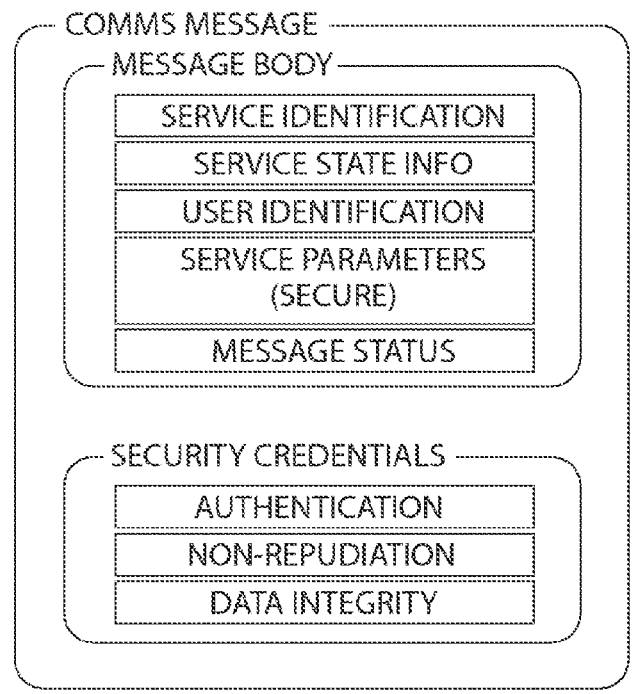
FIG. 85 depicts an abstract definition of the communication protocol.

FIG. 85 depicts the main service facility 142 with various types of electronic transaction facilities 101, each with different communication and security capabilities. The protocol for the electronic transaction facility 101-to-server communication defines an abstract model for the secure communication, which may be configured for the individual electronic transaction facility 101 types. The abstract protocol is agnostic to the data representation schemes (encoding/decoding), communication channel (HTTP, SMS, Raw TCP Sockets) and security models. The MSF 142 Platform may be configured and extended for any valid combinations of these communication factors.

Figure 86:
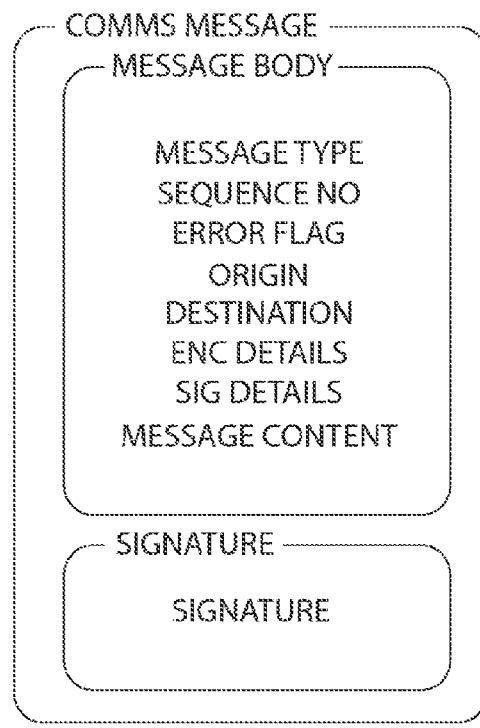
FIG. 86 depicts the logical-schema of the PKI Security model based communication protocol.

FIG. 86 represents the logical-schema of the PKI Security model based communication protocol. The PKI comms message structure may use the header of the message structure to carry the origin and destination identifications, which identifies the electronic transaction facility 101 and MSF's 142 security certificate being referred by the electronic transaction facility 101. The comms message may also contain a signature for the complete body, which can be verified to authenticate the claimed electronic transaction facility's 101 identity. The message content of the comms message may be encrypted with the recipient's encryption keys to ensure that only the recipient can read the data. The integrity and non-repudiation aspects may be taken care of by the signature field. As the complete body is signed by the electronic transaction facility 101, the service request and service parameters cannot be denied by the originator at a later time.

The MSF supports multiple crypto systems and has a set of credentials for each crypto system (RSA, ECC, NERI, etc.). This allows N types of electronic transaction facilities 101 to use whatever crypto system is natively available or supported. The MSF's 142 CA also supports certification for each crypto system.

The C-SAM Comms Message may use a service number and sequence number for identifying the service. Therefore a single data structure may be used to invoke all services. This makes the overall security transaction platform 200 implementation centralized and therefore more manageable. Having a single message structure for all types of service requests may provide added protection from pattern analysis and brute-force type of crypto attacks.

The MSF supports OneWallet (e.g., electronic transaction facility 101) to Legacy POS Transactions. In this type of transactions, the transaction may be carried out by adapting the existing POS (point of sale system, such as a merchant system 170) with a OneWallet (electronic transaction facility 101)-to-POS (merchant facility 170) adapter. The proximity transaction in this case may be between the OneWallet electronic transaction facility 101 and adapter mechanism. The security goal is to protect the data during the communication between the OneWallet and the adapter. As soon as the adapter delivers the user's data to the legacy system, the existing system may take care of the security aspects.

OneWallet-to-merchant electronic transaction facility 101 transactions of this type may be carried out between the OneWallet and MSF empowered POS. Although the proximity transaction happens between the Electronic transaction facility 101 and POS electronic transaction facility 101, the security model may need to cater to the end-to-end security between the electronic transaction facility 101 and the transaction server.

The communication between the electronic transaction facility 101 and the POS may be secured using the symmetric key exchange. The electronic transaction facility 101 and the POS may establish a common symmetric key for a communication session following a standard Key Exchange protocol. The actual transaction data may be transferred in the later stages of the communication session to ensure the maximum security.

Figure 87:
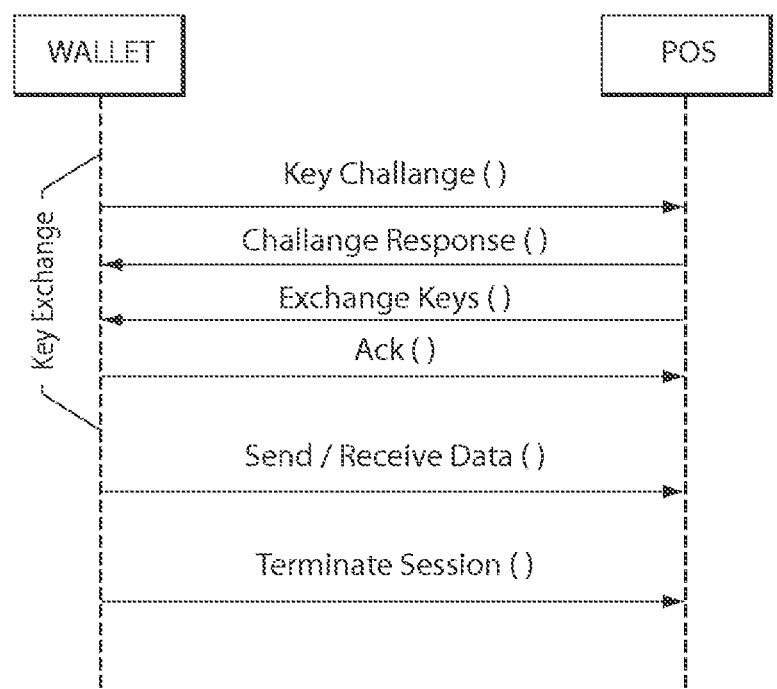
FIG. 87 depicts shows a sample transaction flow.

FIG. 87 shows a sample transaction flow including the Key Exchange. In a typical transaction scenario, the electronic transaction facility 101 software forwards the details of the user's transaction instrument, say a Virtual Card, to the transaction server along-with the necessary transaction attributes. This transaction data is routed through many hops. Each hop added in the transaction path adds a security risk. The MCF 142 Platform may establish end-to-end security credentials between the electronic transaction facility 101 and the transaction server. For example, when the Virtual Card is downloaded from the WSCI, the card info may include the transaction keys for the given user. When the electronic transaction facility 101 uses this data for a transaction with a POS device, it may encrypt (and optionally signs) the data with these keys. This makes it more difficult to retrieve the private data for the intermediate servers, and thus makes the man-in-the-middle type of attacks less likely.

Figure 88:
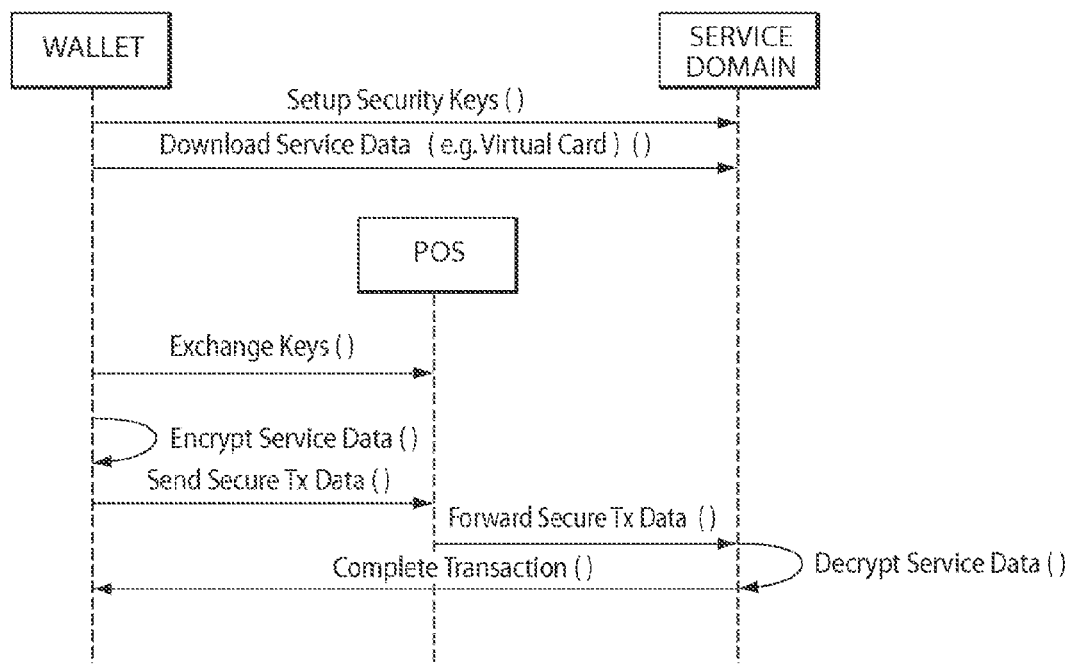
FIG. 88 depicts the end-to-end security setup between the electronic transaction facility and a transaction server.

FIG. 88 shows an outline of the end-to-end security setup between the electronic transaction facility 101 and Transaction Server. Certain electronic transaction facilities 101 are constrained to only communicate with the one server from which the application is downloaded. Here, the option for interacting with service providers 168 is to use a single domain model.

Figure 89:
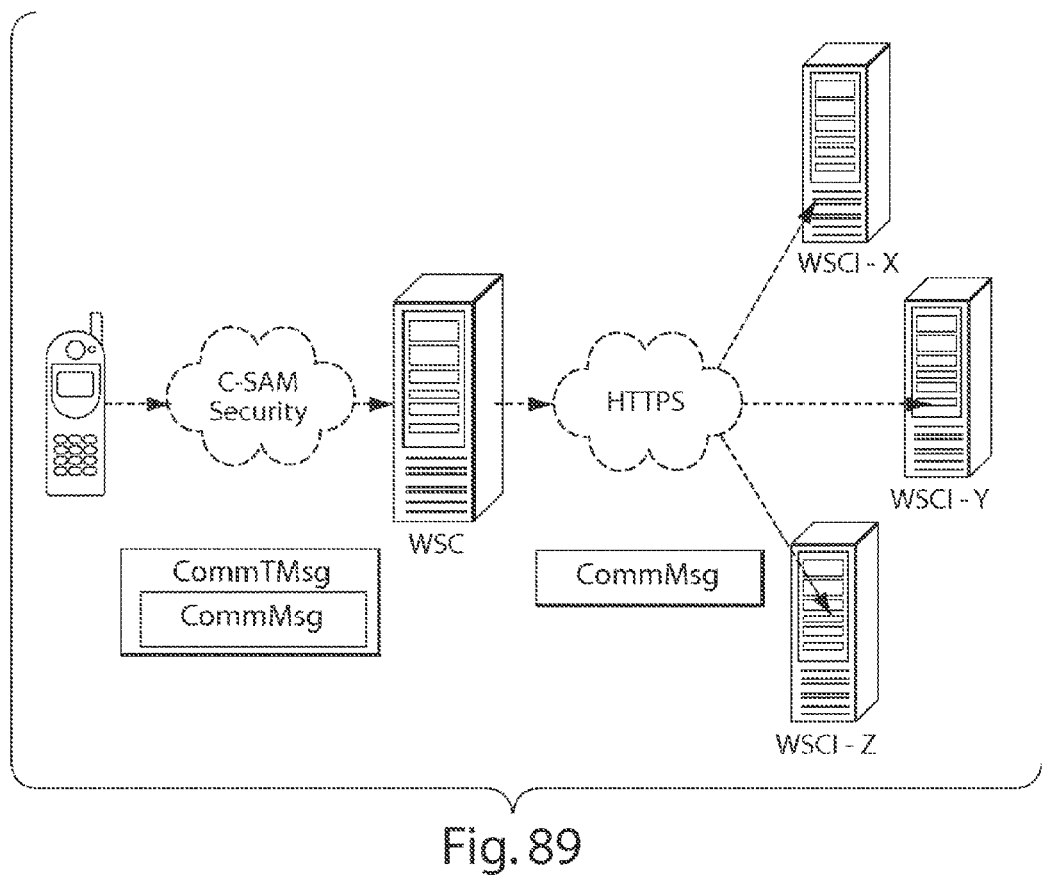
FIG. 89 depicts the Secure Proxy of the main service facility.

The MSF 142 may contain a component called Secure Proxy, which offers the services to the electronic transaction facility 101 for secure communication with service provider 168 servers that are transparent from the rest of the components. The secure proxy services assume that the security credentials are already setup between the electronic transaction facility 101 and the service provider 168. However, often the security credentials may also be set using the same services. The service provider 168 may issue an OTAC over email or land mail to the user. This OTAC may be used to encrypt the key-exchange requests between the Electronic transaction facility 101 and the service provider 168, making the request safe from the proxy. The proxy may forward the electronic transaction facility 101's request (already encrypted for the 168 provider) to the service provider 168 server over the HTTPS, and send the response back to the electronic transaction facility 101. As shown in FIG. 89, this may enable the electronic transaction facility 101 to interact with various service providers 168 using single secure domain.

The MSF 142 platform may offer its services to a wide range of electronic transaction facilities 101, including legacy GSM phones, low-end smart phones, high-end smart phones, PDAs, PCs and custom POS. However, not all electronic transaction facilities 101 are capable of handling full PKI, and therefore a custom security scheme may be designed to ensure the security requirements of such electronic transaction facilities 101. The MSF 142 platform implements a Symmetric Key based security transaction platform 200 for this purpose, where the 128 bit AES keys are used as the security credential and stored at both the ends securely.

The electronic transaction facility 101 software may implement a very lightweight crypto engine. The MSF 142 platform may enable such clients with a Lightweight AES Cipher. The AES cipher supports 128, 192 and 256 bit encryption with the performance optimised for low-capability clients. Also, the code size of this cipher is very small (~3 KB for Java) in order to support the low-end storage capability of the electronic transaction facilities 101. The cipher may use pre-initialised cipher tables to reduce the number of processor calls and the number of computation variables. This may reduce the processor and memory requirements of the cipher, resulting in enhanced performance.

In a memory-centric implementation of the cipher, significant code—size may be devoted to the pre-defined (pre-initialised at runtime) cipher tables, which consumes a large percentage of the available application space. One embodiment of the AES Cipher externalizes these cipher tables and reads/initialises the tables when the engine is ignited from external storage (rather than from within the executable). This approach may allow the application to leverage the available storage space rather than use the scarce application space in constrained electronic transaction facilities 101. This may result in a compact cipher size without compromising the security (as these cipher tables are part of the public domain algorithm of AES). The cipher tables can either be packaged along-with the electronic transaction facility 101 software or can be downloaded by electronic transaction facility 101 at runtime and stored in its data storage space.

Unlike the Public Key based security setup, the biggest challenge in the symmetric security transaction platform 200 is the Key Distribution. The MSF may need to create and/or store the symmetric credentials for each electronic transaction facility 101 securely. In the absence of the pre-installed public key/certificate, the OTAC may be used as the tool for authentication as well as privacy. When the electronic transaction facility 101 initiates the registration process, it sends the user's OTAC encrypted with the OTAC itself. This scheme may ensure the privacy of the user's credentials. Also, the same OTAC may be used to encrypt the server's response. Thus, the OTAC can serve as a shared key between the server and the client. During the initial trust setup, the server and the client share a 128 bit AES key generated using the PRNG. This key is stored at both the server and the client ends securely. When the service message is exchanged between the server-client, the message is encrypted with this Key. This key may also be changed at the end of every communication session. As the OTAC serves as the authentication as well as privacy key, the MSF 142 must not forward anything to the service provider 168 or the electronic transaction facility 101 to establish the dynamic trust.

The MSF 142 platform implements a concept of 'Symmetric Signing' to ensure the authentication and data integrity. In this approach, hash of the message (Message digest) may be encrypted with a shared symmetric key, instead of the sender's private signing key. When the server receives this signature, it may verify the signature by decrypting it with the client's symmetric key. If the signature can be verified, the originator of this message is likely to have the shared secret key of the client. Given the fact that the shared secret key is 256 bit strong AES key, generated using the PRNG, it is difficult to crack it using the standard crypto attacks. Thus, successful verification is a highly probable indictor of the presence of a shared secret with the originator and, therefore, may serve as the authentication mechanism. The symmetric signature is produced by encrypting the message digest of the message. If the message or the signature is corrupted during the communication, the message digest will not match. Given the fact that it is difficult to break the key, the signature is unlikely to be reproduced by an intruder.

The elements depicted in flow charts and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these, and all such implementations are within the scope of the present disclosure. Thus, while the foregoing drawings and description set forth functional aspects of the disclosed systems, no particular arrangement of software for implementing these functional aspects should be inferred from these descriptions unless explicitly stated or otherwise clear from the context.

Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods or processes described above, and steps thereof, may be realized in hardware, software, or any combination of these suitable for a particular application. The hardware may include a general-purpose computer and/or dedicated computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

While the invention has been described in connection with certain preferred embodiments, other embodiments may be understood by those of ordinary skill in the art and are encompassed herein.

What is claimed is:

1. A method of establishing trust among a user, a device, and a service provider, comprising:
    establishing trust between a transaction service provider and an electronic transaction facility deployed on a mobile phone operated by the user comprising registering the electronic transaction facility with the transaction service provider through a registration process that includes the transaction service provider certifying keys generated by the electronic transaction facility, wherein the keys comprise electronic transaction facility identification information;
    establishing trust between the transaction service provider and the user via the trusted electronic transaction facility comprising receiving, decrypting and authenticating an encryption of a first one-time activation code (OTAC) known to the transaction service provider, the first OTAC received by the user from the transaction service provider, input by the user to the electronic transaction facility and encrypted by the electronic transaction facility;
    establishing initial trust between the transaction service provider and a service provider comprising transmitting security certificates between the transaction service provider and the service provider and installing the security certificates as trusted SSL/HTTPS credentials; and
    in response to the user opting to use a transaction service from the service provider, dynamically establishing direct secure transaction trust between the trusted electronic transaction facility and the trusted service provider by the transaction service provider transmitting a certificate representing the electronic transaction facility's security credentials to the trusted service provider and providing a certificate representing the service provider's security credentials to the electronic transaction facility;
    authenticating, by the service provider, the electronic transaction facility by verifying a second OTAC received by the service provider directly from the handheld device after being encrypted by the handheld device using the credentials of the service provider, wherein prior to the authentication the second OTAC is sent from the service provider to the user.

2. The method of claim 1, wherein the user opting to use a service of the service provider references a service provider.

3. The method of claim 2, wherein transmitting the certificate includes transmitting the certificate to the service provider referenced when the user opts to use a service of the service provider.

4. The method of claim 1, wherein the service that the user opts to use from the service provider is a person to person transaction service.

5. A method comprising:
    registering an electronic transaction facility deployed on a mobile device operated by a user with a transaction service provider by certifying electronic transaction facility identifying keys generated by the electronic transaction facility;
    receiving, decrypting and authenticating an encryption of a first one-time activation code (OTAC) known to the transaction service provider from the mobile device, the first OTAC received by the user from the transaction service provider, provided to the electronic transaction facility by the user and encrypted by the electronic transaction facility;
    installing security certificates communicated between the transaction service provider and a service provider as trusted SSL/HTTPS credentials; and
    providing, in response to the user opting to use a transaction service from the service provider, a certificate representing the electronic transaction facility's security credentials to the service provider and providing a certificate representing the service provider's security credentials to the electronic transaction facility;
    authenticating, by the service provider, the electronic transaction facility by verifying a second OTAC received by the service provider directly from the handheld device after being encrypted by the handheld device using the credentials of the service provider, wherein prior to the authentication the second OTAC is sent from the service provider to the user.

6. A method of establishing trust among a user, a device, and a service provider, comprising:

establishing trust between a transaction service provider and an electronic transaction facility deployed on a mobile phone operated by the user comprising registering the electronic transaction facility with the transaction service provider through a registration process that includes the transaction service provider certifying keys generated by the electronic transaction facility, wherein the keys comprise electronic transaction facility identification information;

establishing initial trust of a service provider comprising transmitting security certificates between the transaction service provider and the service provider and installing the security certificates as trusted SSL/HTTPS credentials; and establishing trust between the trusted service provider and the user via the trusted electronic transaction facility comprising the transaction service provider forwarding a key-exchange request and response between the trusted electronic transaction facility and the trusted service provider, wherein the key-exchange request is encrypted by the trusted electronic transaction facility using a first one-time activation code (OTAC) known to the user and to the trusted service provider, the first OTAC input by the user to the electronic transaction facility;

in response to the user opting to use a transaction service from the service provider, dynamically establishing direct secure transaction trust between the trusted electronic transaction facility and the trusted service provider by the transaction service provider transmitting a certificate representing the electronic transaction facility's security credentials to the trusted service provider and providing a certificate representing the service provider's security credentials to the electronic transaction facility;

authenticating, by the service provider, the electronic transaction facility by verifying a second OTAC received by the service provider directly from the handheld device after being encrypted by the handheld device using the credentials of the service provider, wherein prior to the authentication the second OTAC is sent from the service provider to the user.

7. The method of claim 6, wherein the first OTAC known to the user is received by the user in a communication other than via the transaction service provider.

* * * * *